United States Patent
Zhu et al.

(10) Patent No.: US 11,209,437 B2
(45) Date of Patent: Dec. 28, 2021

(54) FLUORESCENT PROBE AND PREPARATION METHOD AND USE THEREOF

(71) Applicant: Fluorescence Diagnosis (shanghai) Biotech Company Ltd., Shanghai (CN)

(72) Inventors: Linyong Zhu, Shanghai (CN); Yi Yang, Shanghai (CN); Dasheng Zhang, Shanghai (CN); Zengmin Du, Shanghai (CN); Bingkun Bao, Shanghai (CN); Qiuning Lin, Shanghai (CN); Xianjun Chen, Shanghai (CN); Lipeng Yang, Shanghai (CN); Chunyan Bao, Shanghai (CN); Yihui Ge, Shanghai (CN); Renmei Liu, Shanghai (CN); Zhengda Chen, Shanghai (CN); Sitong Zhang, Shanghai (CN); Ningfeng Li, Shanghai (CN); Xin Hua, Shanghai (CN)

(73) Assignee: FLUORESCENCE DIAGNOSIS (SHANGHAI) BIOTECH COMPANY, Shanghai (CN)

( * ) Notice: Subject to any disclaimer, the term of this patent is extended or adjusted under 35 U.S.C. 154(b) by 0 days.

(21) Appl. No.: 16/318,868

(22) PCT Filed: Jul. 18, 2017

(86) PCT No.: PCT/CN2017/093271
§ 371 (c)(1),
(2) Date: Jan. 18, 2019

(87) PCT Pub. No.: WO2018/014821
PCT Pub. Date: Jan. 25, 2018

(65) Prior Publication Data
US 2019/0187144 A1   Jun. 20, 2019

(30) Foreign Application Priority Data

Jul. 20, 2016  (CN) .......................... 201610573341.7

(51) Int. Cl.
| | | |
|---|---|---|
| *A61K 49/00* | (2006.01) | |
| *G01N 33/58* | (2006.01) | |
| *C09K 11/06* | (2006.01) | |
| *C07D 473/18* | (2006.01) | |
| *C07D 263/56* | (2006.01) | |
| *C07D 277/64* | (2006.01) | |
| *C07D 409/14* | (2006.01) | |
| *C07D 487/04* | (2006.01) | |
| *C07D 495/04* | (2006.01) | |
| *C07F 7/08* | (2006.01) | |
| *G01N 21/64* | (2006.01) | |
| *G01N 33/533* | (2006.01) | |

(52) U.S. Cl.
CPC ........... *G01N 33/582* (2013.01); *A61K 49/00* (2013.01); *A61K 49/0017* (2013.01); *C07D 263/56* (2013.01); *C07D 277/64* (2013.01); *C07D 409/14* (2013.01); *C07D 473/18* (2013.01); *C07D 487/04* (2013.01); *C07D 495/04* (2013.01); *C07F 7/0816* (2013.01); *C09K 11/06* (2013.01); *G01N 21/6428* (2013.01); *G01N 33/533* (2013.01)

(58) Field of Classification Search
CPC combination set(s) only.
See application file for complete search history.

(56) References Cited

U.S. PATENT DOCUMENTS

| | | |
|---|---|---|
| 2004/0115130 A1 | 6/2004 | Johnsson et al. |
| 2006/0292651 A1 | 12/2006 | Juillerat et al. |
| 2009/0042227 A1 | 2/2009 | Loew et al. |

FOREIGN PATENT DOCUMENTS

| | | |
|---|---|---|
| CN | 1527941 A | 9/2004 |
| CN | 1717496 A | 1/2006 |
| CN | 104745177 A | 7/2015 |
| WO | 02/20499 A1 | 3/2002 |
| WO | 2004/031405 A1 | 4/2004 |
| WO | 2004/072232 A2 | 8/2004 |
| WO | 2008/012296 A1 | 1/2008 |
| WO | 2009/152165 A2 | 12/2009 |
| WO | 2013/142841 A1 | 9/2013 |

OTHER PUBLICATIONS

Komatsu et al., "Real-Time Measurements of Protein Dynamics Using Fluorescence Activation-Coupled Protein Labeling Method," Journal of the American Chemical Society 133 (2011), pp. 6745-6751, cited in the specification.

Liu et al., "A Rapid SNAP-Tag Fluorogenic Probe Based on an Environment-Sensitive Fluorophore for No-Wash Live Cell Imaging," ACS Chemical Biology 9 (2014), pp. 2359-2365, cited in the specification.

Yu et al., "Protein sensing in living cells by molecular rotor-based fluorescence-switchable chemical probes," Chemical Science 7(2016), pp. 301-307, cited in the specification and ISR.

Yu et al., "Protein sensing in living cells by molecular rotor-based fluorescence-switchable chemical probes," Chemical Science, DOI: 10.1039/c5sc02808f (7 pages), corresponding to Cite No. 3 of Non-Patent Literature Documents.

Lukinavičius et al., "A near-infrared fluorophore for live-cell super-resolution microscopy of cellular proteins," Nature Chemistry, Advance Online Publication, Jan. 6, 2013 (8 pages), cited in ISR.

Lee et al., "Superresolution Imaging of Targeted Proteins in Fixed and Living Cells Using Photoactivatable Organic Fluorophores," Journal of the American Chemical Society 132 (2010), p. 15099-15101.

Lai et al., "Fluorescence switchable probes based on a molecular rotor for selective proteins and small molecules detection," Chemical Communications (2015), (6 pages, including cover sheet).

(Continued)

*Primary Examiner* — Heidi Reese
(74) *Attorney, Agent, or Firm* — Xsensus LLP

(57) ABSTRACT

Provided are a fluorescent probe and a preparation process and the use thereof. The fluorescent probe is sensitive and specific to viscosity, and can be used for specific fluorescent labeling of proteins, and can also be used for quantification, detection or kinetic studies of proteins, and the imaging of cells, tissues and living bodies.

15 Claims, 4 Drawing Sheets

Specification includes a Sequence Listing.

(56) References Cited

OTHER PUBLICATIONS

International Search Report dated Oct. 18, 2017, issued in counterpart International Application No. PCT/CN2017/093271 (2 pages, including annex).
Das, J. et al, "Effects of positional and geometrical isomerism on the biological activity of some novel oxazolidinones", Bioorganic & Medicinal Chemistry Letters, 2005, pp. 337-343.
Fujihara, T. et al, "N-Heterocyclic carbene ligands bearing poly(ethylene glycol) chains: effect of the chain length on palladium-catalyzed coupling reactions employing aryl chlorides", Chem. Comm., 2015, p. 17382-17385.
Gaietta, G. et al, "Multicolor and Electron Microscopic Imaging of Connexin Trafficking", Science, Apr. 19, 2002, vol. 296, pp. 503-507.
Gurrapu, S. et al, "Monocarboxylate Transporter 1 Inhibitors as Potential Anticancer Agents", ACS Medicinal Chemistry Letters, 2015, pp. 558-561.
Hao, Y. et al, "Engineering of highly efficient tetrahydroquinoline sensitizers for dye-sensitized solar cells", Tetrahedron, 2012, pp. 552-558.
Keppler, A. et al, "A general method for the covalent labeling of fusion proteins with small molecules in vivo", Nature Biotechnology, 2002, pp. 86-89.
Martinez, M. M., et al, "Synthesis of functionalized thiophenes and oligothiophenes by selective and iterative cross-coupling reactions using indium organometallics", Org. Biomol Chem., 2012, pp. 3892-3898.
Matsumoto, T. et al, "High HOMO levels and narrow energy band gaps of dithienogalloles", RSC Advances, 2015, pp. 55406-55410.
Mollwitz, B. et al, "Directed Evolution of the Suicide Protein O6-Alkylguanine-DNA Alkyltransferase for Increased Reactivity Results in an Alkylated Protein with Exceptional Stability", Biochemistry, 2012, pp. 986-994.
Ono, M. et al, "Push-pull benzothiazole derivatives as probes for detecting beta-amyloid plaques in Alzheimer's brains", Bioorganic & Medicinal Chemistry, 2009, pp. 7002-7007.
Srikun, D. et al, "Organelle-Targetable Fluorescent Probes for Imaging Hydrogen Peroxide in Living Cells via SNAP-Tag Protein Labeling", JACS, 2010, pp. 4455-4465.
Wang, H. et al, "Modifications of DCDHF single molecule fluorophores to impart water solubility", Tetrahedron Letters, 2007, pp. 3471-3474.
Wu, L. et al, "Syntheses of Highly Fluorescent GFP-Chromophore Analogues", J. Am. Chem. Soc., 2008, pp. 4089-4096.
Yan, P. et al, "Amino(oligo)thiophene-Based Environmentally Sensitive Biomembrane Chromophores", J. Org. Chem, 2008, pp. 6587-6594.
Yang, W. et al, "Carboxylate modified benzylidene cyclopentanone dyes fo one- and two-photon excited photodynamic therapy", J. Photochem. Photobiol. A., 2011, pp. 228-235.
Zajac, M. et al, "Donor-π-acceptor benzothiazole-derived dyes with an extended heteroaryl-containing conjugated system: synthesis, DFT study and antimicrobial activity", Tetrahedron, 2008, pp. 10605-10618.

SEQUENCE LISTING

<160> NUMBER OF SEQ ID NOS: 2

<210> SEQ ID NO 1
<211> LENGTH: 549
<212> TYPE: DNA

```
<213> ORGANISM: Homo sapiens

<400> SEQUENCE: 1
atggacaaag actgcgaaat gaagcgcacc accctggata gccctctggg caagctggaa      60
ctgtctgggt gcgaacaggg cctgcaccgt atcatcggcc tgggcaaagg aacatctgcc     120
gccgacgccg tggaagtgcc tgccccagcc gccgtgctgg gcggaccaga gccactgatg     180
caggccaccg cctggctcaa cgcctacttt caccagcctg aggccatcga ggagttccct     240
gtgccagccc tgcaccaccc agtgttccag caggagagct ttacccgcca ggtgctgtgg     300
aaactgctga agtggtgaa gttcggagag gtcatcagct acagccacct ggccgccctg      360
gccggcaatc ccgccgccac cgccgccgtg aaaaccgccc tgagcggaaa tcccgtgccc     420
attctgatcc cctgccaccg ggtggtgcag ggcgacctgg acgtgggggg ctacgagggc     480
gggctcgccg tgaaagagtg gctgctggcc cacgagggcc acagactggg caagcctggg     540
ctgggttaa                                                              549

<210> SEQ ID NO 2
<211> LENGTH: 549
<212> TYPE: DNA
<213> ORGANISM: Homo sapiens

<400> SEQUENCE: 2
atggacaaag actgcgaaat gaagcgcacc accctggata gccctctggg caagctggaa      60
ctgtctgggt gcgaacaggg cctgcaccgt atcatcttcc tgggcaaagg aacatctgcc     120
gccgacgccg tggaagtgcc tgccccagcc gccgtgctgg gcggaccaga gccactgatg     180
caggccaccg cctggctcaa cgcctacttt caccagcctg aggccatcga ggagttccct     240
gtgccagccc tgcaccaccc agtgttccag caggagagct ttacccgcca ggtgctgtgg     300
aaactgctga agtggtgaa gttcggagag gtcatcagct acagccacct ggccgccctg      360
gccggcaatc ccgccgccac cgccgccgtg aaaaccgccc tgagcggaaa tcccgtgccc     420
attctgatcc cctgccaccg ggtggtgcag ggcgacctgg acgtgggggg ctacgagggc     480
gggctcgccg agaaagagtg gctgctggcc cacgagggcc acagactggg caagcctggg     540
ctgggttaa                                                              549
```

FLUORESCENT PROBE AND PREPARATION METHOD AND USE THEREOF

FIELD OF THE INVENTION

The present invention relates to a fluorescent probe and a preparation method and the use thereof.

BACKGROUND OF THE INVENTION

Fluorescence specific labeling is a powerful tool for studying protein function and quantification. Contrast to other study methods, fluorescent labels have the irreplaceable advantages, such as being sensitive, in situ, instant, and visual. Currently, the most often used method of fluorescent labeling proteins is expressing the fluorescent protein in situ on the target protein by gene fusion technology, thereby realizing specific illumination of the target protein and making it possible to perform tracking studies of the target protein in cells or tissues under a fluorescence microscope. Fluorescent protein technology has been developed for a long time, and this technology is relatively mature. However, there are a few shortcomings. For example, fluorescent proteins suffer from a long maturing and folding time, and tendency to aggregate. Once the fluorescent protein is expressed, it is difficult to carry out post-modification; in addition, most fluorescent proteins still have a shortcoming such as less photostability, etc. These shortcomings limit the application of fluorescent proteins in some extent.

In fact, the chromophores structure of fluorescent protein is relatively simple, which makes it very difficult to construct different types or functionalized fluorescent proteins. Furthermore, there is little guideline to follow, and sea screen can only be carried out by means of random mutation. In contrast, organic small molecule fluorescent dyes are rich in molecular structure, but small molecule fluorescent probes still have many defects in protein-specific labeling. Recently, the emergence of chemical tag technology has effectively solved this problem. With chemical tags, the target protein is tagged with a polypeptide or a protein tag with specific recognition function, and small-molecule fluorescent probe-specific protein labeling is achieved by the highly specific binding of the tag to the substrate. Thus, chemistry tag technology not only inherits advantages of gene fusion technology and sufficiently inherits advantages in all aspects of organic dye probes as compared to fluorescent proteins. Currently, SNAP-tag (K. Johnsson et. al. WO 2004031405), CLIP-tag (K. Johnsson. et. al. WO 2008012296), Halo-tag (Wood, Keith V et. al. WO 2004072232), have been commercialized, especially SNAP-tag and CLIP-tag are the most widely used and have been recognized by the market.

Although chemical tag such as SNAP-tag and CLIP-tag are capable of specifically labeling their protein of interest during the labeling process, no matter free probes or labeled probes in the system all emit fluorescent. That is, the probes emits fluorescence within the system, no matter the probe binds to the target or not. This non-characteristic fluorescence emission is clearly a serious problem in current chemical labeling technology. Therefore, in a strict sense, this method still cannot achieve the same specificity as fluorescent protein. The only effective way to solve this problem is washing out the unlabeled probe. Apparently, the application of this technology will be severely limited in situations where it is needed quickly or the probe cannot be washed.

If a method for fluorescent-activated protein-specific labeling for SNAP-tag and CLIP-tag is designed, which remains dark or emits very weak fluorescence before labeling, and the fluorescence of the dye is sharply enhanced once it is bind to the protein. Undoubtedly, this kinds of probes will be able to achieve the same specificity as fluorescent proteins, which will not only eliminate the washing out procedure of free probes, but also greatly reduce the background interference of free probes, furthermore will widen the application of SNAP-tag and CLIP-tag technology. A method for designing a fluorescently activated protein-specific label suitable for this technique must consider a suitable fluorescence ON/OFF switching mechanism. The FRET mechanism is first applied to this design, which additionally adds the ligand with a fluorescence quenching group. Normally, the small molecule fluorescence is quenched by the quenching group; once the ligand binds to the chemical tag, the quenching group is released, to achieve fluorescence activation (T. Komatsu. et. al. J. Am. Chem. Soc. 2011, 133, 6745-6751). However, the introduction of the quenching group greatly increases the molecular volume of the probe, which greatly reduces the labeling speed, and severely limits the real-time tracking and detection of proteins in cells and tissues by the probe. Furthermore, there must be a good energy level match between the fluorescent probe and the quenching group, which makes the FRET design of long wavelength fluorescent probes become very difficult, for example, the red light emitting dye. In addition, some dyes that are extremely sensitive to fluorescence have also been used to design fluorescent probes (T K Liu. et. al. ACS Chem. Biol. 2014, 9, 2359-2365). These probes exhibit no fluorescence or weak fluorescence when the dyes are in polar fluids, such as cell fluid. When the ligand binds to the protein, the probe is placed in the non-polar pocket of the protein, result the probe emits stronger fluorescence. However, on the one hand, due to the presence of a more polar hydration layer on the surface of the protein, the fluorescence enhancement of the probe is limited; on the other hand, the cell or tissue itself is a very complex system, and the polarity of each organelle changes very much greatly, which can lead to polar-sensitive probes with a high background in cell or tissue imaging. Recently, the literature (T Y Wang et. al. Chem Sci. 2016, 7, 301-307) reported a molecular rotor fluorescent probe with viscosity sensitivity, which is sterically hindered after protein ligands are covalently bound to proteins. The action reduces the molecular rotor's degree of freedom, thereby allowing fluorescent of the probe to be activated. However, in this literature, the fluorescence intensity of the probe after fluorescence activation is dim, and the fluorescence quantum yield is very low. Therefore, the method reported in this literature cannot be used as qualified fluorescent protein tags for labeling, tracking, localization and quantification of target proteins.

SUMMARY

We have found that by linking the ligand moiety to the electron donor moiety of the viscosity-sensitive fluorescent dye, the fluorescence intensity of the viscosity-sensitive fluorescent dye can be greatly enhanced after the ligand bond to the target protein, thereby obtaining a novel structure of fluorescence probes. These probes are sensitive to the viscosity and can be used for proteins specific labeling, which exhibit fast labeling speed, dramatic fluorescence enhancement and wide application range, and can be effectively used for labeling, tracking, localization and quantification of target proteins.

In view of the above, there is provided a fluorescent probe comprising: a ligand moiety A, an optional linker moiety C and a fluorescent dye moiety, the fluorescent dye moiety is a viscosity sensitive fluorescent dye group, which comprises an electron donor moiety D, a conjugated system moiety B and an electron acceptor moiety, said ligand moiety A being a group capable of specifically recognizing and labeling a target protein tagged with a protein tag or a fusion protein, and optionally, said ligand moiety A being capable of specifically recognizing and covalently labeling a target protein tagged with a protein tag or a fusion protein; wherein, the ligand moiety A is directly covalently attached to the electron donor moiety D of the fluorescent dye moiety, or is covalently attached to the electron donor moiety D of the fluorescent dye moiety via a linker moiety C.

Optionally, the fluorescent probe described above has a structure as shown in the Formula (I),

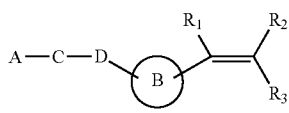
(I)

wherein the linker moiety C is an optionally present group, which is selected from the group consisting of an alkylene group, or a modified alkylene group;
the structural moiety represented by the Formula (I-R) in the Formula (I) is a fluorescent dye moiety,

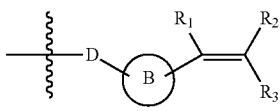
(I-R)

wherein, the electron donor moiety -D- is $—NX_1—X_2—$, $X_1$ is selected from hydrogen, an alkyl group or a modified alkyl group, $X_2$ is selected from an alkylene group or a modified alkylene group, $X_1$, $X_2$ are optionally linked to each other, and form an aliphatic heterocycle with the nitrogen atom;
the conjugated system moiety B is formed by conjugating at least one selected from the group consisting of a double bond, a triple bond, an aromatic ring, and an aromatic hetero ring, and has a structure represented by the following Formula (I-1), optionally, the hydrogen atoms contained are independently replaced with one or more substituents selected from the group consisting of a halogen atom, nitro, a hydrophilic group, an alkyl group, and a modified alkyl group, and the substituents are optionally bonded to each other to form an alicyclic or heterocyclic ring;

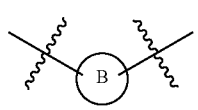
(I-1)

Optionally, the structure of formula (I-1) is linked to $X_1$ and $X_2$ to form an aliphatic heterocyclic ring;
the electron acceptor moiety has a structure represented by the following Formula (I-2),

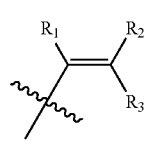
(I-2)

wherein,
$R_1$ is selected from the group consisting of hydrogen, a halogen atom, nitro, an alkyl group, an aryl group, a heteroaryl group, a hydrophilic group or a modified alkyl group;
$R_2$ is selected from the group consisting of cyano, carboxyl, a keto group, an ester group, an amide group, a phosphonic acid group, a phosphonate group, sulfo, a sulfonate group, sulfone, sulfoxide group, an aryl group, a heteroaryl group, an alkyl group or a modified alkyl group;
$R_3$ is cyano;
In certain embodiment, the electron acceptor moiety optionally forms a cyclic structure of the following Formulas (I-2-a), (I-2-b):

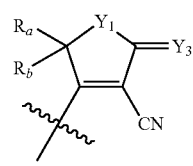
(I-2-a)

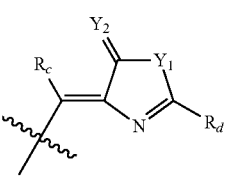
(I-2-b)

wherein, $R_a$, $R_b$ are independently selected from the group consisting of hydrogen, a hydrophilic group, an alkyl group, and a modified alkyl group, and $R_a$ and $R_b$ are optionally bonded to each other to form an alicyclic or heterocyclic ring;
$Y_1$ is selected from the group consisting of $—O—$, $—S—$, $—(S=O)—$, and $—(NR_i)—$, wherein $R_i$ is selected from hydrogen, an alkyl group or a modified alkyl group;
$Y_2$ is selected from the group consisting of $=O$, $=S$, $=S=O$ and $=NR_i$ wherein $R_i$ is selected from hydrogen, an alkyl group or a modified alkyl group;
$Y_3$ is selected from the group consisting of $=O$, $=S$, $=S=O$ and $=NR_i$ wherein $R_i$ is selected from hydrogen, an alkyl group or a modified alkyl group;
or, $Y_3$ is $=C(R_e)(CN)$;
$R_e$ is selected from the group consisting of cyano, carboxyl, a keto group, an ester group, an amide group, phosphonic acid group, a phosphonate group, sulfo, a sulfonate group, sulfone, sulfoxide, an aryl group, a heteroaryl group, an alkyl group or a modified alkyl group;
when $R_2$ or $R_e$ is an aryl group or a heteroaryl group, optionally, the hydrogen atom on the ring is independently replaced with a substituent selected from a halogen atom, nitro, a hydrophilic group, an alkyl group or a modified alkyl group; optionally, the substituents are linked to each other to form a saturated or unsaturated alicyclic or heteroalicyclic ring;

wherein, said alkyl group is a saturated aliphatic straight or branched alkyl group of 1 to 30 carbon atoms;

said alkylene group is a saturated aliphatic straight or branched alkylene group of 1 to 30 carbon atoms;

said modified alkyl group is an alkyl group wherein any carbon atom contained is independently replaced with one or more substituents selected from halogen atom, —O—, —OH, —CO—, —NO$_2$, —CN, —S—, —SO$_2$—, —(S=O),

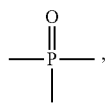

phenyl, phenylene, a primary amino group, a secondary amino group, a tertiary amino group, a quaternary ammonium salt group, a saturated or unsaturated monocyclic or bicyclic cycloalkylene group, a bridged aliphatic heterocyclic ring; the modified alkyl group has 1 to 300 carbon atoms, the carbon-carbon single bond optionally being replaced independently by a carbon-carbon double bond or a carbon-carbon triple bond; said modified alkylene group is an alkylene group wherein any carbon atom contained is independently replaced with one or more substituents independently selected from halogen atom, —O—, —OH, —CO—, —NO$_2$, —CN, —S—, —SO$_2$—, —(S=O),

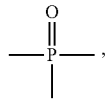

phenyl, phenylene, a primary amino group, a secondary amino group, a tertiary amino group, a quaternary ammonium salt group, a saturated or unsaturated monocyclic or bicyclic cycloalkylene group, a bridged aliphatic heterocyclic ring, the modified alkylene group has 1 to 30 carbon atoms, the carbon-carbon single bond optionally being replaced independently by a carbon-carbon double bond or a carbon-carbon triple bond;

said alicyclic ring is a saturated or unsaturated 4- to 10-membered monocyclic or polycyclic alicyclic ring;

said heteroalicyclic ring is a saturated or unsaturated 4- to 10-membered monocyclic or polycyclic heterocyclic ring having at least one heteroatom selected from N, O, S or Si, on the heteroalicyclic ring. When the heteroalicyclic ring contains an S atom, it is optionally —S— or —SO$_2$—; the heterocyclic ring is optionally substituted with halogen atom, nitro, an alkyl group, an aryl group, a hydrophilic group, and a modified alkyl group;

said aryl or aromatic ring is 5 to 10 membered monocyclic or fused bicyclic ring;

the heteroaryl or aromatic heterocyclic ring is a 5- to 10-membered monocyclic or fused bicyclic ring containing at least one heteroatom selected from N, O, S or Si in the ring;

said halogen atoms are each selected independently from the group consisting of F, Cl, Br, I;

said hydrophilic group is hydroxyl, sulfo, sulfuric acid group, phosphoric acid group, primary amino group, secondary amino group or tertiary amino group and substituendum thereof;

said monocyclic cycloalkylene group is a 4- to 7-membered cycloalkylene group;

said bicyclic cycloalkylene group is a 5- to 7-membered bicyclic cycloalkylene group;

said bridged aliphatic heterocyclic ring is a 5- to 20-membered bridged aliphatic heterocyclic ring containing at least one heteroatom selected from N, O, or S in the ring.

Optionally, the fluorescent probe described above is characterized in that: the protein tag is a purified product, an unpurified product, or an in situ state present in a cell or tissue;

Optionally, the protein tag is O$_6$-alkylguanine-DNA alkyltransferase (SNAP-tag) or a mutant thereof, alkylcytosine transferase (CLIP-tag) or a mutant thereof;

Optionally, the mutant of the O$_6$-alkylguanine-DNA alkyltransferase is selected from the group consisting of SNAP F33G or SNAP V164E;

Optionally, the protein tag is O$_6$-alkylguanine-DNA alkyltransferase (SNAP-tag) or a mutant thereof;

The ligand moiety A is derived from an O$_6$-alkylguanine derivative, an alkyl 4-chloropyrimidine derivative or an alkylcytosine derivative;

Optionally, the ligand moiety A suitable for the SNAP-tag is derived from an O$_6$-alkylguanine derivative or an alkyl 4-chloropyrimidine derivative; optionally, the ligand moiety A suitable for the CLIP-tag is derived from an alkylcytosine derivative;

Optionally, the ligand moiety A- is selected from the following structures:

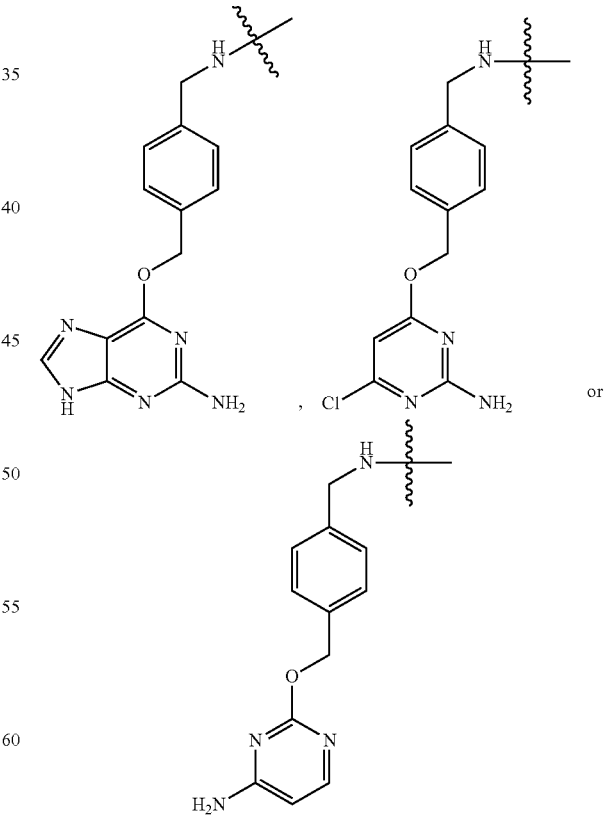

Optionally, the modified alkyl group or the modified alkylene group is independently a group containing one or more substituents selected from —OH, —O—, -ethylene glycol moiety (i.e. —(CH$_2$CH$_2$O)n-), C$_1$ to C$_8$ alkyl groups, C$_1$ to C$_8$ alkoxy, C$_1$ to C$_8$ acyloxy, C$_1$ to C$_8$ haloalkyl, monosaccharide moiety, disaccharide moiety, polysaccharide moiety, —O—CO—, —NH—CO—, —(—NH—CHR—CO—)$_n$, —SO$_2$—O—, —SO—, —SO$_2$—NH—, —S—S—, —CH=CH—, —C≡C—, a halogen atom, cyano, nitro, o-nitrophenyl, phenacyl, a phosphate group or a phosphonate group, wherein n is from 1 to 100, and R is selected from H or an α-amino acid residue;

Optionally, the C$_1$ to C$_8$ alkyl group is methyl, ethyl, propyl, isopropyl, and the C$_1$ to C$_8$ alkoxy group is methoxy, ethoxy, propoxy, isopropoxy, the C$_1$ to C$_8$ acyloxy is acetoxy, propionyloxy, isopropionyloxy, C$_1$ to C$_8$ haloalkyl is trifluoromethyl, chloromethyl, bromomethyl;

Optionally, the aliphatic heterocyclic ring is azetidine, pyrrolidine, piperidine, tetrahydrofuran, tetrahydropyran, morpholine, thiomorpholine;

Optionally, the heteroaryl ring is thiophene, furan, and pyrrole.

Optionally, the linker moiety is selected from the group consisting of —(C=O)—, —(CH$_2$CH$_2$O)$_n$—, wherein n is 1 to 20;

Optionally, X$_1$ is a C$_{1-50}$ straight or branched alkyl group optionally substituted by one or more groups selected from hydroxyl, cyano, halogen atom, carboxyl, and quaternary ammonium group, or a C$_{2-50}$ ether chain group having 1 to 10 oxygen atoms and optionally substituted by one or more groups selected from a sulfonic acid group or carboxyl, and X$_2$ is a C$_{1-50}$ straight or branched alkylene groups optionally substituted by one or more groups selected from hydroxyl, cyano, halogen atom, carboxyl, quaternary ammonium group; or a C$_{2-50}$ ether chain group having 1 to 10 oxygen atoms and optionally substituted by one or more groups selected from a sulfonic acid group or carboxyl; or, —NX$_1$—X$_2$— forms any one of groups of the following Formulas (I-1-1) to (I-1-2):

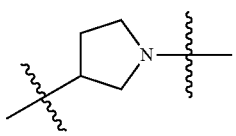
(I-1-1)

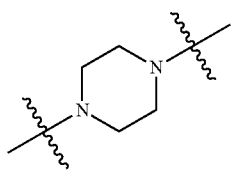
(I-1-2)

Optionally, X$_1$ is a C$_{1-10}$ straight or branched alkyl group optionally substituted with one or more groups selected from hydroxyl, cyano, halogen atom, carboxyl, and quaternary ammonium group, and X$_2$ is a C$_{1-10}$ straight or branched alkylene group optionally substituted with one or more groups selected from hydroxyl, cyano, a halogen atom, carboxyl, and a quaternary ammonium group.

Optionally, the above fluorescent probe is characterized in that two adjacent substituents in the conjugated system moiety B are linked to each other to form a saturated or unsaturated alicyclic ring or aliphatic heterocyclic ring;

Optionally, H of the CH in the conjugated system moiety B is replaced with halogen atom, nitro, hydrophilic group, alkyl group or modified alkyl group;

Optionally, the conjugated system moiety B contains NH; optionally, H on the NH is replaced with an alkyl group or a modified alkyl group;

Optionally, the conjugated system moiety B is selected from the structures of the following Formulas (I-1-1) to (I-1-28):

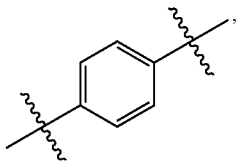
(I-1-1)

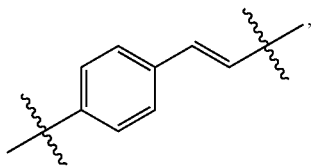
(I-1-2)

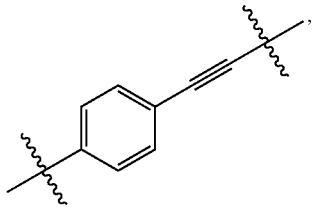
(I-1-3)

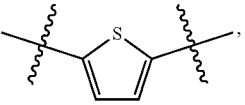
(I-1-4)

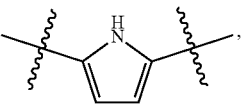
(I-1-5)

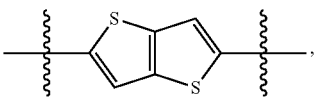
(I-1-6)

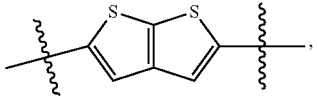
(I-1-7)

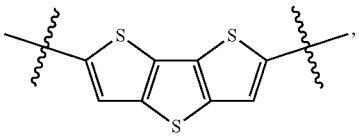
(I-1-8)

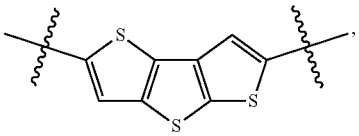
(I-1-9)

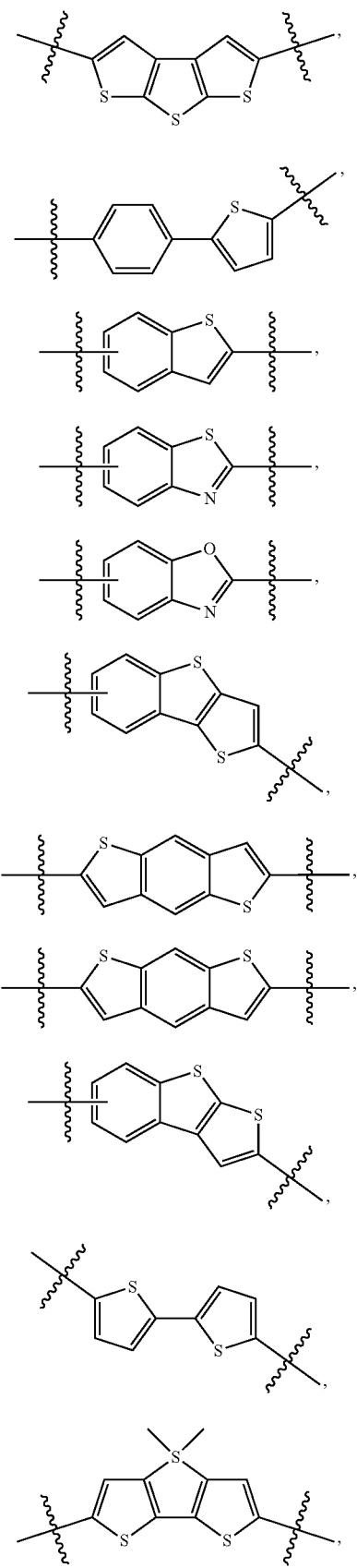
Optionally, the conjugated system moiety B and X₁ are linked to each other to form an alicyclic heterocyclic ring as shown below.

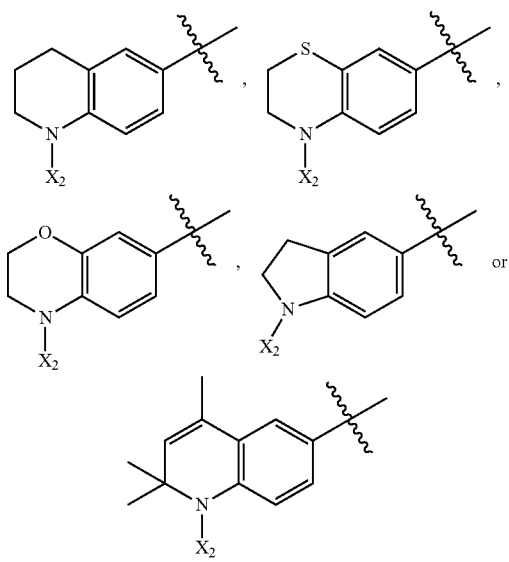

wherein, $X_2$ is as defined in claim 2 or 3.

Optionally, the fluorescent probe described above, wherein $R_a$, $R_b$ in the Formula (I-2-a) form

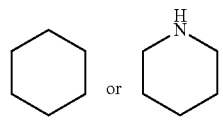

with the bonded carbon atoms;

Optionally, the $R_2$ and $R_e$ are independently selected from the following structures, or a bicyclic or polycyclic fused aromatic ring or fused aromatic heterocyclic ring formed by the following structures themselves or fused with each other: preferably are a bicyclic or a tricyclic fused aromatic ring or fused aromatic heterocyclic ring;

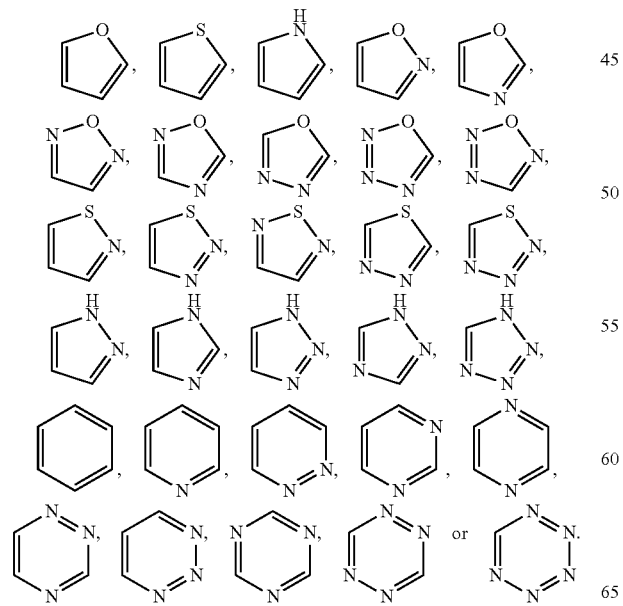

Optionally, H of CH in the above structures of $R_2$ or $R_e$ is replaced by halogen atom, nitro, hydrophilic group, alkyl group or modified alkyl group; optionally, $R_2$ or $R_e$ is a group containing NH selected from the above structure, and optionally, the H on the NH is replaced with an alkyl group or a modified alkyl group;

Alternatively, the $R_2$ and $R_e$ are independently selected from modified alkyl group: the modified alkyl group contains a keto group, an ester group or an amide group, and is bonded to alkenyl carbon of the Formula (I-2) or of formula (I-2-a) via a carbonyl group in the keto, ester or amide group;

Optionally, the structure of the Formula (I-2) is selected from the group consisting of the following Formulas (I-2-1) to (I-2-19):

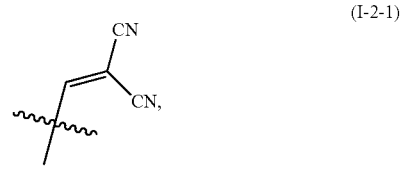
(I-2-1)

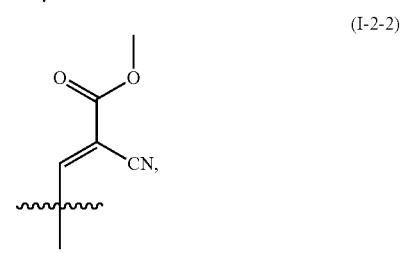
(I-2-2)

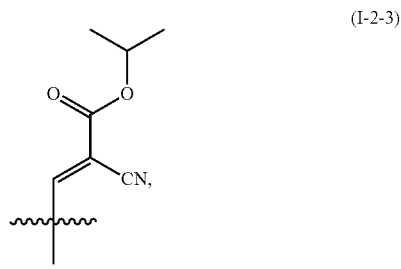
(I-2-3)

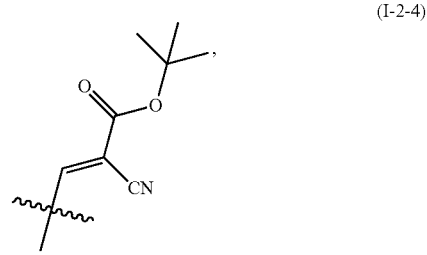
(I-2-4)

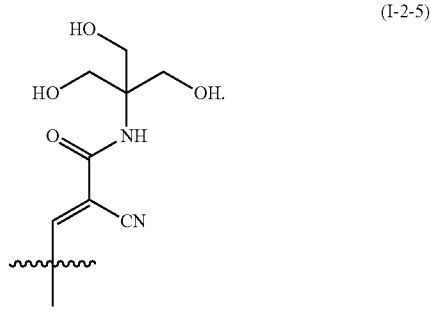
(I-2-5)

(I-2-6)
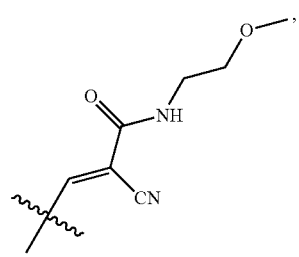
(I-2-7)
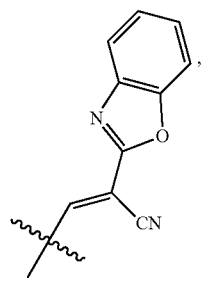
(I-2-8)
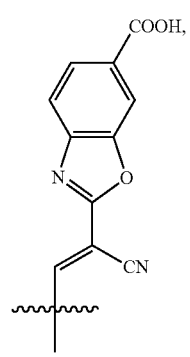
(I-2-9)
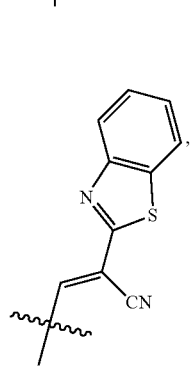
(I-2-10)
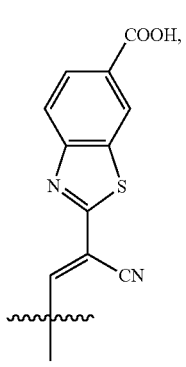
(I-2-11)
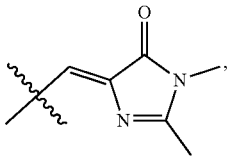
(I-2-12)
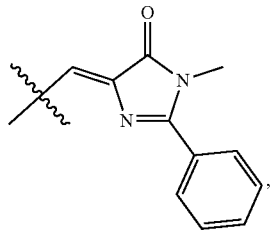
(I-2-13)
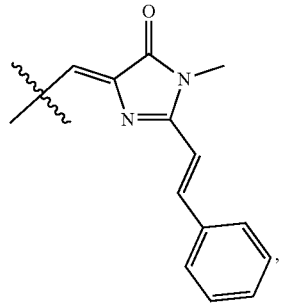
(I-2-14)
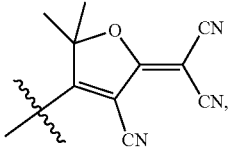
(I-2-15)
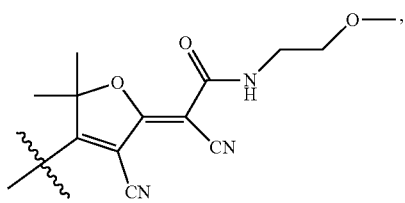
(I-2-16)
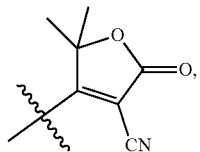
(I-2-17)
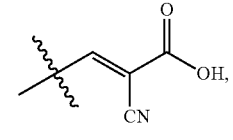
(I-2-18)
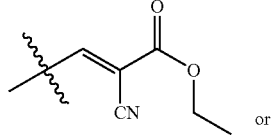
or -continued
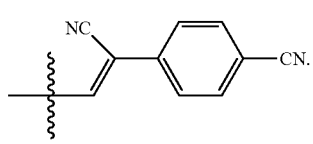
(I-2-19)
Optionally, the fluorescent probe described above is selected from the following structures:
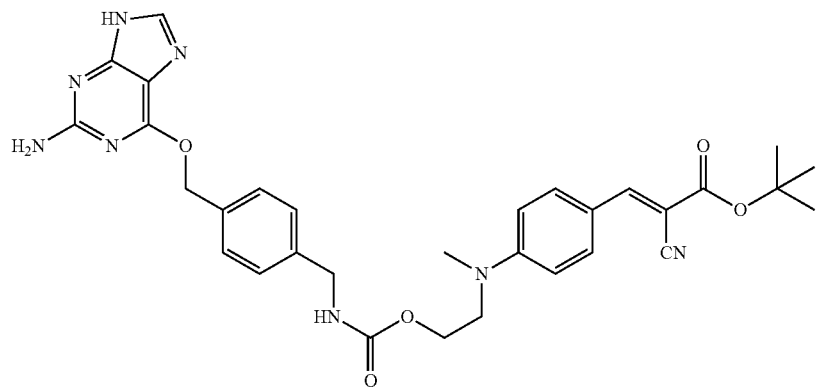
Probe 1
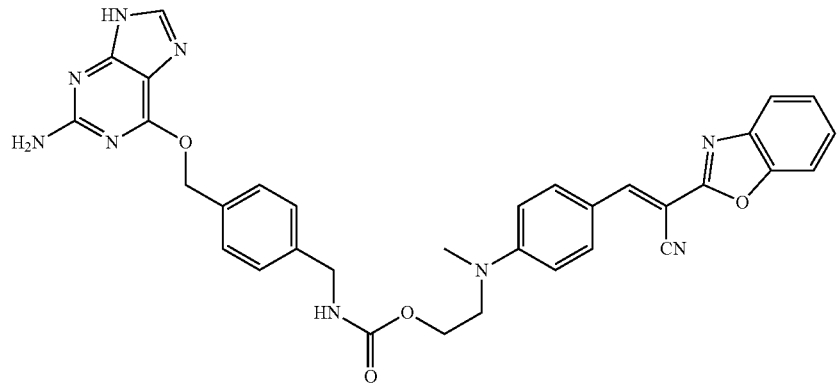
Probe 2
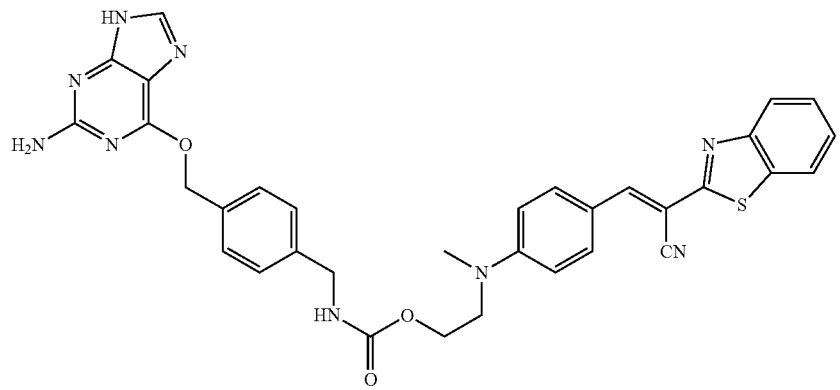
Probe 3

-continued
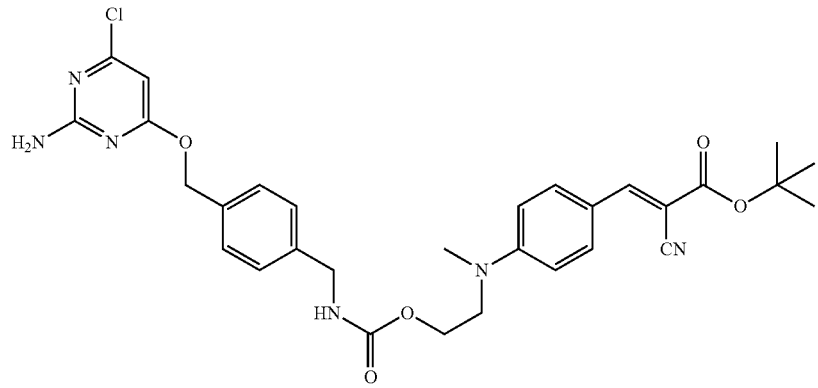
Probe 4
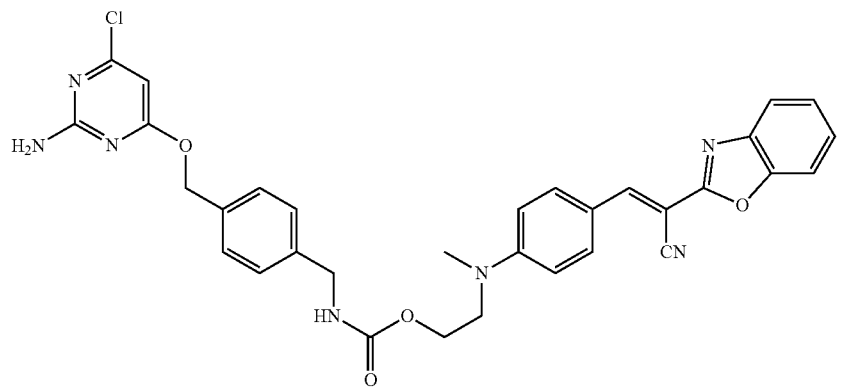
Probe 5
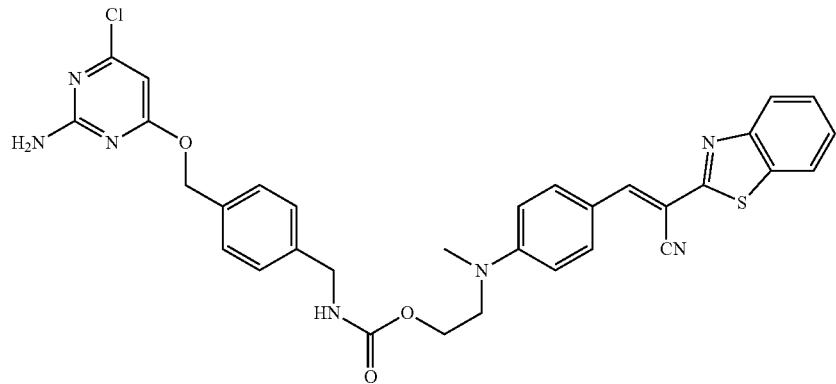
Probe 6
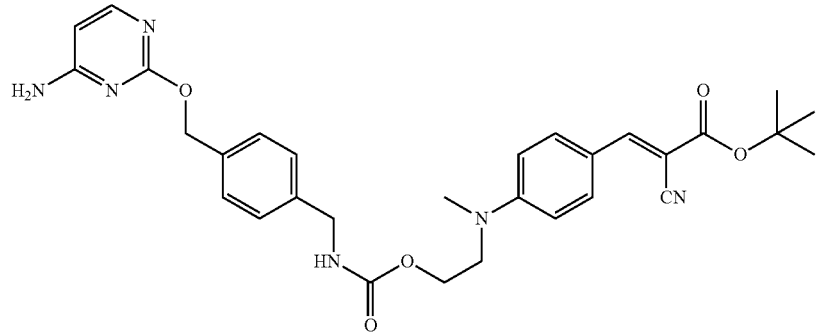
Probe 7

-continued
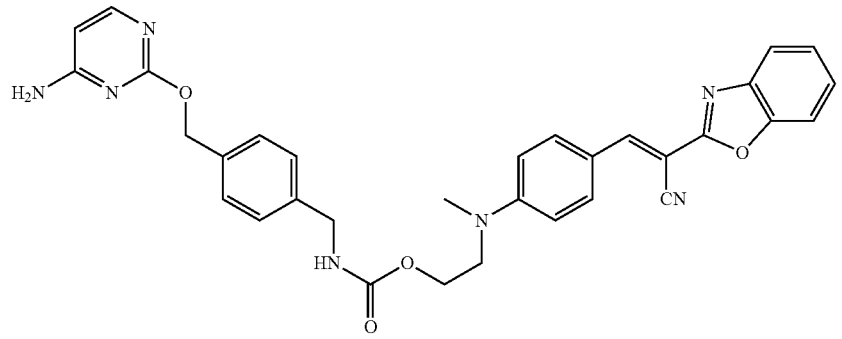
Probe 8
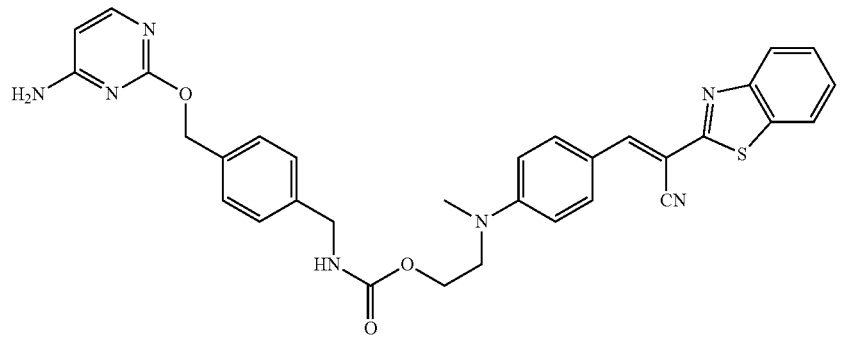
Probe 9
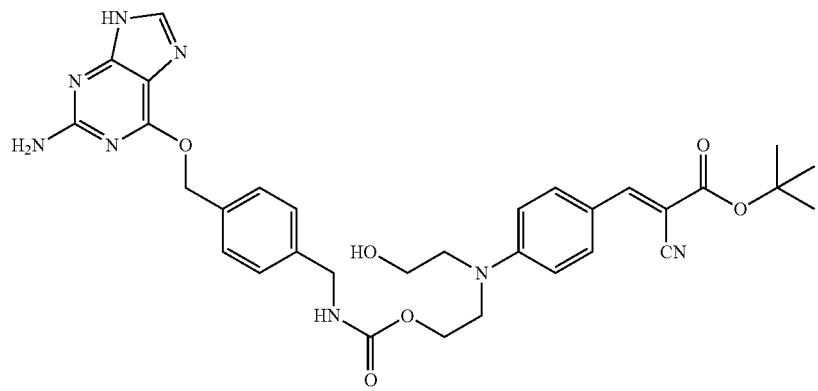
Probe 10
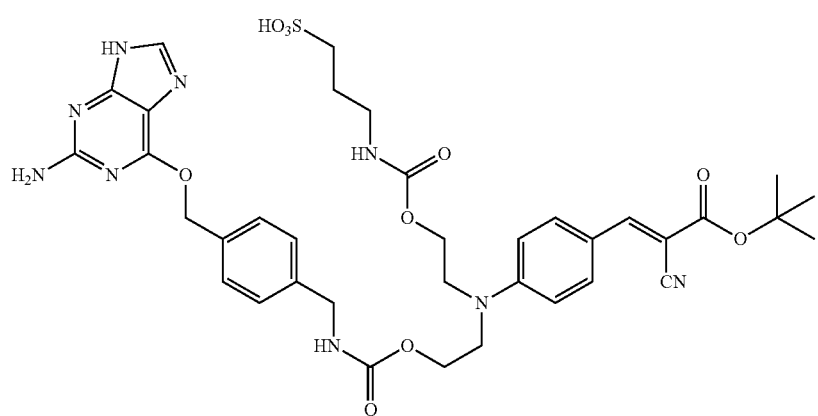
Probe 11

-continued
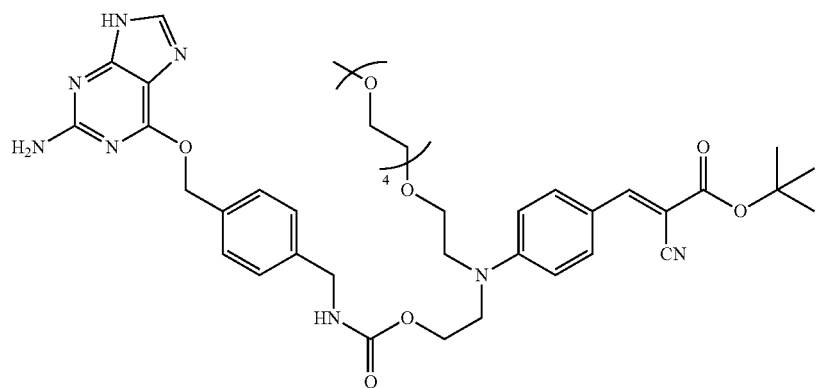
Probe 12
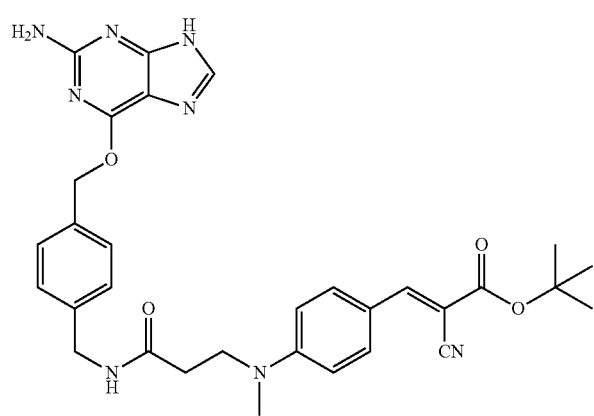
Probe 13
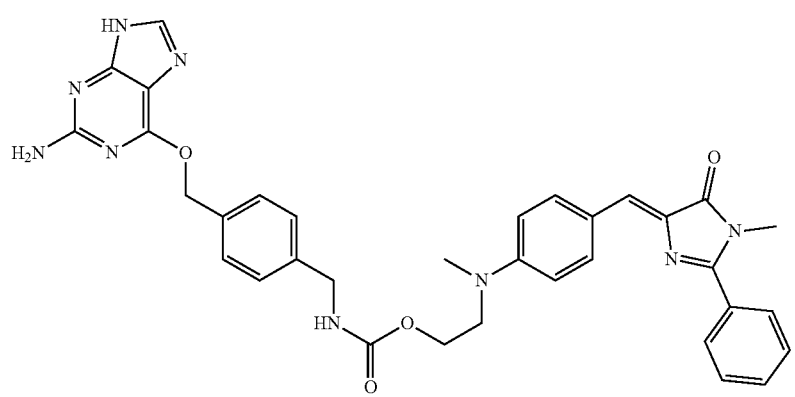
Probe 14
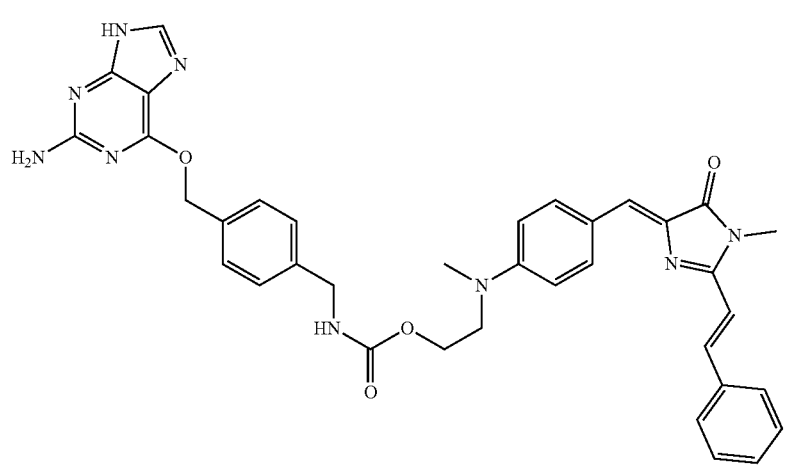
Probe 15

-continued
Probe 16
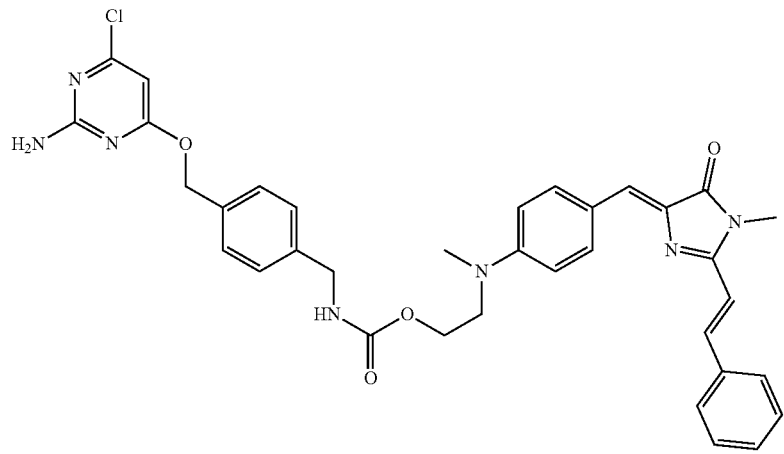
Probe 17
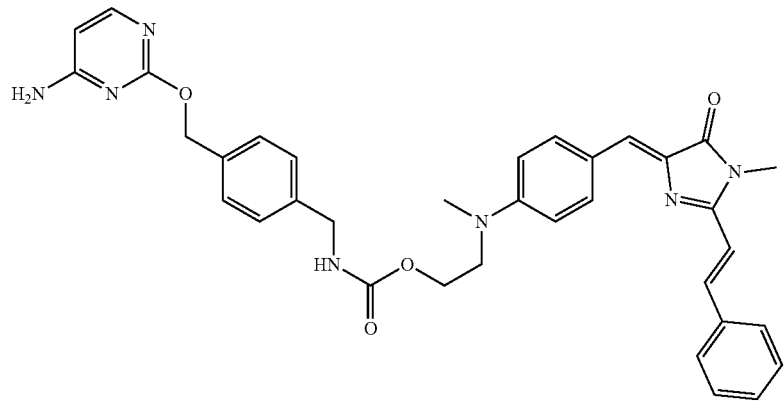
Probe 18
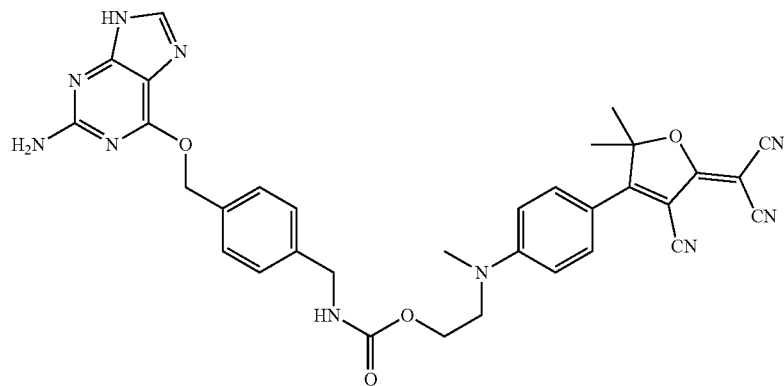
Probe 19
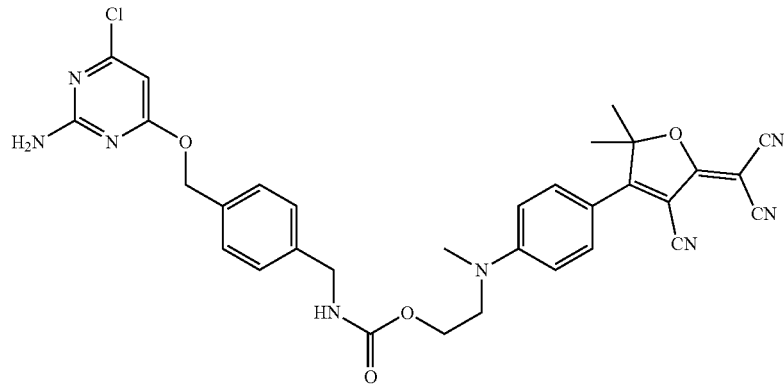

-continued
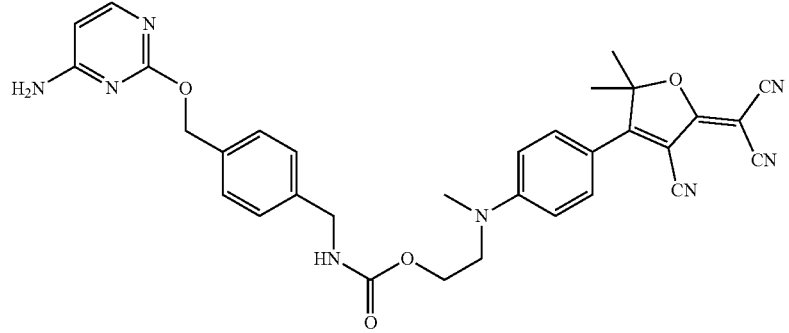
Probe 20
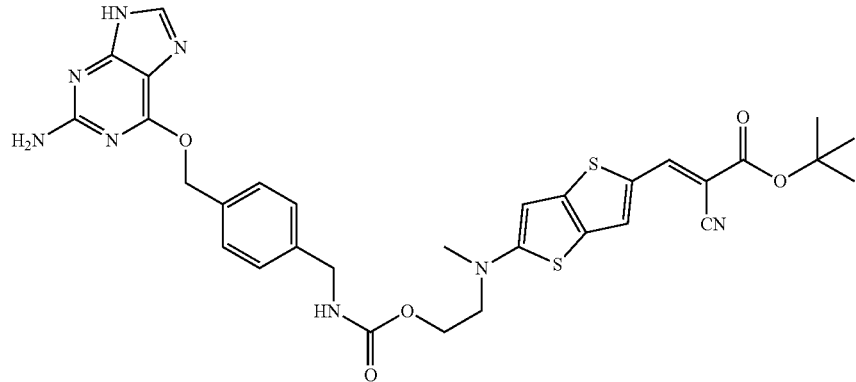
Probe 21
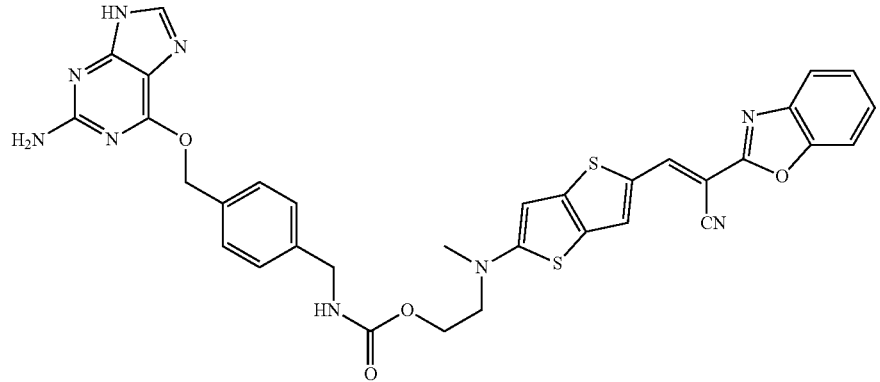
Probe 22
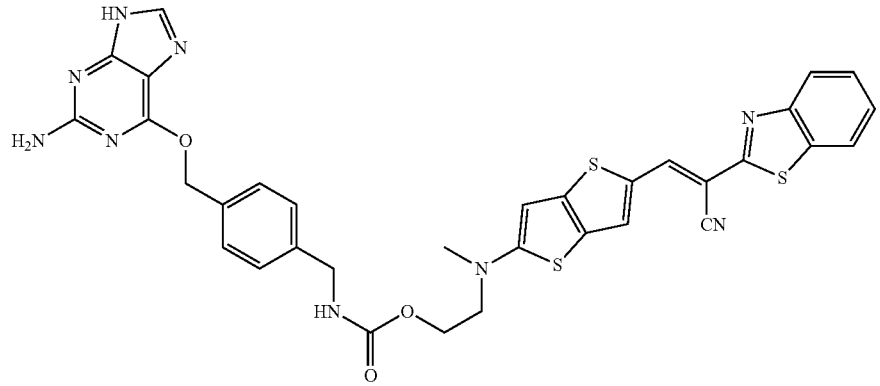
Probe 23

-continued
Probe 24
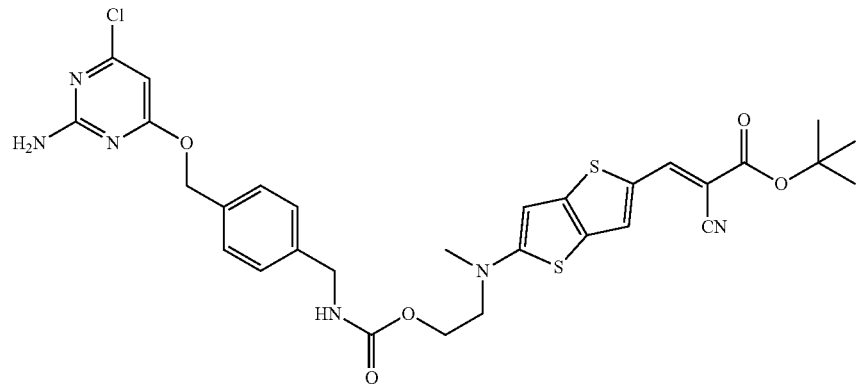
Probe 25
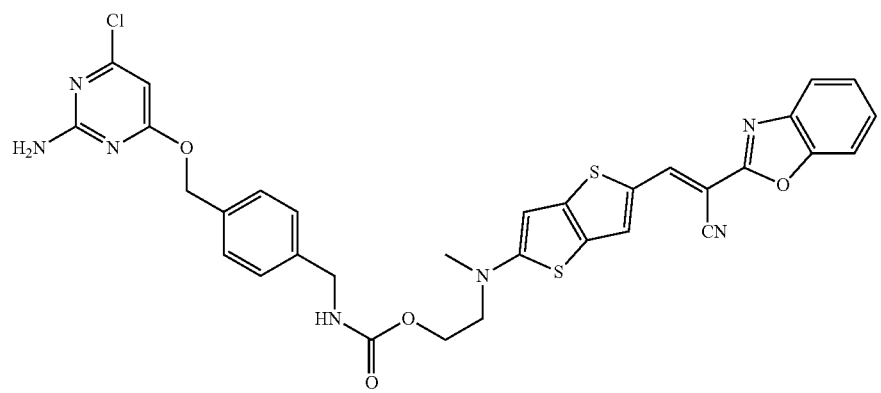
Probe 26
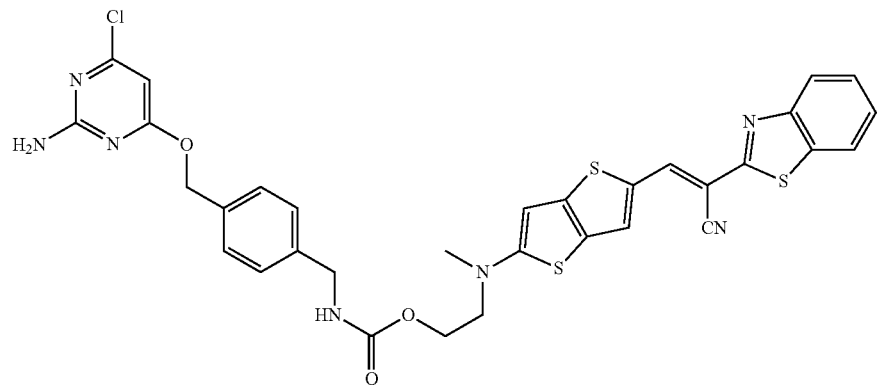
Probe 27
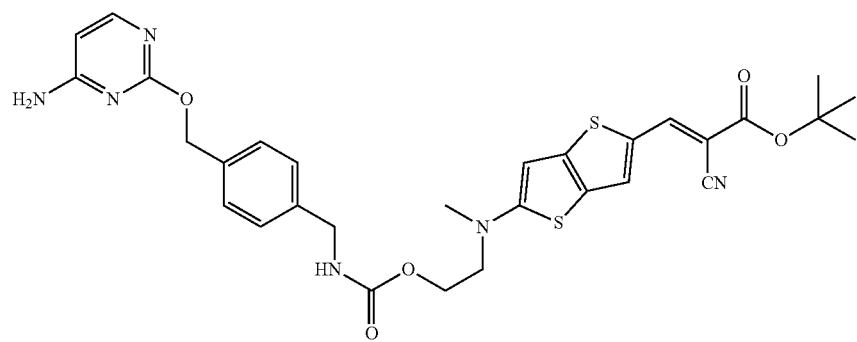

-continued
Probe 28
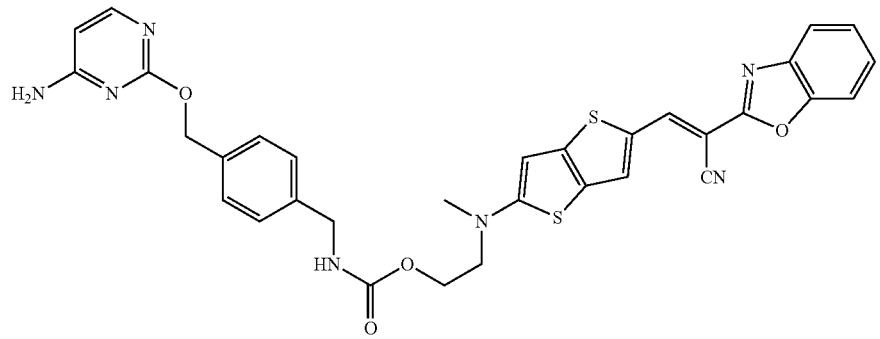
Probe 29
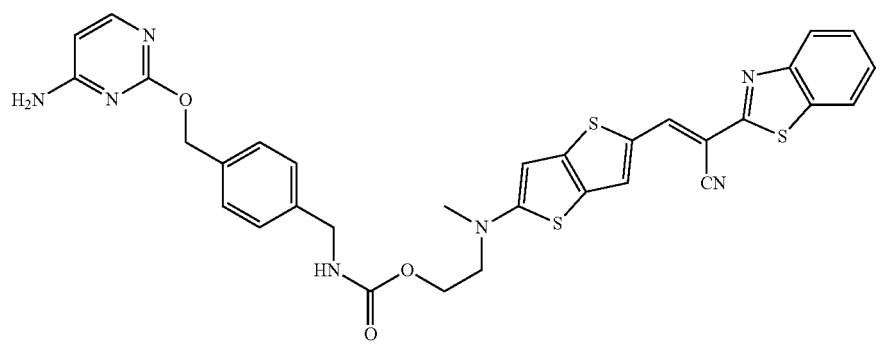
Probe 30
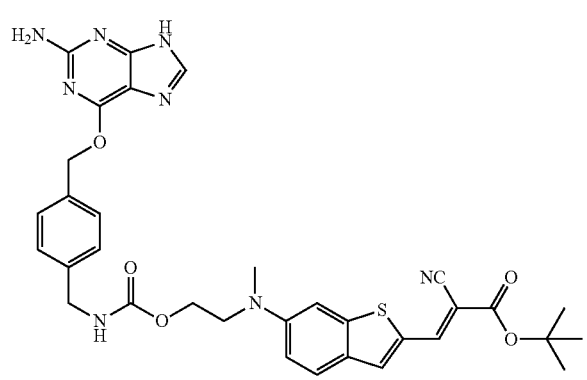
Probe 31
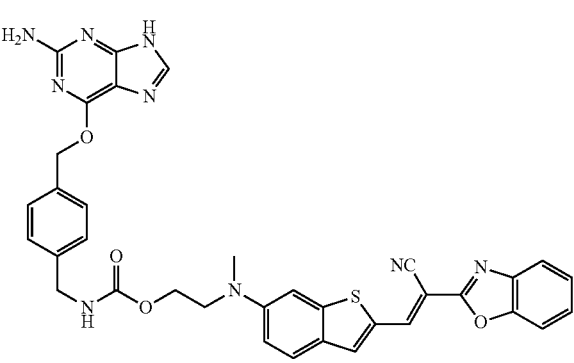
Probe 32
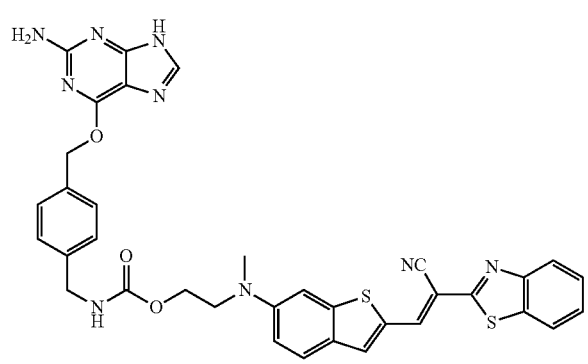
Probe 33
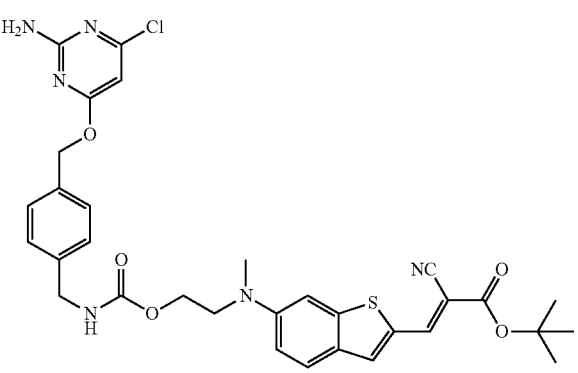

-continued
Probe 34
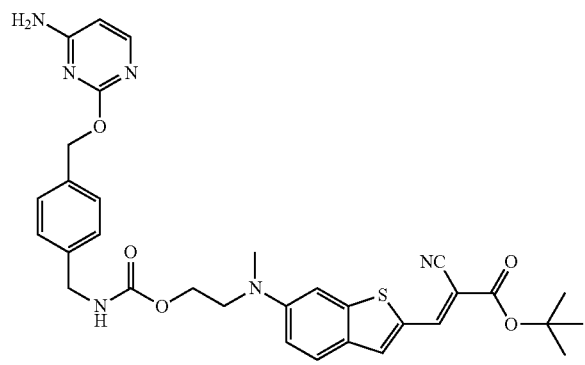
Probe 35
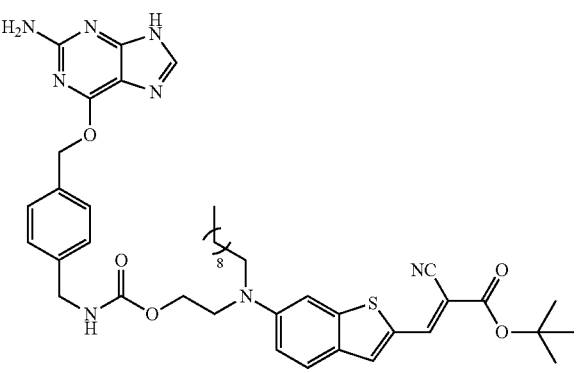
Probe 36
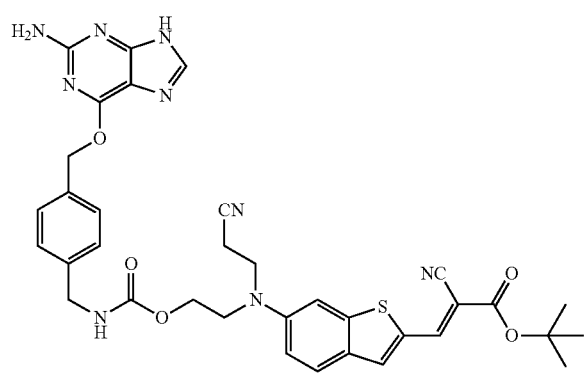
Probe 37
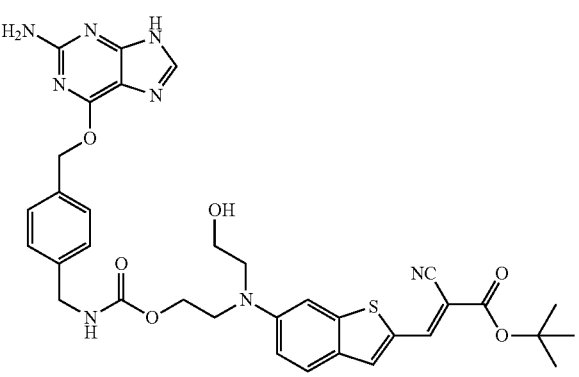
Probe 38
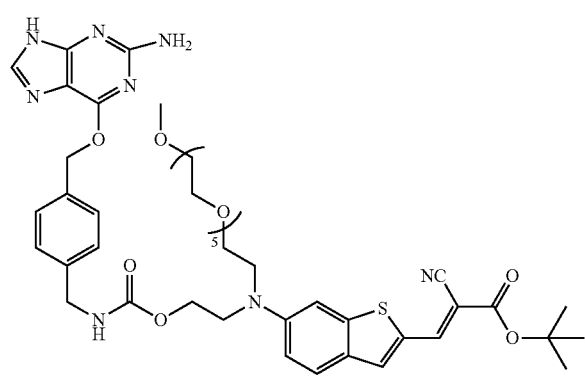
Probe 39
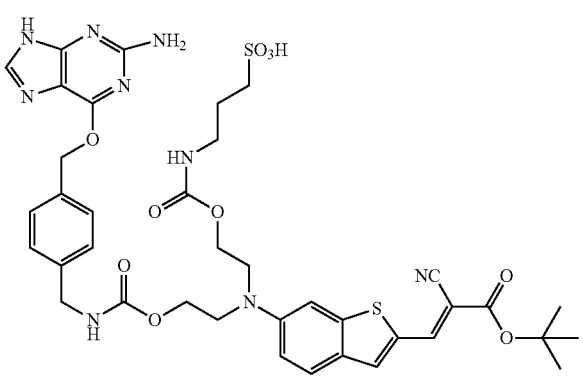
Probe 40
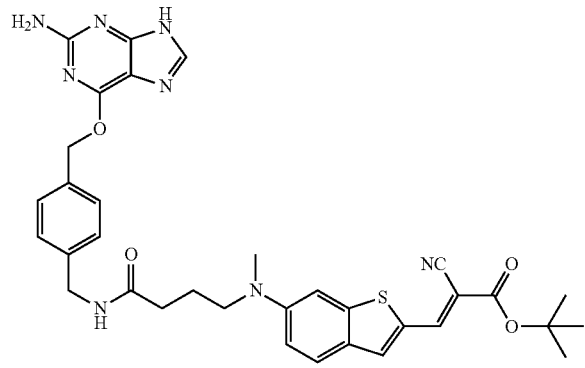
Probe 41
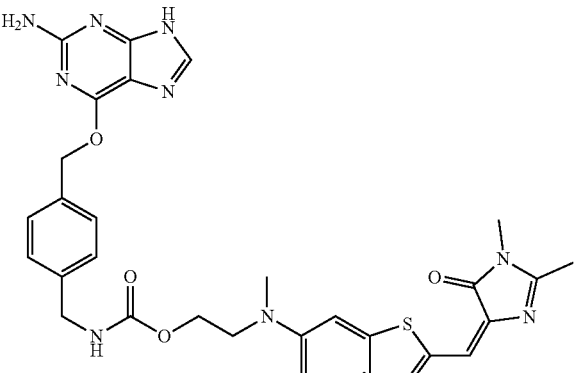

Probe 42
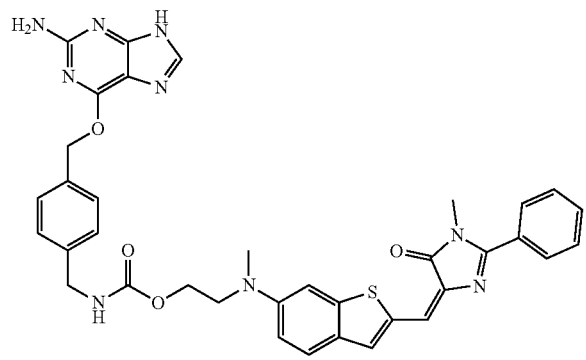
Probe 43
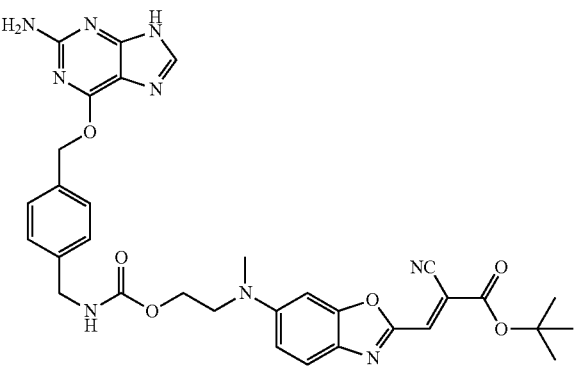
Probe 44
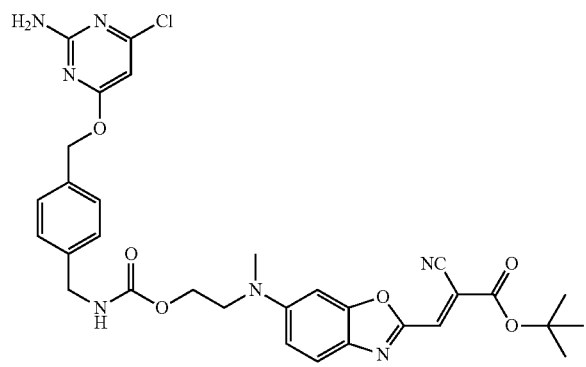
Probe 45
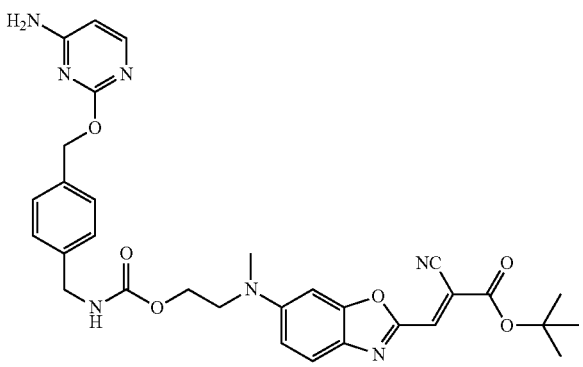
Probe 46
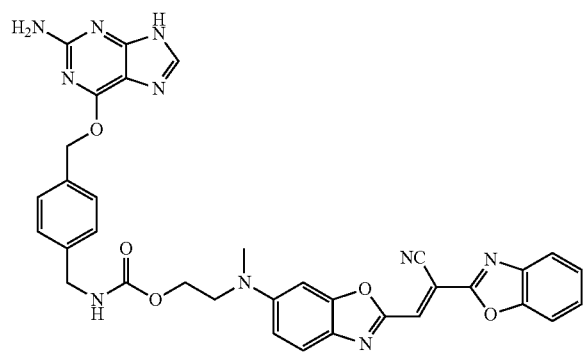
Probe 47
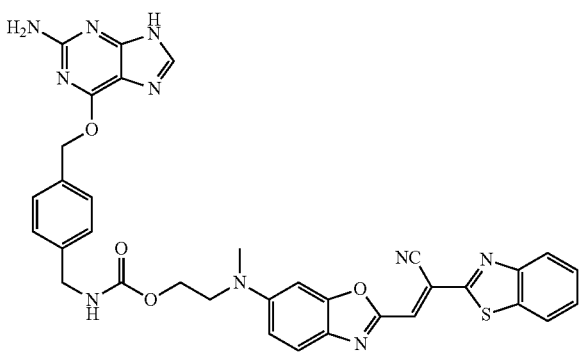
Probe 48
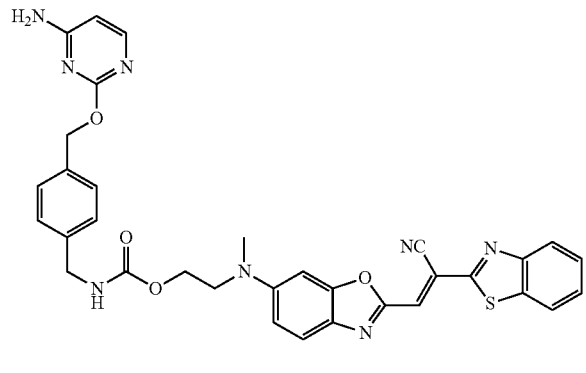
Probe 49
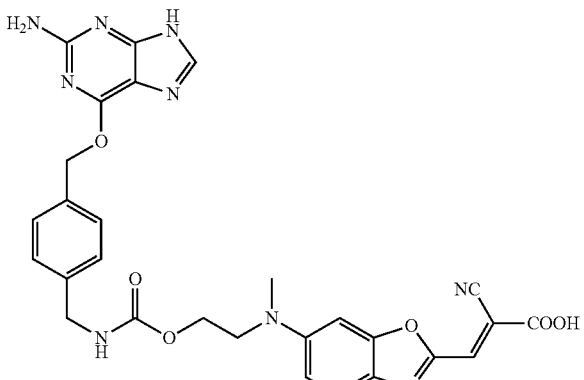

-continued
Probe 50
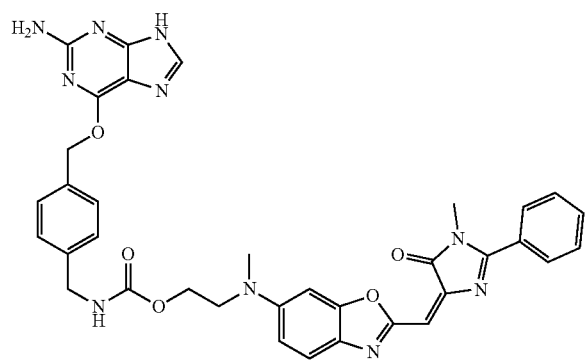
Probe 51
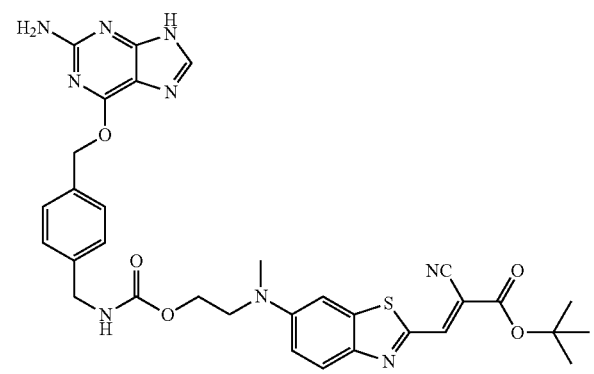
Probe 52
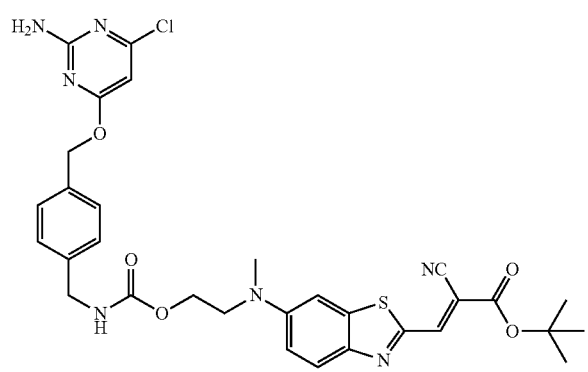
Probe 53
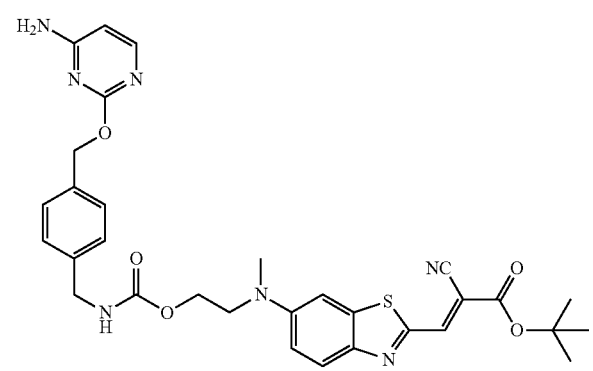
Probe 54
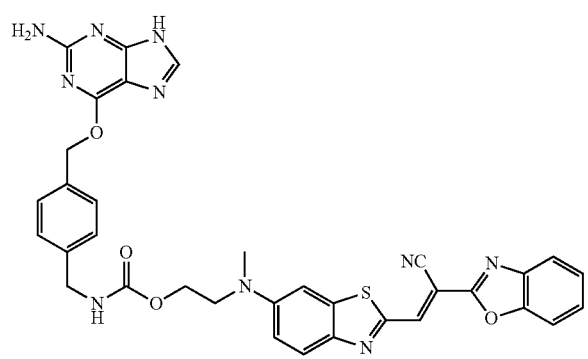
Probe 55
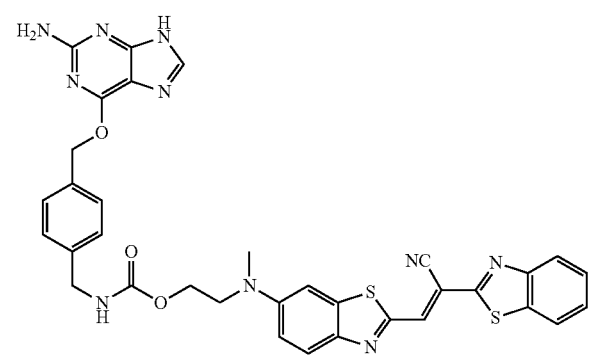
Probe 56
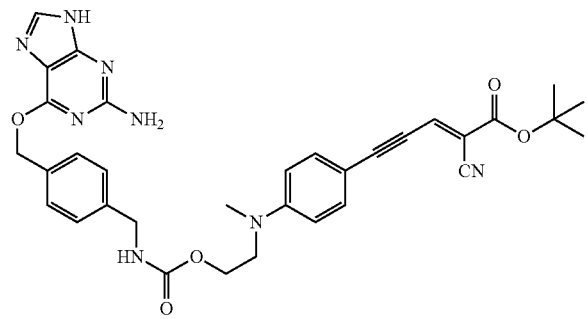
Probe 57
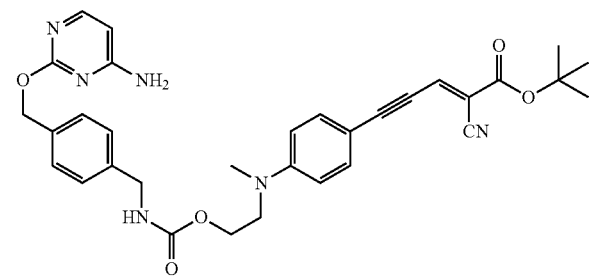

-continued
Probe 58
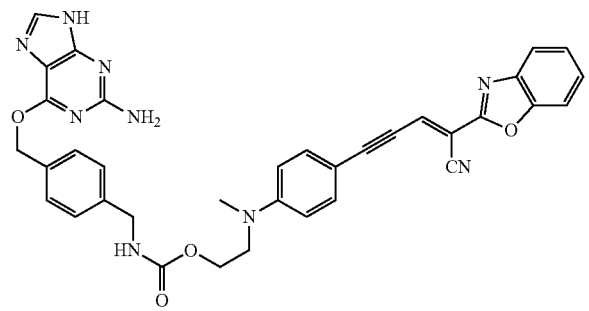
Probe 59
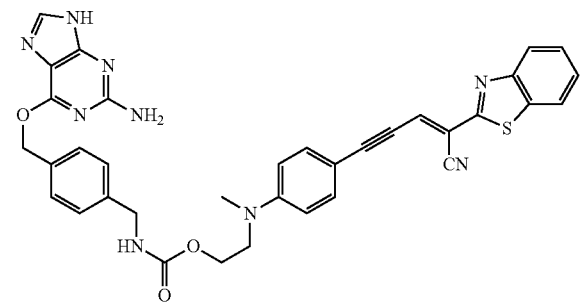
Probe 60
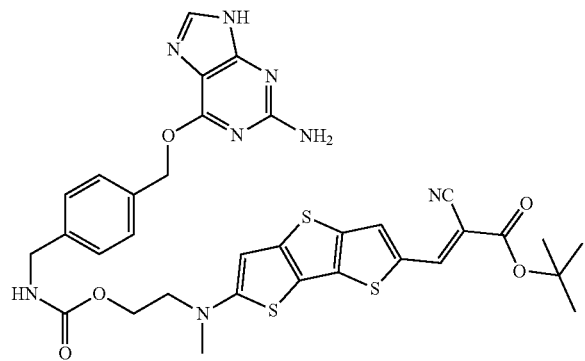
Probe 61
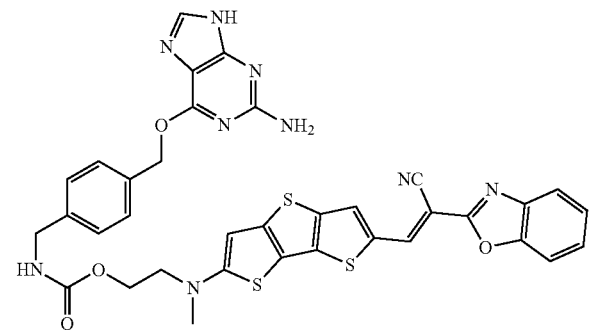
Probe 62
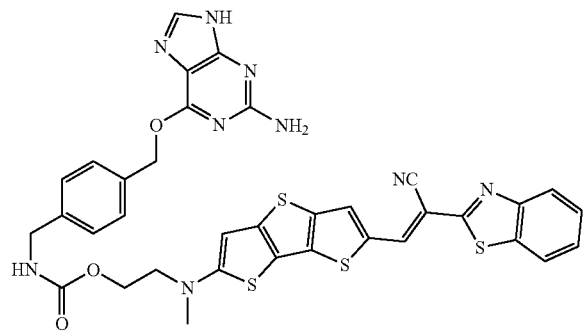
Probe 63
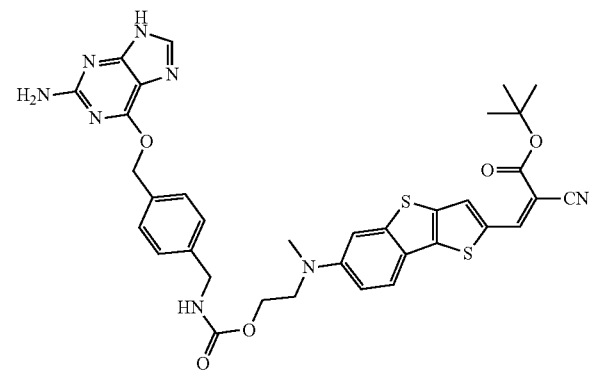
Probe 64
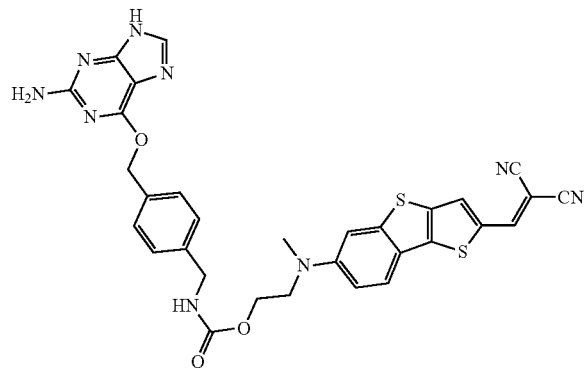
Probe 65
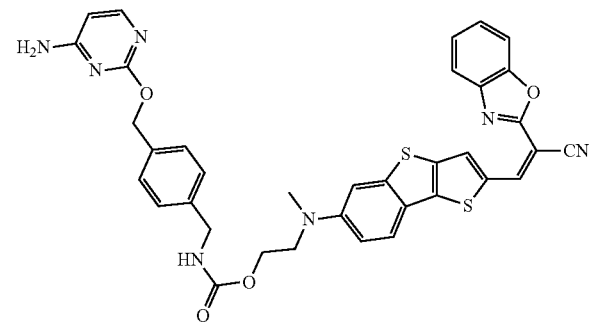

-continued
Probe 66
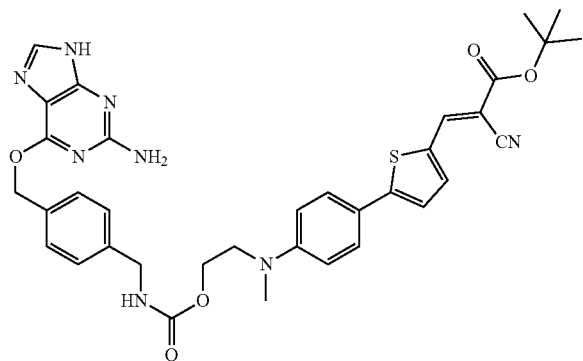
Probe 67
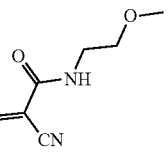
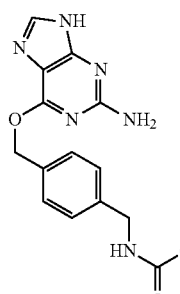
Probe 68
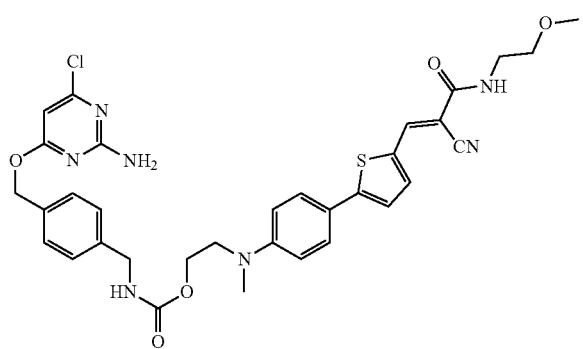
Probe 69
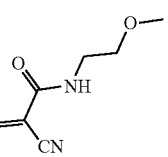
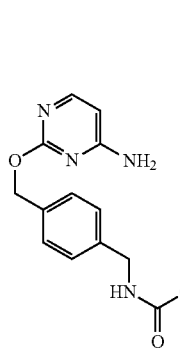
Probe 70
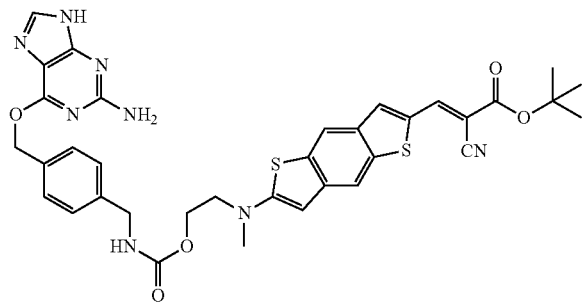
Probe 71
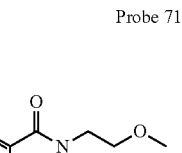
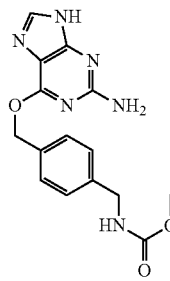
Probe 72
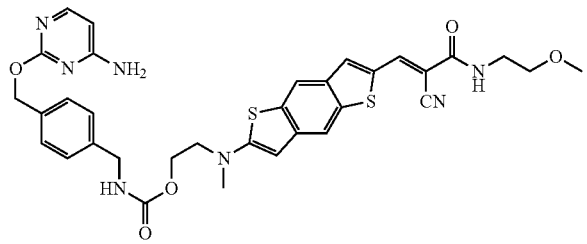
Probe 73
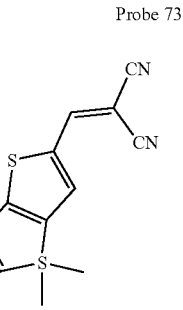
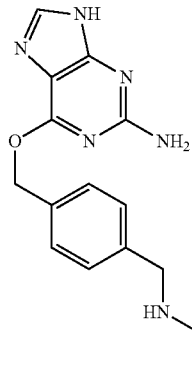

Probe 74
Probe 75
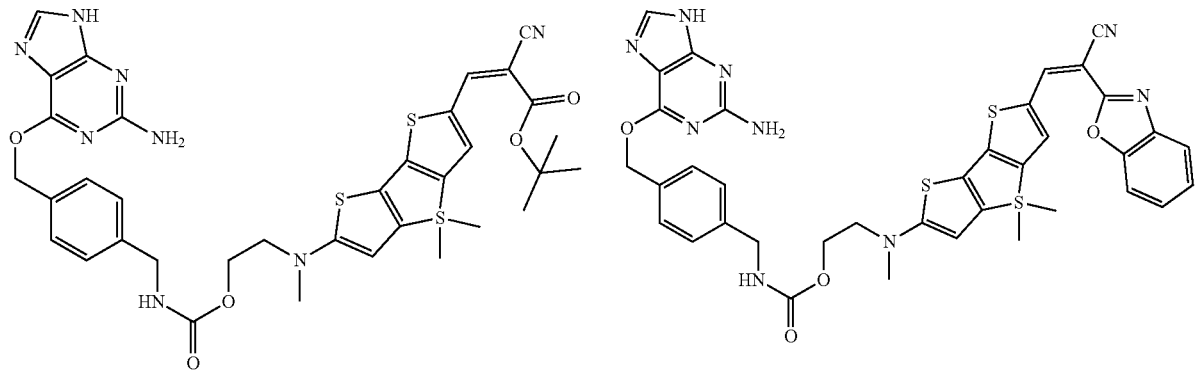
Probe 76
Probe 77
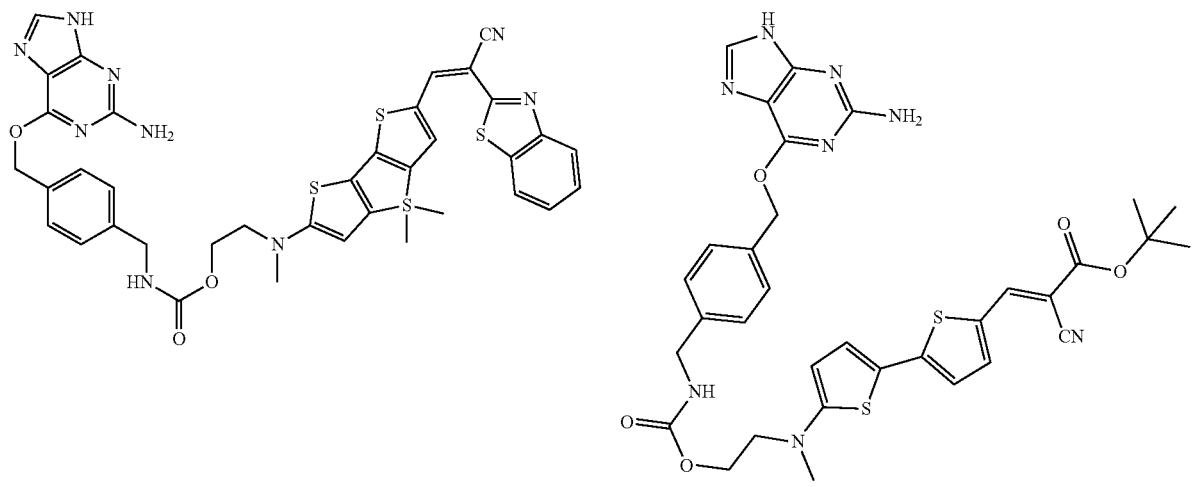
Probe 78
Probe 79
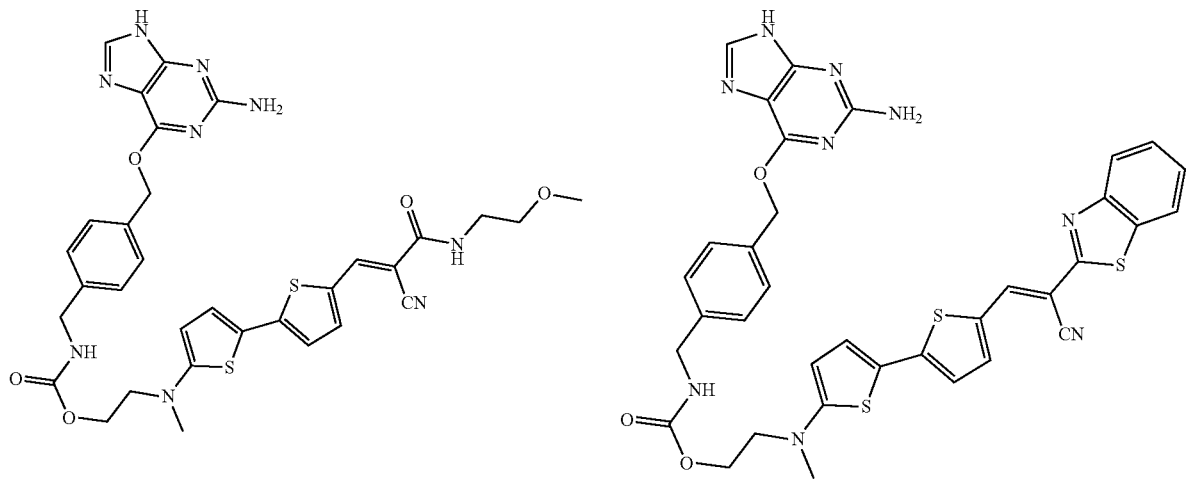

-continued
Probe 80
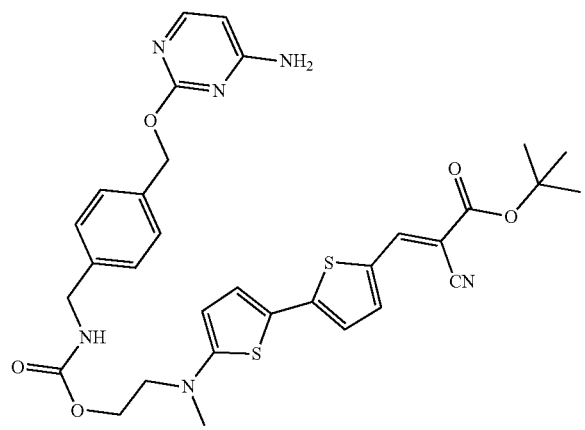
Probe 81
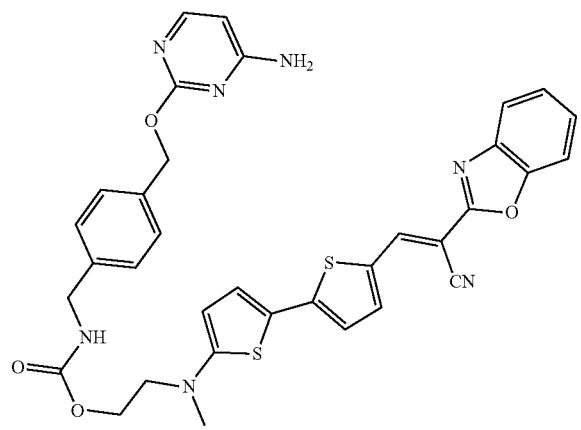
Probe 82
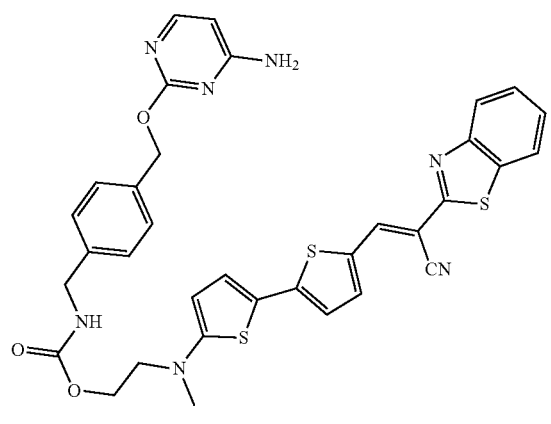
Probe 83
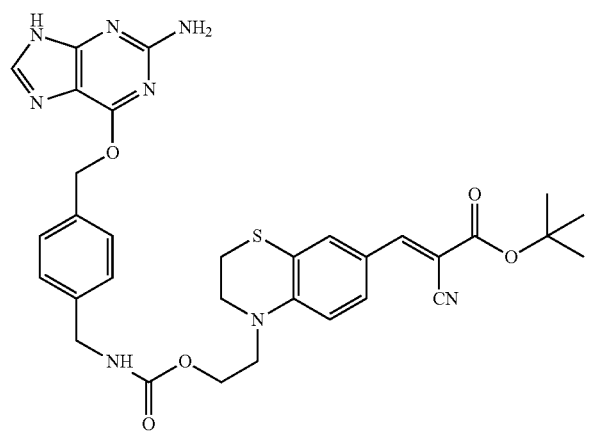
Probe 84
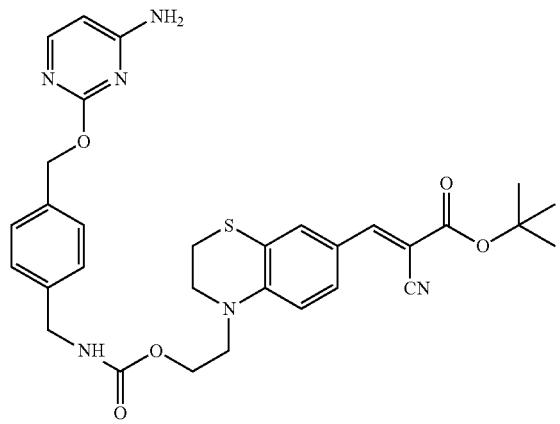
Probe 85
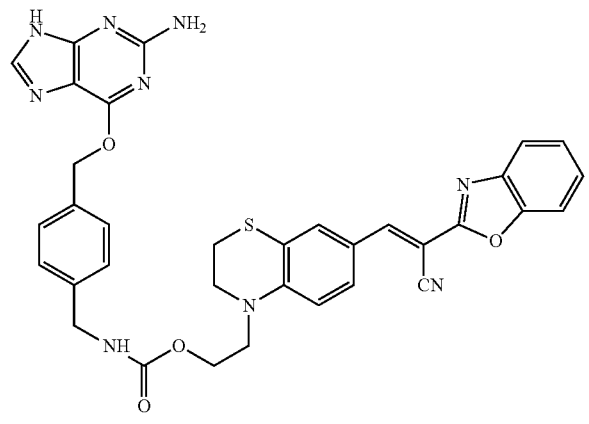

-continued
Probe 86
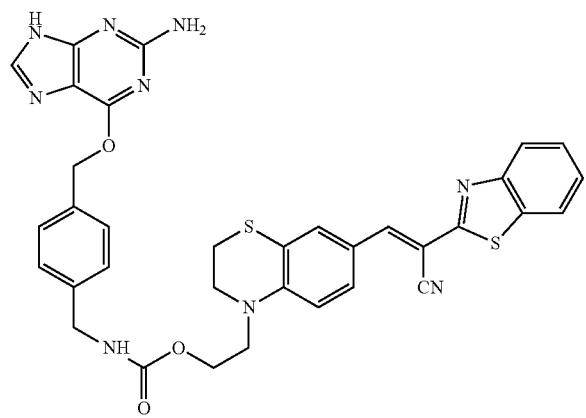
Probe 87
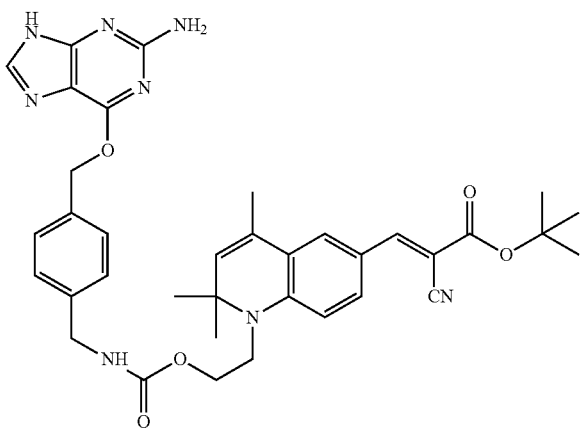
Probe 88
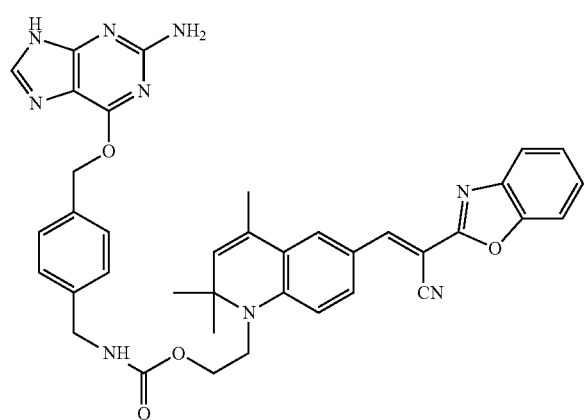
Probe 89
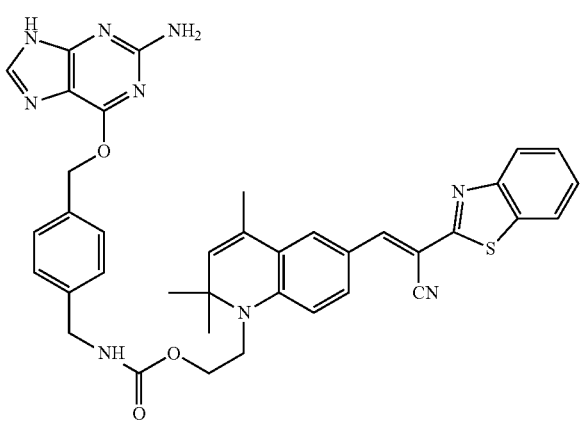
Probe 90
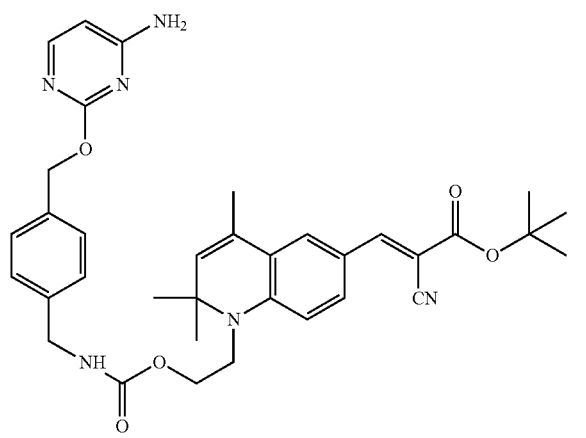
Probe 91
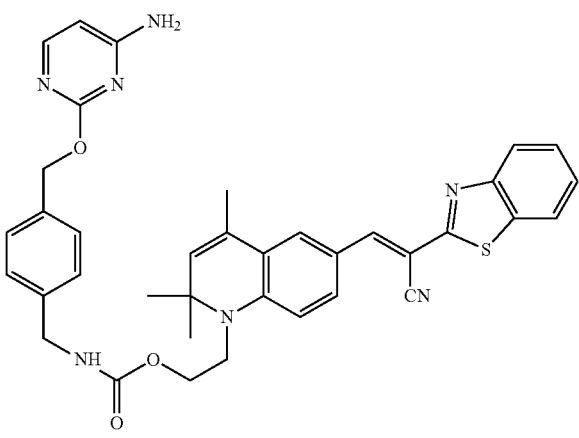

Probe 92
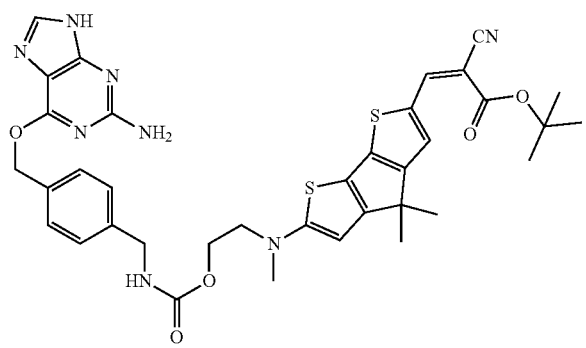
Probe 93
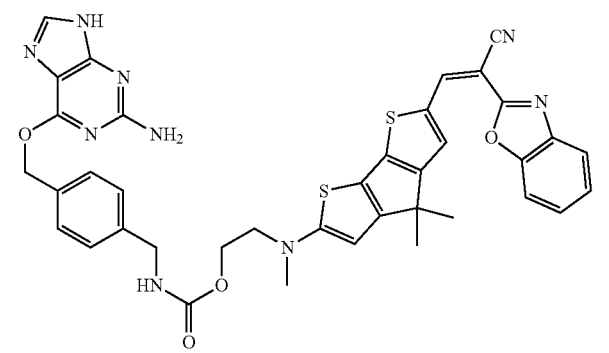
Probe 94
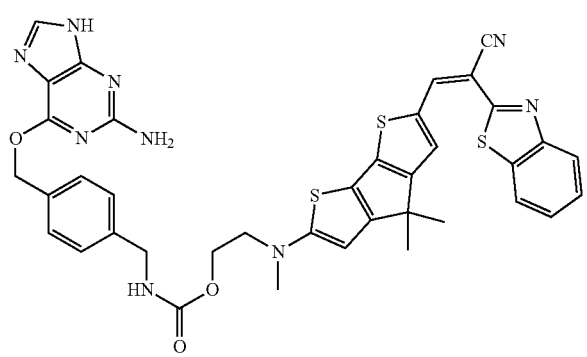
Probe 95
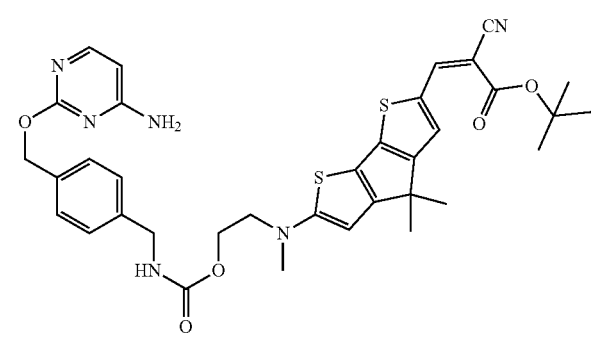
Probe 96
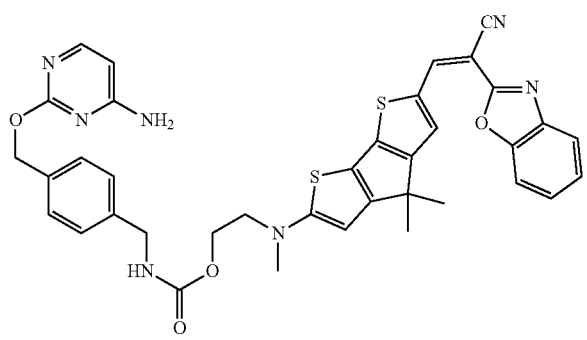
Probe 97
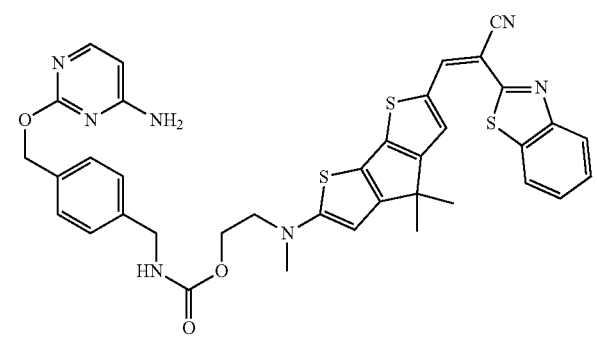
Probe 98
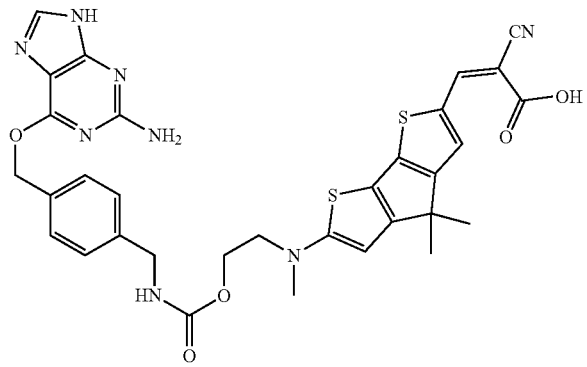
Probe 101
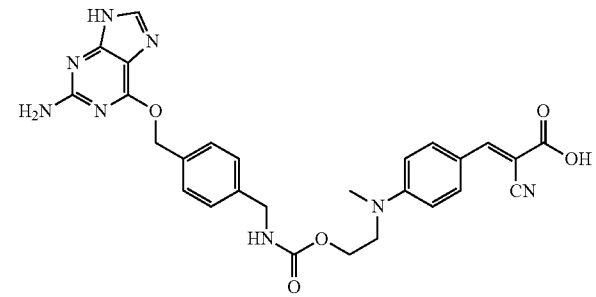

-continued
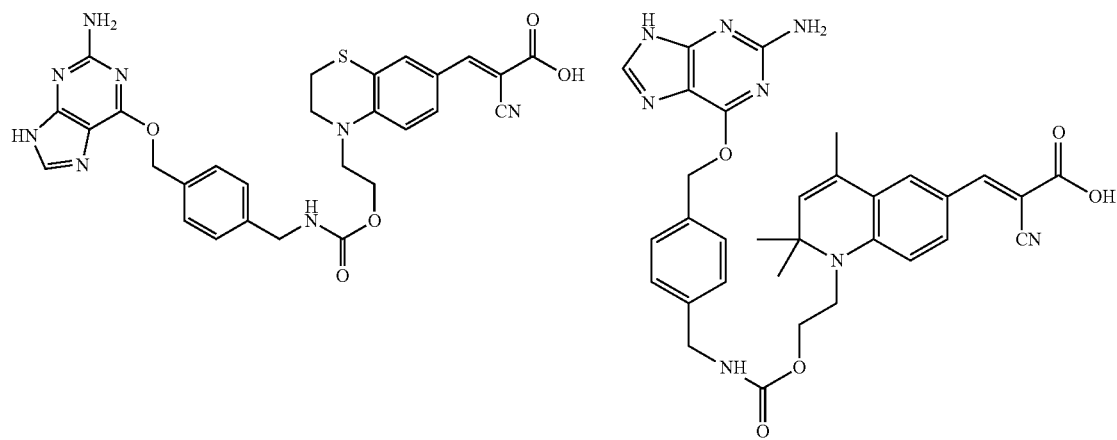
Probe 103
Probe 105
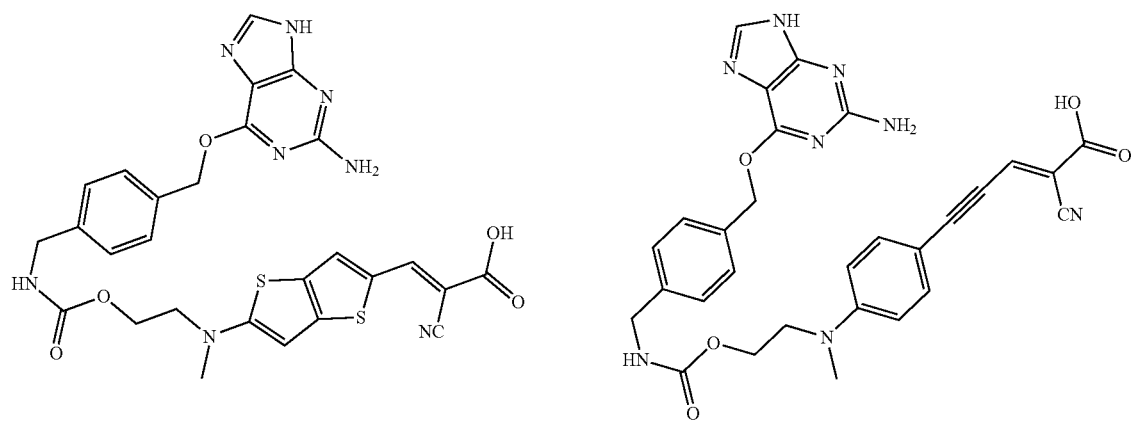
Probe 107
Probe 109
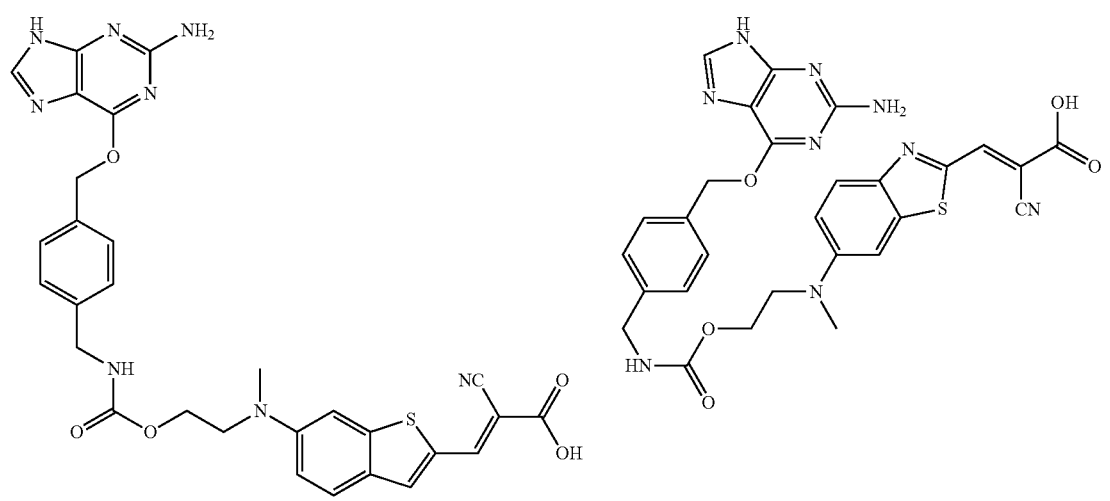
Probe 111
Probe 114

Probe 117

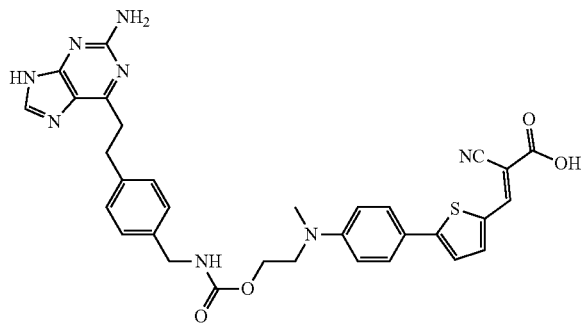

Probe 120

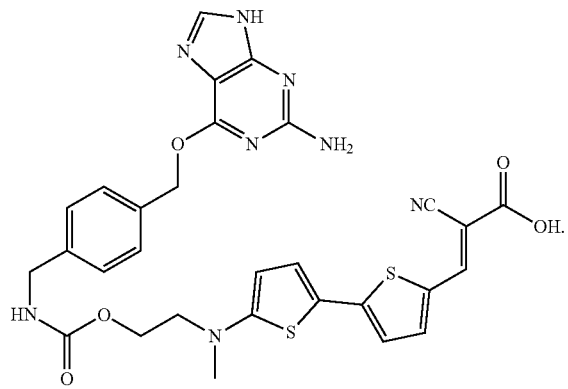

In another aspect, there is provided a process for preparing the fluorescent probe as described above, comprising a step of reacting a fluorescent dye of formula (II) with a ligand and an optionally linker:

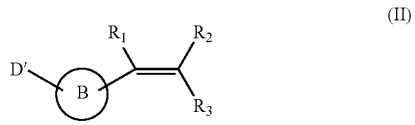
(II)

wherein, after reaction, D' forms a D-group that bonds to the linker moiety or the ligand moiety.

In another aspect, there is also provided a fluorescent activated protein specific labeling method, comprising the following steps: contacting the fluorescent probe described above with a target protein of a protein tag or a fusion protein tag, labeling reaction taking place at the ligand moiety of the fluorescent probe with the protein tag, and the fluorescent probe is labeled onto the protein tag; optionally, the fluorescent probe is covalently labeled on the protein tag;

Optionally, a reaction medium of the labeling reaction is selected from a pure protein solution, a cell lysate or an in situ medium in which the target protein of the protein tag or the fused protein tag is located; optionally, the in situ medium is intracellular media, organelle media, living tissue media, blood or body fluids.

In another aspect, there are further provided uses of the above-mentioned fluorescent probe for protein fluorescent labeling, quantification, detection or kinetic studies of proteins, and use in imaging of cells, tissues, and living bodies.

In another aspect, a probe kit is provided, comprising the fluorescent probe described above.

Optionally, the probe kit further comprises a biocompatible medium; optionally, the biocompatible medium is at least one selected from dimethyl sulfoxide, a buffer, and physiological saline; optionally, the buffer includes phosphate buffer.

The above-described protein tag or the target protein moiety to which the tag is fused can be prepared by existing genetic engineering techniques.

The above-mentioned viscosity-sensitive fluorescent dyes mean that the fluorescence intensity of the dye responds to the viscosity of the solution, and as the viscosity of the solution increases, the fluorescence intensity increases. Optionally, the viscosity-sensitive fluorescent dye is an organic dye molecule which, under the same concentration and excitation wavelength, at 25° C. has a ratio of the maximum fluorescence emission intensity of the dye in glycerol to the fluorescence intensity in methanol of greater than 2, preferably more than 5, more preferably more than 10. The concentration of the viscosity-sensitive dye ranges from $1 \times 10^{-7}$ M to $1 \times 10^{-5}$ M.

Depending on the circumstances, the person skilled in the art can select the corresponding label and ligand as needed.

Those skilled in the art can use correspondingly instrumentation equipment to track and monitor the target protein of the protein tag or the fusion protein tag. The instrument equipment used, as needed, includes equipment and facilities capable of testing or displaying fluorescent, such as fluorescence spectrometer and fluorescent microscopes, confocal fluorescence microscopes, microplate readers, flow cytometers, and in vivo imagers.

The operator can select different types of dyes with different emission/excitation wavelengths as needed.

According to an embodiment of one aspect of the present invention, the fluorescent probe has a wide range of fluorescence emission wavelengths.

According to an embodiment of another aspect of the present invention, the fluorescence intensity of the fluorescent probe is enhanced as the viscosity of the environment increase, is sensitive to viscosity, and has viscosity responsiveness.

According to an embodiment of another aspect of the present invention, the fluorescent probe can be used for a specific label of a target protein of a protein tag or a fusion protein tag, and fluorescence can be activated after the fluorescent probe binds to the protein tag, the fluorescent probe has good fluorescent molecular switching properties, and the fluorescence activation factor is high and the fluorescence activation brightness is high.

According to an embodiment of another aspect of the present invention, the fluorescent probe has a good linear relationship between the fluorescence intensity and the protein tag concentration, which can be used for quantitative detection of a target protein.

According to an embodiment of another aspect of the present invention, the fluorescent probe can achieve specific labeling intracellular protein tags and achieve fluorescence-specific imaging, and the probe fluorescence is not affected by the intracellular environment.

According to an embodiment of another aspect of the present invention, a fluorescent probe can be used as a powerful tool for labeling cell subcellular organelle marker, such as labeling nucleus, mitochondria, Golgi, endoplasmic reticulum, whole cells, cytoskeleton, extracellular membrane, lysosomes, cell inner membrane or the like.

According to an embodiment of another aspect of the present invention, the spectra of fluorophores of different fluorescent probes do not interfere with each other, and the fluorescent probes of different color systems of the present invention can perform multi-color labeling on samples, and can simultaneously perform orthogonal labeled imaging.

According to an embodiment of another aspect of the present invention, the fluorescence of the fluorescent probe is not affected by the internal environment of the animal, and can be applied to living animal, for example, specifically labels a SNAP protein tag expressed in liver, and exhibits a strong fluorescent signal.

According to an embodiment of another aspect of the present invention, a fluorescent probe can be used to track and monitor the degradation process of a target protein.

According to an embodiment of another aspect of the present invention, the fluorescent probe monitors the assembly and degradation processes of biological macromolecules in mammalian cells in real time.

According to an embodiment of another aspect of the present invention, the fluorescent probe can perform rapid contrast imaging of a tissue that is not suitable for washing, such as tissue, living body, and the like.

According to an embodiment of another aspect of the present invention, the fluorescent probe does not exhibit any detection signal when the fluorescent probe does not label the target protein of the protein tag or the fusion protein tag, and does not interfere with the detection of the sample, and can realize rapid quantitative detection of target protein in complex samples, and can also track the dynamics of the labeling reaction process.

EXAMPLES

Figure 1:
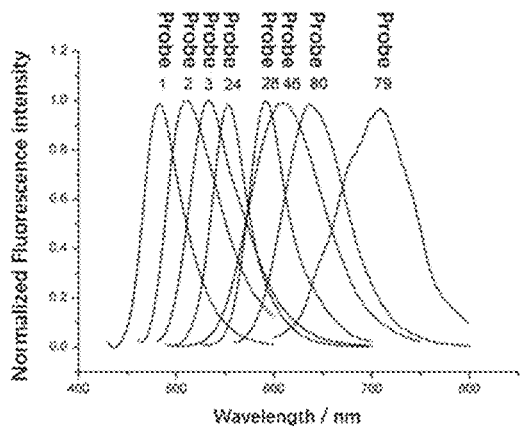
FIG. 1. The fluorescence emission diagram of activated fluorescence of different wavelengths after different probes are bound to protein tags.

Specific examples of the present invention will be described in detail below. It should be understood that the specific examples described herein are merely illustrative description of the present invention and are not intended to limit the present invention.

Example 1

A fluorescence-activated covalently labeling fluorescent probe 1 for SNAP protein tags was constructed using a molecular rotor as a viscosity-sensitive fluorescent dye.

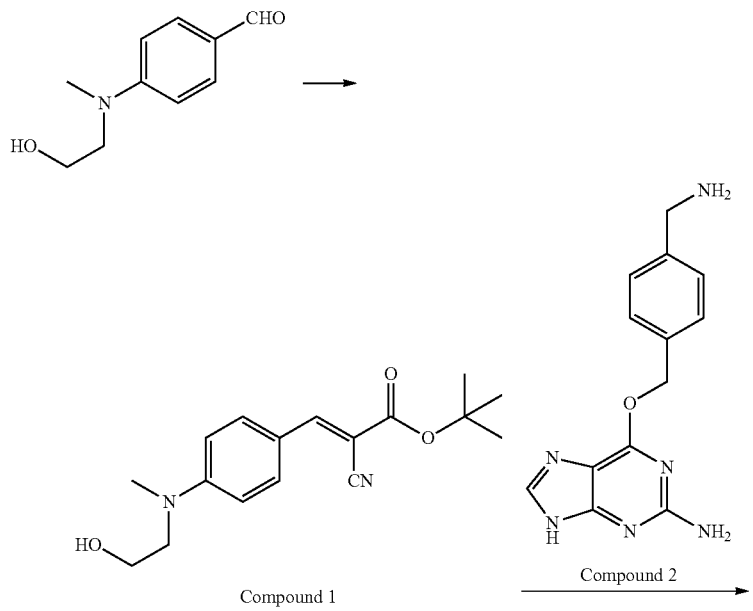

Compound 1

Compound 2

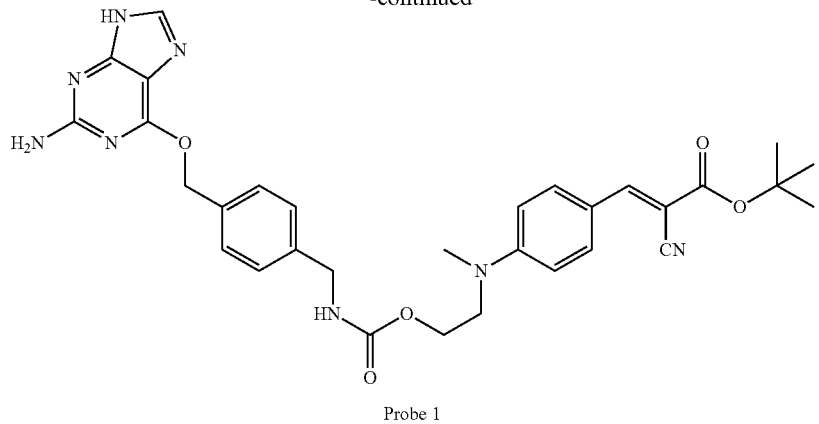

Probe 1

Compound 1

To a solution of N-methyl-N-(2-hydroxyethyl)-4-aminobenzaldehyde (0.358 g, 2 mmol) and tert-butyl cyanoacetate (0.338 g, 2.4 mmol) in 50 mL anhydrous ethanol, a catalytic amount of anhydrous zinc chloride was added. The obtained mixture was heated in an oil bath for 5 hrs under the protection of Ar. After the reaction was completed, the solution was cooled at room temperature, a part of the solvent was removed by rotary evaporation. A large amount of precipitate was formed. The precipitate was separated by filtration, thoroughly washed with cooled ethanol twice and finally dried in vacuo to give a pure yellow compound 1 (0.49 g, 81%). $^1$H-NMR (400 MHz, DMSO-$d_6$): δ=8.01 (s, 1H), 7.97 (d, 2H, J=9.2 Hz), 6.85 (d, 2H, J=9.2 Hz), 4.79 (bt, 1H), 3.55-3.59 (m, 4H), 3.08 (s, 3H), 1.50 (s, 9H).

Compound 2

The synthesis was carried out with reference to the method disclosed in Antje Keppler et. al. Nat Biotechnology. 2002, 21, 86-89. $^1$H-NMR (400 MHz, DMSO-$d_6$): δ=7.82 (s, 1H), 7.39 (m, 4H), 6.27 (s, 2H), 5.45 (s, 2H), 3.71 (s, 2H).

Probe 1

Compound 1 (0.302 g, 1.0 mmol) and 4-dimethylaminopyridine (0.146 g, 1.2 mmol) were dissolved in 20 mL anhydrous dichloromethane, p-nitro phenyl chloroformate (0.242 g, 1.2 mmol) in 10 mL anhydrous dichloromethane was added dropwise under the protection of Ar. The obtained mixture was stirred and kept at room temperature for 1 hr under the protection of Ar. After the reaction was completed, the solvent was completely removed by rotary evaporation. The residue was re-dissolved in anhydrous N,N-dimethylformamide (DFM), compound 2 (0.324 g, 1.2 mmol) was added in the presence of anhydrous triethylamine (TEA) (0.16 ml, 1.2 mmol). The obtained mixture was stirred at room temperature for another 30 min under the protection of Ar. After the reaction was completed, the solvent was completely removed by rotary evaporation. The residue was purified by gel silica gel column chromatography to give a pure Probe 1, at a yield of 70%. $^1$H-NMR (400 MHz, DMSO-$d_6$): δ=12.42 (s, 1H), 10.01 (s, 1H), 8.01 (s, 1H), 7.97 (d, 2H, J=9.2 Hz), 7.81 (s, 1H), 7.40 (m, 4H), 6.85 (d, 2H, J=9.2 Hz), 6.29 (s, 2H), 5.46 (s, 2H), 4.79 (bt, 1H), 4.40 (d, 2H, J=4.90 Hz), 3.55-3.59 (m, 4H), 3.08 (s, 3H), 1.50 (s, 9H).

Example 2

A fluorescence-activated covalently labeling fluorescent probe 2 for SNAP protein tags was constructed using a molecular rotor as a viscosity-sensitive fluorescent dye.

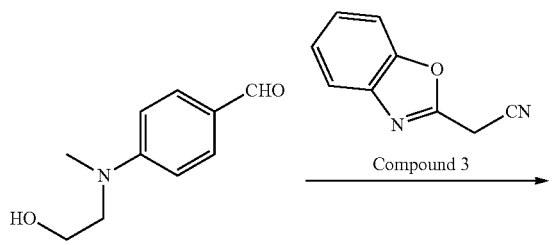

Compound 3

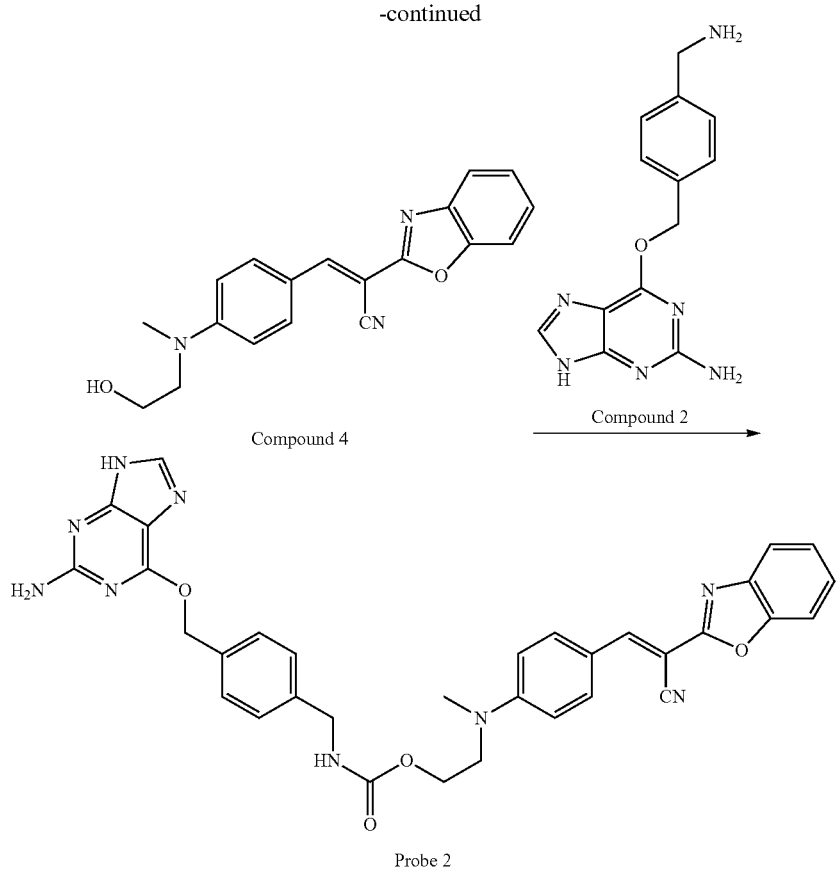

Compound 3

The synthesis was carried out with reference to the method disclosed in J. Das et. al. Bioorg. Med. Chem. Lett. 2005, 15, 337-343. $^1$H-NMR (400 MHz, CDCl$_3$): δ=7.74 (d, 1H, J=4.0 Hz), 7.55 (d, 1H, J=4.0 Hz), 7.36-7.42 (m, 2H), 4.12 (s, 2H).

Compound 4

This compound was obtained by following the general procedure for compound 1. $^1$H-NMR (400 MHz, DMSO-d$_6$): δ=8.11-8.07 (m, 2H), 8.01-7.97 (m, 3H), 7.70 (d, 1H, J=8.8 Hz), 7.46-7.43 (m, 1H), 6.27 (dd, 1H, J=9.2, 1.6 Hz), 6.02 (s, 1H), 3.88 (t, 2H, J=5.6 Hz), 3.64 (t, 2H, J=5.6 Hz), 3.15 (s, 3H).

Probe 2

This probe was obtained by following the general procedure for probe 1, and the yield was 75%. $^1$H-NMR (400 MHz, DMSO-d$_6$): δ=12.41 (s, 1H), 10.01 (s, 1H), 8.11-8.07 (m, 2H), 8.01-7.97 (m, 3H), 7.81 (s, 1H), 7.70 (d, 1H, J=8.8 Hz), 7.46-7.43 (m, 1H), 7.41 (m, 4H), 6.29 (s, 2H), 6.27 (dd, 1H, J=9.2, 1.6 Hz), 6.02 (s, 1H), 5.46 (s, 2H), 4.40 (d, 2H, J=4.9 Hz), 3.88 (t, 2H, J=5.6 Hz), 3.64 (t, 2H, J=5.6 Hz), 3.15 (s, 3H).

Example 3

A fluorescence-activated covalently labeling fluorescent probe 3 for SNAP protein tags was constructed using a molecular rotor as a viscosity-sensitive fluorescent dye.

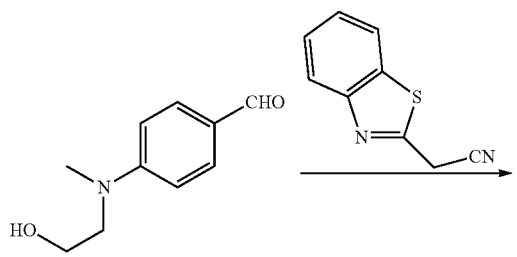

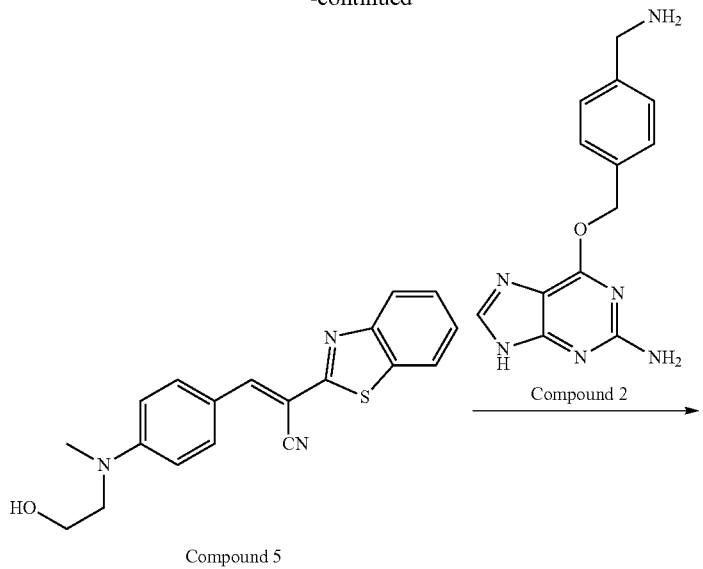

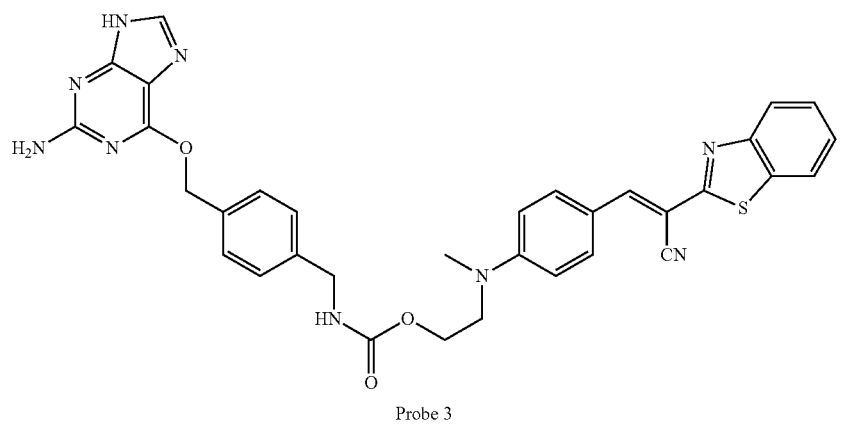

Probe 3

Compound 5

This compound was obtained by following the general procedure for compound 1, and the yield was 95%. $^1$H-NMR (400 MHz, CDCl$_3$): δ=8.09 (s, 1H), 8.02 (d, 1H, J=8.0 Hz), 7.98 (d, 2H, J=9.2 Hz), 7.86 (d, 1H, J=8.4 Hz), 7.48 (t, 1H, J=7.8 Hz), 7.36 (t, 1H, J=7.36 Hz), 6.73 (d, 2H, J=9.2 Hz), 3.88 (t, 2H, J=5.6 Hz), 3.64 (t, 2H, J=5.6 Hz), 3.15 (s, 3H).

Probe 3

This probe was obtained by following the general procedure for probe 1, and the yield was 65%. $^1$H-NMR (400 MHz, DMSO-d$_6$): δ=12.40 (s, 1H), 10.02 (s, 1H), 8.09 (s, 1H), 8.02 (d, 1H, J=8.0 Hz), 7.98 (d, 2H, J=9.2 Hz), 7.86 (d, 1H, J=8.4 Hz), 7.81 (s, 1H), 7.48 (t, 1H, J=7.8 Hz), 7.40 (m, 4H), 7.36 (t, 1H, J=7.36 Hz), 6.73 (d, 2H, J=9.2 Hz), 6.29 (s, 2H), 5.46 (s, 2H), 4.40 (d, 1H, J=4.8 Hz), 3.88 (t, 2H, J=5.6 Hz), 3.64 (t, 2H, J=5.6 Hz), 3.15 (s, 3H).

Example 4

A fluorescence-activated covalently labeling fluorescent probe 4 for SNAP protein tags was constructed using a molecular rotor as a viscosity-sensitive fluorescent dye.

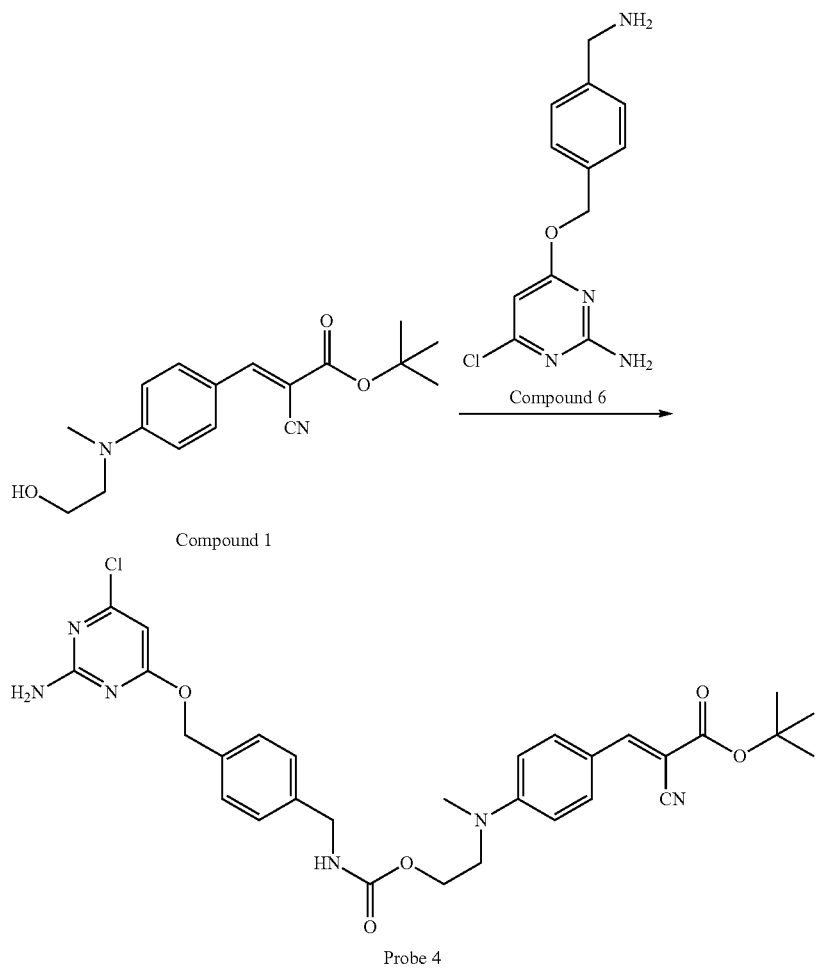

Compound 6

The synthesis was carried out with reference to the method disclosed in the literature (Srikun D 1 et. al JACS 2010, 132, 4455-4465). ¹H-NMR (400 MHz, DMSO-d₆): δ=7.33 (d, 2H, J=8.0 Hz), 7.31 (d, 2H, J=8.0 Hz), 7.10 (brs, 2H), 6.10 (s, 1H), 5.25 (s, 2H), 3.68 (s, 2H).

Probe 4

This probe was obtained by following the general procedure for probe 1, and the yield was 61%. ¹H-NMR (400 MHz, DMSO-d₆): ¹H-NMR (400 MHz, DMSO-d₆): δ=9.99 (brs, 1H), 8.01 (s, 1H), 7.97 (d, 2H, J=9.2 Hz), 7.39 (d, 2H), 7.26 (d, 2H, J=8.4 Hz), 7.09 (s, 2H), 6.85 (d, 2H, J=9.2 Hz), 6.10 (s, 1H), 5.26 (s, 2H), 4.79 (bt, 1H), 4.36 (s, 2H), 3.55-3.59 (m, 4H), 3.08 (s, 3H), 1.50 (s, 9H).

Example 5

A fluorescence-activated covalently labeling fluorescent probe 5 for SNAP protein tags was constructed using a molecular rotor as a viscosity-sensitive fluorescent dye.

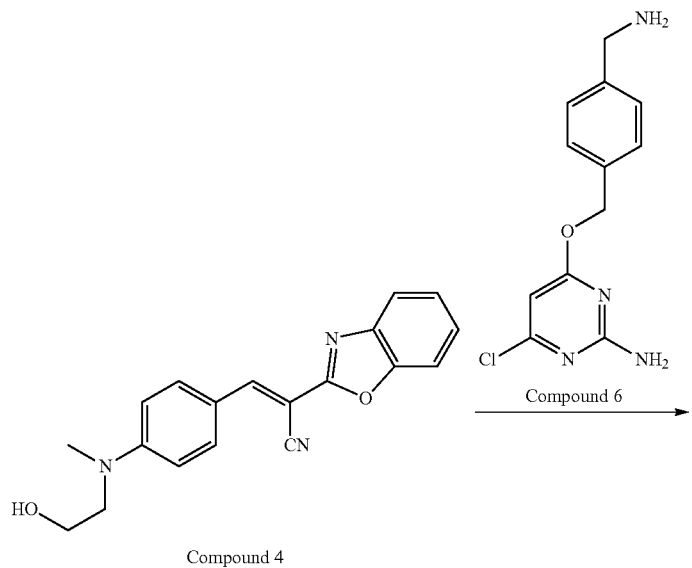

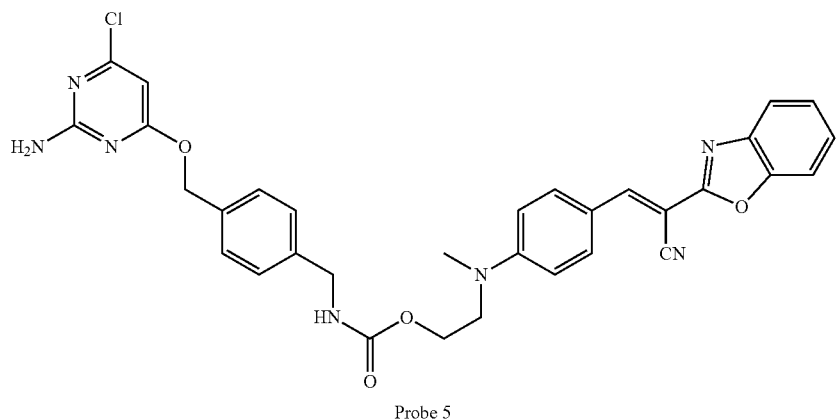

Probe 5

Probe 5

This probe was obtained by following the general procedure for probe 1, and the yield was 59%. 1H-NMR (400 MHz, DMSO-d6): δ=9.97 (s, 1H), 8.11-8.07 (m, 2H), 8.01-7.97 (m, 3H), 7.70 (d, 1H, J=8.8 Hz), 7.46-7.43 (m, 1H), 7.39 (d, 2H, J=8.4 Hz), 7.26 (d, 2H, J=8.4 Hz), 7.10 (s, 2H), 6.27 (dd, 1H, J=9.2, 1.6 Hz), 6.10 (s, 1H), 6.02 (s, 1H), 5.26 (s, 2H), 4.36 (s, 2H), 3.88 (t, 2H, J=5.6 Hz), 3.64 (t, 2H, J=5.6 Hz), 3.15 (s, 3H).

Example 6

A fluorescence-activated covalently labeling fluorescent probe 6 for SNAP protein tags was constructed using a molecular rotor as a viscosity-sensitive fluorescent dye.

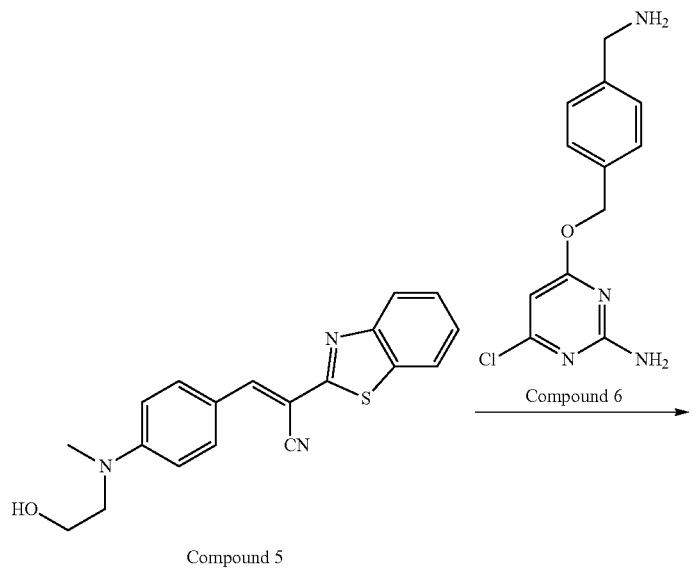

Compound 5

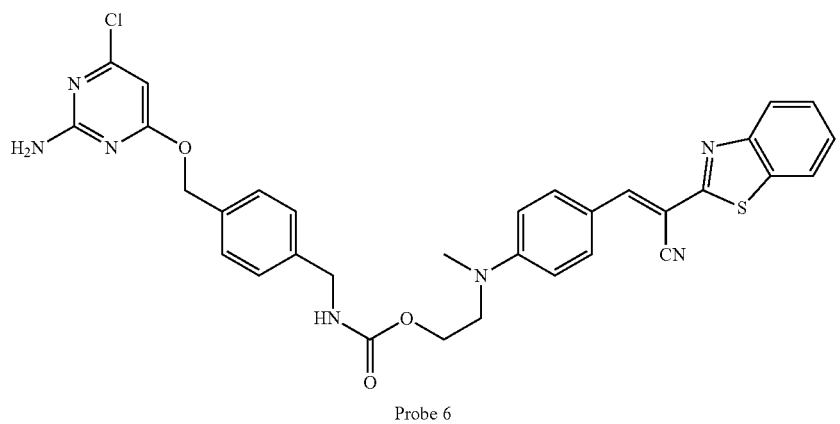

Probe 6

Probe 6

This probe was obtained by following the general procedure for probe 1, and the yield was 55%. $^1$H-NMR (400 MHz, CDCl$_3$): δ=9.98 (brs, 1H), 8.09 (s, 1H), 8.02 (d, 1H, J=8.0 Hz), 7.98 (d, 2H, J=9.2 Hz), 7.86 (d, 1H, J=8.4 Hz), 7.48 (t, 1H, J=7.8 Hz), 7.39 (d, 2H, J=8.4 Hz), 7.36 (t, 1H, J=8.4 Hz), 7.26 (d, 2H, J=8.0 Hz), 7.09 (s, 2H), 6.73 (d, 2H, J=9.2 Hz), 6.10 (s, 1H), 5.26 (s, 2H), 4.36 (s, 2H), 3.88 (t, 2H, J=5.6 Hz), 3.64 (t, 2H, J=5.6 Hz), 3.15 (s, 3H).

Example 7

A fluorescence-activated covalently labeling fluorescent probe 7 for CLIP protein tags was constructed using a molecular rotor as a viscosity-sensitive fluorescent dye.

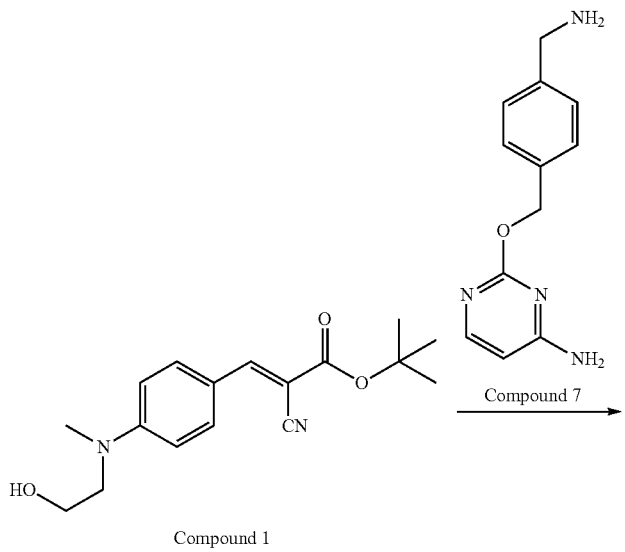

Compound 1

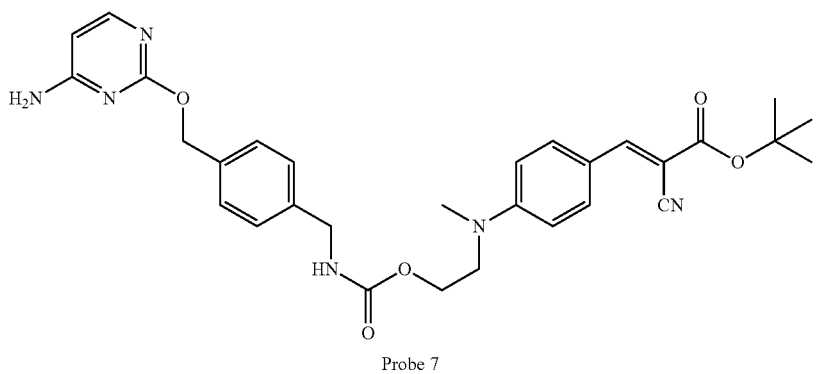

Compound 7

The synthesis was carried out with reference to the method disclosed in the literature. $^1$H-NMR (400 MHz, CD$_3$OD): δ=7.84 (d, 1H, J=6.0 Hz), 7.40 (d, 2H, J=8.0 Hz), 7.31 (d, 2H, J=8.0 Hz), 6.14 (d, 1H, J=6.0), 5.29 (s, 2H), 3.78 (s, 2H).

Probe 7

This probe was obtained by following the general procedure for probe 1, and the yield was 66%. $^1$H-NMR (400 MHz, DMSO-d$_6$): δ=8.01 (s, 1H), 7.97 (d, 2H, J=9.2 Hz), 7.93 (d, 2H, J=8.0 Hz), 7.75 (s, 1H), 7.33 (d, 2H, J=8.0 Hz), 7.19 (d, 2H, J=8.0 Hz) 6.85 (d, 2H, J=9.2 Hz), 6.06 (d, 1H, J=5.6 Hz), 5.27 (s, 2H), 5.16 (s, 2H), 4.45 (d, 2H, J=5.6 Hz), 3.55-3.59 (m, 4H), 3.08 (s, 3H), 1.50 (s, 9H).

Example 8

A fluorescence-activated covalently labeling fluorescent probe 8 for CLIP protein tags was constructed using a molecular rotor as a viscosity-sensitive fluorescent dye.

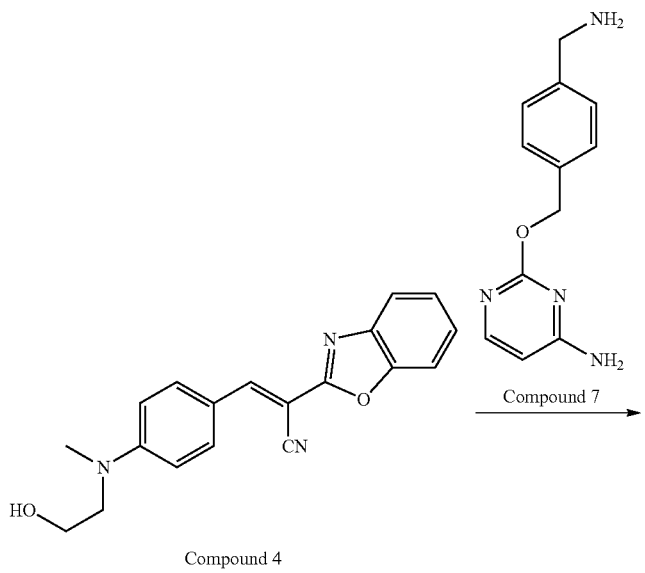

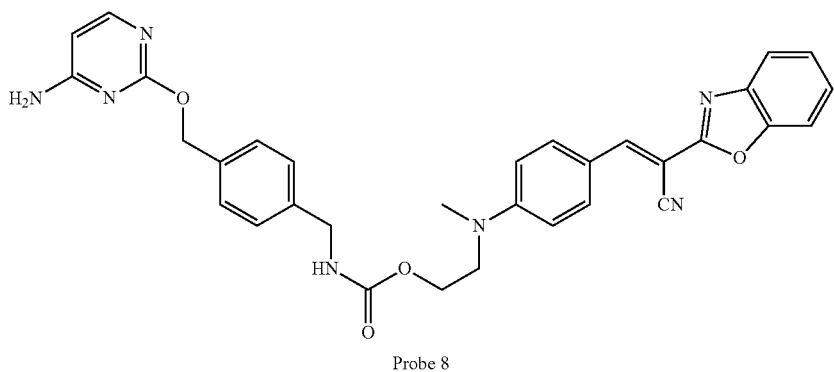

Probe 8

Probe 8

This probe was obtained by following the general procedure for probe 1, and the yield was 60%. $^1$H-NMR (400 MHz, DMSO-$d_6$): δ=8.11-8.07 (m, 2H), 8.01-7.97 (m, 3H), 7.93 (d, 1H, J=5.6 Hz), 7.75 (s, 1H), 7.70 (d, 1H, J=8.8 Hz), 7.46-7.43 (m, 1H), 7.33 (d, 2H, J=8.0 Hz), 7.19 (d, 2H, J=8.0 Hz), 6.27 (dd, 1H, J=9.2, 1.6 Hz), 6.10 (d, 1H, J=5.6 Hz), 6.02 (s, 1H), 5.27 (s, 2H), 5.16 (s, 2H), 4.45 (d, 2H, J=5.6 Hz), 3.88 (t, 2H, J=5.6 Hz), 3.64 (t, 2H, J=5.6 Hz), 3.15 (s, 3H).

Example 9

A fluorescence-activated covalently labeling fluorescent probe 9 for CLIP protein tags was constructed using a molecular rotor as a viscosity-sensitive fluorescent dye.

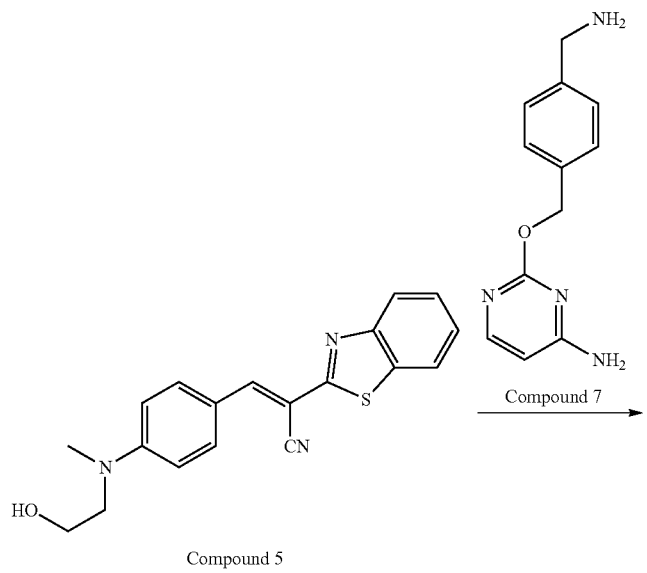

Compound 5

Compound 7

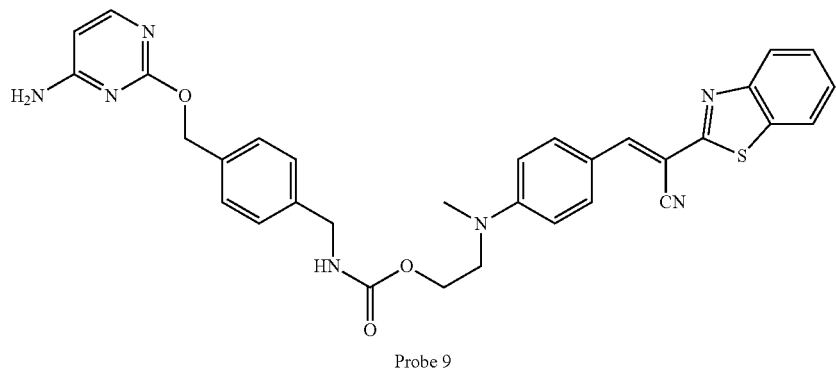

Probe 9

Probe 9

This probe was obtained by following the general procedure for probe 1, and the yield was 65%. 1H-NMR (400 MHz, CDCl3): δ=8.09 (s, 1H), 8.02 (d, 1H, J=8.0 Hz), 7.98 (d, 2H, J=9.2 Hz), 7.93 (d, 1H, J=5.6), 7.86 (d, 1H, J=8.4 Hz), 7.75 (s, 1H), 7.48 (t, 1H, J=7.8 Hz), 7.36 (t, 1H, J=7.36 Hz), 7.33 (d, 2H, J=8.0 Hz), 7.19 (d, 2H, J=8.0 Hz), 6.73 (d, 2H, J=9.2 Hz), 6.06 (d, 1H, J=5.6 Hz), 5.27 (s, 2H), 5.16 (s, 2H), 4.45 (d, 2H, J=5.6 Hz), 3.88 (t, 2H, J=5.6 Hz), 3.64 (t, 2H, J=5.6 Hz), 3.15 (s, 3H).

Example 10

A fluorescence-activated covalently labeling fluorescent probe 10 for SNAP protein tags was constructed using a molecular rotor as a viscosity-sensitive fluorescent dye.

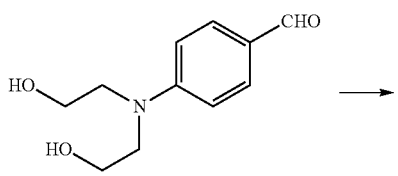

-continued

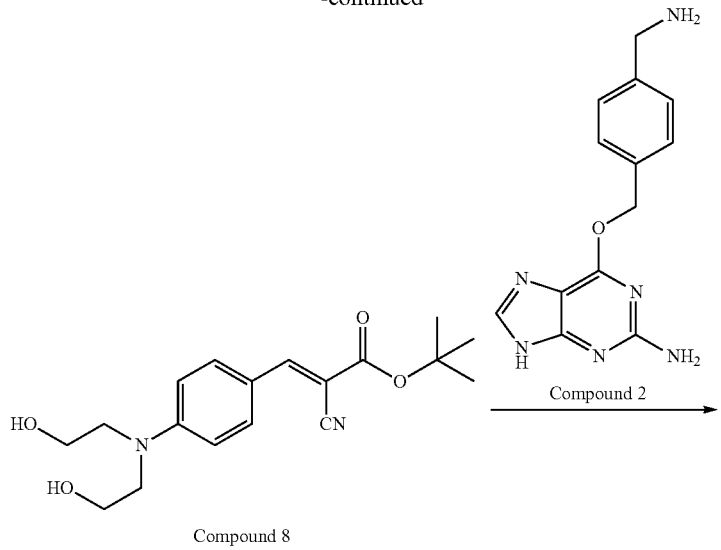

Compound 8

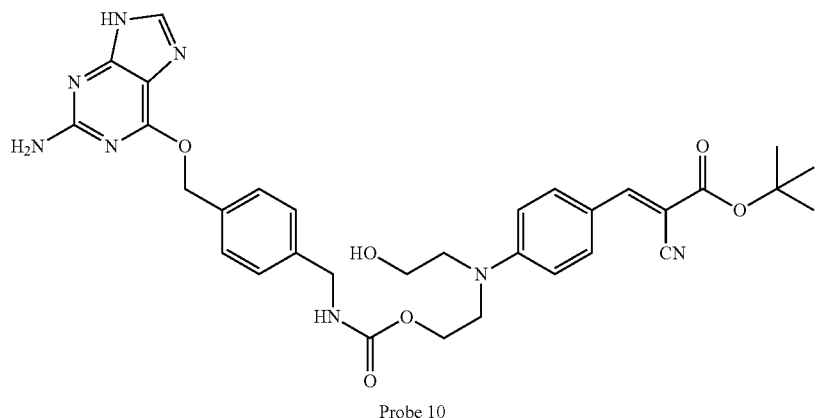

Probe 10

Compound 8

This compound was obtained by following the general procedure for compound 1, and the yield was 95%. $^1$H-NMR (400 MHz, DMSO-d$_6$): δ=8.01 (s, 1H), 7.97 (d, 2H, J=9.2 Hz), 6.85 (d, 2H, J=9.2 Hz), 4.79 (bt, 1H), 3.85 (t, 4H, J=5.6 Hz), 3.60 (t, 4H, J=5.6 Hz), 1.50 (s, 9H).

Probe 10

This probe was obtained by following the general procedure for probe 1, and the yield was 35%. $^1$H-NMR (400 MHz, DMSO-d$_6$): δ=12.42 (s, 1H), 10.01 (s, 1H), 8.01 (s, 1H), 7.97 (d, 2H, J=9.2 Hz), 7.81 (s, 1H), 7.40 (m, 4H), 6.85 (d, 2H, J=9.2 Hz), 6.29 (s, 2H), 5.46 (s, 2H), 4.79 (bt, 1H), 4.40 (d, 2H, J=4.90 Hz), 3.87 (m, 4H), 3.61 (m, 4H), 1.51 (s, 9H).

Example 11

A fluorescence-activated covalently labeling fluorescent probe 11 for SNAP protein tags was constructed using a molecular rotor as a viscosity-sensitive fluorescent dye.

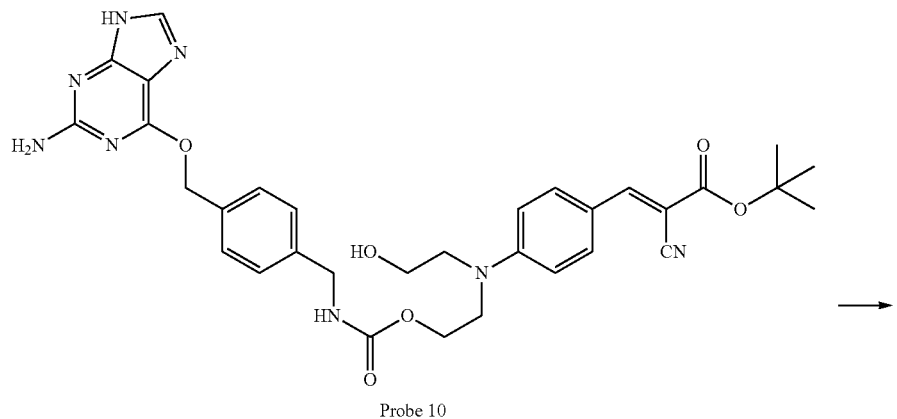

Probe 10

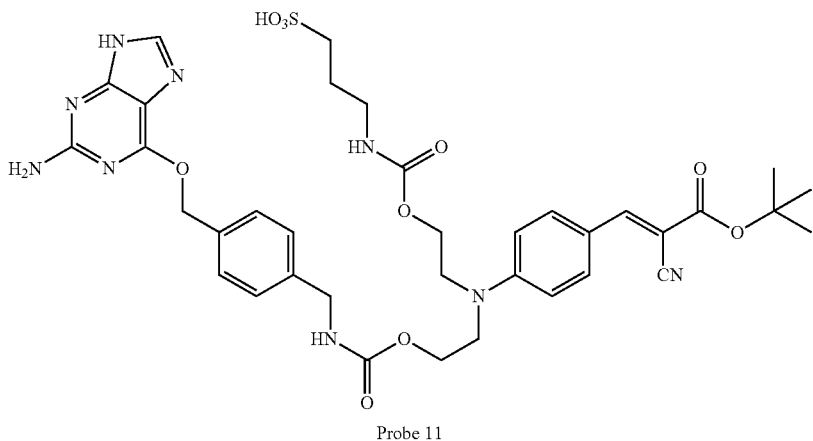

Probe 11

Probe 11

Compound 1 (0.629 g, 1.0 mmol) and 4-dimethylaminopyridine (0.146 g, 1.2 mmol) were dissolved in 20 mL anhydrous DMF, p-nitrophenylchloroformate (0.242 g, 1.2 mmol) in 10 mL anhydrous dichloromethane was added dropwise under the protection of Ar. The obtained mixture was stirred and kept at room temperature for 1 hr. Then, 3-amino-propanesulfonic acid (0.168 g, 1.2 mmol) was added in the presence of TEA (0.16 ml, 1.2 mmol). The obtained mixture was stirred at room temperature for another 30 min under the protection of Ar. After the reaction was completed, the solvent was completely removed by rotary evaporation, and the residue was separated by a reverse phase column to give a pure probe 11 of 0.397 g, and the yield was 50%. 1H-NMR (400 MHz, DMSO-d6): δ=12.42 (s, 1H), 10.01 (s, 1H), 8.01 (s, 1H), 7.97 (d, 2H, J=9.2 Hz), 7.81 (s, 1H), 7.40 (m, 4H), 6.85 (d, 2H, J=9.2 Hz), 6.29 (s, 2H), 5.46 (s, 2H), 4.79 (bt, 1H), 4.40 (d, 2H, J=4.90 Hz), 3.81 (t, 4H, J=6.0 Hz), 3.60 (t, 4H, J=6.0 Hz), 3.21 (t, 2H, 5.6 Hz), 2.71 (t, 2H, 5.6 Hz), 2.31 (m, 2H), 1.51 (s, 9H).

Example 12

A fluorescence-activated covalently labeling fluorescent probe 12 for SNAP protein tags was constructed using a molecular rotor as a viscosity-sensitive fluorescent dye.

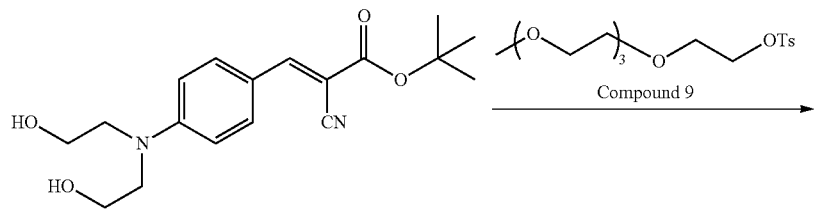

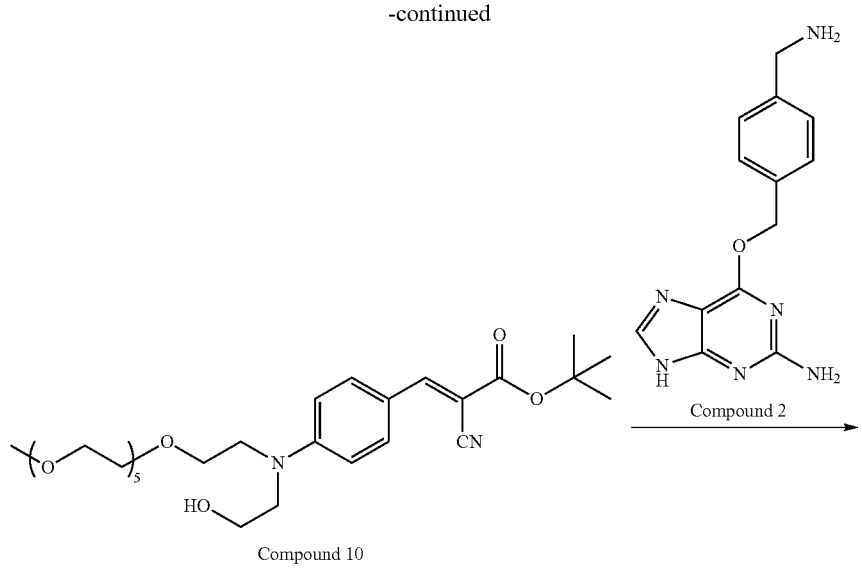

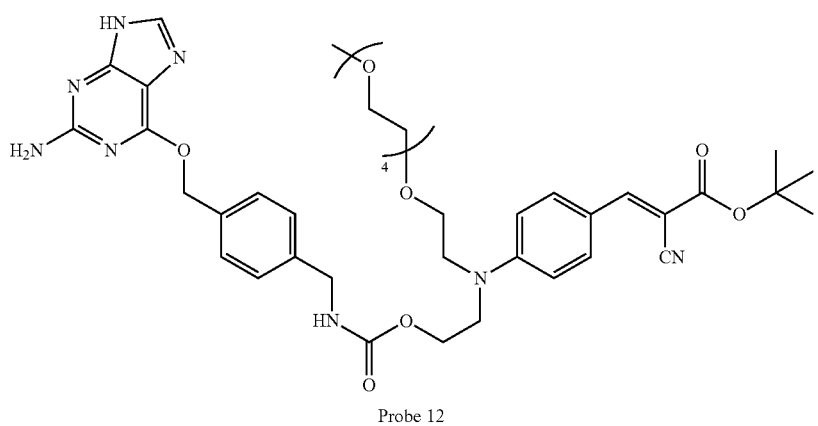

Probe 12

Compound 9

The synthesis was carried out with reference to the method disclosed in the literature (Tetsuaki Fujhara et al. Chem Comm, 2015, 51, 17382-17385). $^1$H-NMR (400 MHz, CDCl$_3$): δ=7.75 (d, 2H, J=8.2 Hz), 7.30 (d, 2H, J=7.8 Hz), 4.11 (t, 2H, J=4.8 Hz), 3.52-3.65 (m, 16H), 3.37 (s, 3H), 2.50 (s, 3H).

Compound 10

Compound 8 (0.664 g, 2 mmol) was dissolved in 10 mL anhydrous DMF, cooled to 0° C. under the protection of Ar, 60% NaH (0.088 g, 2.2 mmol) was added. The obtained mixture was stirred for 5 min under the protection of Ar. Then, Compound 9 (0.781 g, 2 mmol) was added. After slowly returning to room temperature and stirring for 3.5 hrs, 0.5 ml water was added to quench the reaction. The solvent was completely removed by rotary evaporation, and the residue was purified by gel silica gel column chromatography to give a pale yellow oil of 0.396 g, and the yield was 36%. $^1$H-NMR (400 MHz, DMSO-d$_6$): δ=8.01 (s, 1H), 7.97 (d, 2H, J=9.2 Hz), 6.85 (d, 2H, J=9.2 Hz), 3.56-3.68 (m, 24H), 3.38 (s, 3H), 1.50 (s, 9H).

Probe 12

This probe was obtained by following the general procedure for probe 1, and the yield was 71%. $^1$H-NMR (400 MHz, DMSO-d$_6$): δ=12.42 (s, 1H), 10.01 (s, 1H), 8.01 (s, 1H), 7.97 (d, 2H, J=9.2 Hz), 7.81 (s, 1H), 7.40 (m, 4H), 6.85 (d, 2H, J=9.2 Hz), 6.29 (s, 2H), 5.46 (s, 2H), 4.40 (d, 2H, J=4.8 Hz), 3.56-3.68 (m, 24H), 3.38 (s, 3H), 1.50 (s, 9H).

Example 13

A fluorescence-activated covalently labeling fluorescent probe 13 for SNAP protein tags was constructed using a molecular rotor as a viscosity-sensitive fluorescent dye.

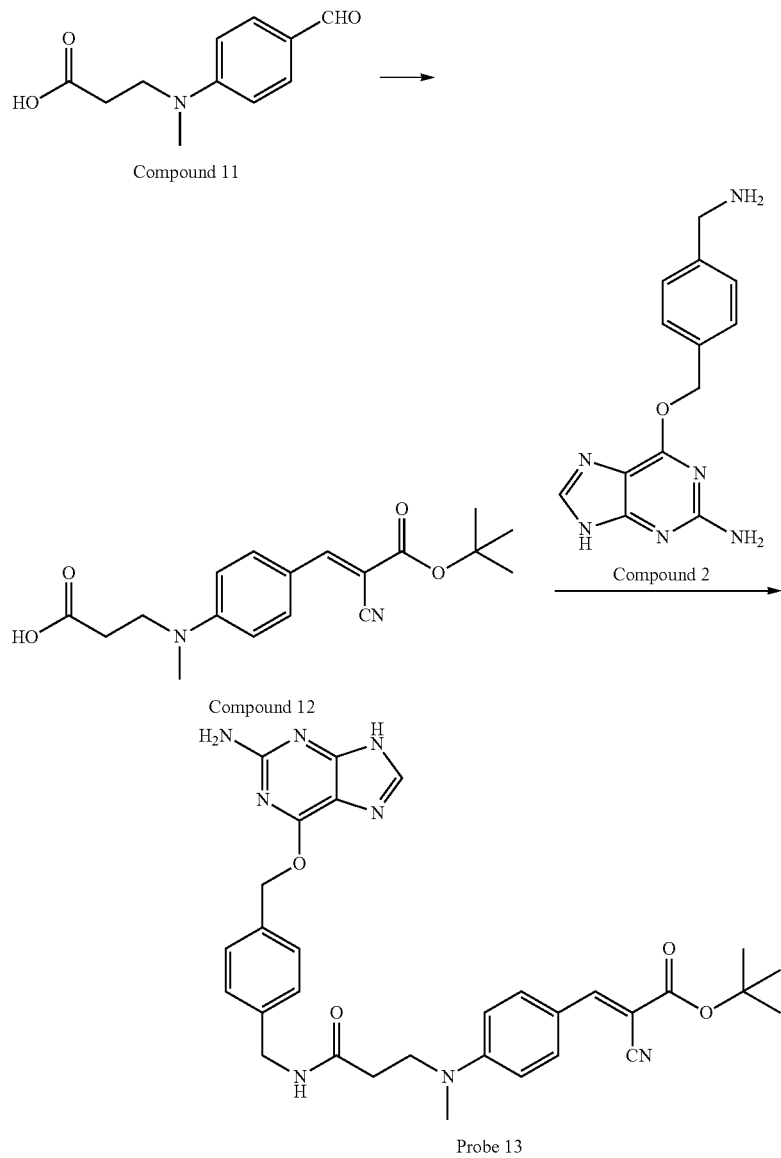

Compound 11

The synthesis was carried out by the method disclosed in the literature (Yang W et al. J. Photochem. Photobiol. A. 2011, 222, 228-235). $^1$H-NMR (400 MHz, D$_2$O): δ=9.43 (s, 1H), 7.72 (d, 2H, J=9.0 Hz), 6.81 (d, 2H, J=9.0 Hz), 3.71 (t, 2H, J=7.36 Hz), 3.03 (s, 3H), 2.44 (t, 2H, J=7.2 Hz).

Compound 12

This compound was obtained by following the general procedure for compound 1, and the yield was 91%. $^1$H-NMR (400 MHz, D$_2$O): δ=8.01 (s, 1H), 7.72 (d, 2H, J=9.0 Hz), 6.81 (d, 2H, J=9.0 Hz), 3.71 (t, 2H, J=7.36 Hz), 3.03 (s, 3H), 2.44 (t, 2H, J=7.2 Hz), 1.49 (s, 9H).

Probe 13

Compound 12 (0.33 g, 1 mmol), benzotriazole-1-yl-oxytripyrrolidinylphosphonium hexafluorophosphate (0.625 g, 1.2 mmol) and compound 2 (0.324 g, 1.2 mmol) were put in a 50 ml round-bottom flask, to which 15 ml anhydrous DMF and 0.3 nil of triethylamine were added. The obtained mixture was stirred and kept at room temperature for 0.5 hr under the protection of Ar. After the reaction was completed, the solvent was completely removed by rotary evaporation, and the residue was purified by gel silica gel column chromatography to give a pale yellow solid, 0.524 g. The yield was 90%. $^1$H-NMR (400 MHz, D$_2$O): δ=12.43 (s, 1H), 10.00 (s, 1H), 8.01 (s, 1H), 7.81 (s, 1H), 7.72 (d, 2H, J=9.0 Hz), 7.40 (m, 4H), 6.81 (d, 2H, J=9.0 Hz), 6.29 (s, 2H), 5.46 (s, 2H), 4.40 (d, 2H, J=4.8 Hz), 3.71 (t, 2H, J=7.36 Hz), 3.03 (s, 3H), 2.47 (t, 2H, J=7.2 Hz), 1.49 (s, 9H).

Example 14

A fluorescence-activated covalently labeling fluorescent probe 14 for SNAP protein tags was constructed using a molecular rotor as a viscosity-sensitive fluorescent dye.

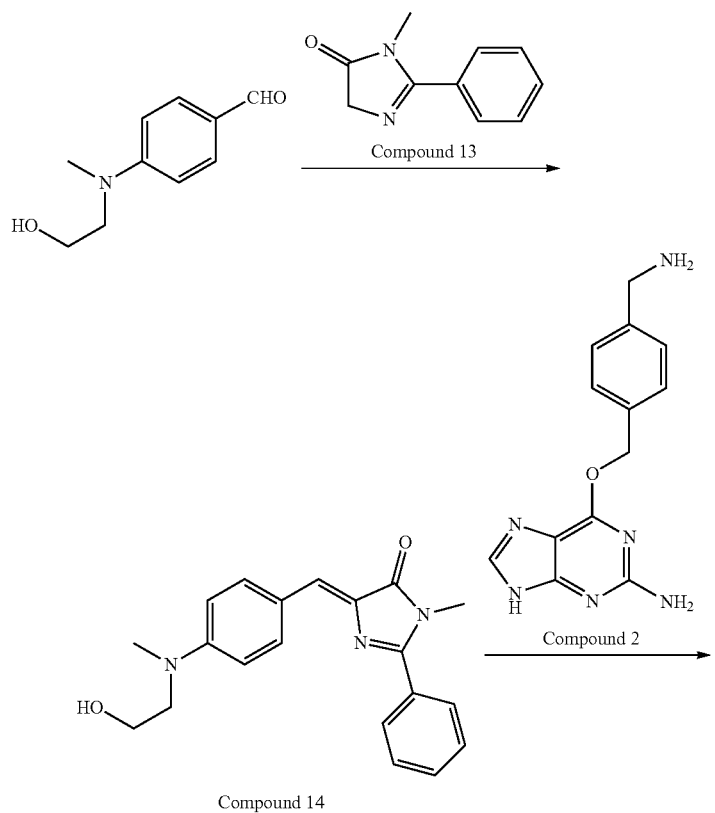

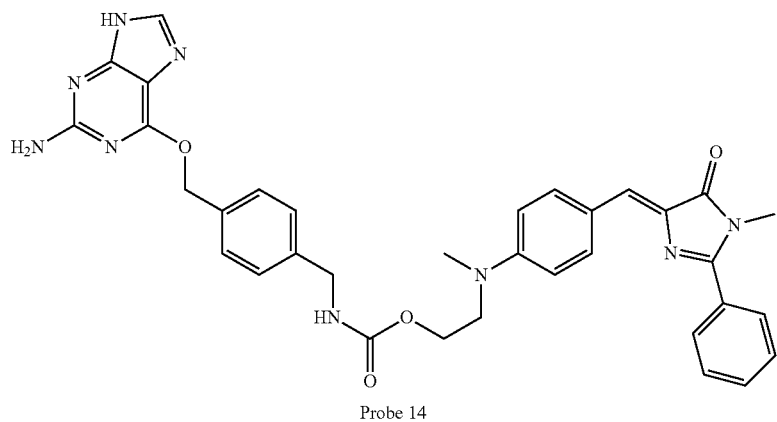

Compound 13

Probe 14

Compound 13

The synthesis was carried out by the method disclosed in literature (L. X. Wu, K. Burgess, J. Am. Chem. Soc. 2008, 130, 4089-4096). $^1$H-NMR (400 MHz, CDCl$_3$): δ=7.63-7.48 (m, 5H), 4.27 (s, 2H), 3.13 (s, 3H).

Compound 14

This compound was obtained by following the general procedure for compound 1, and the yield was 99%. $^1$H-NMR (400 MHz, CDCl$_3$): δ=8.03 (s, 1H), 7.97 (d, 2H, J=9.2 Hz), 6.85 (d, 2H, J=9.2 Hz), 4.27 (s, 2H), 3.55-3.59 (m, 4H), 3.08 (s, 3H), 3.13 (s, 3H).

Probe 14

This probe was obtained by following the general procedure for probe 1, and the yield was 70%. $^1$H-NMR (400 MHz, DMSO-d$_6$): δ=12.42 (s, 1H), 10.01 (s, 1H), 8.01 (s, 1H), 7.96 (d, 2H, J=9.2 Hz), 7.81 (s, 1H), 7.63-7.48 (m, 5H), 7.40 (m, 4H), 6.84 (d, 2H, J=9.2 Hz), 6.29 (s, 2H), 5.46 (s, 2H), 4.40 (d, 2H, J=4.8 Hz), 4.27 (s, 2H), 3.55-3.59 (m, 4H), 3.13 (s, 3H), 3.03 (s, 3H).

Example 15

A fluorescence-activated covalently labeling fluorescent probe 15 for SNAP protein tags was constructed using a molecular rotor as a viscosity-sensitive fluorescent dye.

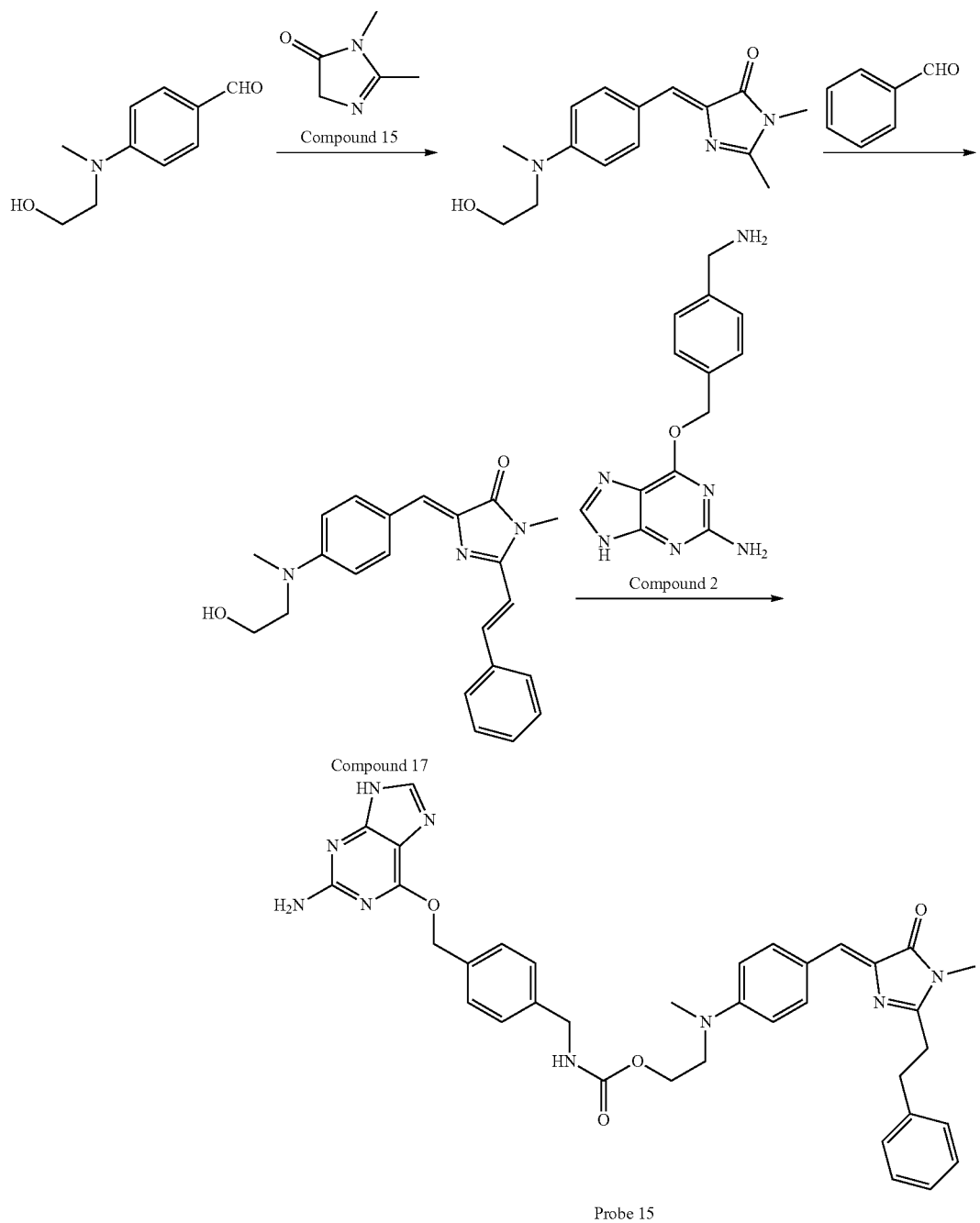

Compound 15

The synthesis was carried out by the method disclosed in literature (L. X. Wu, K. Burgess, J. Am. Chem. Soc. 2008, 130, 4089-4096). $^1$H-NMR (400 MHz, CDCl$_3$): δ=3.98 (q, 2H, J=2.4 Hz), 3.01 (s, 3H), 2.15 (t, 3H, J=2.4 Hz).

Compound 16

This compound was obtained by following the general procedure for compound 1, and the yield was 97%. $^1$H-NMR (400 MHz, DMSO-d$_6$): δ=8.00 (s, 1H), 7.97 (d, 2H, J=9.2 Hz), 6.85 (d, 2H, J=9.2 Hz), 3.98 (q, 2H, J=2.4 Hz), 3.55-3.59 (m, 4H), 3.08 (s, 3H), 3.01 (s, 3H), 2.15 (t, 3H, J=2.4 Hz).

Compound 17

Compound 16 (0.546 g, 2 mmol), benzaldehyde (0.530 g, 5 mmol) and anhydrous zinc chloride (0.545 g, 4 mmol) were dissolved in 100 ml anhydrous toluene. The mixture was heated to reflux in an oil bath for 48 hrs, After the reaction was completed, the solvent was completely removed by rotary evaporation, and the residue was dissolved in 100 ml of methylene dichloride, washed with water three times, and the organic phase is dried over anhydrous sodium sulfate, and the solvent was was completely removed by rotary evaporation, and the residue was purified by gel silica gel column chromatography to give a red-brown solid 0.181 g. The yield was 25%. $^1$H-NMR (400 MHz, DMSO-d$_6$): δ=8.21 (d, 2H, J=8.8 Hz), 8.00 (d, 1H, J=16 Hz), 7.85 (d, 2H, J=8.0 Hz), 7.45-7.38 (m, 3H), 7.24 (s, 1H), 7.01 (s, 1H), 6.92 (d, 2H, J=8.8 Hz), 3.85 (t, 2H, J=5.6 Hz), 3.60 (t, 2H, J=5.6 Hz), 3.10 (s, 3H).

Probe 15

This probe was obtained by following the general procedure for probe 1, and the yield was 66%. $^1$H-NMR (400 MHz, DMSO-d$_6$): δ=12.42 (s, 1H), 10.01 (s, 1H), 8.21 (d, 2H, J=8.8 Hz), 8.00 (d, 1H, J=16 Hz), 7.85 (d, 2H, J=8.0 Hz), 7.81 (s, 1H), 7.45-7.38 (m, 7H), 7.24 (s, 1H), 7.01 (s, 1H), 6.92 (d, 2H, J=8.8 Hz), 6.29 (s, 2H), 5.46 (s, 2H), 4.40 (d, 2H, J=4.8 Hz), 3.85 (t, 2H, J=5.6 Hz), 3.60 (t, 2H, J=5.6 Hz), 3.10 (s, 3H).

Example 16

A fluorescence-activated covalently labeling fluorescent probe 16 for SNAP protein tags was constructed using a molecular rotor as a viscosity-sensitive fluorescent dye.

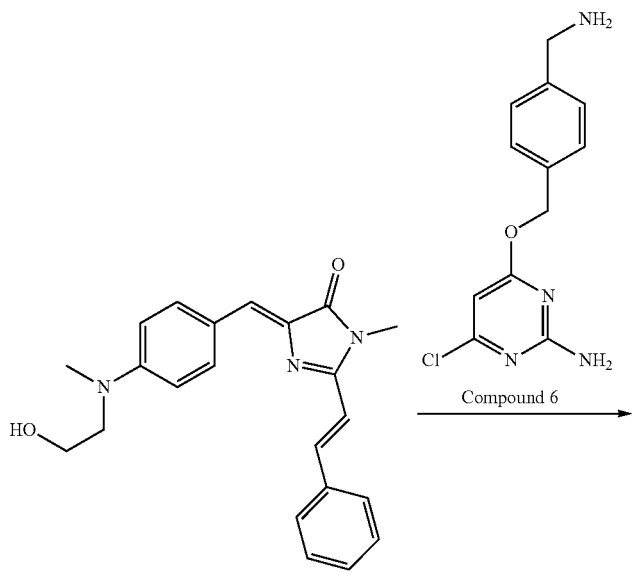

Compound 17

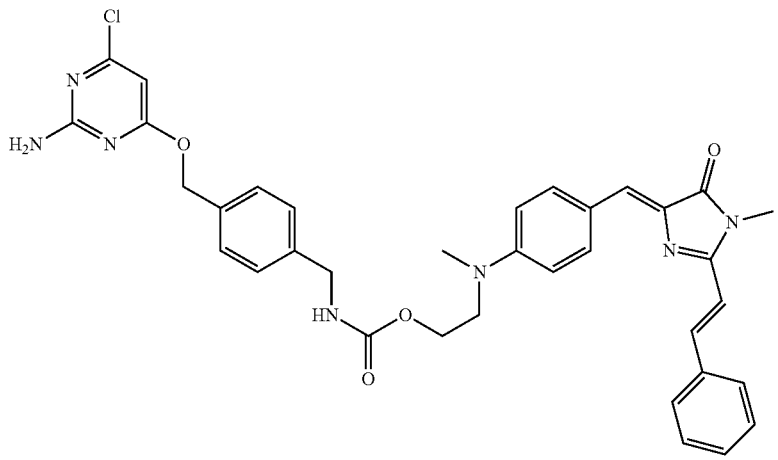

Probe 16

Probe 16

This probe was obtained by following the general procedure for probe 1, and the yield was 78%. $^1$H-NMR (400 MHz, DMSO-$d_6$): δ=9.99 (brs, 1H), 8.21 (d, 2H, J=8.8 Hz), 8.00 (d, 1H, J=16 Hz), 7.85 (d, 2H, J=8.0 Hz), 7.45-7.39 (m, 3H), 7.35 (d, 2H, J=8.4 Hz), 7.26 (d, 2H, J=8.4 Hz), 7.24 (s, 1H), 7.09 (s, 2H), 7.01 (s, 1H), 6.92 (d, 2H, J=8.8 Hz), 6.10 (s, 1H), 5.26 (s, 2H), 4.36 (s, 2H), 3.85 (t, 2H, J=5.6 Hz), 3.60 (t, 2H, J=5.6 Hz), 3.10 (s, 3H).

Example 17

A fluorescence-activated covalently labeling fluorescent probe 17 for CLIP protein tags was constructed using a molecular rotor as a viscosity-sensitive fluorescent dye.

Probe 17

This probe was obtained by following the general procedure for probe 1, and the yield was 71%. $^1$H-NMR (400 MHz, DMSO-$d_6$): δ=8.21 (d, 2H, J=8.8 Hz), 8.00 (d, 1H, J=16 Hz), 7.93 (d, 1H, J=5.6), 7.85 (d, 2H, J=8.0 Hz), 7.75 (s, 1H), 7.45-7.38 (m, 3H), 7.33 (d, 2H, J=8.0 Hz), 7.24 (s, 1H), 7.19 (d, 2H, J=8.0 Hz), 7.01 (s, 1H), 6.92 (d, 2H, J=8.8 Hz), 6.06 (d, 1H, J=5.6 Hz), 5.27 (s, 2H), 5.16 (s, 2H), 4.45 (d, 2H, J=5.6 Hz), 3.85 (t, 2H, J=5.6 Hz), 3.60 (t, 2H, J=5.6 Hz), 3.10 (s, 3H).

Example 18

A fluorescence-activated covalently labeling fluorescent probe 18 for SNAP protein tags was constructed using a molecular rotor as a viscosity-sensitive fluorescent dye.

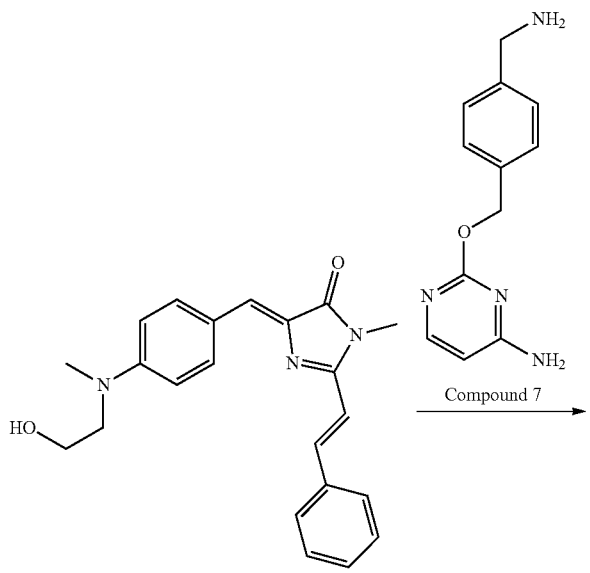

Compound 17

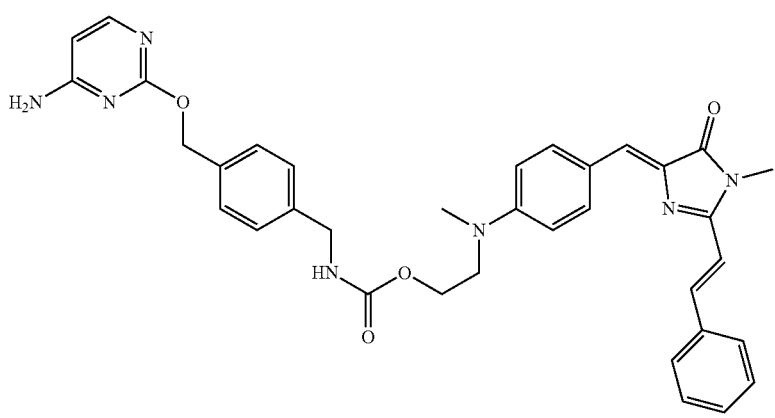

Probe 17

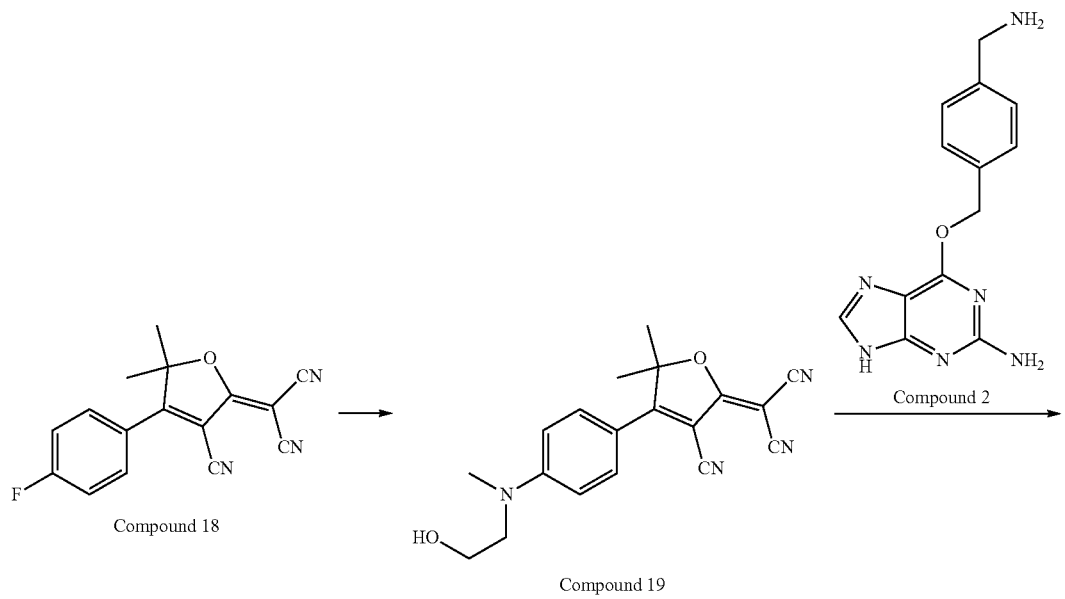

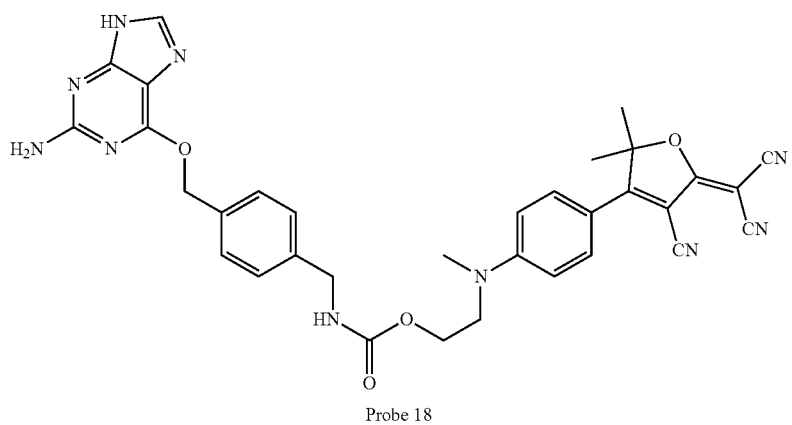

Probe 18

Compound 18

The synthesis was carried out by the method disclosed in the literature (Wang H. et al. Tetra Let, 2007, 48, 3471-3474). $^1$H-NMR (400 MHz, DMSO-d$_6$): δ=8.05 (m, 2H), 7.01 (m, 2H), 1.83 (s, 6H).

Compound 19

Compound 18 (0.279 g, 1 mmol) was dissolved in 20 ml of anhydrous pyridine, ml of N-methyl-N-hydroxyethyl was added, and heated in an oil bath at 40° C. overnight under the protection of Ar, After the reaction was completed, the solvent was completely removed by rotary evaporation, and the residue was purified by gel silica gel column chromatography to give a red product 0.187 g. The yield was 56%.

$^1$H-NMR (400 MHz, DMSO-d$_6$): δ=8.05 (m, 2H), 7.01 (m, 2H), 3.85 (t, 2H, J=5.6 Hz), 3.60 (t, 2H, J=5.6 Hz), 3.10 (s, 3H), 1.83 (s, 6H).

Probe 18

This probe was obtained by following the general procedure for probe 1, and the yield was 56%. $^1$H-NMR (400 MHz, DMSO-d$_6$): δ=8.05 (m, 2H), 7.01 (m, 2H), 3.85 (t, 2H, J=5.6 Hz), 3.60 (t, 2H, J=5.6 Hz), 3.10 (s, 3H), 1.83 (s, 6H).

Example 19

A fluorescence-activated covalently labeling fluorescent probe 19 for SNAP protein tags was constructed using a molecular rotor as a viscosity-sensitive fluorescent dye.

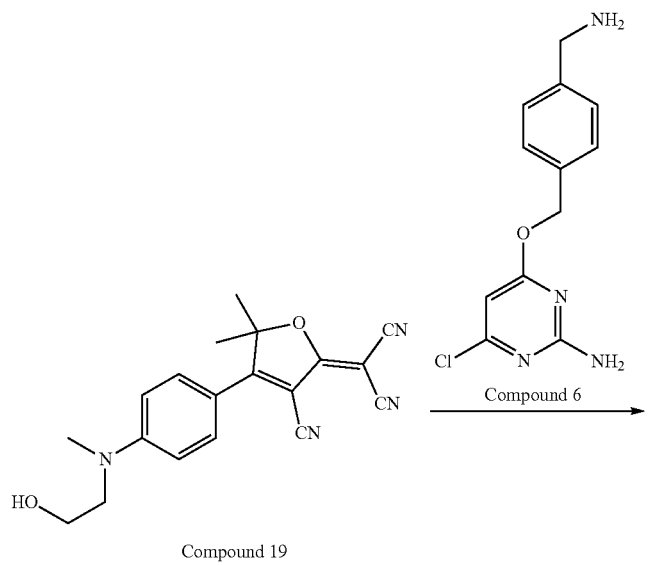
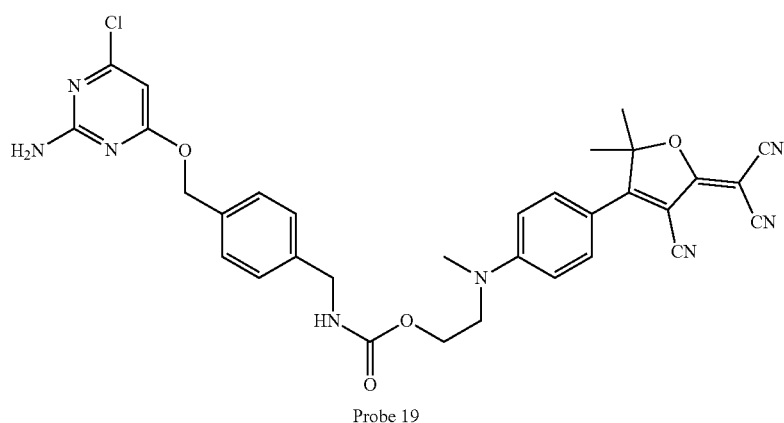
Probe 19
This probe was obtained by following the general procedure for probe 1, and the yield was 75%. $^1$H-NMR (400 MHz, DMSO-d$_6$): δ=9.90 (brs, 1H), 8.05 (m, 2H), 7.39 (d, 2H, J=8.4 Hz), 7.26 (d, 2H, J=8.4 Hz), 7.09 (s, 2H), 7.01 (m, 2H), 6.10 (s, 1H), 5.26 (s, 2H), 4.36 (s, 2H), 3.85 (t, 2H, J=5.6 Hz), 3.60 (t, 2H, J=5.6 Hz), 3.10 (s, 3H), 1.83 (s, 6H).
Example 20
A fluorescence-activated covalently labeling fluorescent probe 20 for CLIP protein tags was constructed using a molecular rotor as a viscosity-sensitive fluorescent dye.

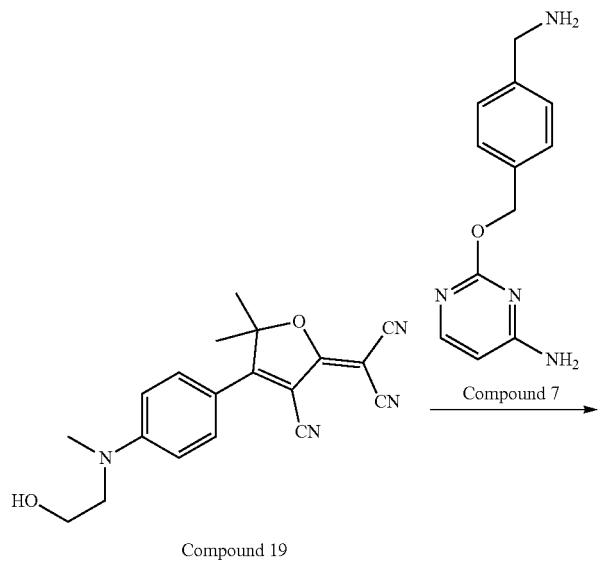

Compound 19 → Compound 7

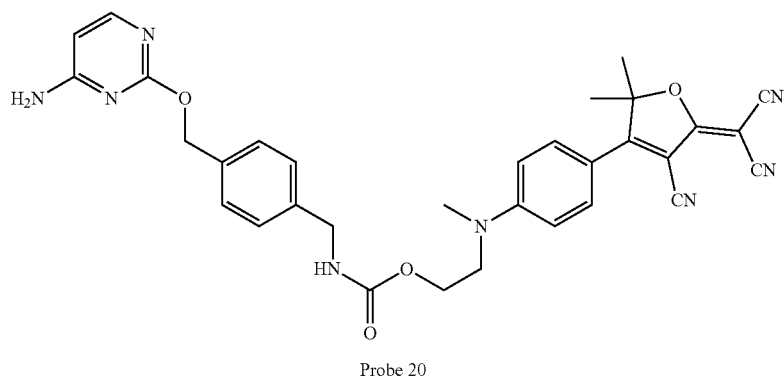

Probe 20

Probe 20

This probe was obtained by following the general procedure for probe 1, and the yield was 71%. $^1$H-NMR (400 MHz, DMSO-$d_6$): δ=8.05 (m, 2H), 7.93 (d, 1H, J=5.6), 7.75 (s, 1H), 7.33 (d, 2H, J=8.0 Hz), 7.19 (d, 2H, J=8.0 Hz), 7.01 (m, 2H), 6.06 (d, 1H, J=5.6 Hz), 5.27 (s, 2H), 5.16 (s, 2H), 4.45 (d, 2H, J=5.6 Hz), 3.85 (t, 2H, J=5.6 Hz), 3.60 (t, 2H, J=5.6 Hz), 3.10 (s, 3H), 1.83 (s, 6H).

Example 21

A fluorescence-activated covalently labeling fluorescent probe 21 for SNAP protein tags was constructed using a molecular rotor as a viscosity-sensitive fluorescent dye.

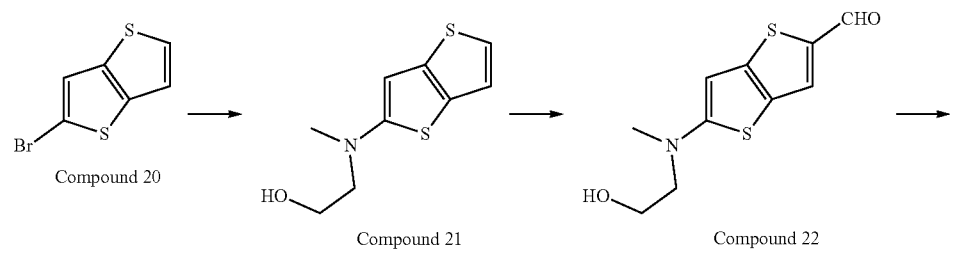

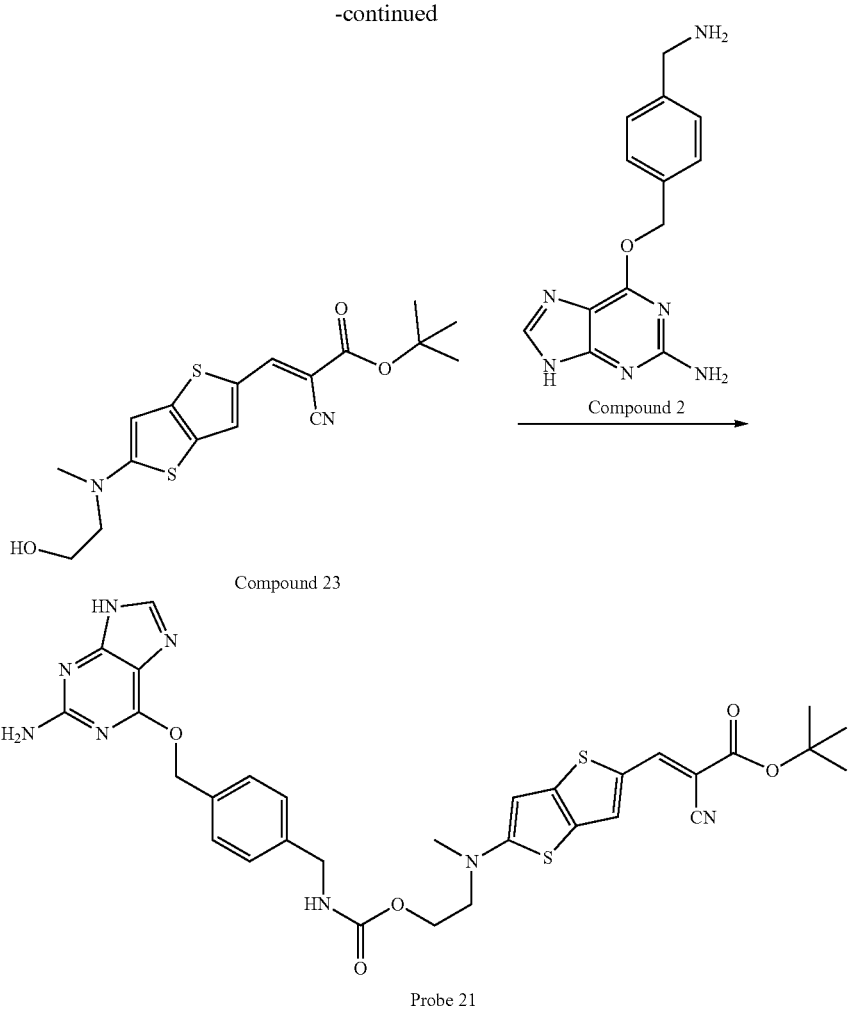

Compound 20

The synthesis was carried out by the method disclosed in the literature (WO 2013142841 (A1) 2013 Sep. 26). $^1$H-NMR (400 MHz, CDCl$_3$): δ=7.92 (s, 1H), 7.63 (d, 1H, J=5.2 Hz), 7.31 (d, 1H, J=5.2 Hz).

Compound 21

Compound 20 (0.438 g, 2 mmol) was dissolved in 15 mL of N-methyl-N-hydroxyethylamine, copper powder (6.4 mg, 0.01 mmol), cuprous iodide (19 mg, 0.01 mmol), tripotassium phosphate (0.850 g, 4 mmol) were added, and heated in an oil bath at 80° C. overnight under the protection of Ar. After the reaction was completed, cooled at room temperature, the system was poured into 50 mL of water and was extracted three times with 50 ml dichloromethane; the organic phases were combined, and the solvent was completely removed by rotary evaporation. After separation by column chromatography, 0.362 g of a yellow product was obtained, and the yield was 85%. $^1$H-NMR (400 MHz, CDCl$_3$): δ=7.92 (s, 1H), 7.63 (d, 1H, J=5.2 Hz), 7.31 (d, 1H, J=5.2 Hz), 3.85 (t, 2H, J=5.6 Hz), 3H, J=5.6 Hz), 3.10 (s, 3H).

Compound 22

Compound 21 (0.426 g, 2 mmol) was dissolved in 50 ml of anhydrous dichloromethane, 1 ml of triethylamine was added, and acetic anhydride (0.3 ml, 3 mmol) was slowly added dropwise under an ice bath. After the temperature was raised to room temperature, the system was stirred for 3 hrs. After the reaction was completed, 100 ml water was added. The organic phase was separated, and the aqueous phase was extracted twice with 50 ml dichloromethane. The organic phase was combined and dried over anhydrous sodium sulfate. The solvent was completely removed by rotary evaporation. The residue was directly used in the next step without being further purified.

The residue was dissolved in 50 nil of dichloromethane. 5 ml of DMF was added, 2 ml of phosphorus oxychloride was added under an ice bath, and the mixture was stirred under the protection of Ar for 0.5 h. The system was slowly warmed at room temperature and stirring was continued for 5 hrs; after the reaction was completed, saturated sodium carbonate solution was added to adjust pH to 10.0; stirring was carried out at room temperature overnight, and the organic phase was separated the next day, and the aqueous phase was extracted three times with 50 ml of dichloromethane, and the organic phase was combined and washed twice with saturated brine. The organic phase was dried over anhydrous sodium sulfate. The solvent was completely removed by rotary evaporation, and the residue was purified by gel silica gel column chromatography to give a yellow solid 0.285 g, and the yield was 59%. $^1$H-NMR (400 MHz, CDCl$_3$): δ=10.01 (s, 1H), 7.92 (s, 1H), 7.63 (s, 1H) 3.85 (t, 2H, J=5.6 Hz), 3.60 (t, 2H, J=5.6 Hz), 3.10 (s, 3H).

Compound 23

This compound was obtained by following the general procedure for compound 1, and the yield was 89%. $^1$H-NMR (400 MHz, DMSO-d$_6$): δ=8.22 (s, 1H), 8.02 (s, 1H), 6.43 (s, 1H), 3.85 (t, 2H, J=5.6 Hz), 3.60 (t, 2H, J=5.6 Hz), 3.10 (s, 3H), 1.49 (s, 9H).

Probe 21

This probe was obtained by following the general procedure for probe 1, and the yield was 65%. $^1$H-NMR (400 MHz, DMSO-d$_6$): δ=12.22 (s, 1H), 10.01 (s, 1H), 8.22 (s, 1H), 8.02 (s, 1H), 7.81 (s, 1H), 7.40 (m, 4H), 6.43 (s, 1H), 6.28 (s, 2H), 5.45 (s, 2H), 4.41 (d, 2H, J=4.8 Hz), 3.85 (t, 2H, J=5.6 Hz), 3.60 (t, 2H, J=5.6 Hz), 1.49 (s, 9H).

Example 22

A fluorescence-activated covalently labeling fluorescent probe 22 for SNAP protein tags was constructed using a molecular rotor as a viscosity-sensitive fluorescent dye.

Compound 24

This compound was obtained by following the general procedure for compound 1, and the yield was 93%. $^1$H-NMR (400 MHz, CDCl$_3$): δ=8.22 (s, 1H), 8.02 (s, 1H), 7.74 (d, 1H, J=4.0 Hz), 7.55 (d, 1H, J=4.0 Hz), 7.36-7.42 (m, 2H), 6.43 (s, 1H), 3.75 (t, 2H, J=5.6 Hz), 3.55 (t, 2H, J=5.6 Hz), 3.10 (s, 3H).

Probe 22

This probe was obtained by following the general procedure for probe 1, and the yield was 66%. $^1$H-NMR (400 MHz, DMSO-d$_6$): δ=12.02 (s, 1H), 10.00 (s, 1H), 8.22 (s, 1H), 8.02 (s, 1H), 7.81 (s, 1H), 7.74 (d, 1H, J=4.0 Hz), 7.55 (d, 1H, J=4.0 Hz), 7.36-7.42 (m, 6H), 6.43 (s, 1H), 6.28 (s, 2H), 5.45 (s, 2H), 4.41 (d, 2H, J=4.8 Hz), 3.75 (t, 2H, J=5.6 Hz), 3.55 (t, 2H, J=5.6 Hz), 3.10 (s, 3H).

Example 23

A fluorescence-activated covalently labeling fluorescent probe 23 for SNAP protein tags was constructed using a molecular rotor as a viscosity-sensitive fluorescent dye.

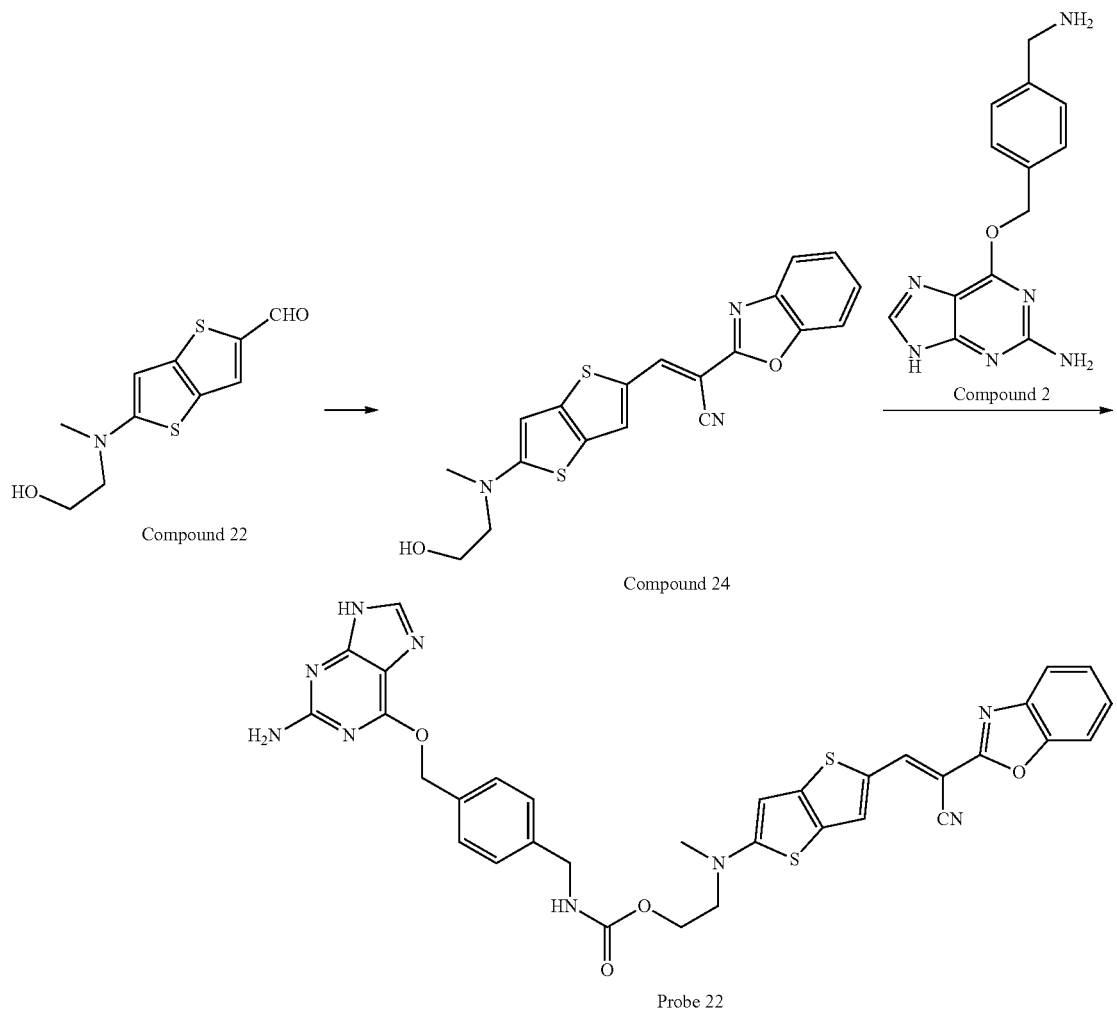

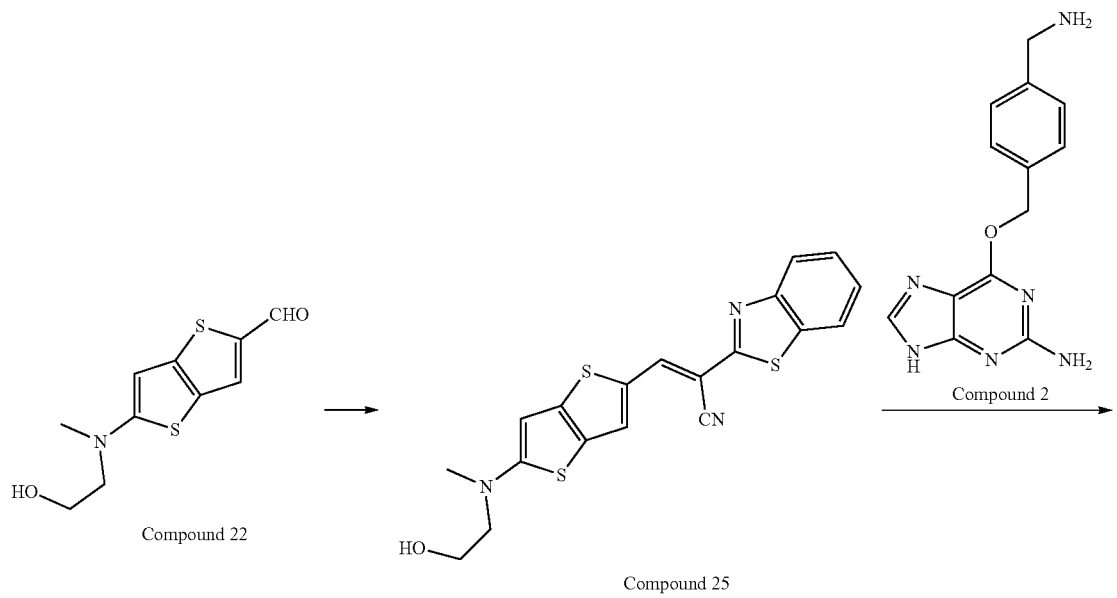

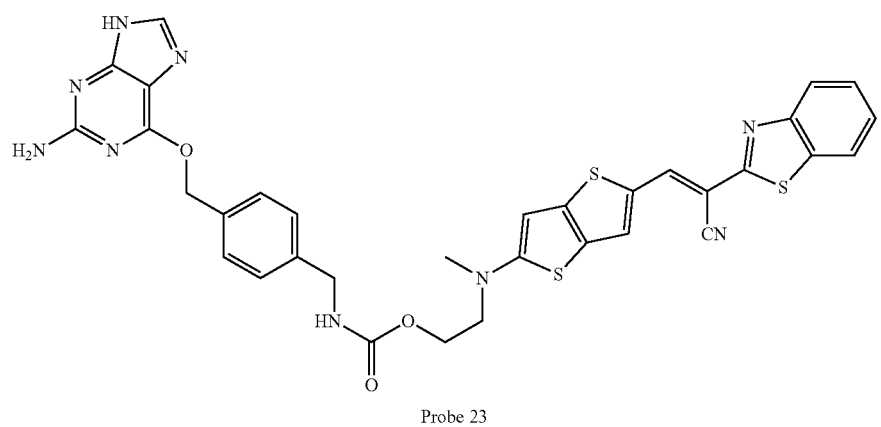

Probe 23

Compound 25

This compound was obtained by following the general procedure for compound 1, and the yield was 88%. $^1$H-NMR (400 MHz, DMSO-d$_6$): δ=8.22 (s, 1H), 8.09 (d, 1H, J=8.0 Hz), 8.02 (s, 1H), 7.90 (d, 1H, J=8.0 Hz), 7.53 (t, 1H, J=8.0 Hz), 7.45 (t, 1H, J=8.0 Hz), 6.43 (s, 1H), 3.85 (t, 2H, J=5.6 Hz), 3.60 (t, 2H, J=5.6 Hz), 3.10 (s, 3H).

Probe 23

This Probe was obtained by following the general procedure for Probe 1, and the yield was 56%. $^1$H-NMR (400 MHz, DMSO-d$_6$): δ=12.32 (s, 1H), 10.03 (s, 1H), 8.22 (s, 1H), 8.09 (d, 1H, J=8.0 Hz), 8.02 (s, 1H), 7.90 (d, 1H, J=8.0 Hz), 7.81 (s, 1H), 7.53 (t, 1H, J=8.0 Hz), 7.45 (t, 1H, J=8.0 Hz), 7.40 (m, 4H), 6.43 (s, 1H), 6.29 (s, 2H), 5.46 (s, 2H), 4.40 (d, 2H, J=4.8 Hz), 3.85 (t, 2H, J=5.6 Hz), 3.60 (t, 2H, J=5.6 Hz), 3.10 (s, 3H).

Example 24

A fluorescence-activated covalently labeling fluorescent probe 24 for SNAP protein tags was constructed using a molecular rotor as a viscosity-sensitive fluorescent dye.

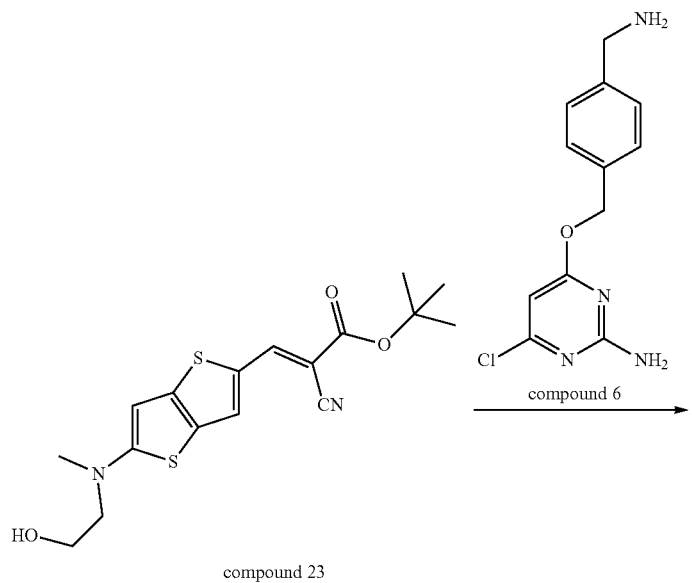

compound 23

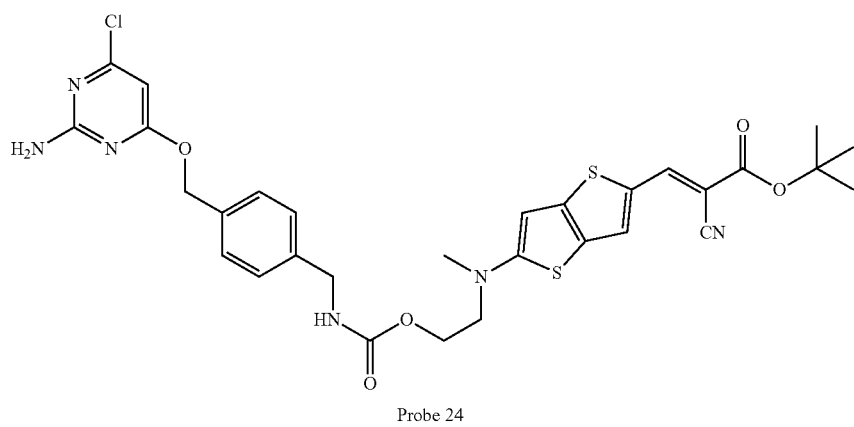

Probe 24

Probe 24

This probe was obtained by following the general procedure for probe 1, and the yield was 58%. $^1$H-NMR (400 MHz, DMSO-d$_6$): δ=9.98 (brs, 1H), 8.22 (s, 1H), 8.02 (s, 1H), 7.39 (d, 2H, J=8.4 Hz), 7.26 (d, 2H, J=8.4 Hz), 7.09 (s, 2H), 6.43 (s, 1H), 6.10 (s, 1H), 5.26 (s, 2H), 4.36 (s, 2H), 3.85 (t, 2H, J=5.6 Hz), 3.60 (t, 2H, J=5.6 Hz), 3.10 (s, 3H), 1.49 (s, 9H).

Example 25

A fluorescence-activated covalently labeling fluorescent probe 25 for SNAP protein tags was constructed using a molecular rotor as a viscosity-sensitive fluorescent dye.

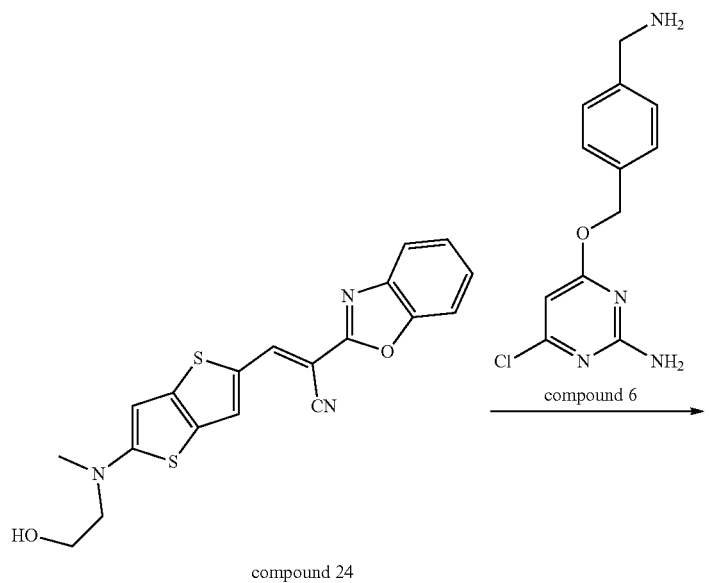

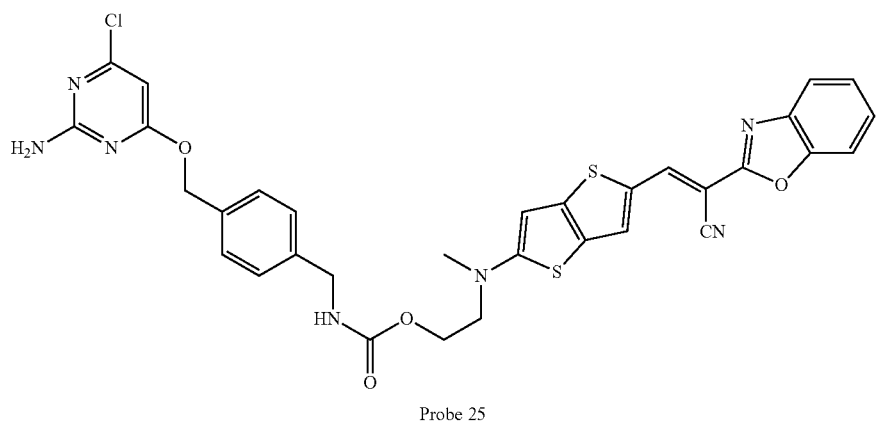

Probe 25

This probe was obtained by following the general procedure for probe 1, and the yield was 63%. $^1$H-NMR (400 MHz, DMSO-d$_6$): δ=9.99 (brs, 1H), 8.22 (s, 1H), 8.02 (s, 1H), 7.74 (d, 1H, J=4.0 Hz), 7.55 (d, 1H, J=4.0 Hz), 7.44 (d, 2H, J=8.4 Hz), 7.36-7.42 (m, 2H), 7.26 (d, 2H, J=8.4 Hz), 7.09 (s, 2H), 6.43 (s, 1H), 6.10 (s, 1H), 5.26 (s, 2H), 4.36 (s, 2H), 3.75 (t, 2H, J=5.6 Hz), 3.55 (t, 2H, J=5.6 Hz), 3.10 (s, 3H).

Example 26

A fluorescence-activated covalently labeling fluorescent probe 26 for SNAP protein tags was constructed using a molecular rotor as a viscosity-sensitive fluorescent dye.

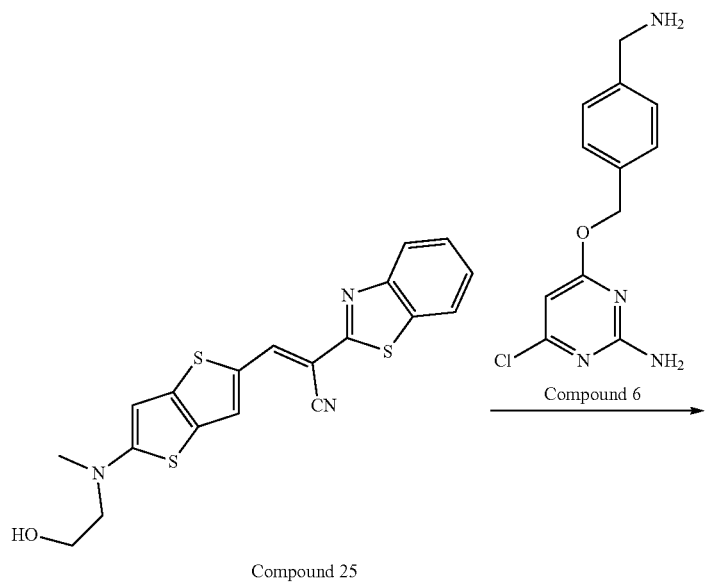

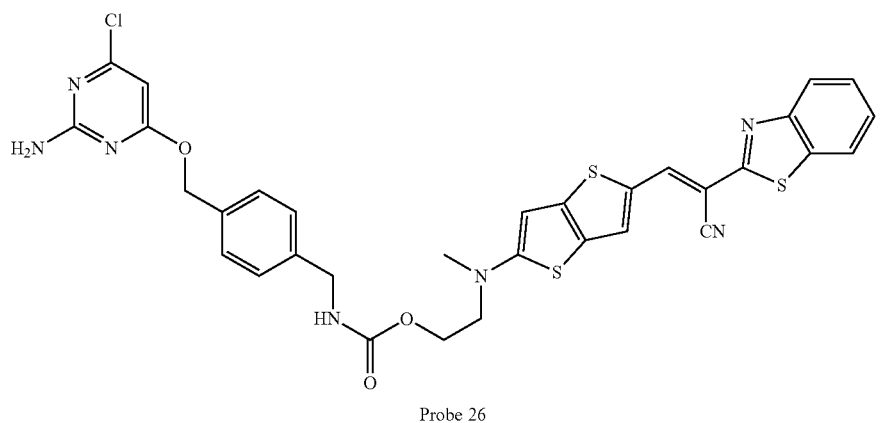

Probe 26

Probe 26

This probe was obtained by following the general procedure for probe 1, and the yield was 58%. $^1$H-NMR (400 MHz, DMSO-d$_6$): δ=9.98 (brs, 1H), 8.22 (s, 1H), 8.09 (d, 1H, J=8.0 Hz), 8.02 (s, 1H), 7.90 (d, 1H, J=8.0 Hz), 7.53 (t, 1H, J=8.0 Hz), 7.45 (t, 1H, J=8.0 Hz), 7.39 (d, 2H, J=8.4 Hz), 7.26 (d, 2H, J=8.4 Hz), 7.09 (s, 2H), 6.43 (s, 1H), 6.10 (s, 1H), 5.26 (s, 2H), 4.36 (s, 2H), 3.85 (t, 2H, J=5.6 Hz), 3.60 (t, 2H, J=5.6 Hz), 3.10 (s, 3H).

Example 27

A fluorescence-activated covalently labeling fluorescent probe 27 for CLIP protein tags was constructed using a molecular rotor as a viscosity-sensitive fluorescent dye.

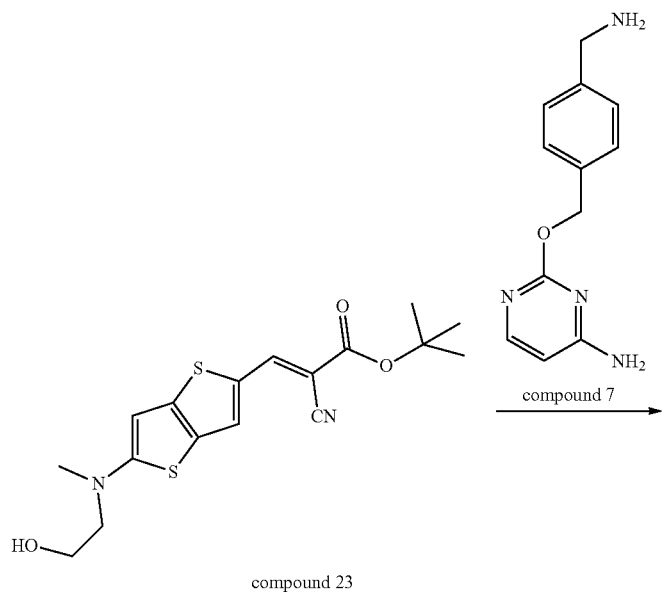

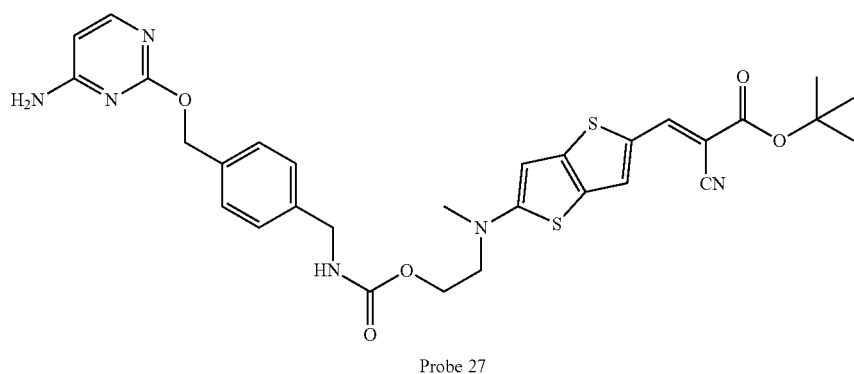

Probe 27

Probe 27

This probe was obtained by following the general procedure for probe 1, and the yield was 61%. $^1$H-NMR (400 MHz, DMSO-d$_6$): δ=8.22 (s, 1H), 8.02 (s, 1H), 7.93 (d, 1H, J=5.6), 7.75 (s, 1H), 7.33 (d, 2H, J=8.0 Hz), 7.19 (d, 2H, J=8.0 Hz), 6.43 (s, 1H), 6.06 (d, 1H, J=5.6 Hz), 5.27 (s, 2H), 5.16 (s, 2H), 4.45 (d, 2H, J=5.6 Hz), 3.85 (t, 2H, J=5.6 Hz), 3.60 (t, 2H, J=5.6 Hz), 3.10 (s, 3H), 1.49 (s, 9H).

Example 28

A fluorescence-activated covalently labeling fluorescent probe 28 for CLIP protein tags was constructed using a molecular rotor as a viscosity-sensitive fluorescent dye.

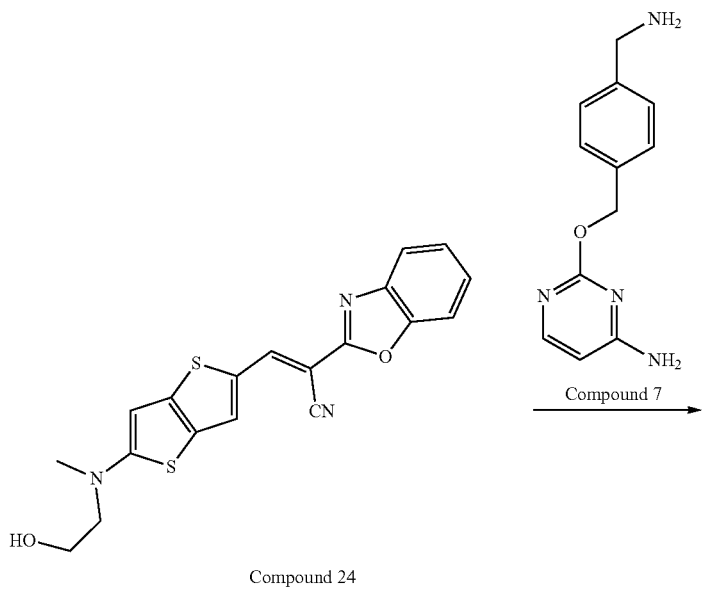

Compound 24

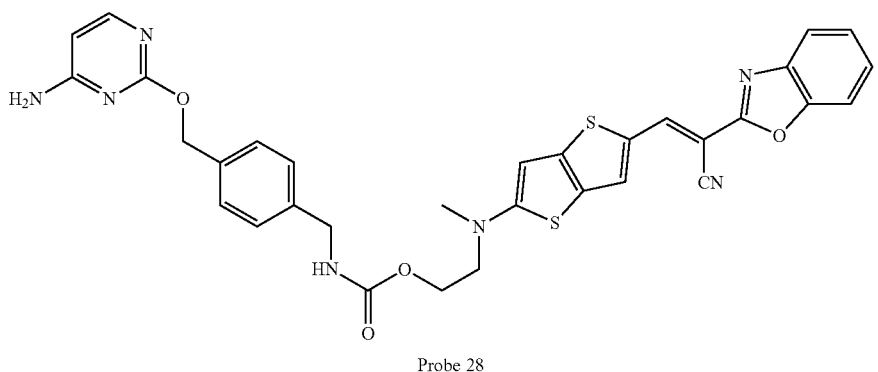

Probe 28

Probe 28

This probe was obtained by following the general procedure for probe 1, and the yield was 63%. $^1$H-NMR (400 MHz, DMSO-$d_6$): δ=8.22 (s, 1H), 8.02 (s, 1H), 7.93 (d, 1H, J=5.6), 7.77 (s, 1H), 7.74 (d, 1H, J=4.0 Hz), 7.55 (d, 1H, J=4.0 Hz), 7.36-7.42 (m, 2H), 7.30 (d, 2H, J=8.0 Hz), 7.19 (d, 2H, J=8.0 Hz), 6.43 (s, 1H), 6.06 (d, 1H, J=5.6 Hz), 5.27 (s, 2H), 5.16 (s, 2H), 4.45 (d, 2H, J=5.6 Hz), 3.75 (t, 2H, J=5.6 Hz), 3.55 (t, 2H, J=5.6 Hz), 3.10 (s, 3H).

Example 29

A fluorescence-activated covalently labeling fluorescent probe 29 for CLIP protein tags was constructed using a molecular rotor as a viscosity-sensitive fluorescent dye.

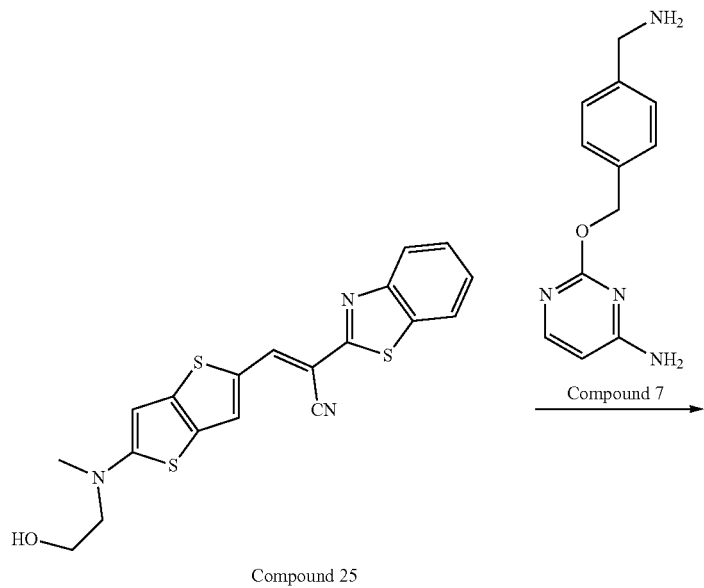

Compound 25

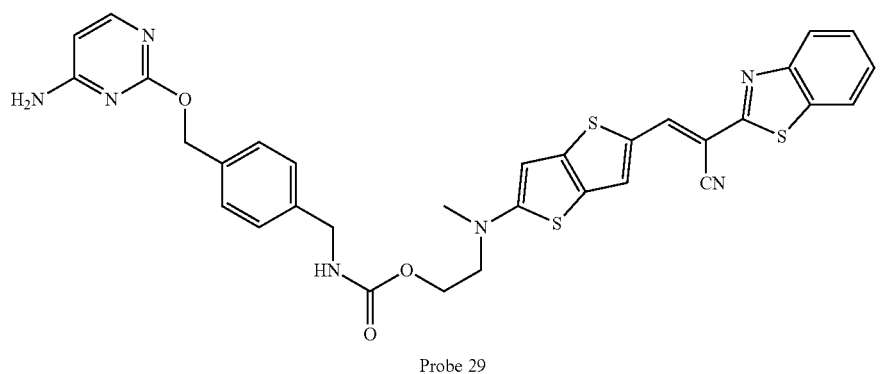

Probe 29

Probe 29

This probe was obtained by following the general procedure for probe 1, and the yield was 61%. $^1$H-NMR (400 MHz, DMSO-$d_6$): δ=8.22 (s, 1H), 8.09 (d, 1H, J=8.0 Hz), 8.02 (s, 1H), 7.96 (d, 1H, J=5.6), 7.90 (d, 1H, J=8.0 Hz), 7.75 (s, 1H), 7.53 (t, 1H, J=8.0 Hz), 7.45 (t, 1H, J=8.0 Hz), 7.33 (d, 2H, J=8.0 Hz), 7.19 (d, 2H, J=8.0 Hz), 6.43 (s, 1H), 6.06 (d, 1H, J=5.6 Hz), 5.27 (s, 2H), 5.16 (s, 2H), 4.45 (d, 2H, J=5.6 Hz), 3.85 (t, 2H, J=5.6 Hz), 3.60 (t, 2H, J=5.6 Hz), 3.10 (s, 3H).

Example 30

A fluorescence-activated covalently labeling fluorescent probe 30 for SNAP protein tags was constructed using a molecular rotor as a viscosity-sensitive fluorescent dye.

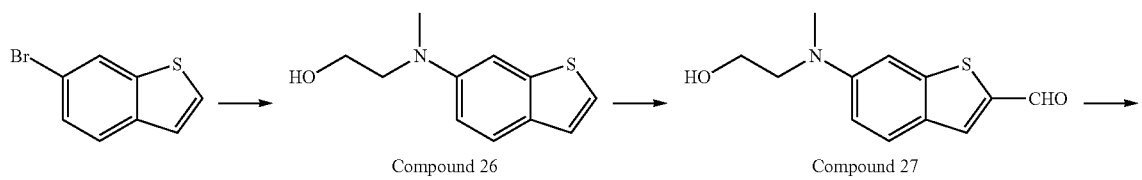

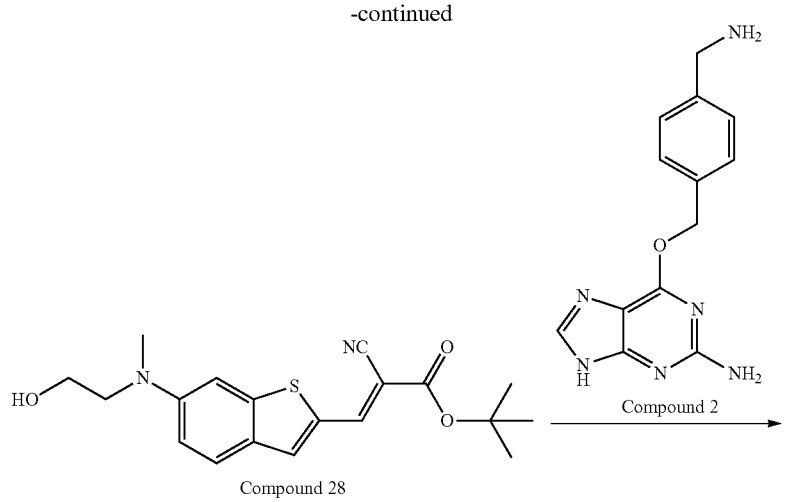

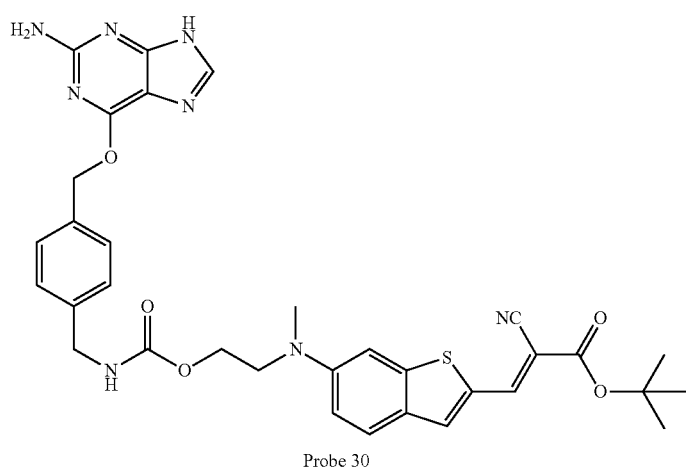

Probe 30

Compound 26

This compound was obtained by following the general procedure for compound 21, and the yield was 87%. $^1$H-NMR (400 MHz, CDCl$_3$): δ=8.02 (s, 1H), 7.66 (d, 1H, J=8.4 Hz), 7.44-7.48 (m, 1H), 7.41 (m, 1H), 7.29 (m, 1H), 3.60 (t, 2H, J=5.6 Hz), 3.34 (t, J=8.0 Hz, 3H), 3.10 (s, 3H).

Compound 27

This compound was obtained by following the general procedure for compound 22, and the yield was 56%. $^1$H-NMR (400 MHz, CDCl$_3$): δ=9.92 (s, 1H), 7.81 (s, 1H), 7.68 (d, J=9.0 Hz, 1H), 6.92 (d, J=2.0 Hz, 1H), 6.82 (d, J=9.1, 2.3 Hz, 1H), 3.61 (t, J=8.0 Hz, 3H), 3.34 (t, J=8.0 Hz, 3H), 3.10 (s, 3H).

Compound 28

This compound was obtained by following the general procedure for compound 1, and the yield was 91%. $^1$H-NMR (400 MHz, CDCl$_3$): δ=8.22 (s, 1H), 8.02 (s, 1H), 6.43 (s, 1H), 3.61 (t, J=8.0 Hz, 3H), 3.34 (t, J=8.0 Hz, 3H), 3.11 (s, 3H), 1.48 (s, 9H).

Probe 30

This probe was obtained by following the general procedure for probe 1, and the yield was 66%. $^1$H-NMR (400 MHz, CDCl$_3$): δ=12.42 (s, 1H), 10.01 (s, 1H), 8.20 (s, 1H), 7.81 (s, 2H), 7.68 (d, J=9.0 Hz, 1H), 7.40 (m, 4H), 6.92 (d, J=2.0 Hz, 1H), 6.82 (d, J=9.1, 2.3 Hz, 1H), 6.29 (s, 2H), 5.46 (s, 2H), 4.40 (d, 2H, J=4.8 Hz), 3.61 (t, J=8.0 Hz, 3H), 3.34 (t, J=8.0 Hz, 3H), 3.11 (s, 3H), 1.51 (s, 9H).

Example 31

A fluorescence-activated covalently labeling fluorescent probe 31 for SNAP protein tags was constructed using a molecular rotor as a viscosity-sensitive fluorescent dye.

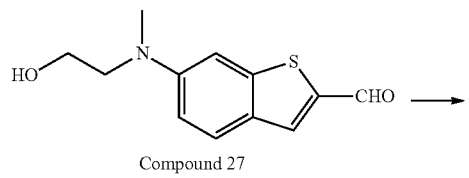

Compound 27

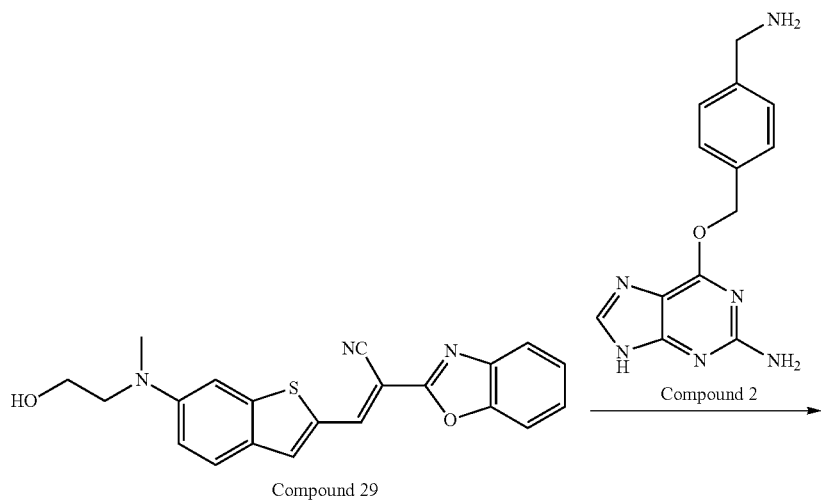

Compound 29

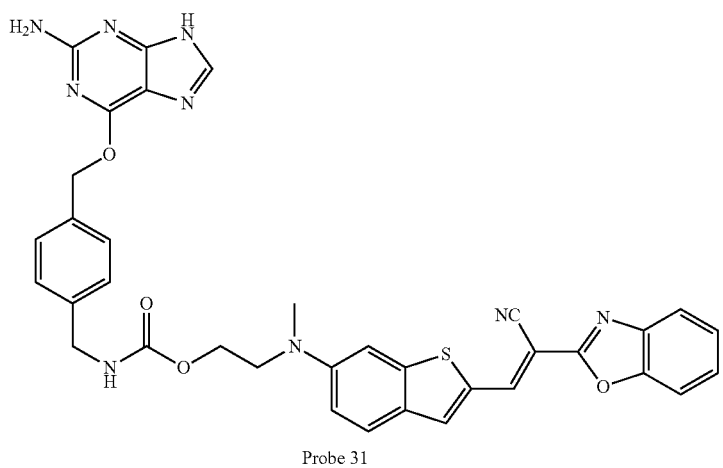

Probe 31

Compound 29

This compound was obtained by following the general procedure for compound 4, and the yield was 93%. $^1$H-NMR (400 MHz, DMSO-d$_6$): δ=8.45 (s, 1H), 8.09 (d, J=8.00 Hz, 2H), 8.07 (s, 1H), 7.94 (d, J=8.00 Hz, 2H), 7.51 (m, 1H), 7.41 (m, 1H), 6.45 (s, 1H), 3.61 (t, 3H, J=8.0 Hz), 3.34 (t, J=8.0 Hz, 3H), 3.21 (s, 3H).

Probe 31

This probe was obtained by following the general procedure for probe 1, and the yield was 71%. $^1$H-NMR (400 MHz, DMSO-d$_6$): δ=12.42 (s, 1H), 10.01 (s, 1H), 8.45 (s, 1H), 8.09 (d, J=8.00 Hz, 2H), 8.07 (s, 1H), 7.94 (d, J=8.00 Hz, 2H), 7.81 (s, 1H), 7.51 (m, 1H), 7.41 (m, 5H), 6.45 (s, 1H), 6.29 (s, 2H), 5.46 (s, 2H), 4.40 (d, 2H, J=4.8 Hz), 3.61 (t, 3H, J=8.0 Hz), 3.34 (t, J=8.0 Hz, 3H), 3.21 (s, 3H).

Example 32

A fluorescence-activated covalently labeling fluorescent probe 32 for SNAP protein tags was constructed using a molecular rotor as a viscosity-sensitive fluorescent dye.

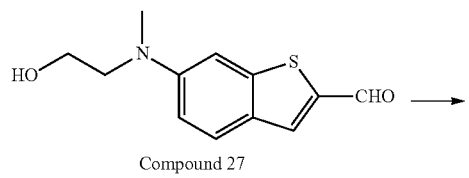

Compound 27

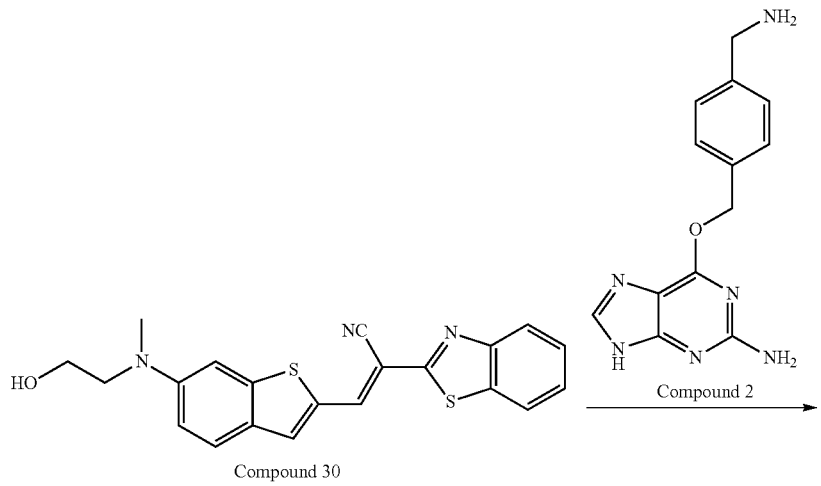

Compound 30

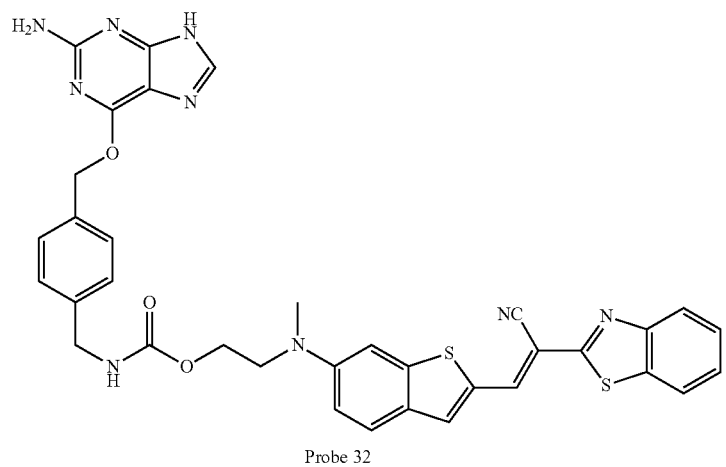

Probe 32

Compound 30

This compound was obtained by following the general procedure for compound 1, and the yield was 89%. $^1$H-NMR (400 MHz, DMSO-d$_6$): δ=8.09 (d, 1H, J=8.00 Hz), 7.94 (d, 1H, J=8.00 Hz), 7.81 (s, 1H), 7.68 (d, J=9.0 Hz, 1H), 7.51 (m, 1H), 7.41 (m, 1H), 6.92 (d, J=2.0 Hz, 1H), 6.82 (d, J=9.1, 2.3 Hz, 1H), 6.45 (s, 1H), 3.61 (t, 2H, J=8.0 Hz), 3.34 (t, 2H, J=8.0 Hz), 3.21 (s, 3H).

Probe 32

This probe was obtained by following the general procedure for probe 1, and the yield was 66%. $^1$H-NMR (400 MHz, DMSO-d$_6$): δ=12.42 (s, 1H), 10.01 (s, 1H), 8.09 (d, 1H, J=8.00 Hz), 7.94 (d, 1H, J=8.00 Hz), 7.81 (s, 2H), 7.68 (d, J=9.0 Hz, 1H), 7.51 (m, 1H), 7.41 (m, 5H), 6.92 (d, J=2.0 Hz, 1H), 6.82 (d, J=9.1, 2.3 Hz, 1H), 6.45 (s, 1H), 6.29 (s, 2H), 5.46 (s, 2H), 4.40 (d, 2H, J=4.8 Hz), 3.62 (t, 2H, J=8.0 Hz), 3.36 (t, J=8.0 Hz, 2H), 3.21 (s, 3H).

Example 33

A fluorescence-activated covalently labeling fluorescent probe 33 for SNAP protein tags was constructed using a molecular rotor as a viscosity-sensitive fluorescent dye

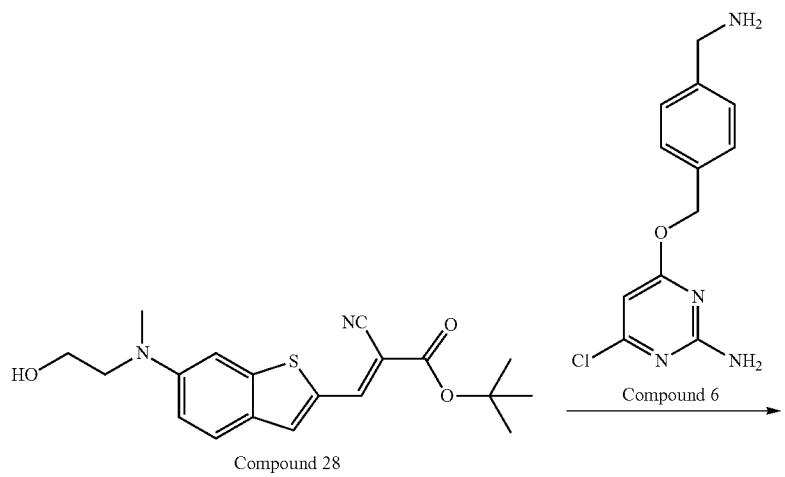
Probe 33
Probe 33
This probe was obtained by following the general procedure for probe 1, and the yield was 61%. 1H-NMR (400 MHz, CDCl₃): δ=9.99 (brs, 1H), 8.22 (s, 1H), 8.02 (s, 1H), 7.39 (d, 2H, J=8.4 Hz), 7.26 (d, 2H, J=8.4 Hz), 7.09 (s, 2H), 6.43 (s, 1H), 6.10 (s, 1H), 5.26 (s, 2H), 4.36 (s, 2H), 3.61 (t, J=8.0 Hz, 3H), 3.34 (t, J=8.0 Hz, 3H), 3.21 (s, 3H), 1.48 (s, 9H).
Example 34
A fluorescence-activated covalently labeling fluorescent probe 34 for CLIP protein tags was constructed using a molecular rotor as a viscosity-sensitive fluorescent dye.
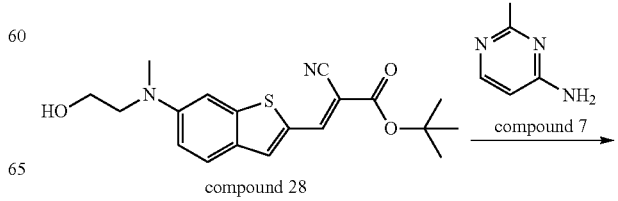

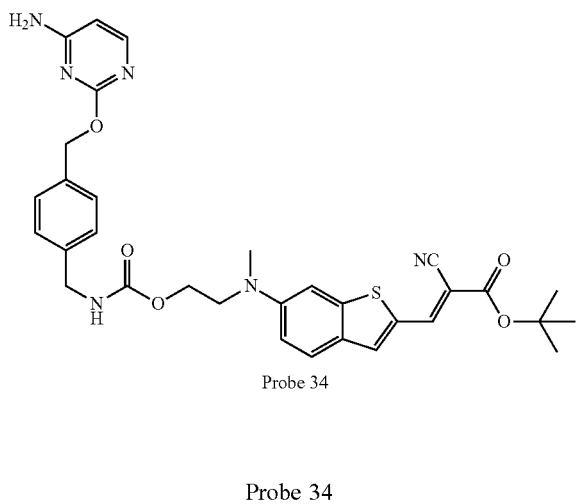

Probe 34

This probe was obtained by following the general procedure for probe 1, and the yield was 61%. ¹H-NMR (400 MHz, CDCl₃): δ=8.22 (s, 1H), 8.02 (s, 1H), 7.93 (d, 1H, J=5.6), 7.75 (s, 1H), 7.33 (d, 2H, J=8.0 Hz), 7.19 (d, 2H, J=8.0 Hz), 6.43 (s, 1H), 6.06 (d, 1H, J=5.6 Hz), 5.27 (s, 2H), 5.16 (s, 2H), 4.45 (d, 2H, J=5.6 Hz), 3.62 (t, J=8.0 Hz, 3H), 3.35 (t, J=8.0 Hz, 3H), 3.21 (s, 3H), 1.48 (s, 9H).

Example 35

A fluorescence-activated covalently labeling fluorescent probe 35 for SNAP protein tags was constructed using a molecular rotor as a viscosity-sensitive fluorescent dye.

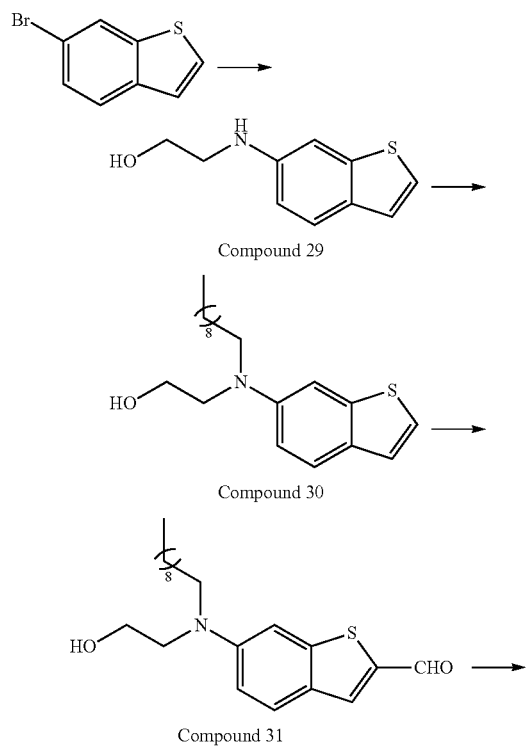

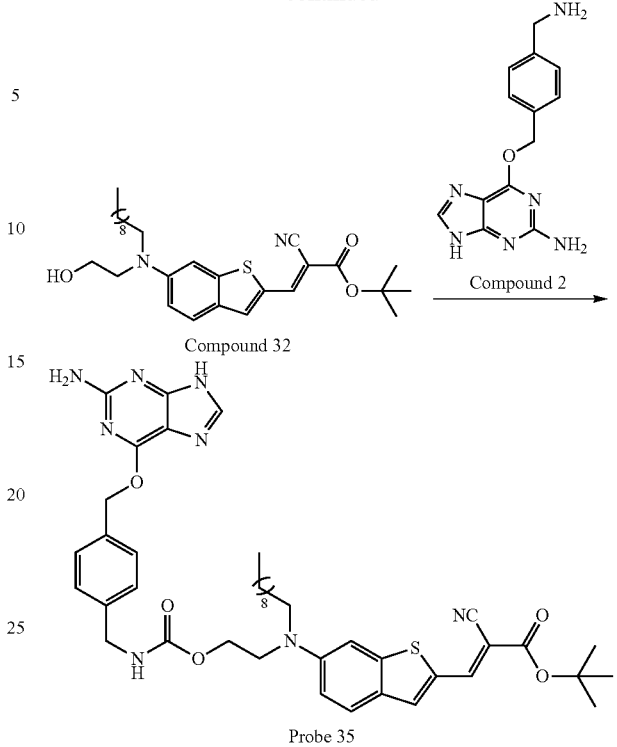

Compound 29

This compound was obtained by following the general procedure for compound 26, and the yield was 42%. ¹H-NMR (400 MHz, CDCl₃): δ=7.62 (d, 1H), 7.81 (s, 1H), 7.68 (d, 1H, J=9.0 Hz), 6.92 (d, 1H, J=2.0 Hz), 6.82 (dd, 1H, J₁=9.0 Hz, J₂=2.4 Hz), 3.62 (t, J=8.0 Hz, 3H), 3.35 (t, J=8.0 Hz, 3H).

Compound 30

Compound 29 (0.965 g, 5 mmol) was dissolved in 50 ml acetonitrile in a 100 ml round-bottom flask, and potassium carbonate (1.38 g, 10 mmol) and bromohexane (1.33 g, 6 mmol) were added. The resulting mixture was heated to reflux in an oil bath under the protection of Ar. After the reaction was completed, filtering was carried out, and the solvent was removed by rotary evaporation. The residue was dissolved in 100 ml ethyl acetate, then washed with water, saturated brine, respectively. The organic phase was dried over anhydrous sodium sulfate. The solvent was completely removed by rotary evaporation. The residue was purified by gel silica gel column chromatography to give a waxy solid 1.182 g, and the yield was 71%. ¹H-NMR (400 MHz, CDCl₃): δ=7.64 (d, 1H, J=8.8 Hz), 7.81 (s, 1H), 7.68 (d, 1H, J=9.0 Hz), 6.92 (d, 1H, J=2.0 Hz), 6.82 (m, 1H), 3.62 (t, J=8.0 Hz, 3H), 3.35 (t, J=8.0 Hz, 3H), 3.12-3.09 (t, 2H, J=7.6 Hz), 1.59-1.65 (m, 24H), 0.89 (t, 3H, J=2.0 Hz).

Compound 31

This compound was obtained by following the general procedure for compound 27, and the yield was 56%. 1H-NMR (400 MHz, CDCl3): δ=9.92 (s, 1H), 7.81 (s, 1H), 7.68 (d, 1H, J=9.0 Hz), 6.92 (d, 1H, J=2.0 Hz), 6.82 (m, 1H), 3.62 (t, J=8.0 Hz, 3H), 3.35 (t, J=8.0 Hz, 3H), 3.12-3.09 (t, 2H, J=7.6 Hz), 1.59-1.65 (m, 24H), 0.89 (t, 3H, J=2.0 Hz).

Compound 32

This compound was obtained by following the general procedure for compound 1, and the yield was 87%. $^1$H-NMR (400 MHz, CDCl$_3$): δ=8.01 (s, 1H), 7.81 (s, 1H), 7.68 (d, 1H, J=9.0 Hz), 6.92 (d, 1H, J=2.0 Hz), 6.82 (m, 1H), 3.62 (t, J=8.0 Hz, 3H), 3.35 (t, J=8.0 Hz, 3H), 3.12-3.09 (t, 2H, J=7.6 Hz), 1.59-1.65 (m, 33H), 0.89 (t, 3H, J=2.0 Hz).

Probe 35

This probe was obtained by following the general procedure for probe 1, and the yield was 60%. $^1$H-NMR (400 MHz, CDCl$_3$): δ=12.42 (s, 1H), 10.01 (s, 1H), 8.01 (s, 1H), 7.83 (s, 1H), 7.78 (s, 1H), 7.68 (d, 1H, J=9.0 Hz), 7.40 (m, 4H), 6.92 (d, 1H, J=2.0 Hz), 6.82 (m, 1H), 6.29 (s, 2H), 5.46 (s, 2H), 4.40 (d, 2H, J=4.8 Hz), 3.62 (t, J=8.0 Hz, 3H), 3.35 (t, J=8.0 Hz, 3H), 3.12-3.09 (t, 2H, J=7.6 Hz), 1.59-1.65 (m, 33H), 0.89 (t, 3H, J=2.0 Hz).

Example 36

A fluorescence-activated covalently labeling fluorescent probe 36 for SNAP protein tags was constructed using a molecular rotor as a viscosity-sensitive fluorescent dye.

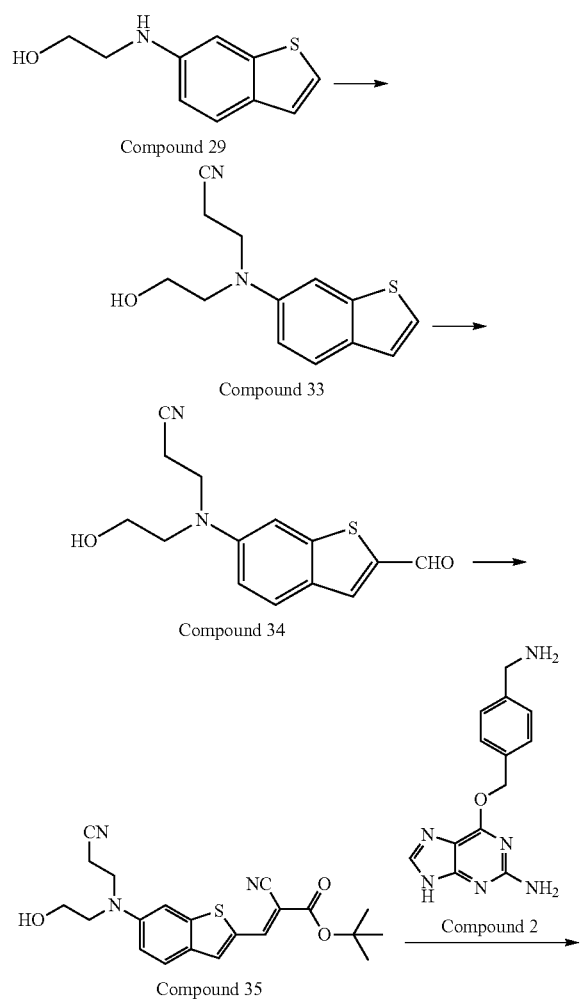

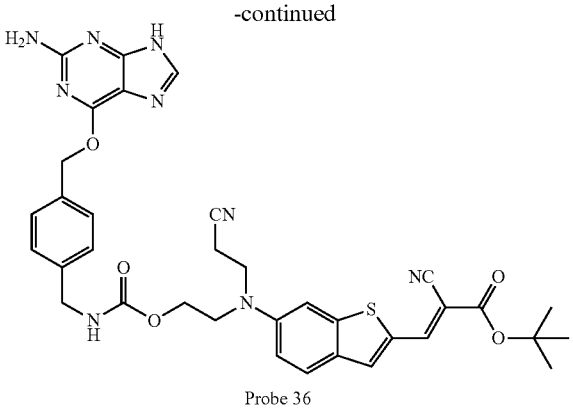

Probe 36

Compound 33

Compound 29 (0.580 g, 3 mmol) was dissolved in 60 ml of toluene in a 100 ml round-bottom flask, 1 ml of acrylonitrile and 1 ml of acetic acid were added, heated to reflux in an oil bath for 24 h under the protection of Ar. After the reaction was completed, the system was poured into 100 ml of water, the organic phase was separated, and the aqueous phase was extracted twice with 50 ml of dichloromethane. The organic phases were combined and dried over anhydrous sodium sulfate. The solvent was completely removed by rotary evaporation, and the residue was purified by gel silica gel column chromatography to give a product 0.487 g. The yield was 66%. $^1$H-NMR (400 MHz, CDCl$_3$): δ=7.62 (d, 1H), 7.81 (s, 1H), 7.68 (d, 1H, J=9.0 Hz), 6.92 (d, 1H, J=2.0 Hz), 6.82 (dd, 1H, J$_1$=9.0 Hz, J$_2$=2.4 Hz), 3.72 (t, 2H, J=6.8 Hz), 3.62 (t, J=8.0 Hz, 3H), 3.35 (t, J=8.0 Hz, 3H), 2.57 (t, 2H, J=6.8 Hz).

Compound 34

This compound was obtained by following the general procedure for compound 27, and the yield was 43%. $^1$H-NMR (400 MHz, CDCl$_3$): δ=9.97 (s, 1H), 7.60 (d, 1H), 7.80 (s, 1H), 7.68 (d, 1H, J=9.0 Hz), 6.92 (d, 1H, J=2.0 Hz), 6.82 (dd, 1H, J$_1$=9.0 Hz, J$_2$=2.4 Hz), 3.72 (t, 2H, J=6.8 Hz), 3.62 (t, J=8.0 Hz, 3H), 3.35 (t, J=8.0 Hz, 3H), 2.57 (t, 2H, J=6.8 Hz).

Compound 35

This compound was obtained by following the general procedure for compound 1, and the yield was 91%. $^1$H-NMR (400 MHz, CDCl$_3$): δ=8.00 (s, 1H), 7.60 (d, 1H), 7.80 (s, 1H), 7.68 (d, 1H, J=9.0 Hz), 6.92 (d, 1H, J=2.0 Hz), 6.82 (dd, 1H, J$_1$=9.0 Hz, J$_2$=2.4 Hz), 3.72 (t, 2H, J=6.8 Hz), 3.62 (t, J=8.0 Hz, 3H), 3.35 (t, J=8.0 Hz, 3H), 2.57 (t, 2H, J=6.8 Hz), 1.49 (s, 9H).

Probe 36

This probe was obtained by following the general procedure for probe 1, and the yield was 55%. $^1$H-NMR (400 MHz, CDCl$_3$): δ=12.42 (s, 1H), 10.01 (s, 1H), 8.00 (s, 1H), 7.81 (s, 1H), 7.68 (d, 1H, J=9.0 Hz), 7.60 (d, 1H), 7.40 (m, 4H), 6.92 (d, 1H, J=2.0 Hz), 6.82 (m, 1H), 6.29 (s, 2H), 5.46 (s, 2H), 4.40 (d, 2H, J=4.8 Hz), 3.72 (t, 2H, J=6.8 Hz), 3.62 (t, J=8.0 Hz, 3H), 3.35 (t, J=8.0 Hz, 3H), 2.57 (t, 2H, J=6.8 Hz), 1.49 (s, 9H).

Example 37

A fluorescence-activated covalently labeling fluorescent probe 37 for SNAP protein tags was constructed using a molecular rotor as a viscosity-sensitive fluorescent dye.

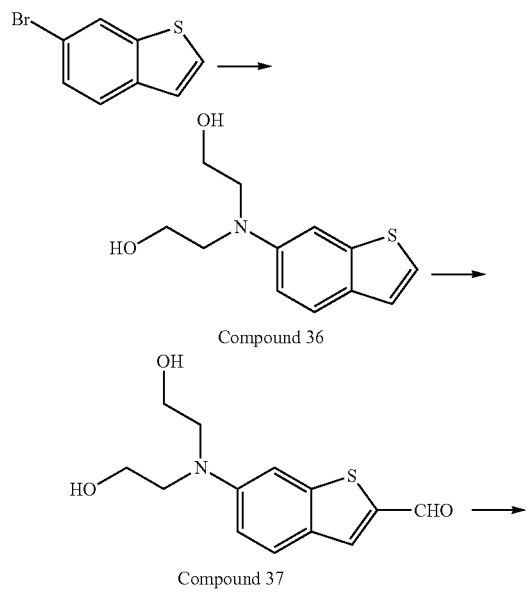

Compound 36

This compound was obtained by following the general procedure for compound 21, and the yield was 67%. $^1$H-NMR (400 MHz, CDCl$_3$): δ=7.62 (d, 1H, J=8.8 Hz), 7.15 (d, 1H, J=5.6 Hz), 7.08-7.01 (m, 2H), 6.81 (d, 1H, J=2.4 Hz), 3.62 (t, 4H, J=8.0 Hz), 3.35 (t, 4H, J=8.0 Hz).

Compound 37

This compound was obtained by following the general procedure for compound 27, and the yield was 67%. $^1$H-NMR (400 MHz, CDCl$_3$): δ=9.99 (s, 1H), 7.81 (s, 1H), 7.68 (d, 1H, J=9.0 Hz), 6.92 (d, 1H, J=2.0 Hz), 6.81 (m, 1H), 3.62 (t, 4H, J=8.0 Hz), 3.35 (t, 4H, J=8.0 Hz).

Compound 38

This compound was obtained by following the general procedure for compound 1, and the yield was 96%. $^1$H-NMR (400 MHz, CDCl$_3$): δ=8.00 (s, 1H), 7.83 (s, 1H), 7.69 (d, 1H, J=9.0 Hz), 6.92 (d, 1H, J=2.0 Hz), 6.81 (m, 1H), 3.62 (t, 4H, J=8.0 Hz), 3.35 (t, 4H, J=8.0 Hz), 1.49 (s, 9H).

Probe 37

This probe was obtained by following the general procedure for probe 1, and the yield was 44%. $^1$H-NMR (400 MHz, CDCl$_3$): δ=12.42 (s, 1H), 9.99 (s, 1H), 8.00 (s, 1H), 7.83 (s, 1H), 7.81 (s, 1H), 7.69 (d, 1H, J=9.0 Hz), 7.40 (m, 4H), 6.92 (d, 1H, J=2.0 Hz), 6.81 (m, 1H), 6.29 (s, 2H), 5.46 (s, 2H), 4.40 (d, 2H, J=4.8 Hz), 3.62 (t, 4H, J=8.0 Hz), 3.35 (t, 4H, J=8.0 Hz), 1.49 (s, 9H).

Example 38

A fluorescence-activated covalently labeling fluorescent probe 38 for SNAP protein tags was constructed using a molecular rotor as a viscosity-sensitive fluorescent dye.

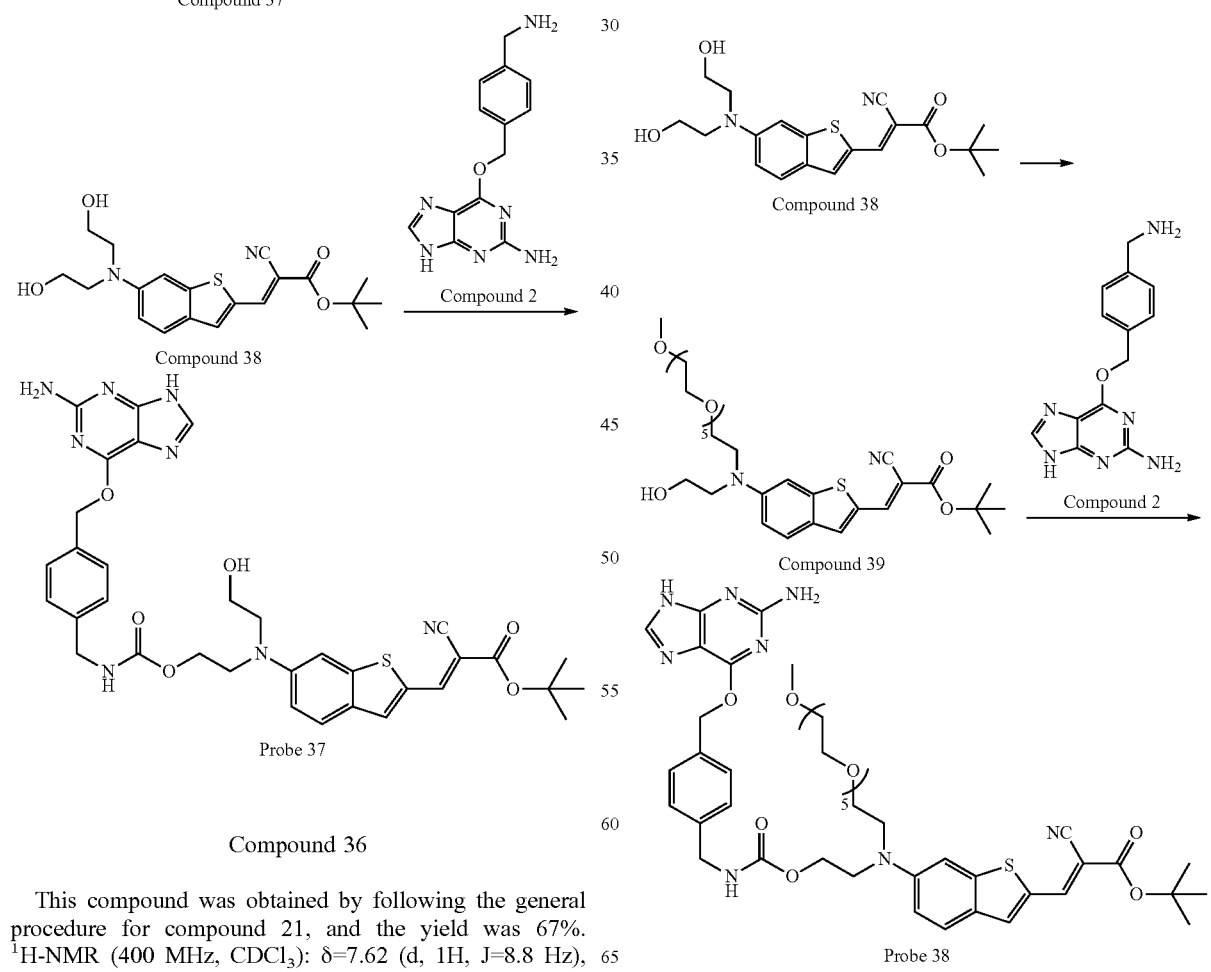

Compound 39

This compound was obtained by following the general procedure for compound 10, and the yield was 45%. ¹H-NMR (400 MHz, CDCl₃): δ=8.00 (s, 1H), 7.83 (s, 1H), 7.69 (d, 1H, J=9.0 Hz), 6.92 (d, 1H, J=2.0 Hz), 6.81 (m, 1H), 3.56-3.68 (m, 24H), 3.38 (s, 3H), 1.49 (s, 9H).

Probe 38

This probe was obtained by following the general procedure for probe 1, and the yield was 67%. ¹H-NMR (400 MHz, CDCl₃): δ=12.42 (s, 1H), 10.01 (s, 1H), 8.00 (s, 1H), 7.83 (s, 1H), 7.81 (s, 1H), 7.69 (d, 1H, J=9.0 Hz), 7.40 (m, 4H), 6.92 (d, 1H, J=2.0 Hz), 6.81 (m, 1H), 6.29 (s, 2H), 5.46 (s, 2H), 4.40 (d, 2H, J=4.8 Hz), 3.56-3.68 (m, 24H), 3.38 (s, 3H), 1.49 (s, 9H).

Example 39

A fluorescence-activated covalently labeling fluorescent probe 39 for SNAP protein tags was constructed using a molecular rotor as a viscosity-sensitive fluorescent dye.

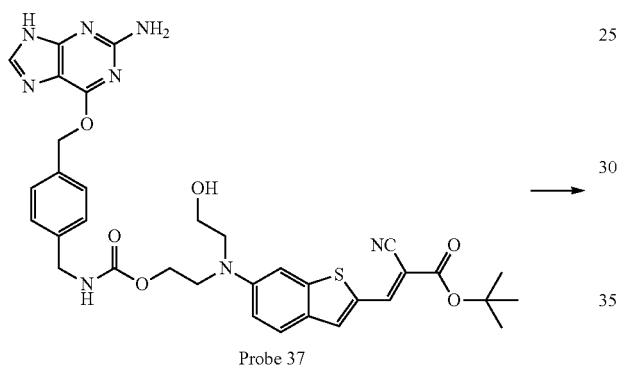

Probe 37

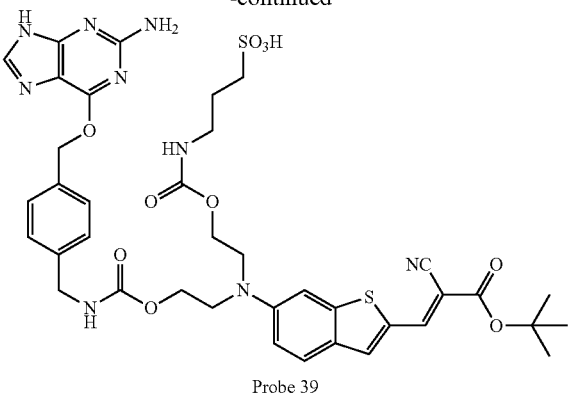

Probe 39

Probe 39

This probe was obtained by following the general procedure for probe 11, and the yield was 65%. ¹H-NMR (400 MHz, CDCl₃): δ=12.42 (s, 1H), 9.99 (s, 1H), 8.00 (s, 1H), 7.83 (s, 1H), 7.81 (s, 1H), 7.69 (d, 1H, J=9.0 Hz), 7.40 (m, 4H), 6.92 (d, 1H, J=2.0 Hz), 6.81 (m, 1H), 6.29 (s, 2H), 5.46 (s, 2H), 4.40 (d, 2H, J=4.8 Hz), 3.62 (t, 4H, J=8.0 Hz), 3.35 (t, 4H, J=8.0 Hz), 3.21 (t, 2H, 5.6 Hz), 2.71 (t, 2H, 5.6 Hz), 2.31 (m, 2H), 1.49 (s, 9H).

Example 40

A fluorescence-activated covalently labeling fluorescent probe 40 for SNAP protein tags was constructed using a molecular rotor as a viscosity-sensitive fluorescent dye.

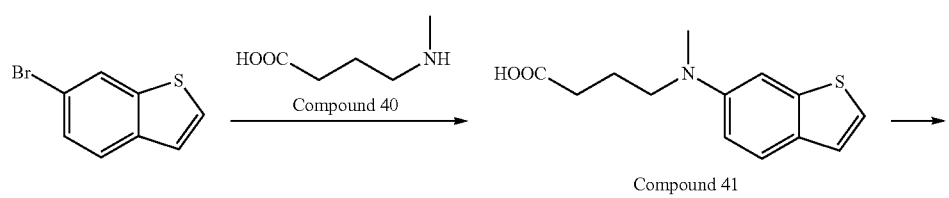

Compound 41

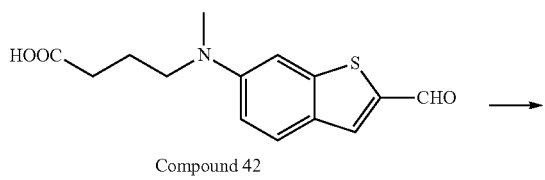

Compound 42

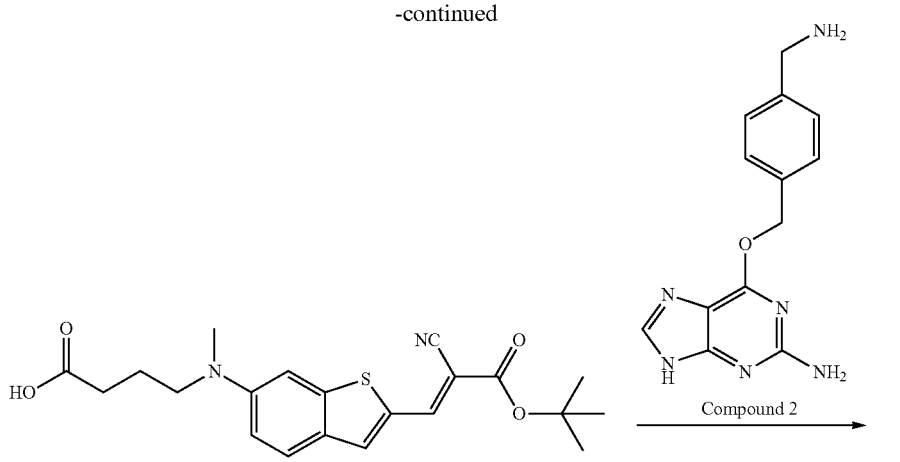

Compound 2

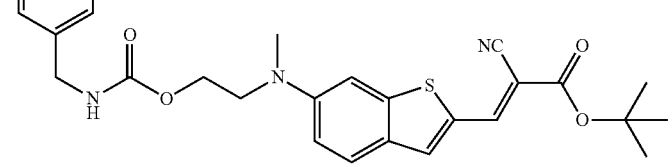

Probe 40

Compound 41

This compound was obtained by following the general procedure for compound 27, and the yield was 68%. $^1$H-NMR (400 MHz, CDCl$_3$): δ=7.62 (d, 1H), 7.81 (s, 1H), 7.68 (d, 1H, J=9.0 Hz), 6.92 (d, 1H, J=2.0 Hz), 6.82 (dd, 1H, J$_1$=9.0 Hz, J$_2$=2.4 Hz), 3.55 (t, 2H, J=7.6 Hz), 3.35 (t, 2H, J=6.8 Hz), 3.13 (s, 3H), 1.24 (m, 2H).

Probe 40

This probe was obtained by following the general procedure for probe 13, and the yield was 88%. $^1$H-NMR (400 MHz, CDCl$_3$): δ=12.42 (s, 1H), 10.01 (s, 1H), 7.81 (s, 1H), 7.82 (s, 1H), 7.81 (s, 1H), 7.68 (d, 1H, J=9.0 Hz), 7.40 (m, 4H), 6.92 (d, 1H, J=2.0 Hz), 6.82 (m, 1H), 6.29 (s, 2H), 5.46 (s, 2H), 4.40 (d, 2H, J=4.8 Hz), 3.55 (t, 2H, J=7.6 Hz), 3.35 (t, 2H, J=6.8 Hz), 3.13 (s, 3H), 1.24 (m, 2H).

Example 41

A fluorescence-activated covalently labeling fluorescent probe 41 for SNAP protein tags was constructed using a molecular rotor as a viscosity-sensitive fluorescent dye.

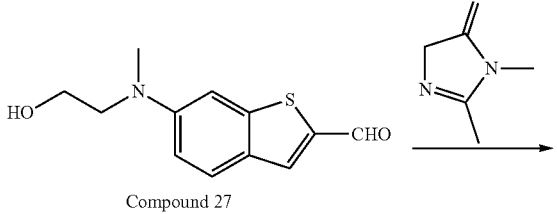

Compound 27

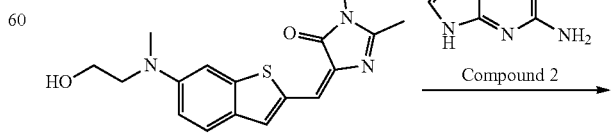

Compound 44     Compound 2

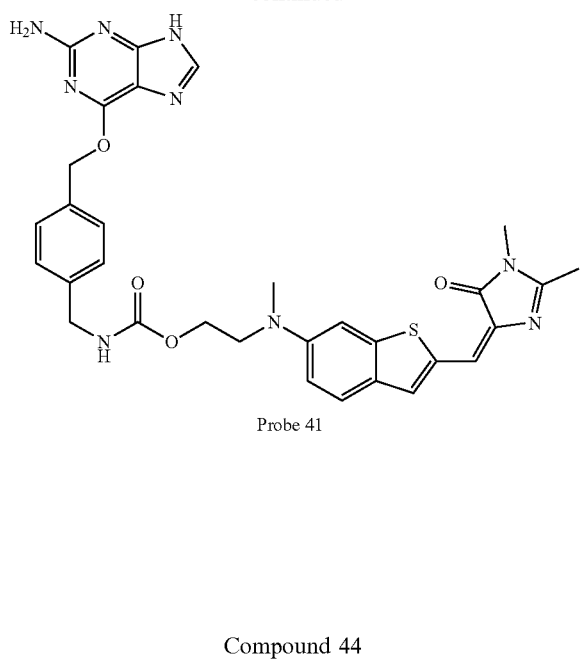

Compound 44

This compound was obtained by following the general procedure for compound 14, and the yield was 91%. ¹H-NMR (400 MHz, CDCl₃): δ=8.22 (s, 1H), 8.02 (s, 1H), 6.43 (s, 1H), 3.61 (t, J=8.0 Hz, 3H), 3.34 (t, J=8.0 Hz, 3H), 3.11 (s, 3H), 3.00 (s, 3H), 2.15 (t, 3H, J=2.4 Hz), 1.48 (s, 9H).

Probe 41

This probe was obtained by following the general procedure for probe 1, and the yield was 55%. ¹H-NMR (400 MHz, CDCl₃): δ=12.42 (s, 1H), 10.01 (s, 1H), 8.22 (s, 1H), 8.02 (s, 1H), 7.81 (s, 1H), 7.40 (m, 4H), 6.43 (s, 1H), 6.29 (s, 2H), 5.46 (s, 2H), 4.40 (d, 2H, J=4.8 Hz), 3.61 (t, J=8.0 Hz, 3H), 3.34 (t, J=8.0 Hz, 3H), 3.11 (s, 3H), 3.00 (s, 3H), 2.15 (t, 3H, J=2.4 Hz), 1.48 (s, 9H).

Example 42

A fluorescence-activated covalently labeling fluorescent probe 42 for SNAP protein tags was constructed using a molecular rotor as a viscosity-sensitive fluorescent dye.

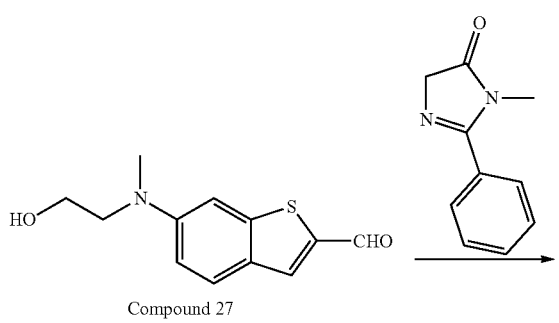

Compound 27

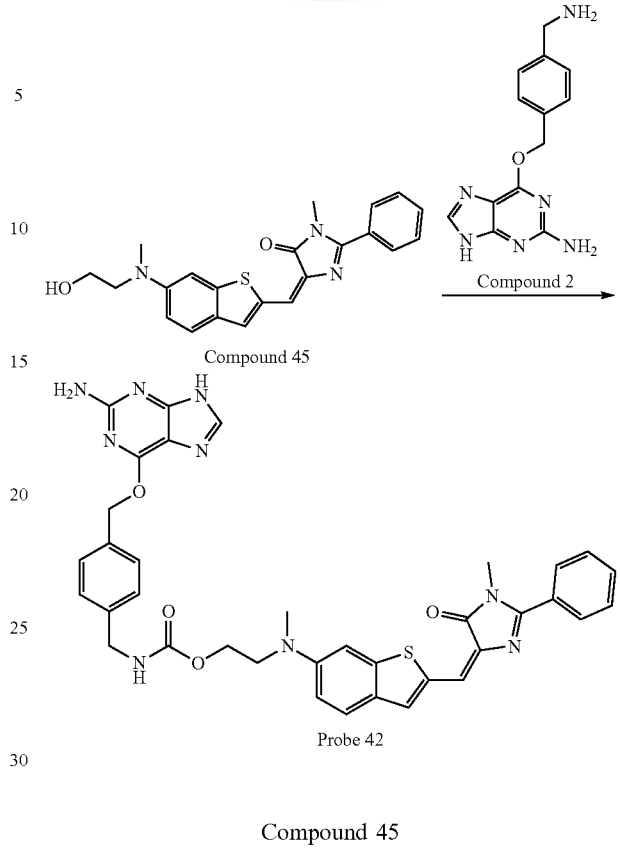

Compound 45

This compound was obtained by following the general procedure for compound 1, and the yield was 93%. ¹H-NMR (400 MHz, CDCl₃): δ=8.22 (s, 1H), 8.02 (s, 1H), 7.63-7.68 (m, 5H), 6.43 (s, 1H), 3.61 (t, 2H, J=8.0 Hz), 3.34 (t, 2H, J=8.0 Hz), 3.15 (s, 3H), 3.11 (s, 3H).

Probe 42

This probe was obtained by following the general procedure for probe 1, and the yield was 56%. ¹H-NMR (400 MHz, CDCl₃): δ=12.42 (s, 1H), 10.01 (s, 1H), 8.22 (s, 1H), 8.02 (s, 1H), 7.81 (s, 1H), 7.63-7.68 (m, 5H), 6.43 (s, 1H), 7.40 (m, 4H), 6.29 (s, 2H), 5.46 (s, 2H), 4.40 (d, 2H, J=4.8 Hz), 3.61 (t, J=8.0 Hz, 3H), 3.34 (t, J=8.0 Hz, 3H), 3.15 (s, 3H), 3.11 (s, 3H).

Example 43

A fluorescence-activated covalently labeling fluorescent probe 43 for SNAP protein tags was constructed using a molecular rotor as a viscosity-sensitive fluorescent dye.

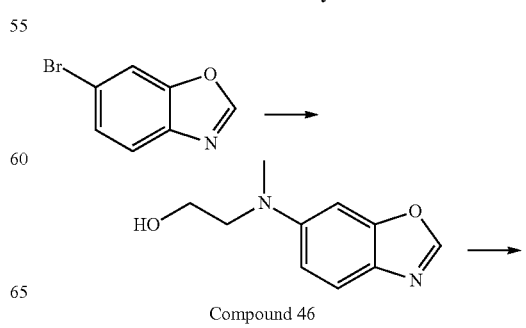

Compound 46

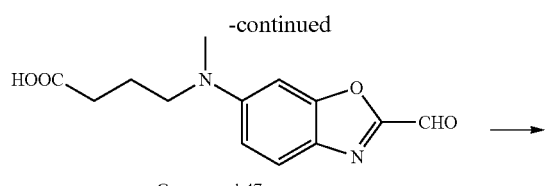

Compound 47

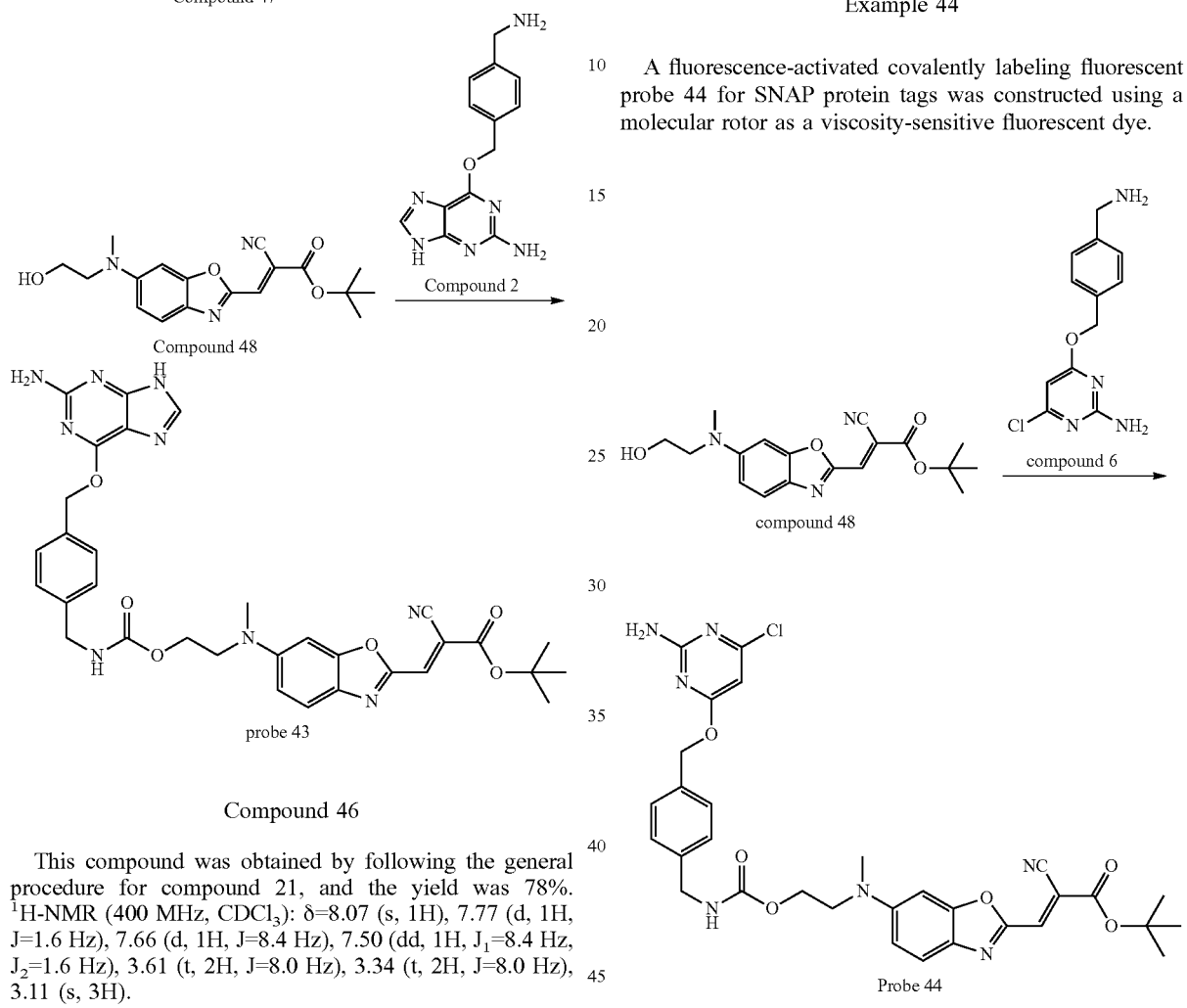

Compound 46

This compound was obtained by following the general procedure for compound 21, and the yield was 78%. ¹H-NMR (400 MHz, CDCl₃): δ=8.07 (s, 1H), 7.77 (d, 1H, J=1.6 Hz), 7.66 (d, 1H, J=8.4 Hz), 7.50 (dd, 1H, J₁=8.4 Hz, J₂=1.6 Hz), 3.61 (t, 2H, J=8.0 Hz), 3.34 (t, 2H, J=8.0 Hz), 3.11 (s, 3H).

Compound 47

This compound was obtained by following the general procedure for compound 22, and the yield was 81%. ¹H-NMR (400 MHz, CDCl₃): δ=9.99 (s, 1H), 7.61 (d, 1H, J=1.6 Hz), 7.49 (d, 1H, J=8.4 Hz), 7.40 (dd, 1H, J₁=8.4 Hz, J₂=1.6 Hz), 3.61 (t, 2H, J=8.0 Hz), 3.34 (t, 2H, J=8.0 Hz), 3.11 (s, 3H).

Compound 48

This compound was obtained by following the general procedure for compound 1, and the yield was 98%. ¹H-NMR (400 MHz, CDCl₃): δ=8.01 (s, 1H), 7.61 (d, 1H, J=1.6 Hz), 7.49 (d, 1H, J=8.4 Hz), 7.40 (dd, 1H, J₁=8.4 Hz, J₂=1.6 Hz), 3.61 (t, 2H, J=8.0 Hz), 3.34 (t, 2H, J=8.0 Hz), 3.11 (s, 3H), 1.50 (s, 9H).

Probe 43

This probe was obtained by following the general procedure for probe 1, and the yield was 66%. ¹H-NMR (400 MHz, CDCl₃): δ=12.42 (s, 1H), 10.01 (s, 1H), 8.01 (s, 1H), 7.81 (s, 1H), 7.61 (d, 1H, J=1.6 Hz), 7.49 (d, 1H, J=8.4 Hz), 7.40 (m, 5H), 6.29 (s, 2H), 5.46 (s, 2H), 4.40 (d, 2H, J=4.8 Hz), 3.61 (t, 2H, J=8.0 Hz), 3.34 (t, 2H, J=8.0 Hz), 3.11 (s, 3H), 1.50 (s, 9H).

Example 44

A fluorescence-activated covalently labeling fluorescent probe 44 for SNAP protein tags was constructed using a molecular rotor as a viscosity-sensitive fluorescent dye.

Probe 44

This probe was obtained by following the general procedure for probe 1, and the yield was 61%. ¹H-NMR (400 MHz, CDCl₃): δ=9.99 (brs, 1H), 8.01 (s, 1H), 7.61 (d, 1H, J=1.6 Hz), 7.49 (d, 1H, J=8.4 Hz), 7.40 (m, 1H), 7.33 (d, 2H, J=8.4 Hz), 7.26 (d, 2H, J=8.4 Hz), 7.09 (s, 2H), 6.10 (s, 1H), 5.26 (s, 2H), 4.36 (s, 2H), 3.61 (t, 2H, J=8.0 Hz), 3.34 (t, 2H, J=8.0 Hz), 3.11 (s, 3H), 1.50 (s, 9H).

Example 45

A fluorescence-activated covalently labeling fluorescent probe 45 for CLIP protein tags was constructed using a molecular rotor as a viscosity-sensitive fluorescent dye.

135

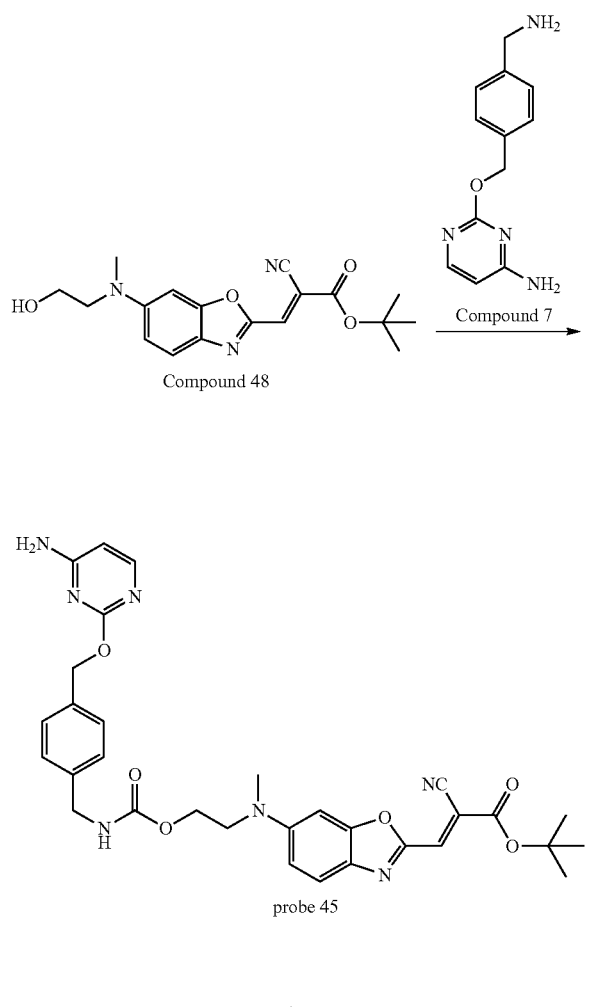 [SMILES: CN(CCO)c1ccc2nc(/C=C(\C#N)C(=O)OC(C)(C)C)oc2c1 ; NCc1ccc(COc2nccc(N)n2)cc1 ; CN(CCOC(=O)NCc1ccc(COc2nccc(N)n2)cc1)c1ccc2nc(/C=C(\C#N)C(=O)OC(C)(C)C)oc2c1]

Probe 45

This probe was obtained by following the general procedure for probe 1, and the yield was 67%. $^1$H-NMR (400 MHz, CDCl$_3$): δ=8.01 (s, 1H), 7.89 (d, 1H, J=5.6), 7.75 (s, 1H), 7.61 (d, 1H, J=1.6 Hz), 7.49 (d, 1H, J=8.4 Hz), 7.40 (dd, 1H, J$_1$=8.4 Hz, J$_2$=1.6 Hz), 7.33 (d, 2H, J=8.0 Hz), 7.19 (d, 2H, J=8.0 Hz), 6.06 (d, 1H, J=5.6 Hz), 5.27 (s, 2H), 5.16 (s, 2H), 4.45 (d, 2H, J=5.6 Hz), 3.61 (t, 2H, J=8.0 Hz), 3.34 (t, 2H, J=8.0 Hz), 3.11 (s, 3H), 1.50 (s, 9H).

Example 46

A fluorescence-activated covalently labeling fluorescent probe 46 for SNAP protein tags was constructed using a molecular rotor as a viscosity-sensitive fluorescent dye.

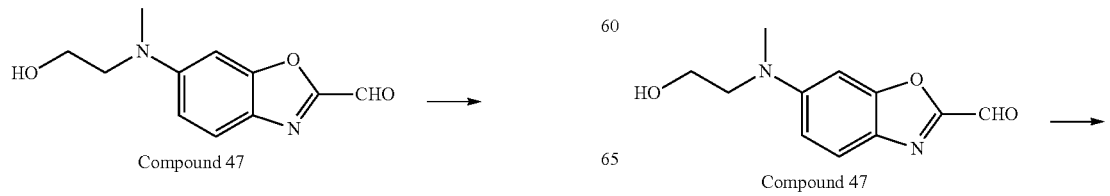

Compound 47

136

-continued

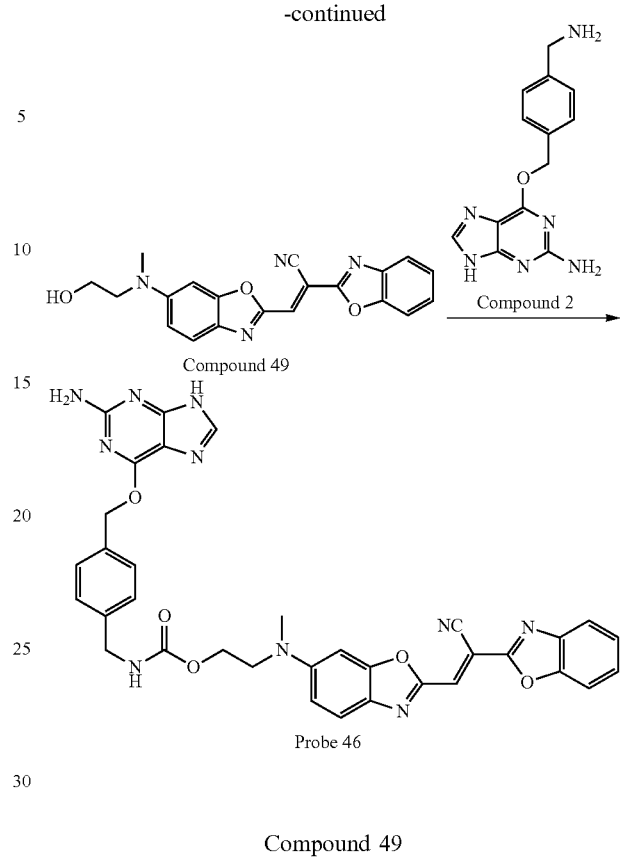

Probe 46

Compound 49

This compound was obtained by following the general procedure for compound 1, and the yield was 97%. $^1$H-NMR (400 MHz, CDCl$_3$): δ=7.99 (s, 1H), 7.61 (d, 1H, J=1.6 Hz), 7.74 (d, 1H, J=4.0 Hz), 7.55 (d, 1H, J=4.0 Hz), 7.49 (d, 1H, J=8.4 Hz), 7.36-7.42 (m, 3H), 3.61 (t, 2H, J=8.0 Hz), 3.34 (t, 2H, J=8.0 Hz), 3.11 (s, 3H).

Probe 46

This probe was obtained by following the general procedure for probe 1, and the yield was 65%. $^1$H-NMR (400 MHz, CDCl$_3$): δ=12.32 (s, 1H), 10.01 (s, 1H), 7.99 (s, 1H), 7.81 (s, 1H), 7.61 (d, 1H, J=1.6 Hz), 7.74 (d, 1H, J=4.0 Hz), 7.55 (d, 1H, J=4.0 Hz), 7.49 (d, 1H, J=8.4 Hz), 7.32-7.37 (m, 3H), 7.40 (m, 4H), 6.29 (s, 2H), 5.46 (s, 2H), 4.40 (d, 2H, J=4.8 Hz), 3.61 (t, 2H, J=8.0 Hz), 3.34 (t, 2H, J=8.0 Hz), 3.11 (s, 3H).

Example 47

A fluorescence-activated covalently labeling fluorescent probe 47 for SNAP protein tags was constructed using a molecular rotor as a viscosity-sensitive fluorescent dye.

Compound 47

-continued

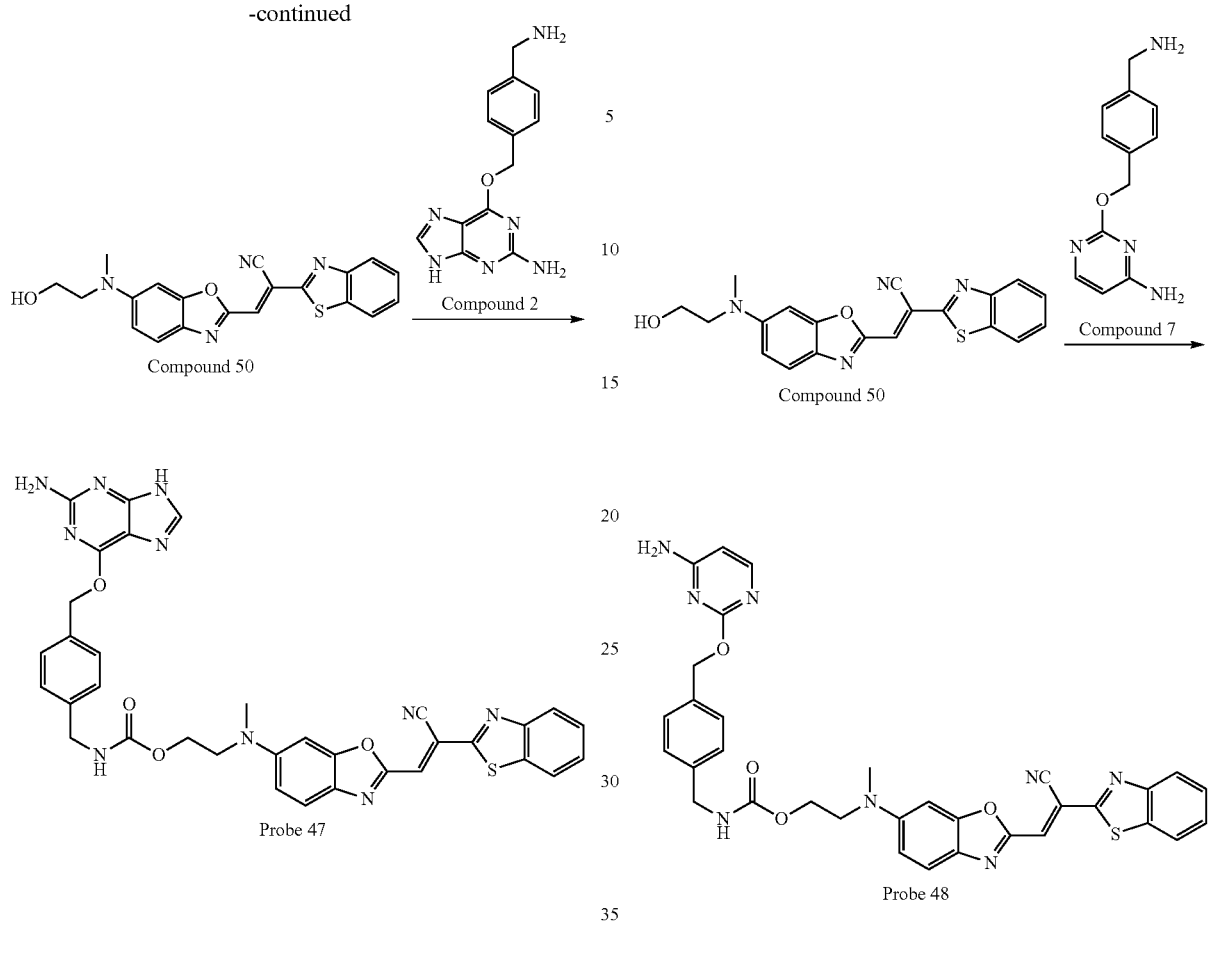

Compound 50

This compound was obtained by following the general procedure for compound 1, and the yield was 97%. $^1$H-NMR (400 MHz, CDCl$_3$): δ=8.04 (d, 1H, J=8.0 Hz), 7.90 (d, 1H, J=8.0 Hz), 7.99 (s, 1H), 7.61 (d, 1H, J=1.6 Hz), 7.53 (t, 1H, J=8.0 Hz), 7.49 (d, 1H, J=8.4 Hz), 7.45 (t, 1H, J=8.0 Hz), 7.40 (dd, 1H, J$_1$=8.4 Hz, J$_2$=1.6 Hz), 3.61 (t, 2H, J=8.0 Hz), 3.34 (t, 2H, J=8.0 Hz), 3.11 (s, 3H).

Probe 47

This probe was obtained by following the general procedure for probe 1, and the yield was 61%. $^1$H-NMR (400 MHz, CDCl$_3$): δ=12.42 (s, 1H), 10.01 (s, 1H), 8.04 (d, 1H, J=8.0 Hz), 7.90 (d, 1H, J=8.0 Hz), 7.99 (s, 1H), 7.81 (s, 1H), 7.61 (d, 1H, J=1.6 Hz), 7.53 (t, 1H, J=8.0 Hz), 7.49 (d, 1H, J=8.4 Hz), 7.45 (t, 1H, J=8.0 Hz), 7.40 (m, 5H), 6.29 (s, 2H), 5.46 (s, 2H), 4.40 (d, 2H, J=4.8 Hz), 3.61 (t, 2H, J=8.0 Hz), 3.34 (t, 2H, J=8.0 Hz), 3.11 (s, 3H).

Example 48

A fluorescence-activated covalently labeling fluorescent probe 48 for CLIP protein tags was constructed using a molecular rotor as a viscosity-sensitive fluorescent dye.

Probe 48

This probe was obtained by following the general procedure for probe 1, and the yield was 97%. $^1$H-NMR (400 MHz, CDCl$_3$): δ=8.04 (d, 1H, J=8.0 Hz), 7.93 (d, 1H, J=5.6), 7.90 (d, 1H, J=8.0 Hz), 7.99 (s, 1H), 7.75 (s, 1H), 7.61 (d, 1H, J=1.6 Hz), 7.53 (t, 1H, J=8.0 Hz), 7.49 (d, 1H, J=8.4 Hz), 7.45 (t, 1H, J=8.0 Hz), 7.40 (dd, 1H, J$_1$=8.4 Hz, J$_2$=1.6 Hz), 7.33 (d, 2H, J=8.0 Hz), 7.19 (d, 2H, J=8.0 Hz), 6.06 (d, 1H, J=5.6 Hz), 5.27 (s, 2H), 5.16 (s, 2H), 4.45 (d, 2H, J=5.6 Hz), 3.61 (t, 2H, J=8.0 Hz), 3.34 (t, 2H, J=8.0 Hz), 3.11 (s, 3H).

Example 49

A fluorescence-activated covalently labeling fluorescent probe 49 for SNAP protein tags was constructed using a molecular rotor as a viscosity-sensitive fluorescent dye.

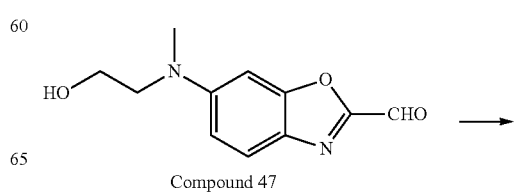

Compound 47

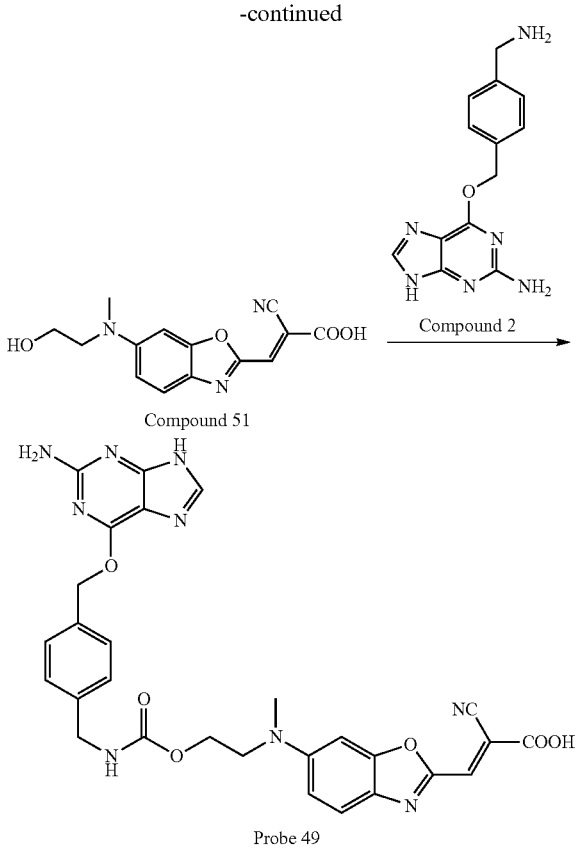

Compound 51

This compound was obtained by following the general procedure for compound 1, and the yield was 87%. $^1$H-NMR (400 MHz, CDCl$_3$): δ=7.99 (s, 1H), 7.61 (d, 1H, J=1.6 Hz), 7.49 (d, 1H, J=8.4 Hz), 7.40 (dd, 1H, J$_1$=8.4 Hz, J$_2$=1.6 Hz), 3.61 (t, 2H, J=8.0 Hz), 3.34 (t, 2H, J=8.0 Hz), 3.11 (s, 3H).

Probe 49

This probe was obtained by following the general procedure for probe 1, and the yield was 31%. $^1$H-NMR (400 MHz, DMSO-d$_6$): δ=12.32 (s, 1H), 10.05 (s, 1H), 8.01 (s, 1H), 7.81 (s, 1H), 7.61 (d, 1H, J=1.6 Hz), 7.49 (d, 1H, J=8.4 Hz), 7.40 (m, 5H), 6.29 (s, 2H), 5.46 (s, 2H), 4.40 (d, 2H, J=4.8 Hz), 3.61 (t, 2H, J=8.0 Hz), 3.34 (t, 2H, J=8.0 Hz), 3.11 (s, 3H).

Example 50

A fluorescence-activated covalently labeling fluorescent probe 50 for SNAP protein tags was constructed using a molecular rotor as a viscosity-sensitive fluorescent dye.

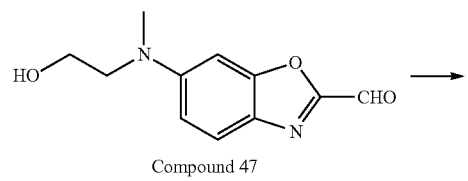

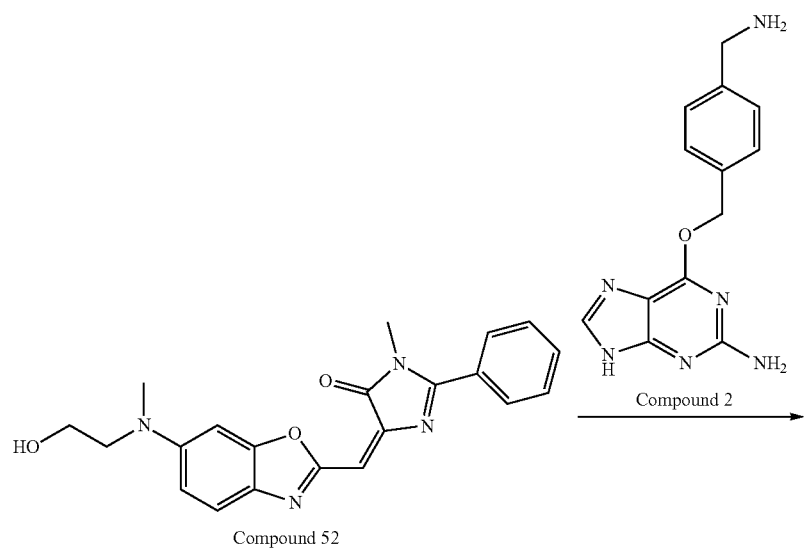

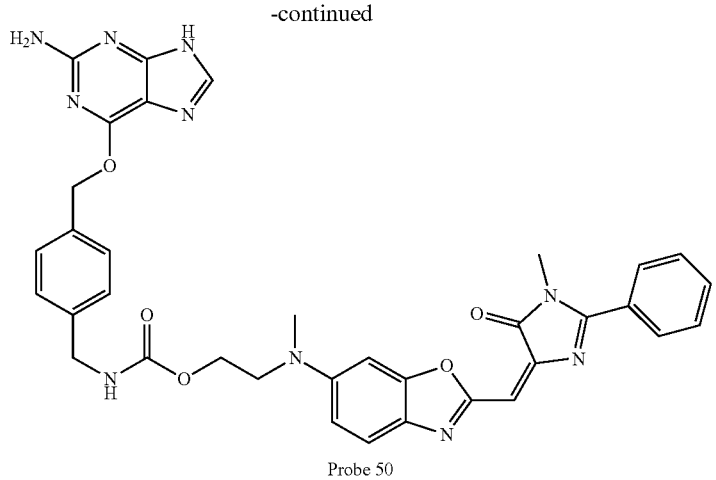

Probe 50

Compound 52

This compound was obtained by following the general procedure for compound 1, and the yield was 91%. $^1$H-NMR (400 MHz, CDCl$_3$): δ=7.98 (s, 1H), 7.64-7.48 (m, 7H), 7.40 (dd, 1H, J$_1$=8.4 Hz, J$_2$=1.6 Hz), 3.61 (t, 2H, J=8.0 Hz), 3.34 (t, 2H, J=8.0 Hz), 3.13 (s, 3H), 3.11 (s, 3H).

Probe 50

This probe was obtained by following the general procedure for probe 1, and the yield was 67%. $^1$H-NMR (400 MHz, CDCl$_3$): δ=12.42 (s, 1H), 10.01 (s, 1H), 7.98 (s, 1H), 7.81 (s, 1H), 7.64-7.48 (m, 7H), 7.40 (m, 5H), 6.29 (s, 2H), 5.46 (s, 2H), 4.40 (d, 2H, J=4.8 Hz), 3.61 (t, 2H, J=8.0 Hz), 3.34 (t, 2H, J=8.0 Hz), 3.13 (s, 3H), 3.11 (s, 3H).

Example 51

A fluorescence-activated covalently labeling fluorescent probe 51 for SNAP protein tags was constructed using a molecular rotor as a viscosity-sensitive fluorescent dye.

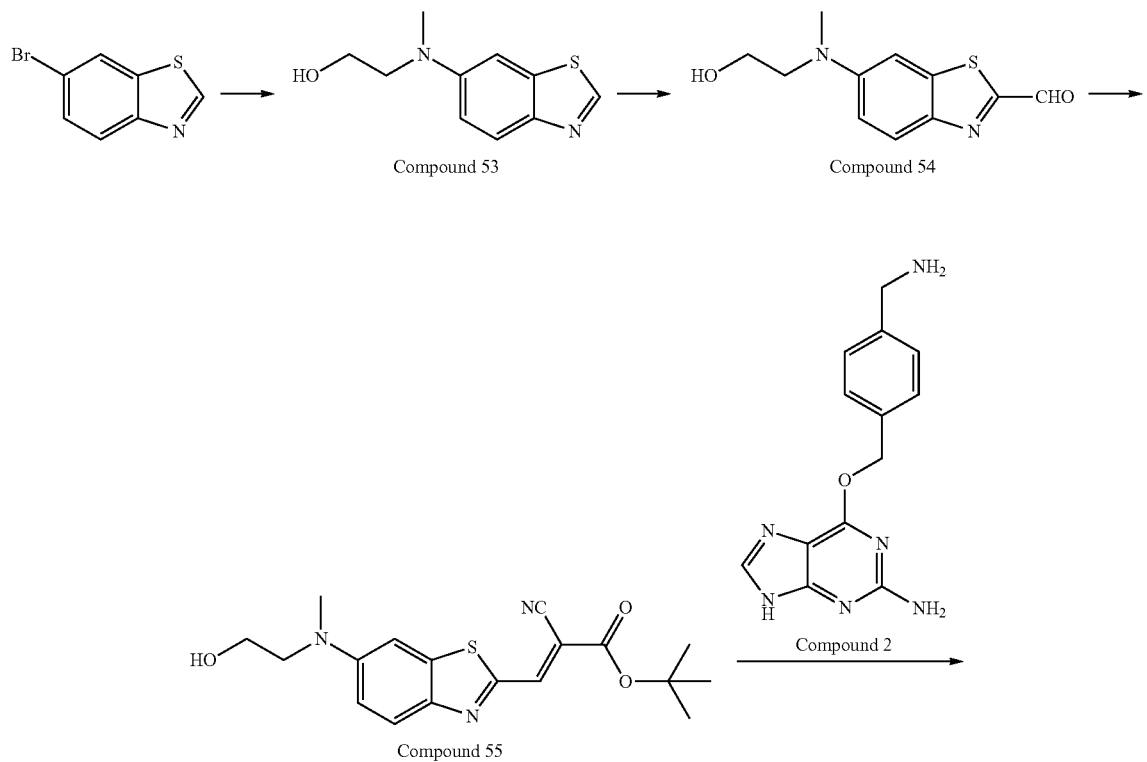

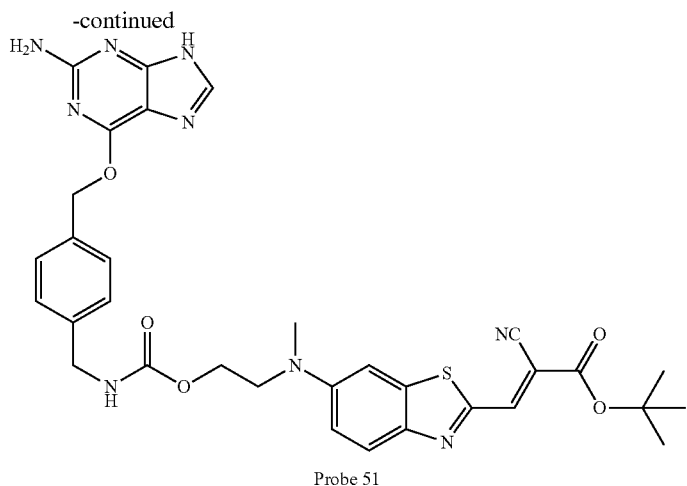

Probe 51

Compound 53

This compound was obtained by following the general procedure for compound 21, and the yield was 81%. $^1$H-NMR (400 MHz, CDCl$_3$): δ=8.67 (s, 1H), 7.95 (d, 1H, J=10.0 Hz), 7.15 (d, 1H, J=2.4 Hz), 7.00 (dd, 1H, J$_1$=8.8 Hz, J$_2$=2.4 Hz), 3.61 (t, 2H, J=8.0 Hz), 3.34 (t, 2H, J=8.0 Hz), 3.10 (s, 3H).

Compound 54

This compound was obtained by following the general procedure for compound 22, the yield was 56%. $^1$H-NMR (400 MHz, CDCl$_3$): δ=10.06 (s, 1H), 8.03 (d, 1H, J=10.0 Hz), 7.07-7.04 (m, 2H), 3.61 (t, 2H, J=8.0 Hz), 3.34 (t, 2H, J=8.0 Hz), 3.10 (s, 3H).

Compound 55

This compound was obtained by following the general procedure for compound 1, and the yield was 96%. $^1$H-NMR (400 MHz, CDCl$_3$): δ=8.03 (d, 1H, J=10.0 Hz), 7.95 (s, 1H), 7.07-7.04 (m, 2H), 3.61 (t, 2H, J=8.0 Hz), 3.34 (t, 2H, J=8.0 Hz), 3.10 (s, 3H), 1.50 (s, 9H).

Probe 51

This probe was obtained by following the general procedure for probe 1, and the yield was 61%. $^1$H-NMR (400 MHz, DMSO-d$_6$): δ=12.42 (s, 1H), 10.01 (s, 1H), 8.03 (d, 1H, J=10.0 Hz), 7.95 (s, 1H), 7.81 (s, 1H), 7.40 (m, 4H), 7.07-7.04 (m, 2H), 6.29 (s, 2H), 5.46 (s, 2H), 4.40 (d, 2H, J=4.8 Hz), 3.61 (t, 2H, J=8.0 Hz), 3.34 (t, 2H, J=8.0 Hz), 3.10 (s, 3H), 1.50 (s, 9H).

Example 52

A fluorescence-activated covalently labeling fluorescent probe 52 for SNAP protein tags was constructed using a molecular rotor as a viscosity-sensitive fluorescent dye.

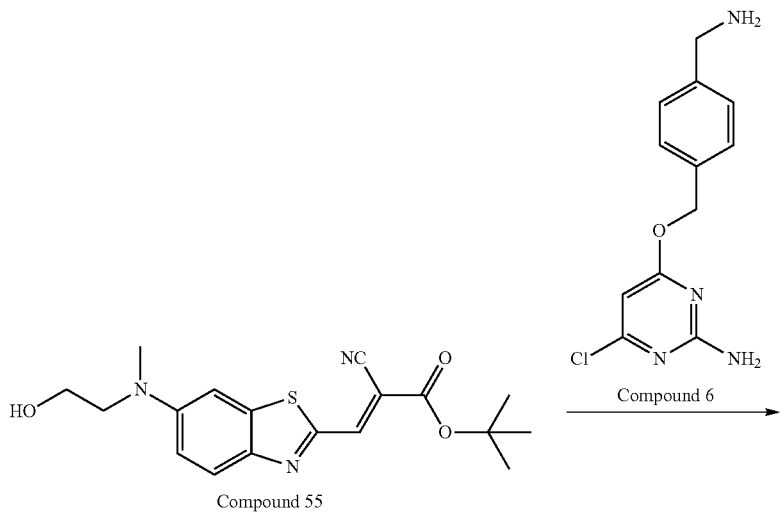

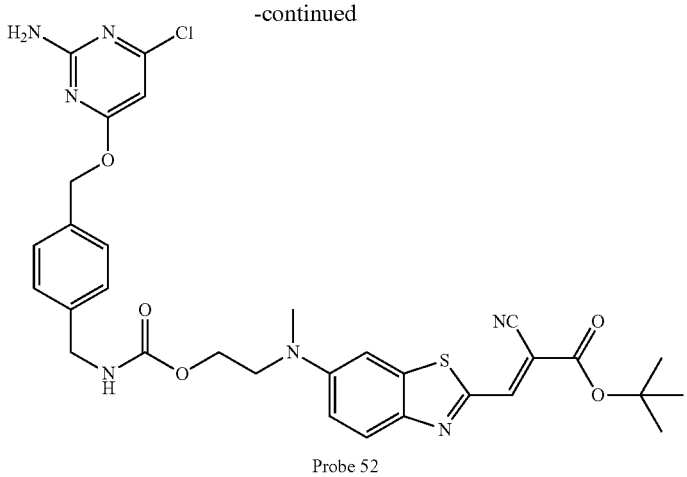

Probe 52

Probe 52

This probe was obtained by following the general procedure for probe 1, and the yield was 69%. $^1$H-NMR (400 MHz, CDCl$_3$): δ=9.99 (brs, 1H), 8.03 (d, 1H, J=10.0 Hz), 7.95 (s, 1H), 7.39 (d, 2H, J=8.4 Hz), 7.26 (d, 2H, J=8.4 Hz), 7.19 (s, 2H), 7.07-7.04 (m, 2H), 6.10 (s, 1H), 5.26 (s, 2H), 4.36 (s, 2H), 3.61 (t, 2H, J=8.0 Hz), 3.34 (t, 2H, J=8.0 Hz), 3.10 (s, 3H), 1.50 (s, 9H).

Example 53

A fluorescence-activated covalently labeling fluorescent probe 52 for CLIP protein tags was constructed using a molecular rotor as a viscosity-sensitive fluorescent dye.

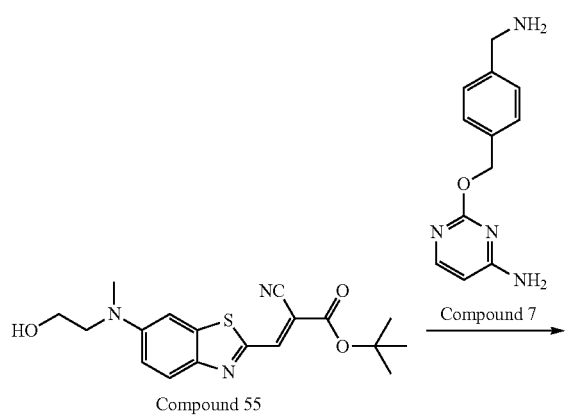

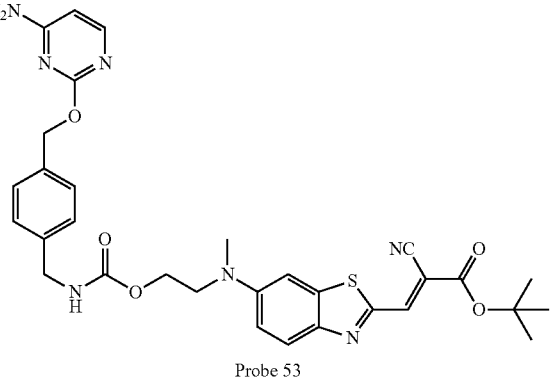

Probe 53

Probe 53

This probe was obtained by following the general procedure for probe 1, and the yield was 61%. $^1$H-NMR (400 MHz, CDCl$_3$): δ=8.03 (d, 1H, J=10.0 Hz), 7.95 (s, 1H), 7.90 (d, 1H, J=5.6), 7.75 (s, 1H), 7.33 (d, 2H, J=8.0 Hz), 7.19 (d, 2H, J=8.0 Hz), 7.07-7.04 (m, 2H), 6.06 (d, 1H, J=5.6 Hz), 5.27 (s, 2H), 5.16 (s, 2H), 4.45 (d, 2H, J=5.6 Hz), 3.61 (t, 2H, J=8.0 Hz), 3.34 (t, 2H, J=8.0 Hz), 3.10 (s, 3H), 1.50 (s, 9H).

Example 54

A fluorescence-activated covalently labeling fluorescent probe 54 for SNAP protein tags was constructed using a molecular rotor as a viscosity-sensitive fluorescent dye.

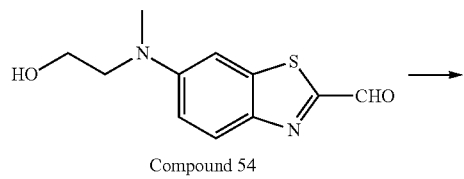

Compound 54

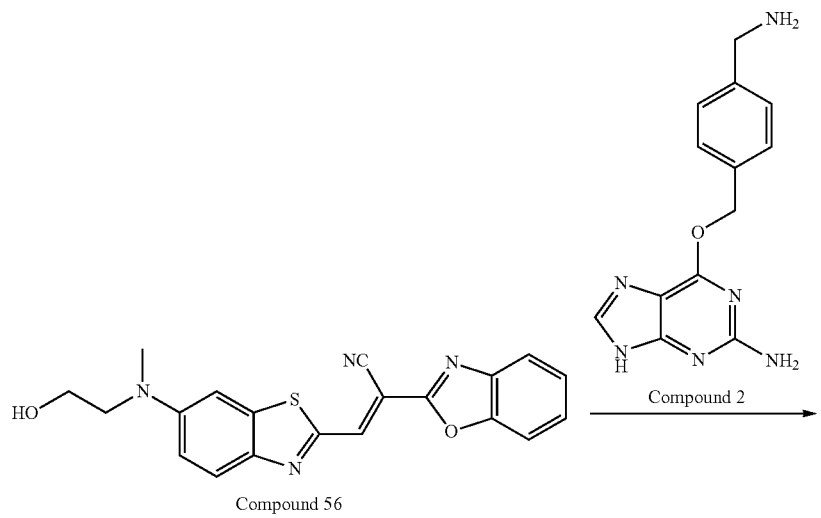

Compound 56

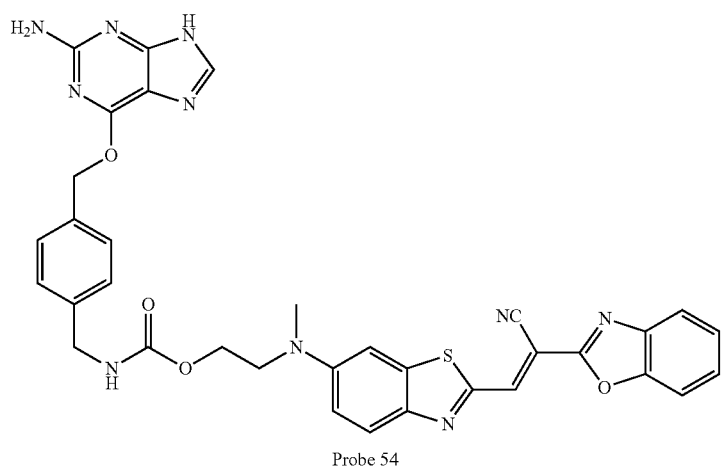

Probe 54

Compound 56

This compound was obtained by following the general procedure for compound 1, and the yield was 81%. $^1$H-NMR (400 MHz, CDCl$_3$): δ=8.03 (d, 1H, J=10.0 Hz), 7.95 (s, 1H), 7.74 (d, 1H, J=4.0 Hz), 7.55 (d, 1H, J=4.0 Hz), 7.36-7.42 (m, 2H), 7.07-7.04 (m, 2H), 3.61 (t, 2H, J=8.0 Hz), 3.34 (t, 2H, J=8.0 Hz), 3.10 (s, 3H).

Probe 54

This probe was obtained by following the general procedure for probe 1, and the yield was 65%. $^1$H-NMR (400 MHz, DMSO-d$_6$): δ=12.42 (s, 1H), 10.01 (s, 1H), 8.03 (d, 1H, J=10.0 Hz), 7.95 (s, 1H), 7.81 (s, 1H), 7.74 (d, 1H, J=4.0 Hz), 7.55 (d, 1H, J=4.0 Hz), 7.40 (m, 4H), 7.36-7.42 (m, 2H), 7.07-7.04 (m, 2H), 6.29 (s, 2H), 5.46 (s, 2H), 4.40 (d, 2H, J=4.8 Hz), 3.61 (t, 2H, J=8.0 Hz), 3.34 (t, 2H, J=8.0 Hz), 3.10 (s, 3H).

Example 55

A fluorescence-activated covalently labeling fluorescent probe 55 for SNAP protein tags was constructed using a molecular rotor as a viscosity-sensitive fluorescent dye.

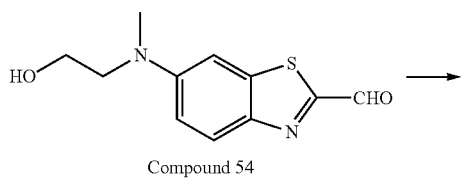

Compound 54

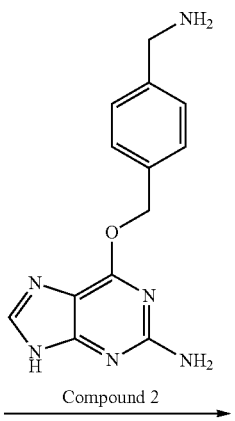

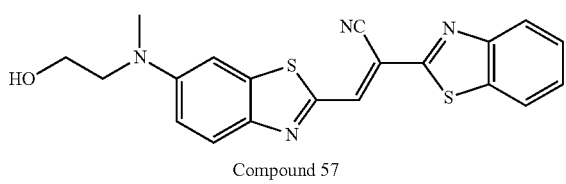

Compound 57

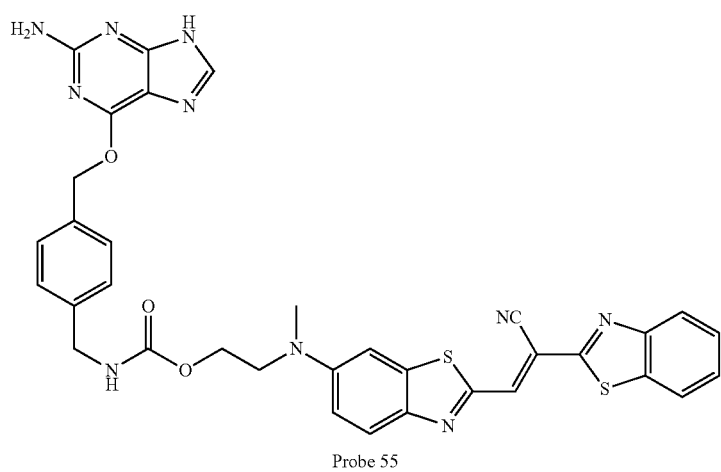

Probe 55

Compound 57

This compound was obtained by following the general procedure for compound 1, and the yield was 97%. ¹H-NMR (400 MHz, CDCl₃): δ=8.04 (d, 1H, J=8.0 Hz), 8.00 (d, 1H, J=10.0 Hz), 7.95 (s, 1H), 7.90 (d, 1H, J=8.0 Hz), 7.53 (t, 1H, J=8.0 Hz), 7.45 (t, 1H, J=8.0 Hz), 7.07-7.04 (m, 2H), 3.61 (t, 2H, J=8.0 Hz), 3.34 (t, 2H, J=8.0 Hz), 3.10 (s, 3H).

Probe 55

This probe was obtained by following the general procedure for probe 1, and the yield was 66%. ¹H-NMR (400 MHz, DMSO-d₆): δ=8.04 (d, 1H, J=8.0 Hz), 8.00 (d, 1H, J=10.0 Hz), 7.95 (s, 1H), 7.90 (d, 1H, J=8.0 Hz), 7.53 (t, 1H, J=8.0 Hz), 7.45 (t, 1H, J=8.0 Hz), 7.07-7.04 (m, 2H), 3.61 (t, 2H, J=8.0 Hz), 3.34 (t, 2H, J=8.0 Hz), 3.10 (s, 3H).

Example 56

A fluorescence-activated covalently labeling fluorescent probe 56 for SNAP protein tags was constructed using a molecular rotor as a viscosity-sensitive fluorescent dye.

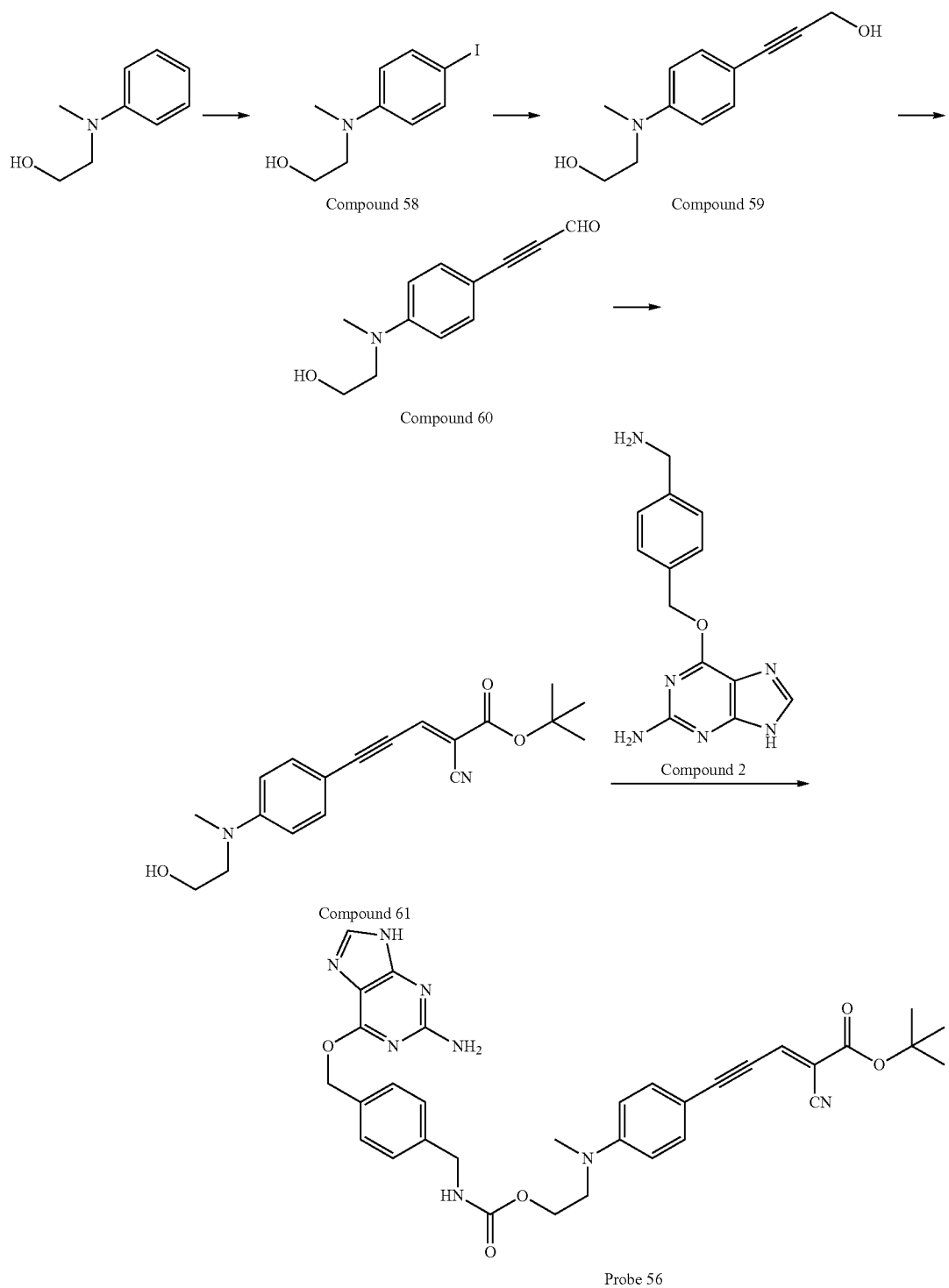

Compound 58

N-methyl-N-hydroxyethylaniline (1.88 g, 12.5 mmol) and NaHCO$_3$ (1.57 g, 18.7 mmol) were dissolved in 48 ml of dichloromethane and 36 ml of water, cooled to 0° C., and I$_2$ (3.0 g, 11.8 mmol) was added slowly, then, the system was gradually warmed to room temperature, stirred for 30 min, the system was diluted with 300 ml of dichloromethane and 40 ml of water; the organic phase was separated, and the organic phase was washed with water, sodium thiosulfate solution and brine, respectively, and dried over anhydrous sodium sulfate; the solvent was completely removed by rotary evaporation, and the residue was purified by gel silica gel column chromatography to give a pure compound 22 (2.46 g, 92%). $^1$H-NMR (400 MHz, CDCl$_3$): δ=7.46 (d, 1H, J=7.60 Hz), 6.56 (d, 1H, J=7.60 Hz), 3.78 (t, 2H, J=4.80 Hz), 3.44 (t, 2H, J=4.80 Hz), 2.94 (s, 3H).

Compound 59

Compound 58 (5.54 g, 20 mmol), Pd(PPh$_3$)$_2$Cl$_2$ (213 mg, 0.3 mmol), cuprous iodide (38 mg, 0.2 mmol) were dissolved in 20 ml of trimethylamine. After stirred at room temperature for 30 min under the protection of Ar, propargyl alcohol (1.53 ml, 26 mmol) was added, and the mixture was stirred at room temperature for 24 hrs. After the reaction was completed, the mixture was filtered, the solvent was completely removed by rotary evaporation, and the residue was purified by gel silica gel column chromatography to give a brown solid of 3.20 g, and the yield was 78%. $^1$H-NMR (400 MHz, CDCl$_3$): δ=7.30 (d, 2H, J=8.8 Hz), 6.60 (d, 2H, J=8.8 Hz), 4.45 (d, 2H, J=4.0 Hz), 3.78 (t, 2H, J=4.80 Hz), 3.44 (t, 2H, J=4.80 Hz), 3.02 (s, 3H).

Compound 60

Compound 59 (2.05 g, 10 mmol) was dissolved in 50 ml of tetrahydrofuran, 10 g of active manganese dioxide was added, and stirred under the protection of Ar for 24 h at room temperature. When the reaction was completed, the solution was filtered, and the solvent was completely removed by rotary evaporation, and the residue was purified by gel silica gel column chromatography to give a brown solid of 1.42 g, and the yield was 70%. $^1$H-NMR (400 MHz, CDCl$_3$): δ=9.37 (s, 1H), 7.49 (d, 2H, J=8.8 Hz), 6.74 (d, 2H, J=8.8 Hz), 3.78 (t, 2H, J=4.80 Hz), 3.44 (t, 2H, J=4.80 Hz), 3.02 (s, 3H).

Compound 61

This compound was obtained by following the general procedure for compound 61, and the yield was 81%. $^1$H-NMR (400 MHz, CDCl$_3$): δ=8.01 (s, 1H), 7.47 (d, 2H, J=8.8 Hz), 6.76 (d, 2H, J=8.8 Hz), 3.78 (t, 2H, J=4.80 Hz), 3.44 (t, 2H, J=4.80 Hz), 3.02 (s, 3H), 1.50 (s, 9H).

Probe 56

This probe was obtained by following the general procedure for probe 1, and the yield was 55%. $^1$H-NMR (400 MHz, CDCl$_3$): δ=12.42 (s, 1H), 10.01 (s, 1H), 8.01 (s, 1H), 7.81 (s, 1H), 7.47 (d, 2H, J=8.8 Hz), 7.40 (m, 4H), 6.76 (d, 2H, J=8.8 Hz), 6.29 (s, 2H), 5.46 (s, 2H), 4.40 (d, 2H, J=4.8 Hz), 3.78 (t, 2H, J=4.80 Hz), 3.44 (t, 2H, J=4.80 Hz), 3.02 (s, 3H), 1.50 (s, 9H).

Example 57

A fluorescence-activated covalently labeling fluorescent probe 57 for CLIP protein tags was constructed using a molecular rotor as a viscosity-sensitive fluorescent dye.

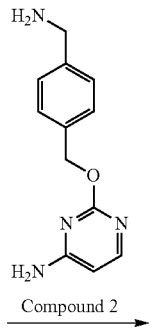

Compound 2

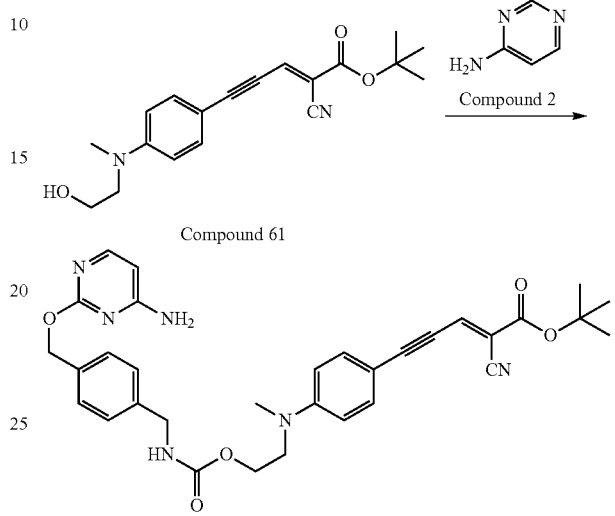

Compound 61

Probe 57

Probe 57

This probe was obtained by following the general procedure for probe 1, and the yield was 61%. $^1$H-NMR (400 MHz, CDCl$_3$): δ=8.01 (s, 1H), 7.93 (d, 1H, J=5.6), 7.75 (s, 1H), 7.47 (d, 2H, J=8.8 Hz), 7.33 (d, 2H, J=8.0 Hz), 7.19 (d, 2H, J=8.0 Hz), 6.76 (d, 2H, J=8.8 Hz), 6.06 (d, 1H, J=5.6 Hz), 5.27 (s, 2H), 5.16 (s, 2H), 4.45 (d, 2H, J=5.6 Hz), 3.78 (t, 2H, J=4.80 Hz), 3.44 (t, 2H, J=4.80 Hz), 3.02 (s, 3H), 1.50 (s, 9H).

Example 58

A fluorescence-activated covalently labeling fluorescent probe 58 for SNAP protein tags was constructed using a molecular rotor as a viscosity-sensitive fluorescent dye.

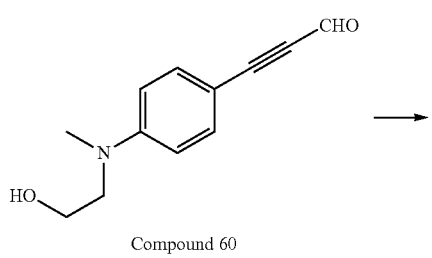

Compound 60

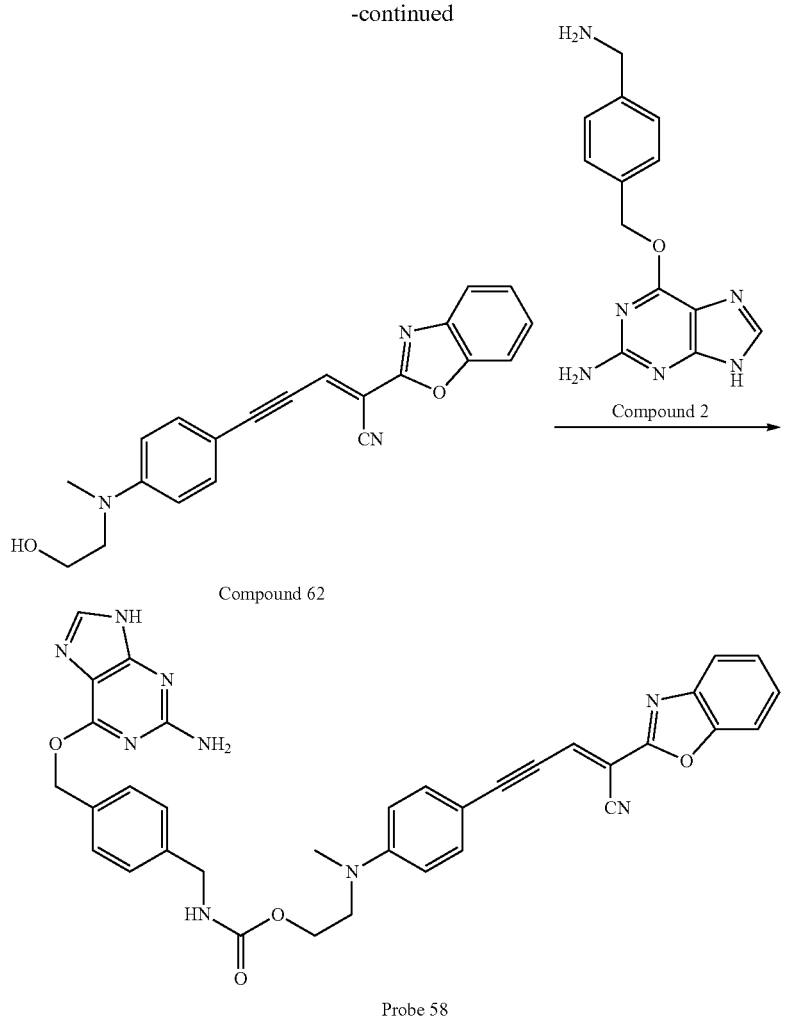

Compound 62

Compound 62

This compound was obtained by following the general procedure for compound 1, and the yield was 90%. $^1$H-NMR (400 MHz, CDCl$_3$): δ=8.01 (s, 1H), 7.74 (d, 1H, J=4.0 Hz), 7.55 (d, 1H, J=4.0 Hz), 7.47 (d, 2H, J=8.8 Hz), 7.36-7.42 (m, 2H), 6.76 (d, 2H, J=8.8 Hz), 3.78 (t, 2H, J=4.80 Hz), 3.44 (t, 2H, J=4.80 Hz), 3.02 (s, 3H).

Probe 58

This probe was obtained by following the general procedure for probe 1, and the yield was 50%. $^1$H-NMR (400 MHz, CDCl$_3$): δ=12.42 (s, 1H), 10.01 (s, 1H), 8.01 (s, 1H), 7.81 (s, 1H), 7.74 (d, 1H, J=4.0 Hz), 7.55 (d, 1H, J=4.0 Hz), 7.47 (d, 2H, J=8.8 Hz), 7.40 (m, 4H), 7.36-7.42 (m, 2H), 6.76 (d, 2H, J=8.8 Hz), 6.29 (s, 2H), 5.46 (s, 2H), 4.40 (d, 2H, J=4.8 Hz), 3.78 (t, 2H, J=4.80 Hz), 3.44 (t, 2H, J=4.80 Hz), 3.02 (s, 3H).

Example 59

A fluorescence-activated covalently labeling fluorescent probe 59 for SNAP protein tags was constructed using a molecular rotor as a viscosity-sensitive fluorescent dye.

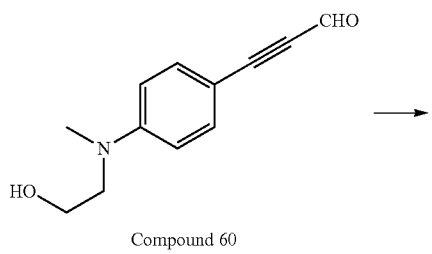

Compound 60

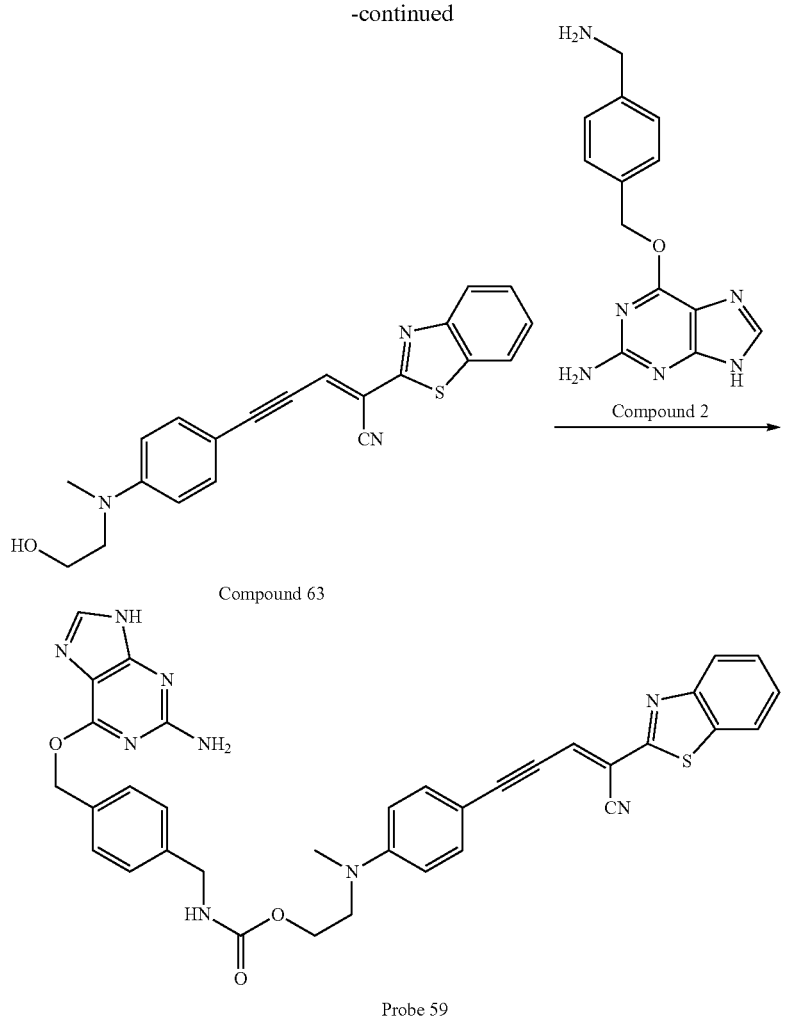

Compound 63

Compound 63

This compound was obtained by following the general procedure for compound 1, and the yield was 90%. $^1$H-NMR (400 MHz, CDCl$_3$): δ=8.04 (d, 1H, J=8.0 Hz), 8.01 (s, 1H), 7.90 (d, 1H, J=8.0 Hz), 7.53 (t, 1H, J=8.0 Hz), 7.47 (d, 2H, J=8.8 Hz), 7.45 (t, 1H, J=8.0 Hz), 6.76 (d, 2H, J=8.8 Hz), 3.78 (t, 2H, J=4.80 Hz), 3.44 (t, 2H, J=4.80 Hz), 3.02 (s, 3H).

Probe 59

This probe was obtained by following the general procedure for probe 1, and the yield was 49%. $^1$H-NMR (400 MHz, CDCl$_3$): δ=12.42 (s, 1H), 10.01 (s, 1H), 8.04 (d, 1H, J=8.0 Hz), 8.01 (s, 1H), 7.90 (d, 1H, J=8.0 Hz), 7.81 (s, 1H), 7.53 (t, 1H, J=8.0 Hz), 7.47 (d, 2H, J=8.8 Hz), 7.45 (t, 1H, J=8.0 Hz), 7.40 (m, 4H), 6.76 (d, 2H, J=8.8 Hz), 6.29 (s, 2H), 5.46 (s, 2H), 4.40 (d, 2H, J=4.8 Hz), 3.78 (t, 2H, J=4.80 Hz), 3.44 (t, 2H, J=4.80 Hz), 3.02 (s, 3H).

Example 60

A fluorescence-activated covalently labeling fluorescent probe 60 for SNAP protein tags was constructed using a molecular rotor as a viscosity-sensitive fluorescent dye.

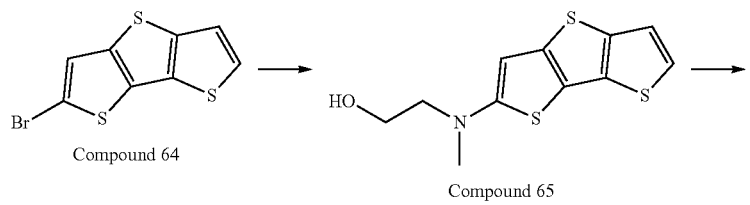

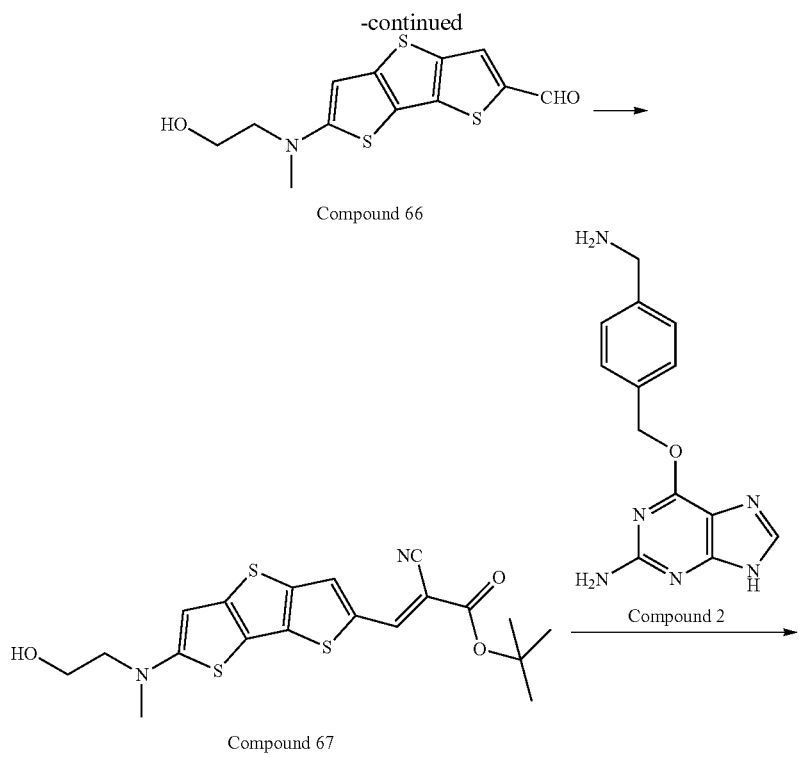

Compound 66

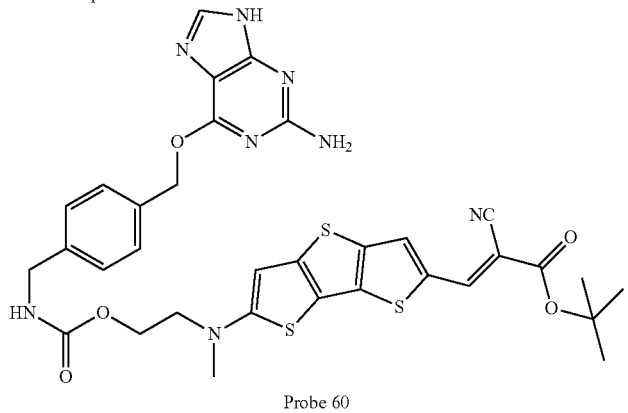

Compound 67

Probe 60

Compound 64

The synthesis was carried out by the method disclosed in WO2009152165 (A2), Dec. 17, 2009. ¹H-NMR (400 MHz, DMSO-d₆): δ=7.84 (s, 1H), 7.37 (s, 1H), 7.24 (s, 1H).

Compound 65

This compound was obtained by following the general procedure for compound 21, and the yield was 85%. ¹H-NMR (400 MHz, DMSO-d₆): δ=7.84 (s, 1H), 7.37 (s, 1H), 7.24 (s, 1H), 3.78 (t, 2H, J=4.80 Hz), 3.44 (t, 2H, J=4.80 Hz), 3.02 (s, 3H).

Compound 66

This compound was obtained by following the general procedure for compound 22, and the yield was 56%. 1H-NMR (400 MHz, DMSO-d₆): δ=10.04 (s, 1H), 7.84 (s, 1H), 7.24 (s, 1H), 3.78 (t, 2H, J=4.80 Hz), 3.44 (t, 2H, J=4.80 Hz), 3.02 (s, 3H).

Compound 67

This compound was obtained by following the general procedure for compound 1, and the yield was 88%. 1H-NMR (400 MHz, DMSO-d₆): δ=8.01 (s, 1H), 7.84 (s, 1H), 7.24 (s, 1H), 3.78 (t, 2H, J=4.80 Hz), 3.44 (t, 2H, J=4.80 Hz), 3.02 (s, 3H), 1.50 (s, 9H).

Probe 60

This probe was obtained by following the general procedure for probe 1, and the yield was 55%. ¹H-NMR (400 MHz, DMSO-d₆): δ=12.42 (s, 1H), 10.01 (s, 1H), 8.01 (s, 1H), 7.84 (s, 1H), 7.81 (s, 1H), 7.40 (m, 4H), 7.24 (s, 1H), 6.29 (s, 2H), 5.46 (s, 2H), 4.40 (d, 2H, J=4.8 Hz), 3.78 (t, 2H, J=4.80 Hz), 3.44 (t, 2H, J=4.80 Hz), 3.02 (s, 3H), 1.50 (s, 9H).

Example 61

A fluorescence-activated covalently labeling fluorescent probe 61 for SNAP protein tags was constructed using a molecular rotor as a viscosity-sensitive fluorescent dye.

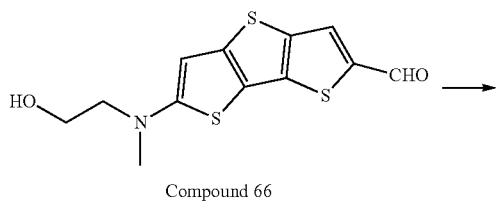

Compound 66

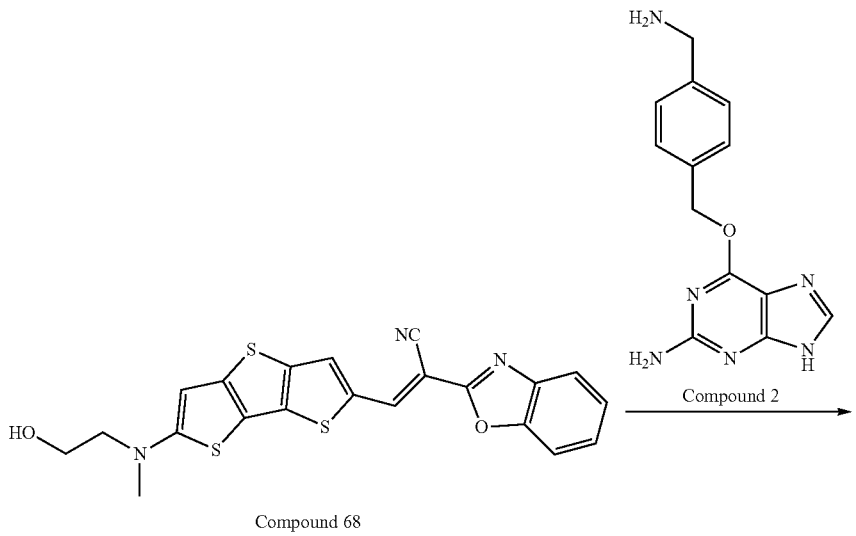

Compound 68

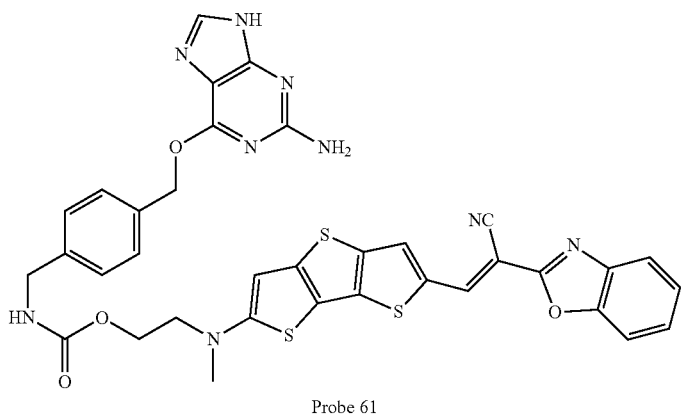

Probe 61

Compound 68

This compound was obtained by following the general procedure for compound 1, and the yield was 99%. $^1$H-NMR (400 MHz, DMSO-d$_6$): δ=8.01 (s, 1H), 7.84 (s, 1H), 7.74 (1H, d, J=4.0 Hz), 7.55 (1H, d, J=4.0 Hz), 7.36-7.42 (2H, m), 7.24 (s, 1H), 3.78 (t, 2H, J=4.80 Hz), 3.44 (t, 2H, J=4.80 Hz), 3.02 (s, 3H).

Probe 61

This probe was obtained by following the general procedure for probe 1, and the yield was 56%. $^1$H-NMR (400 MHz, DMSO-d$_6$): δ=12.42 (s, 1H), 10.01 (s, 1H), 8.01 (s, 1H), 7.84 (s, 1H), 7.81 (s, 1H), 7.74 (1H, d, J=4.0 Hz), 7.55 (1H, d, J=4.0 Hz), 7.36-7.42 (6H, m), 7.24 (s, 1H), 6.29 (s, 2H), 5.46 (s, 2H), 4.40 (d, 2H, J=4.8 Hz), 3.78 (t, 2H, J=4.80 Hz), 3.44 (t, 2H, J=4.80 Hz), 3.02 (s, 3H).

Example 62

A fluorescence-activated covalently labeling fluorescent probe 62 for SNAP protein tags was constructed using a molecular rotor as a viscosity-sensitive fluorescent dye.

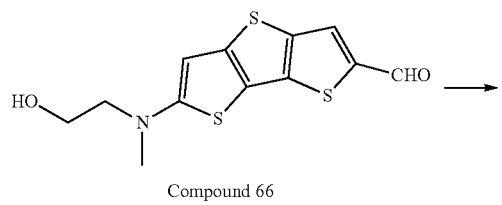

Compound 66

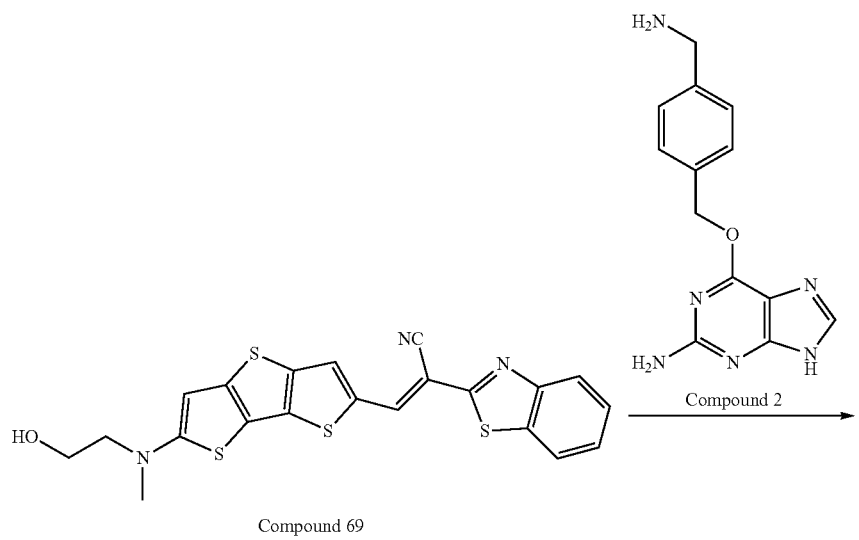

Compound 69

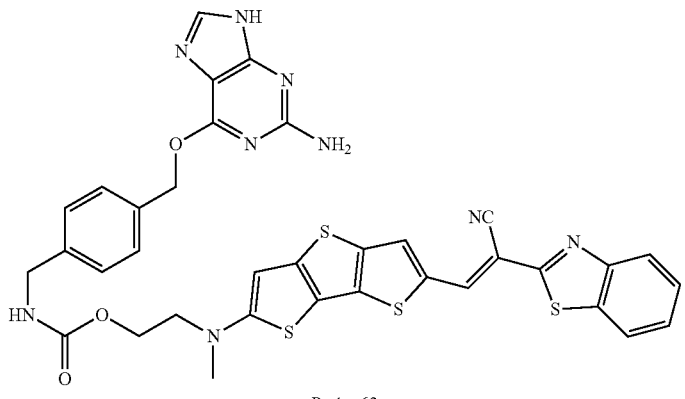

Probe 62

Compound 68

This compound was obtained by following the general procedure for compound 1, and the yield was 99%. $^{1}$H-NMR (400 MHz, DMSO-d$_6$): δ=8.07 (1H, d, J=8.0 Hz), 8.01 (s, 1H), 7.90 (1H, d, J=8.0 Hz), 7.84 (s, 1H), 7.53 (1H, t, J=8.0 Hz), 7.45 (1H, t, J=8.0 Hz), 7.24 (s, 1H), 3.78 (t, 2H, J=4.80 Hz), 3.44 (t, 2H, J=4.80 Hz), 3.02 (s, 3H).

Probe 62

This probe was obtained by following the general procedure for probe 1, and the yield was 56%. $^{1}$H-NMR (400 MHz, DMSO-d$_6$): δ=12.42 (s, 1H), 10.01 (s, 1H), 8.07 (1H, d, J=8.0 Hz), 8.01 (s, 1H), 7.90 (1H, d, J=8.0 Hz), 7.84 (s, 1H), 7.81 (s, 1H), 7.53 (1H, t, J=8.0 Hz), 7.45 (1H, t, J=8.0 Hz), 7.40 (m, 4H), 7.24 (s, 1H), 6.29 (s, 2H), 5.46 (s, 2H), 4.40 (d, 2H, J=4.8 Hz), 3.78 (t, 2H, J=4.80 Hz), 3.44 (t, 2H, J=4.80 Hz), 3.02 (s, 3H).

Example 63

A fluorescence-activated covalently labeling fluorescent probe 63 for SNAP protein tags was constructed using a molecular rotor as a viscosity-sensitive fluorescent dye.

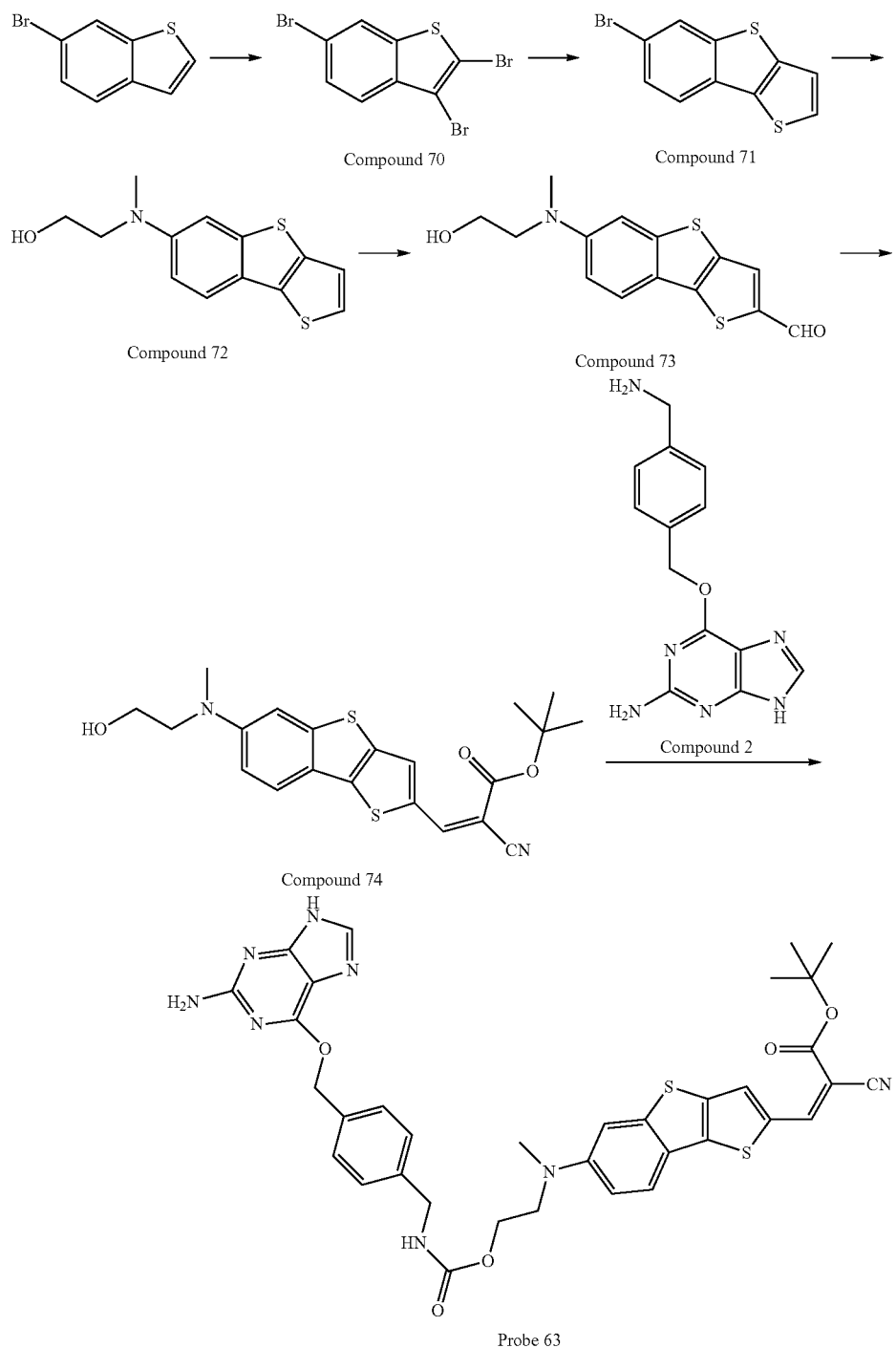

Compound 70

6-Bromo-1-benzothiophene (0.43 g, 2 mmol) was dissolved in 50 ml of dry dihalomethane, potassium acetate (0.4 g, 4 mmol) was added, and bromine (0.32 g, 2 mmol) was added in an ice bath. The system was slowly risen to room temperature. When the reaction was completed, 100 ml of saturated sodium thiosulfate solution was added. The organic phase was separated, and the aqueous phase was extracted three times with dichloromethane, and the organic phase was combined and dried by rotary evaporation, and the residue was purified by gel silica gel column chromatography to give a yellow product 0.64 g. and the yield was 81%. $^1$H-NMR (400 MHz, CDCl$_3$): δ=7.81 (s, 1H). 7.68 (d, J=9.0 Hz, 1H), 6.92 (d, J=2.0 Hz, 1H).

Synthesis of Compound 71

Compound 70 (1.27 g, 3.43 mmol) was dissolved in 50 ml of dry triethylamine, and dichloroditetra(triphenylphosphine) palladium (120.2 mg, 0.171 mmol), cuprous iodide (65.2 mg, 0.343 mmol) and trimethylsilylacetylene (344 mg, 3.43 mmol) were added, heated in an oil bath for 24 h under the protection of Ar. After completion of the reaction, 5 ml of water was added to quench the reaction. The solvent was completely removed by rotary evaporation. The residue was dissolved in diethyl ether, and filtered. Rotary evaporation was carried out to give a residue, which was used in the next step without purification.

The crude product was dissolved in 30 ml of NMP, added with sodium sulfide nonahydrate (0.87 g, 3.63 mmol). The mixture was heated in an oil bath at 190° C. for 12 h under the protection of Ar, cooled at room temperature, and added with 20 ml of saturated ammonium chloride solution, and the resulting was extracted with dichloromethane three times, and the organic phase was combined and dried over anhydrous $Na_2SO_4$, and $Na_2SO_4$ was removed by filtration. The solvent was removed by rotary evaporation to give a residue which was purified by gel silica gel column chromatography to give a yellow solid 0.85 g, and the yield was 49%. $^1$H-NMR (400 MHz, CDCl3): δ=7.87 (m, 1H), 7.71 (m, 1H), 7.51 (d, J=5.4 Hz, 1H), 7.41 (m, 1H), 7.32 (d, J=5.4 Hz, 1H).

Compound 72

This compound was obtained by following the general procedure for compound 21, and the yield was 75%. $^1$H-NMR (400 MHz, CDCl$_3$): δ=7.86 (m, 1H), 7.73 (m, 1H), 7.54 (d, J=5.4 Hz, 1H), 7.41 (m, 1H), 7.32 (d, J=5.4 Hz, 1H), 3.78 (t, 2H, J=4.80 Hz), 3.44 (t, 2H, J=4.80 Hz), 3.02 (s, 3H).

Compound 73

This compound was obtained by following the general procedure for compound 22, and the yield was 56%. $^1$H-NMR (400 MHz, CDCl$_3$): δ=9.71 (s, 1H), 7.87 (m, 1H), 7.71 (m, 1H), 7.51 (d, J=5.4 Hz, 1H), 7.32 (d, J=5.4 Hz, 1H), 3.78 (t, 2H, J=4.80 Hz), 3.44 (t, 2H, J=4.80 Hz), 3.02 (s, 3H).

Compound 74

This compound was obtained by following the general procedure for compound 1, and the yield was 93%. $^1$H-NMR (400 MHz, CDCl$_3$): δ=8.01 (s, 1H), 7.87 (m, 1H), 7.71 (m, 1H), 7.51 (d, J=5.4 Hz, 1H), 7.32 (d, J=5.4 Hz, 1H), 3.78 (t, 2H, J=4.80 Hz), 3.44 (t, 2H, J=4.80 Hz), 3.02 (s, 3H), 1.49 (s, 9H).

Probe 63

This probe was obtained by following the general procedure for probe 1, and the yield was 56%. $^1$H-NMR (400 MHz, CDCl$_3$): δ=12.42 (s, 1H), 10.01 (s, 1H), 7.81 (s, 1H), 8.01 (s, 1H), 7.87 (m, 1H), 7.71 (m, 1H), 7.51 (d, J=5.4 Hz, 1H), 7.40 (m, 4H), 7.32 (d, J=5.4 Hz, 1H), 6.29 (s, 2H), 5.46 (s, 2H), 4.40 (d, 2H, J=4.8 Hz), 3.78 (t, 2H, J=4.80 Hz), 3.44 (t, 2H, J=4.80 Hz), 3.02 (s, 3H), 1.49 (s, 9H).

Example 64

A fluorescence-activated covalently labeling fluorescent probe 64 for SNAP protein tags was constructed using a molecular rotor as a viscosity-sensitive fluorescent dye.

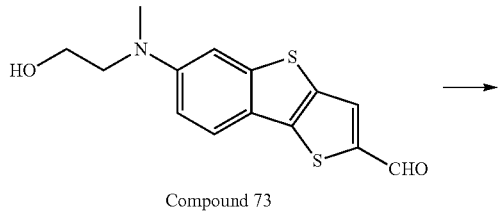

Compound 73

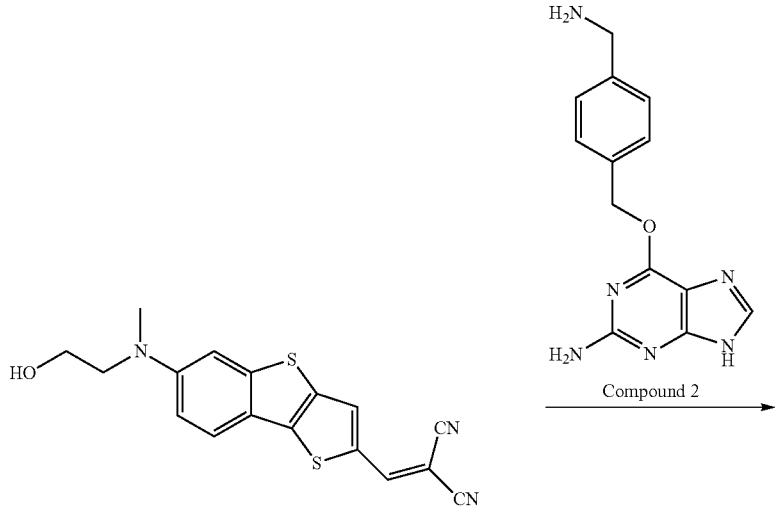

Compound 75

-continued

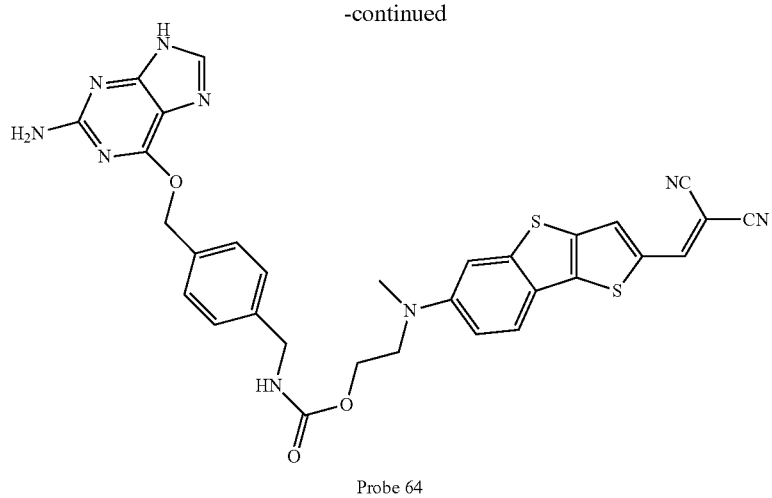

Probe 64

Compound 75

This compound was obtained by following the general procedure for compound 75, and the yield was 98%. ¹H-NMR (400 MHz, CDCl₃): δ=8.01 (s, 1H), 7.87 (m, 1H), 7.71 (m, 1H), 7.51 (d, J=5.4 Hz, 1H), 7.32 (d, J=5.4 Hz, 1H), 3.78 (t, 2H, J=4.80 Hz), 3.44 (t, 2H, J=4.80 Hz), 3.02 (s, 3H).

Probe 64

This probe was obtained by following the general procedure for probe 1, and the yield was 45%. ¹H-NMR (400 MHz, CDCl₃): δ=12.42 (s, 1H), 10.01 (s, 1H), 8.01 (s, 1H), 7.87 (m, 1H), 7.81 (s, 1H), 7.71 (m, 1H), 7.51 (d, J=5.4 Hz, 1H), 7.40 (m, 4H), 7.32 (d, J=5.4 Hz, 1H), 6.29 (s, 2H), 5.46 (s, 2H), 4.40 (d, 2H, J=4.8 Hz), 3.78 (t, 2H, J=4.80 Hz), 3.44 (t, 2H, J=4.80 Hz), 3.02 (s, 3H).

Example 65

A fluorescence-activated covalently labeling fluorescent probe 65 for SNAP protein tags was constructed using a molecular rotor as a viscosity-sensitive fluorescent dye.

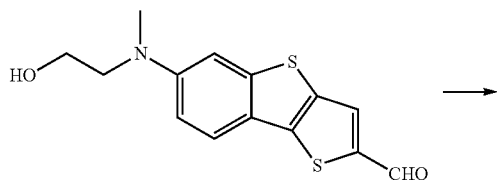

Compound 73

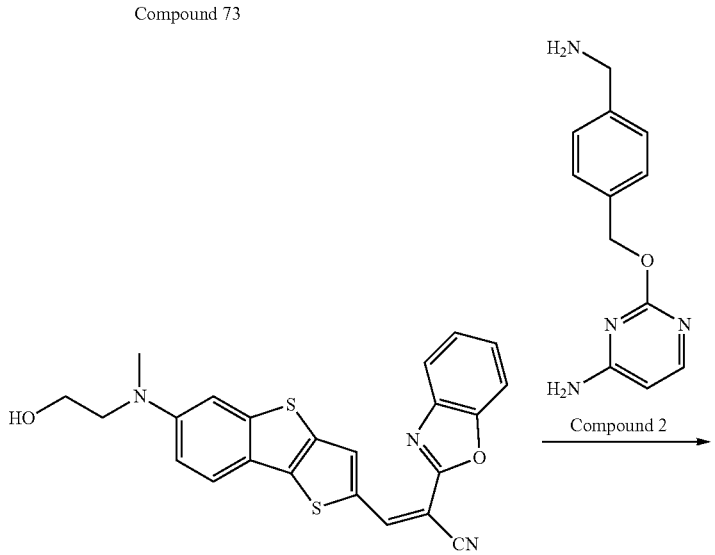

Compound 76

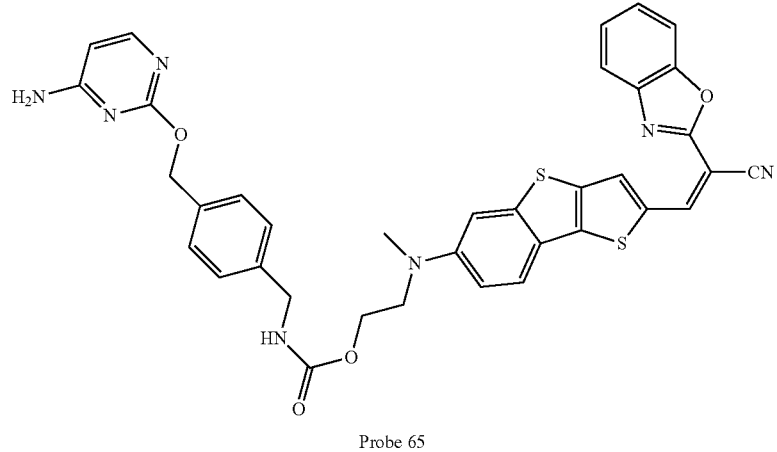

Probe 65

Compound 76

This compound was obtained by following the general procedure for compound 1, and the yield was 91%. $^1$H-NMR (400 MHz, CDCl$_3$): δ=8.01 (s, 1H), 7.87 (m, 1H), 7.74 (d, 1H, J=4.0 Hz), 7.71 (m, 1H)), 7.55 (d, 1H, J=4.0 Hz), 7.51 (d, J=5.4 Hz, 1H), 7.36-7.42 (m, 2H), 7.32 (d, J=5.4 Hz, 1H), 3.78 (t, 2H, J=4.80 Hz), 3.44 (t, 2H, J=4.80 Hz), 3.02 (s, 3H).

Probe 65

This probe was obtained by following the general procedure for probe 1, and the yield was 45%. $^1$H-NMR (400 MHz, CDCl$_3$): δ=8.01 (s, 1H), 7.93 (d, 1H, J=5.6), 7.87 (m, 1H), 7.77 (s, 1H), 7.74 (d, 1H, J=4.0 Hz), 7.71 (m, 1H)), 7.55 (d, 1H, J=4.0 Hz), 7.51 (d, J=5.4 Hz, 1H), 7.36-7.42 (m, 4H), 7.32 (d, J=5.4 Hz, 1H), 7.19 (d, 2H, J=8.0 Hz), 6.06 (d, 1H, J=5.6 Hz), 5.27 (s, 2H), 5.16 (s, 2H), 4.45 (d, 2H, J=5.6 Hz), 3.78 (t, 2H, J=4.80 Hz), 3.44 (t, 2H, J=4.80 Hz), 3.02 (s, 3H).

Example 66

A fluorescence-activated covalently labeling fluorescent probe 66 for SNAP protein tags was constructed using a molecular rotor as a viscosity-sensitive fluorescent dye.

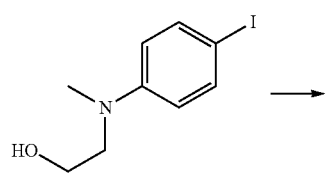

Compound 58

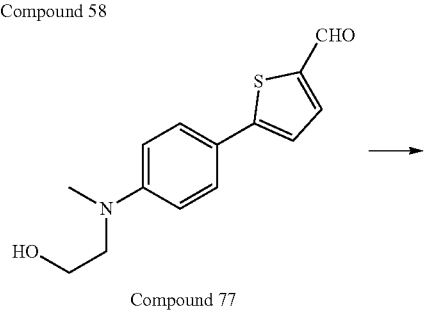

Compound 77

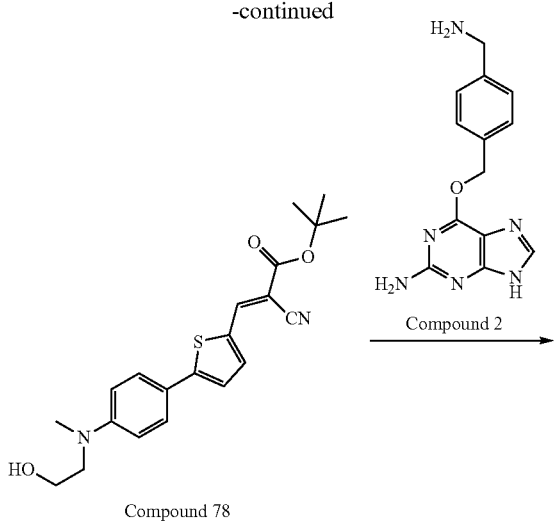

Compound 78

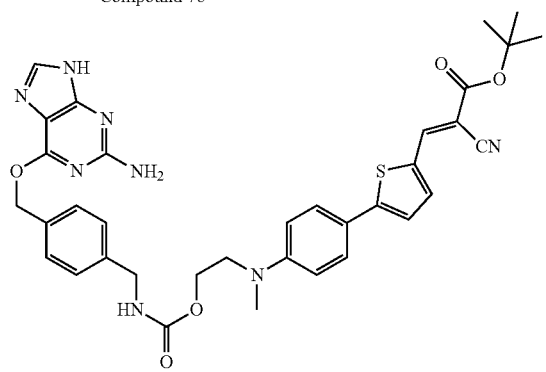

Probe 66

Compound 77

Compound 58 (0.554 g, 2 mmol) and 5-aldehyde-2-thiopheneboronic acid (0.374 g, 2.4 mmol) were dissolved in 10 ml of toluene, 10 ml of ethanol, and 2 ml of 2 N K$_2$CO$_3$ solution was added. After heating in an oil bath at 85° C. for 5 hrs under the protection of Ar, the reaction was completed, and the solution was cooled at room temperature, and then the reaction was quenched with water (10 ml). The organic phase was separated and the aqueous phase was extracted with dichloromethane. The organic phase was combined, washed with brine, dried over anhydrous sodium sulfate and the solvent was removed by rotary evaporation to give a residue which was purified by gel silica gel column chromatography to give a pure product 0.339 g, and the yield was 65%. $^1$H-NMR (400 MHz, CDCl$_3$): δ=9.81 (s, 1H), 7.68 (s, 1H), 7.55 (d, 1H, J=8.00 Hz), 7.25 (d, 2H, J=8.00 Hz), 6.78 (d, 2H, J=8.00 Hz), 3.86 (t, 2H, J=4.80 Hz), 3.56 (t, 2H, J=4.80 Hz), 3.06 (s, 3H).

Compound 78

This compound was obtained by following the general procedure for compound 1, and the yield was 98%. $^1$H-NMR (400 MHz, CDCl$_3$): δ=8.01 (s, 1H), 7.68 (s, 1H), 7.55 (d, 1H, J=8.00 Hz), 7.25 (d, 2H, J=8.00 Hz), 6.78 (d, 2H, J=8.00 Hz), 3.86 (t, 2H, J=4.80 Hz), 3.56 (t, 2H, J=4.80 Hz), 3.06 (s, 3H), 1.50 (s, 9H).

Probe 66

This probe was obtained by following the general procedure for probe 1, and the yield was 54%. $^1$H-NMR (400 MHz, CDCl$_3$): δ=12.42 (s, 1H), 10.01 (s, 1H), 8.01 (s, 1H), 7.81 (s, 1H), 7.68 (s, 1H), 7.55 (d, 1H, J=8.00 Hz), 7.40 (m, 4H), 7.25 (d, 2H, J=8.00 Hz), 6.78 (d, 2H, J=8.00 Hz), 6.29 (s, 2H), 5.46 (s, 2H), 4.40 (d, 2H, J=4.8 Hz), 3.86 (t, 2H, J=4.80 Hz), 3.56 (t, 2H, J=4.80 Hz), 3.06 (s, 3H), 1.50 (s, 9H).

Example 67

A fluorescence-activated covalently labeling fluorescent probe 67 for SNAP protein tags was constructed using a molecular rotor as a viscosity-sensitive fluorescent dye.

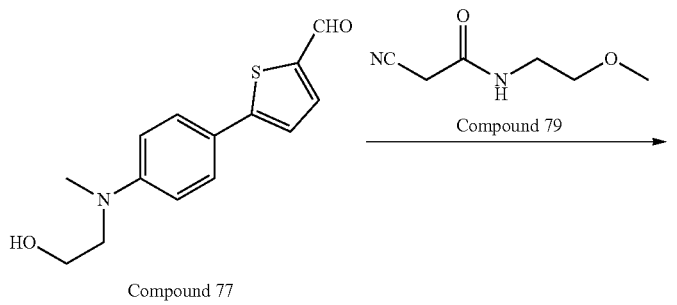

Compound 77

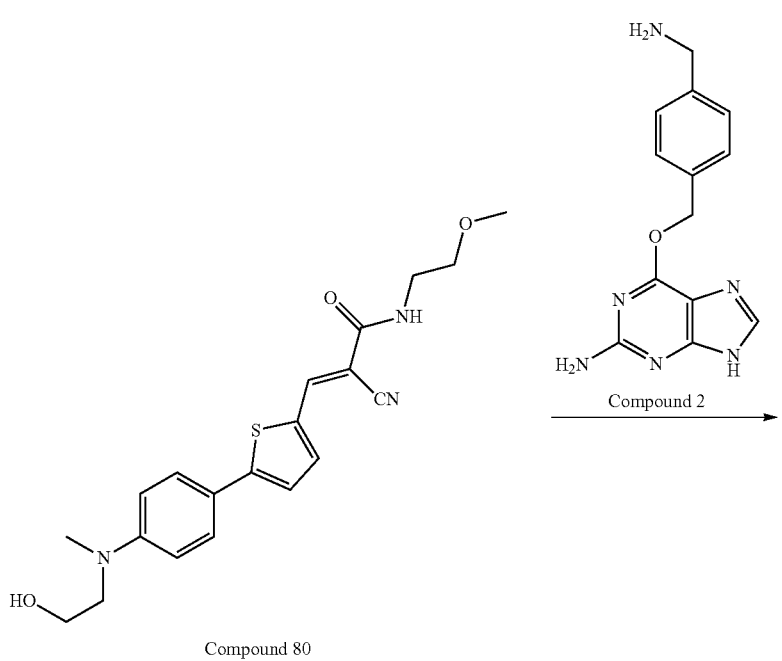

Compound 80

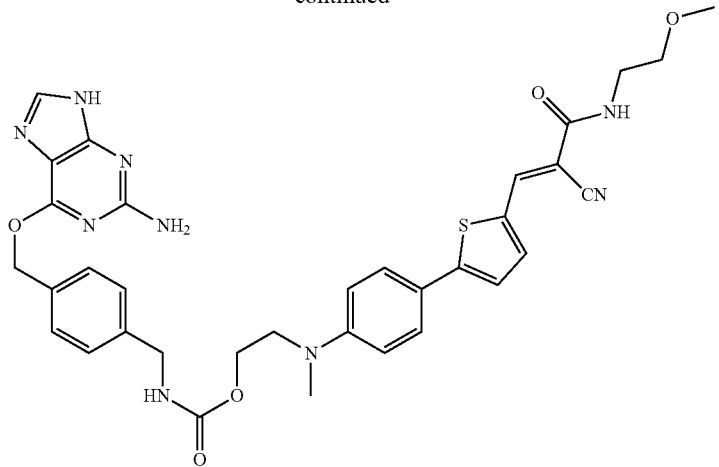

Probe 67

Compound 79

Cyanoacetic acid (1.0 g, 10 mmol) was added to a 25 ml round bottom flask, and 2-methoxyethylamine was added and stirred at room temperature under the protection of Ar. After completion of the reaction, 10 ml of anhydrous diethyl ether was added, and the mixture was separated by ultrasonication, filtered, and dried in vacuo to give a white solid. $^1$H-NMR (400 MHz, CDCl$_3$): δ=6.5 (s, 1H), 3.48-3.52 (m, 4H), 3.38 (s, 3H).

Compound 80

This compound was obtained by following the general procedure for compound 1, and the yield was 91%. $^1$H-NMR (400 MHz, DMSO-d$_6$): δ=8.31 (s, 1H), 8.22 (bt, 1H), 7.82 (d, 1H, J=4.00 Hz), 7.58 (d, 2H, J=8.80 Hz), 7.50 (d, 2H, J=4.00 Hz), 6.77 (d, 2H, J=8.80 Hz), 4.74 (bt, 1H), 3.57 (t, 2H, J=5.20 Hz), 3.41-3.48 (m, 4H), 3.38 (t, 2H, J=5.20 Hz), 3.27 (s, 3H), 3.01 (s, 3H).

Probe 67

This probe was obtained by following the general procedure for probe 1, and the yield was 45%. $^1$H-NMR (400 MHz, DMSO-d$_6$): δ=12.42 (s, 1H), 10.01 (s, 1H), 8.31 (s, 1H), 8.22 (bt, 1H), 7.82 (m, 2H), 7.58 (d, 2H, J=8.80 Hz), 7.50 (d, 2H, J=4.00 Hz), 7.40 (m, 4H), 6.77 (d, 2H, J=8.80 Hz), 6.29 (s, 2H), 5.46 (s, 2H), 4.74 (bt, 1H), 4.40 (d, 2H, J=4.8 Hz), 3.57 (t, 2H, J=5.20 Hz), 3.41-3.48 (m, 4H), 3.38 (t, 2H, J=5.20 Hz), 3.27 (s, 3H), 3.01 (s, 3H).

Example 68

A fluorescence-activated covalently labeling fluorescent probe 68 for SNAP protein tags was constructed using a molecular rotor as a viscosity-sensitive fluorescent dye.

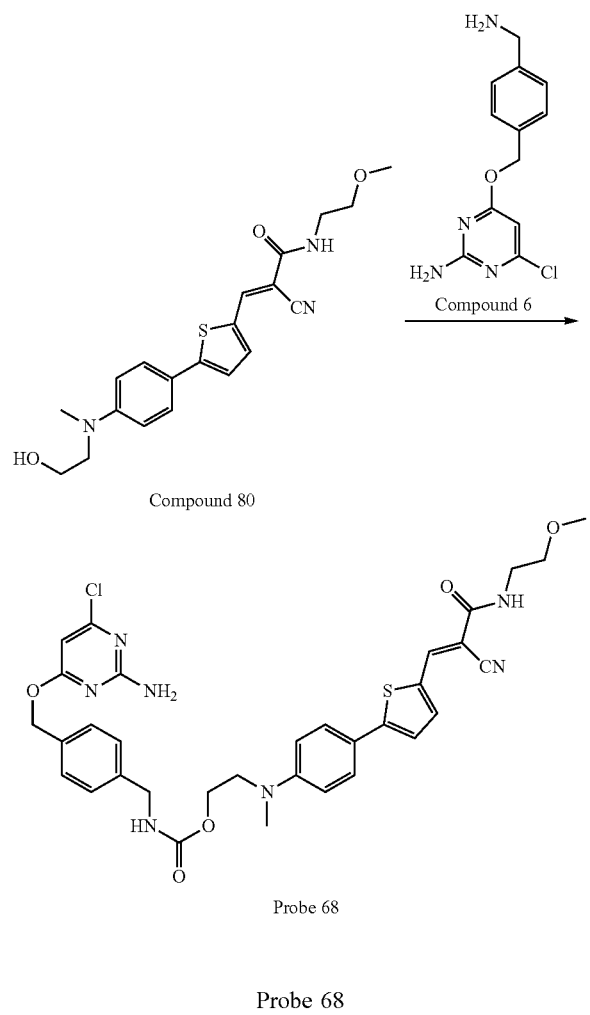

Compound 80

Probe 68

Probe 68

This probe was obtained by following the general procedure for probe 1, and the yield was 56%. $^1$H-NMR (400 MHz, DMSO-d$_6$): δ=9.99 (s, 1H), 8.31 (s, 1H), 8.22 (bt, 1H), 7.82 (d, 1H, J=4.00 Hz), 7.58 (d, 2H, J=8.80 Hz), 7.50 (d, 2H, J=4.00 Hz), 7.39 (d, 2H, J=8.4 Hz), 7.26 (d, 2H, J=8.4 Hz), 7.09 (s, 2H), 6.77 (d, 2H, J=8.80 Hz), 6.10 (s, 1H), 5.26 (s, 2H), 4.74 (bt, 1H), 4.36 (s, 2H), 3.57 (t, 2H, J=5.20 Hz), 3.41-3.48 (m, 4H), 3.38 (t, 2H, J=5.20 Hz), 3.27 (s, 3H), 3.01 (s, 3H).

Example 69

A fluorescence-activated covalently labeling fluorescent probe 69 for CLIP protein tags was constructed using a molecular rotor as a viscosity-sensitive fluorescent dye.

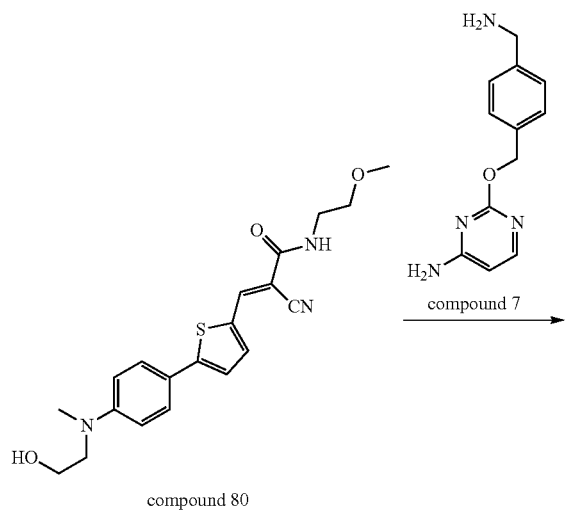

Probe 69

This probe was obtained by following the general procedure for probe 1, and the yield was 61%. $^1$H-NMR (400 MHz, DMSO-d$_6$): δ=8.31 (s, 1H), 8.22 (bt, 1H), 7.93 (d, 1H, J=5.6), 7.82 (d, 1H, J=4.00 Hz), 7.75 (s, 1H), 7.58 (d, 2H, J=8.80 Hz), 7.50 (d, 2H, J=4.00 Hz), 7.33 (d, 2H, J=8.0 Hz), 7.19 (d, 2H, J=8.0 Hz), 6.77 (d, 2H, J=8.80 Hz), 6.06 (d, 1H, J=5.6 Hz), 5.27 (s, 2H), 5.16 (s, 2H), 4.74 (bt, 1H), 4.45 (d, 2H, J=5.6 Hz), 3.57 (t, 2H, J=5.20 Hz), 3.41-3.48 (m, 4H), 3.38 (t, 2H, J=5.20 Hz), 3.27 (s, 3H), 3.01 (s, 3H).

Example 70

A fluorescence-activated covalently labeling fluorescent probe 70 for SNAP protein tags was constructed using a molecular rotor as a viscosity-sensitive fluorescent dye.

-continued

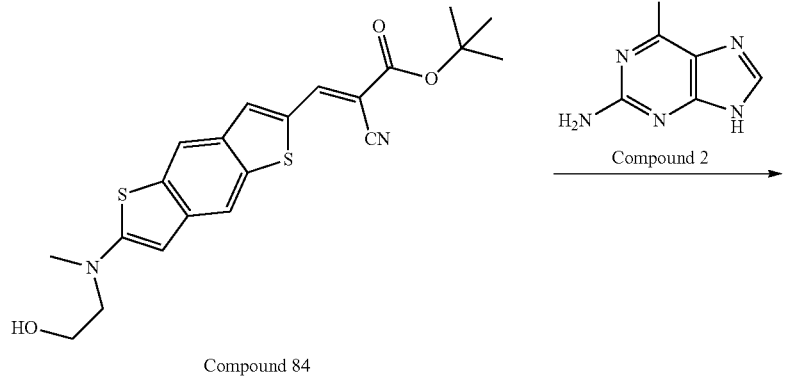

Compound 84

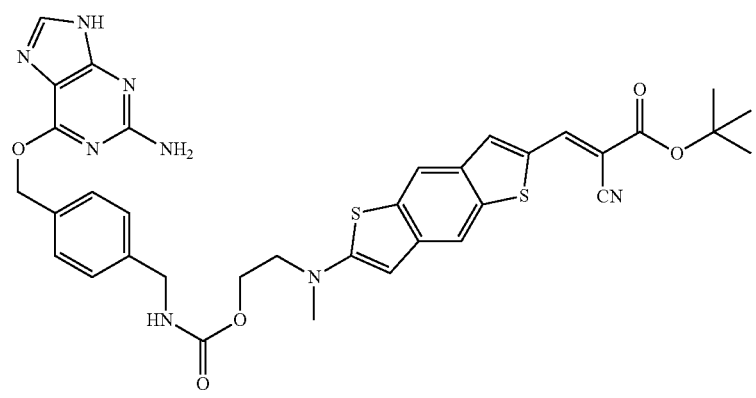

Probe 70

Compound 81

The synthesis was carried out by the method disclosed in the reference (WO2013142841 (A1) Sep. 26, 2013). ¹H-NMR (400 MHz, CDCl₃): δ=7.87 (s, 2H), 7.54 (s, 1H), 7.42 (d, J=5.6 Hz, 1H), 7.39 (d, J=5.6 Hz, 1H).

Compound 82

This compound was obtained by following the general procedure for compound 21, and the yield was 76%. ¹H-NMR (400 MHz, CDCl₃): δ=7.87 (s, 2H), 7.54 (s, 1H), 7.42 (d, J=5.6 Hz, 1H), 7.39 (d, J=5.6 Hz, 1H), 3.86 (t, 2H, J=4.80 Hz), 3.56 (t, 2H, J=4.80 Hz), 3.06 (s, 3H).

Compound 83

This compound was obtained by following the general procedure for compound 22, and the yield was 62%. ¹H-NMR (400 MHz, CDCl3): δ=9.99 (s, 1H), 7.89 (s, 2H), 7.59 (s, 1H), 7.27 (s, 1H), 3.86 (t, 2H, J=4.80 Hz), 3.56 (t, 2H, J=4.80 Hz), 3.06 (s, 3H).

Compound 84

This compound was obtained by following the general procedure for compound 1, and the yield was 88%. ¹H-NMR (400 MHz, CDCl₃): δ=7.89 (s, 2H), 7.59 (s, 1H), 7.27 (s, 1H), 7.05 (s, 1H), 3.86 (t, 2H, J=4.80 Hz), 3.56 (t, 2H, J=4.80 Hz), 3.06 (s, 3H).

Probe 70

This probe was obtained by following the general procedure for probe 1, and the yield was 54%. ¹H-NMR (400 MHz, CDCl₃): δ=12.22 (s, 1H), 10.11 (s, 1H), 7.89 (s, 2H), 7.81 (s, 1H), 7.59 (s, 1H), 7.40 (m, 4H), 7.27 (s, 1H), 7.05 (s, 1H), 6.29 (s, 2H), 5.46 (s, 2H), 4.40 (d, 2H, J=4.8 Hz), 3.86 (t, 2H, J=4.80 Hz), 3.56 (t, 2H, J=4.80 Hz), 3.06 (s, 3H).

Example 71

A fluorescence-activated covalently labeling fluorescent probe 71 for SNAP protein tags was constructed using a molecular rotor as a viscosity-sensitive fluorescent dye.

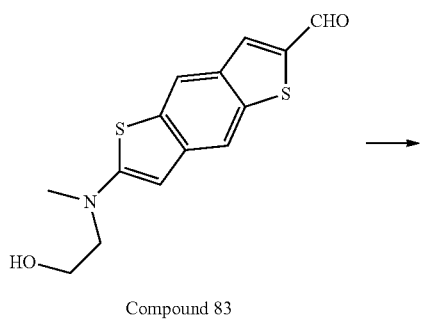

Compound 83

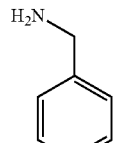

Compound 2

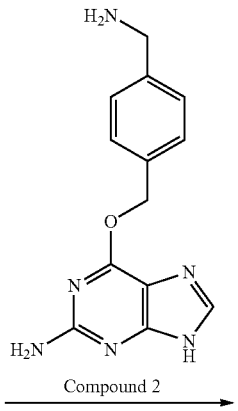

Compound 85

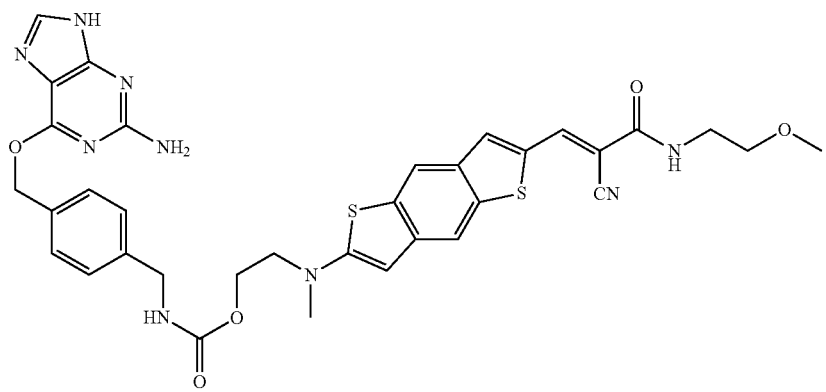

Probe 71

Compound 85

This compound was obtained by following the general procedure for compound 1, and the yield was 95%. $^1$H-NMR (400 MHz, CDCl$_3$): δ=7.98 (s, 1H), 7.89 (s, 2H), 7.59 (s, 1H), 7.27 (s, 1H), 3.86 (t, 2H, J=4.80 Hz), 3.56 (t, 2H, J=4.80 Hz), 3.48-3.50 (m, 4H), 3.38 (s, 3H), 3.06 (s, 3H).

Probe 71

This probe was obtained by following the general procedure for probe 1, and the yield was 66%. $^1$H-NMR (400 MHz, CDCl$_3$): δ=11.92 (s, 1H), 10.21 (s, 1H), 7.98 (s, 1H), 7.89 (s, 2H), 7.81 (s, 1H), 7.59 (s, 1H), 7.40 (m, 4H), 7.27 (s, 1H), 6.29 (s, 2H), 5.46 (s, 2H), 4.40 (d, 2H, J=4.8 Hz), 3.86 (t, 2H, J=4.80 Hz), 3.56 (t, 2H, J=4.80 Hz), 3.48-3.50 (m, 4H), 3.38 (s, 3H), 3.06 (s, 3H).

Example 72

A fluorescence-activated covalently labeling fluorescent probe 72 for CLIP protein tags was constructed using a molecular rotor as a viscosity-sensitive fluorescent dye.

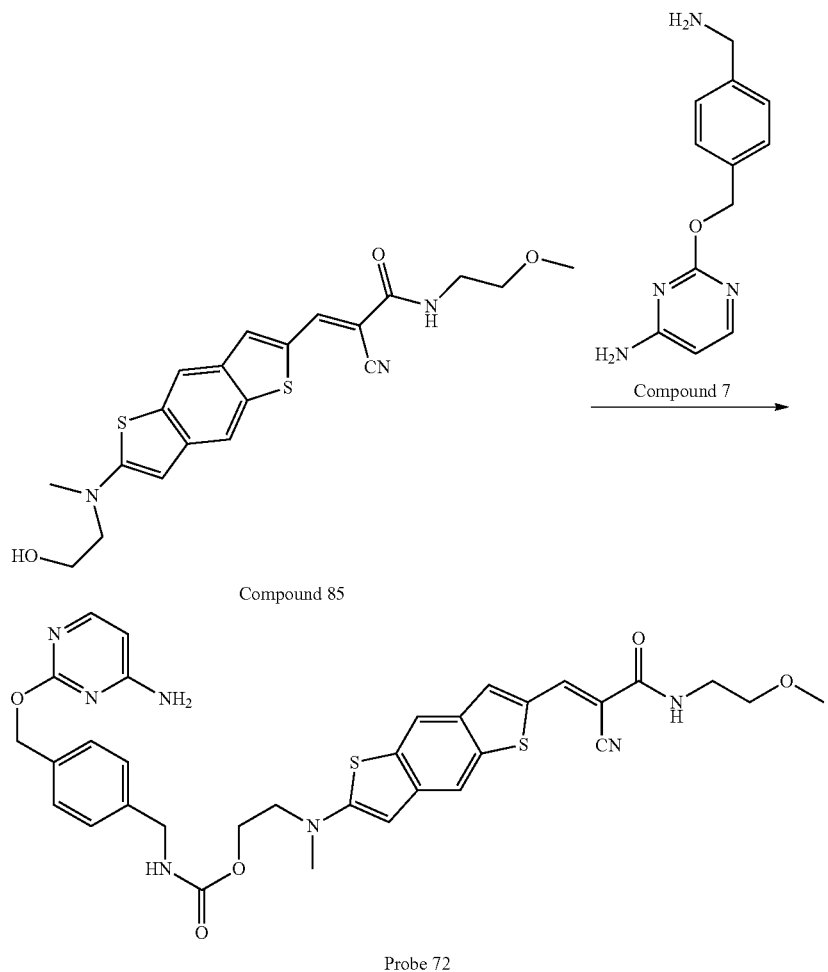

Probe 72

Probe 72

This probe was obtained by following the general procedure for probe 1, and the yield was 56%. $^1$H-NMR (400 MHz, CDCl$_3$): δ=7.98 (s, 1H), 7.93 (d, 1H, J=5.6), 7.89 (s, 2H), 7.75 (s, 1H), 7.59 (s, 1H), 7.33 (d, 2H, J=8.0 Hz), 7.27 (s, 1H), 7.19 (d, 2H, J=8.0 Hz), 6.06 (d, 1H, J=5.6 Hz), 5.27 (s, 2H), 5.16 (s, 2H), 4.45 (d, 2H, J=5.6 Hz), 3.86 (t, 2H, J=4.80 Hz), 3.56 (t, 2H, J=4.80 Hz), 3.48-3.50 (m, 4H), 3.38 (s, 3H), 3.06 (s, 3H).

Example 73

A fluorescence-activated covalently labeling fluorescent probe 73 for SNAP protein tags was constructed using a molecular rotor as a viscosity-sensitive fluorescent dye.

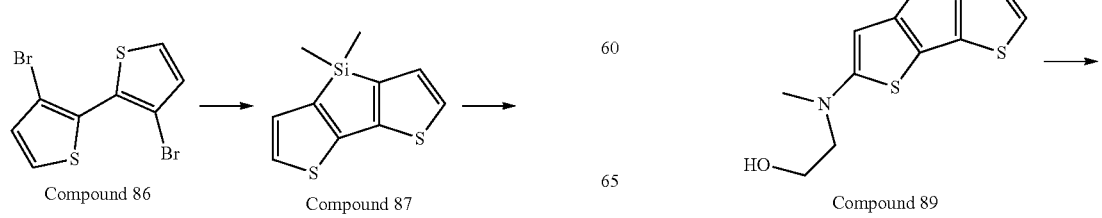

-continued

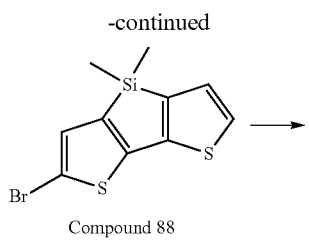

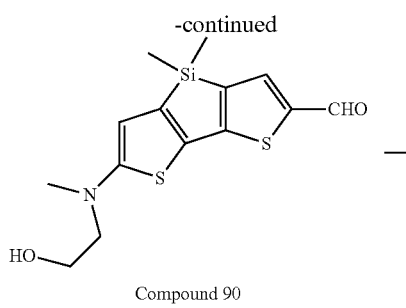

Compound 90

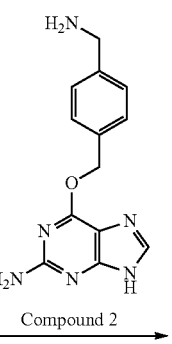

Compound 91

Compound 87

The synthesis was carried out by the method disclosed in the literature (Takuya M. et al. RSC Adv. 2015.5.55406-55410). ¹H-NMR (400 MHz, CDCl₃): δ=7.20 (d, 2H, J=4.8 Hz), 7.07 (d, 2H, J=4.8 Hz), 0.41 (s, 6H).

Compound 88

Compound 87 (0.4 g, 1.8 mmol) was dissolved in 100 ml of anhydrous tetrahydrofuran, cooled to −30° C., added with N-bromodibutimide, stirred under the protection of Ar for 2 hrs, and 5 ml of water was added to quench the reaction. The system was returned to room temperature, and the solvent was completely removed by rotary evaporation, and the residue was dissolved in 100 ml of dichloromethane and washed with water three times. The organic phase was dried over anhydrous Na₂SO₄, and Na₂SO₄ was removed by filtration. The solvent was removed by rotary evaporation to give a residue which was purified by gel silica gel column chromatography to give a white solid 0.31 g, and the yield was 57%. ¹H-NMR (400 MHz, CDCl₃): δ=7.73 (s, 1H), 7.42 (d, 1H, J=4.8 Hz), 7.15 (d, 1H, J=4.8 Hz), 0.46 (s, 6H).

Compound 89

This compound was obtained by following the general procedure for compound 21, and the yield was 76%. ¹H-NMR (400 MHz, CDCl₃): δ=7.73 (s, 1H), 7.42 (d, 1H, J=4.8 Hz), 7.15 (d, 1H, J=4.8 Hz), 3.86 (t, 2H, J=4.80 Hz), 3.56 (t, 2H, J=4.80 Hz), 3.06 (s, 3H), 0.46 (s, 6H).

Compound 90

This compound was obtained by following the general procedure for compound 22, and the yield was 66%. ¹H-NMR (400 MHz, CDCl₃): δ=9.87 (s, 1H), 7.83 (s, 1H), 7.10 (s, 1H), 3.85 (t, 2H, J=4.80 Hz), 3.46 (t, 2H, J=4.80 Hz), 3.06 (s, 3H), 0.46 (s, 6H).

Compound 91

This compound was obtained by following the general procedure for compound 1, and the yield was 98%. ¹H-NMR (400 MHz, CDCl₃): δ=7.83 (s, 1H), 7.11 (s, 1H), 3.85 (t, 2H, J=4.80 Hz), 3.46 (t, 2H, J=4.80 Hz), 3.06 (s, 3H), 0.46 (s, 6H).

Probe 73

This probe was obtained by following the general procedure for probe 1, and the yield was 45%. ¹H-NMR (400 MHz, DMSO-d₆): δ=11.82 (s, 1H), 10.00 (s, 1H), 7.83 (s, 1H), 7.81 (s, 1H), 7.40 (m, 4H), 7.11 (s, 1H), 6.29 (s, 2H), 5.46 (s, 2H), 4.40 (d, 2H, J=4.8 Hz), 3.85 (t, 2H, J=4.80 Hz), 3.46 (t, 2H, J=4.80 Hz), 3.06 (s, 3H), 0.46 (s, 6H).

Example 74

A fluorescence-activated covalently labeling fluorescent probe 74 for SNAP protein tags was constructed using a molecular rotor as a viscosity-sensitive fluorescent dye.

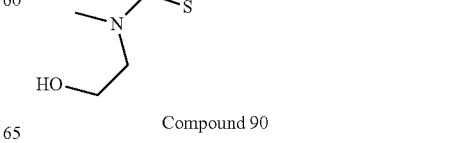

Compound 90

187
-continued

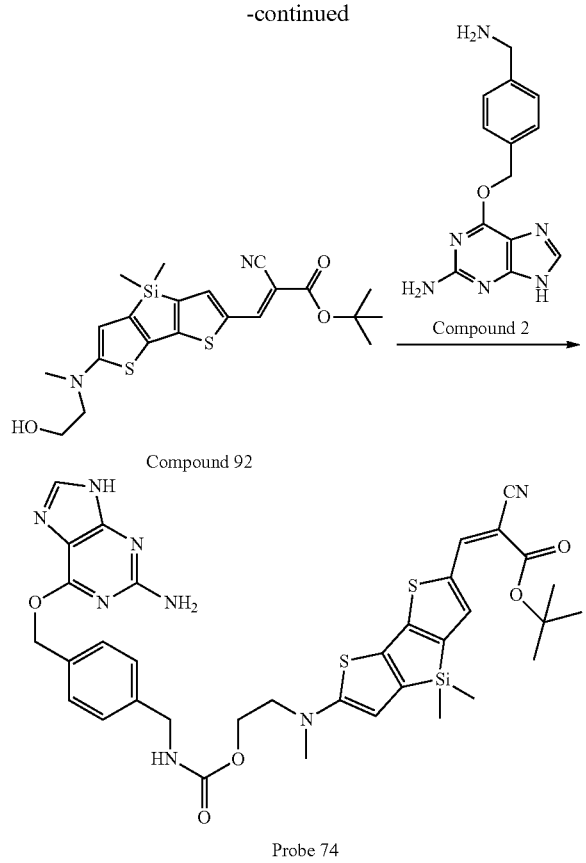

Compound 92

Probe 74

Compound 92

This compound was obtained by following the general procedure for compound 1, and the yield was 98%. ¹H-NMR (400 MHz, CDCl$_3$): δ=7.83 (s, 1H), 7.11 (s, 1H), 3.85 (t, 2H, J=4.80 Hz), 3.46 (t, 2H, J=4.80 Hz), 3.06 (s, 3H), 1.50 (s, 9H), 0.42 (s, 6H).

Probe 74

This probe was obtained by following the general procedure for probe 1, and the yield was 45%. ¹H-NMR (400 MHz, DMSO-d$_6$): δ=10.92 (s, 1H), 9.84 (s, 1H), 7.83 (s, 1H), 7.71 (s, 1H), 7.40 (m, 4H), 7.11 (s, 1H), 6.29 (s, 2H), 5.46 (s, 2H), 4.40 (d, 2H, J=4.8 Hz), 3.85 (t, 2H, J=4.80 Hz), 3.46 (t, 2H, J=4.80 Hz), 3.06 (s, 3H), 1.50 (s, 9H), 0.46 (s, 6H).

Example 75

A fluorescence-activated covalently labeling fluorescent probe 75 for SNAP protein tags was constructed using a molecular rotor as a viscosity-sensitive fluorescent dye.

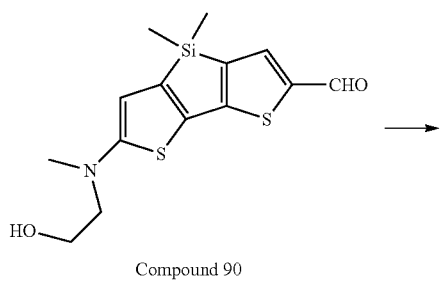

Compound 90

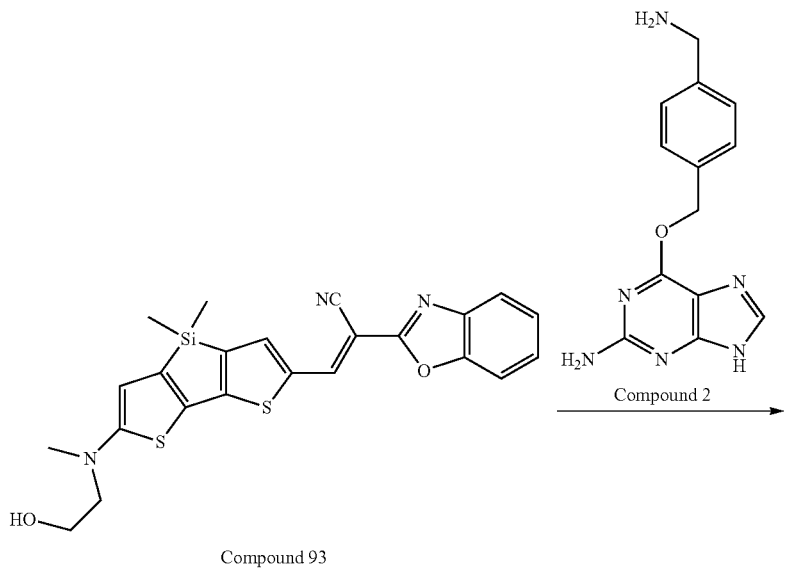

Compound 93

-continued

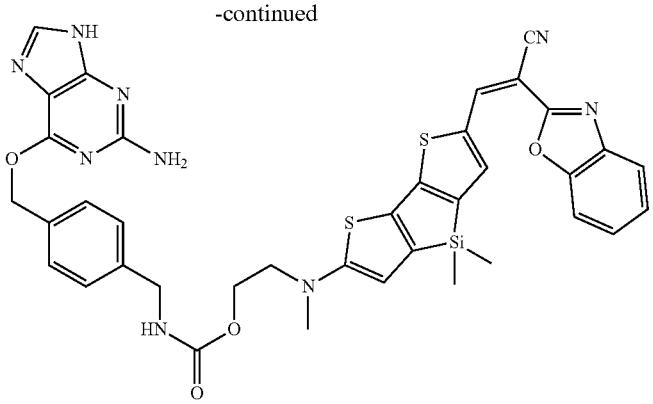

Probe 75

Compound 93

This compound was obtained by following the general procedure for compound 1, and the yield was 91%. $^1$H-NMR (400 MHz, CDCl$_3$): δ=7.83 (s, 1H), 7.74 (1H, d, J=4.0 Hz), 7.55 (1H, d, J=4.0 Hz), 7.36-7.42 (2H, m), 7.11 (s, 1H), 4.12 (2H, s), 3.85 (t, 2H, J=4.80 Hz), 3.46 (t, 2H, J=4.80 Hz), 3.06 (s, 3H), 0.42 (s, 6H).

Probe 75

This probe was obtained by following the general procedure for probe 1, and the yield was 45%. $^1$H-NMR (400 MHz, CDCl$_3$): δ=11.22 (s, 1H), 10.01 (s, 1H), 7.89 (s, 1H), 7.81 (s, 1H), 7.74 (1H, d, J=4.0 Hz), 7.70 (1H, d, J=4.0 Hz), 7.63-7.48 (m, 5H), 7.46 (m, 4H), 7.36-7.42 (2H, m), 7.11 (s, 1H), 6.29 (s, 2H), 5.46 (s, 2H), 4.40 (d, 2H, J=4.8 Hz), 4.12 (2H, s), 3.85 (t, 2H, J=4.80 Hz), 3.46 (t, 2H, J=4.80 Hz), 3.13 (s, 3H), 3.06 (s, 3H), 0.46 (s, 6H).

Example 76

A fluorescence-activated covalently labeling fluorescent probe 76 for CLIP protein tags was constructed using a molecular rotor as a viscosity-sensitive fluorescent dye.

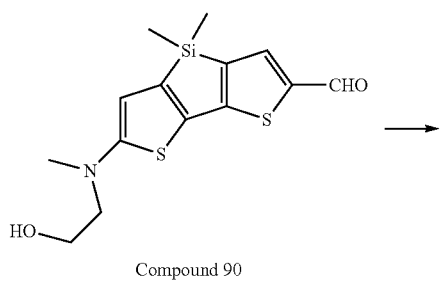

Compound 90

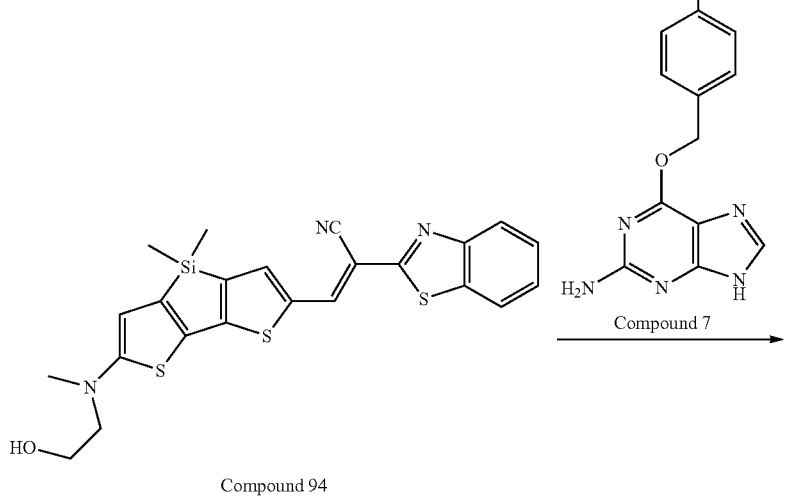

Compound 94

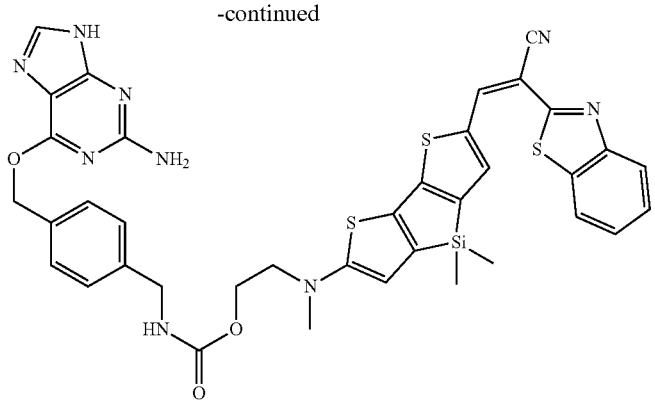

Probe 76

Compound 94

This compound was obtained by following the general procedure for compound 1, and the yield was 98%. $^1$H-NMR (400 MHz, CDCl$_3$): δ=7.99 (s, 1H), 7.11 (s, 1H), 6.50 (s, 1H), 3.85 (t, 2H, J=4.80 Hz), 3.46 (t, 2H, J=4.80 Hz), 3.06 (s, 3H), 0.46 (s, 6H).

Probe 76

This probe was obtained by following the general procedure for probe 1, and the yield was 45%. $^1$H-NMR (400 MHz, CDCl$_3$): δ=12.42 (s, 1H), 10.01 (s, 1H), 7.99 (s, 1H), 7.81 (s, 1H), 7.4 (m, 4H), 7.11 (s, 1H), 6.50 (s, 1H), 6.29 (s, 2H), 5.46 (s, 2H), 4.40 (d, 2H, J=4.8 Hz), 3.85 (t, 2H, J=4.80 Hz), 3.46 (t, 2H, J=4.80 Hz), 3.06 (s, 3H), 0.46 (s, 6H).

Example 77

A fluorescence-activated covalently labeling fluorescent probe 77 for SNAP protein tags was constructed using a molecular rotor as a viscosity-sensitive fluorescent dye.

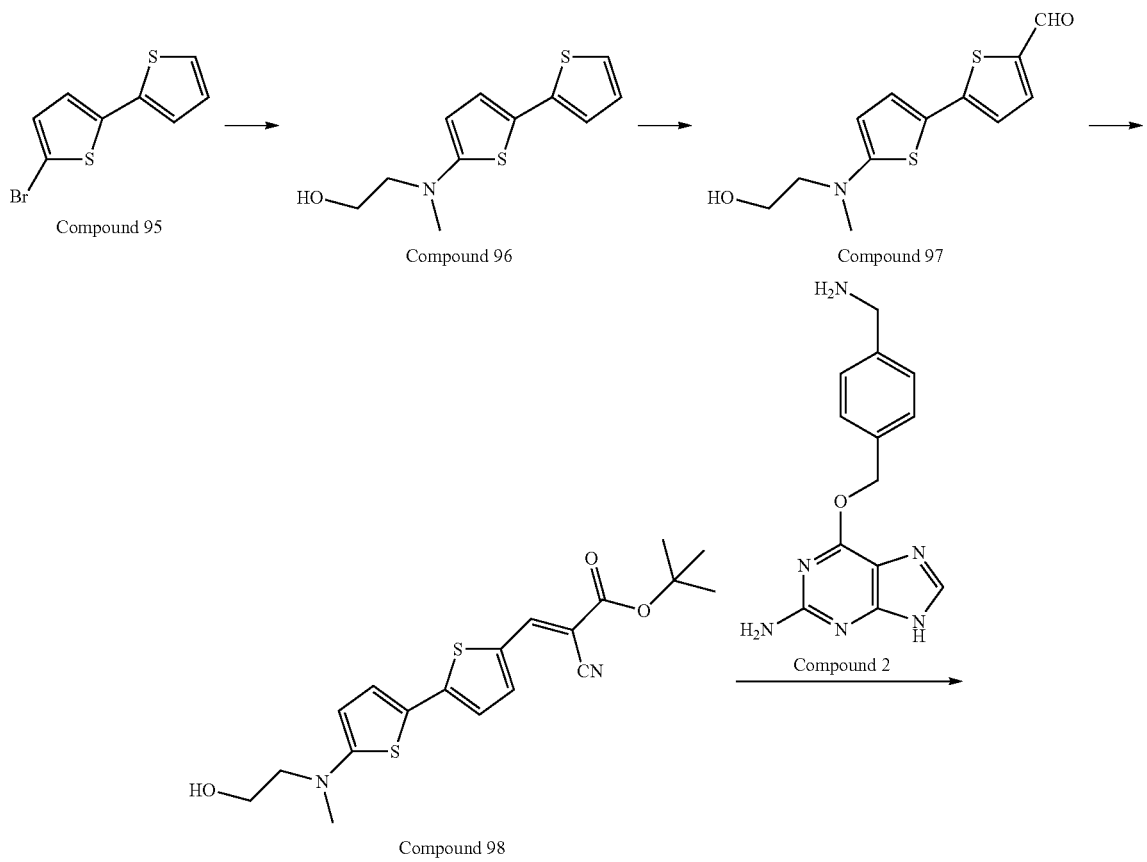

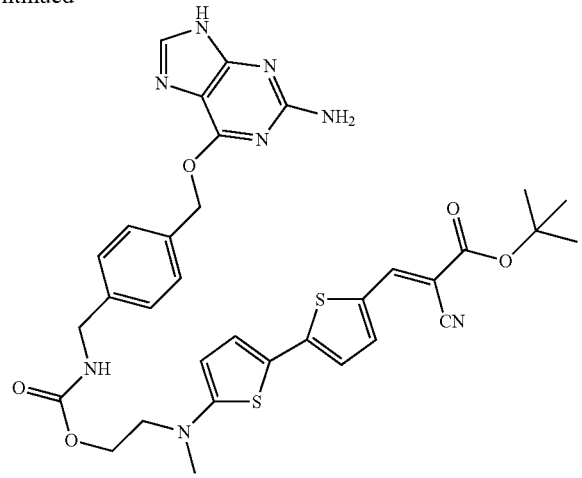

Probe 77

Compound 95

The synthesis was carried out by the method disclosed in the literature (Martinez M. et al. Org. Biomol. Chem. 2012, 10.3892-3898). $^1$H-NMR (400 MHz, CDCl$_3$): δ=7.24 (dd, $J_1$=5.2 Hz, $J_2$=1.2 Hz, 1H), 7.13 (dd, 1H, $J_1$=3.6 Hz, $J_2$=1.2 Hz), 7.03 (dd, 1H, $J_1$=5.2 Hz, $J_2$=1.2 Hz), 6.99 (d, 1H, J=3.8 Hz), 6.93 (d, 1H, J=3.6 Hz).

Compound 96

This compound was obtained by following the general procedure for compound 21, and the yield was 78%. $^1$H-NMR (400 MHz, CDCl$_3$): δ=7.25 (dd, $J_1$=5.2 Hz, $J_2$=1.2 Hz, 1H), 7.13 (dd, 1H, $J_1$=3.6 Hz, $J_2$=1.2 Hz), 7.03 (dd, 1H, $J_1$=5.2 Hz, $J_2$=1.2 Hz), 6.99 (d, 1H, J=3.8 Hz), 6.93 (d, 1H, J=3.6 Hz), 3.85 (t, 2H, J=4.80 Hz), 3.46 (t, 2H, J=4.80 Hz), 3.10 (s, 3H).

Compound 97

This compound was obtained by following the general procedure for compound 22, and the yield was 65%. $^1$H-NMR (400 MHz, DMSO-d$_6$): δ=9.75 (s, 1H), 7.57 (d, 1H, J=4.00 Hz), 7.13 (d, 1H, J=4.00 Hz), 6.95 (d, 1H, J=4.00 Hz), 5.81 (d, 1H, J=4.00 Hz), 3.67 (t, 2H, J=5.60 Hz), 3.35 (t, 2H, J=5.60 Hz), 3.27 (s, 3H), 3.13 (s, 3H).

Compound 98

This compound was obtained by following the general procedure for compound 1, and the yield was 98%. $^1$H-NMR (400 MHz, DMSO-d$_6$): δ=8.00 (s, 1H), 7.57 (d, 1H, J=4.00 Hz), 7.13 (d, 1H, J=4.00 Hz), 6.95 (d, 1H, J=4.00 Hz), 5.81 (d, 1H, J=4.00 Hz), 3.67 (t, 2H, J=5.60 Hz), 3.35 (t, 2H, J=5.60 Hz), 3.13 (s, 3H), 1.50 (s, 9H).

Probe 77

This probe was obtained by following the general procedure for probe 1, and the yield was 45%. $^1$H-NMR (400 MHz, DMSO-d$_6$): δ=11.52 (s, 1H), 10.01 (s, 1H), 8.00 (s, 1H), 7.57 (d, 1H, J=4.00 Hz), 7.81 (s, 1H), 7.40 (m, 4H), 7.13 (d, 1H, J=4.00 Hz), 6.95 (d, 1H, J=4.00 Hz), 6.29 (s, 2H), 5.81 (d, 1H, J=4.00 Hz), 5.46 (s, 2H), 4.40 (d, 2H, J=4.8 Hz), 3.67 (t, 2H, J=5.60 Hz), 3.35 (t, 2H, J=5.60 Hz), 3.27 (s, 3H), 3.13 (s, 3H), 1.50 (s, 9H).

Example 78

A fluorescence-activated covalently labeling fluorescent probe 78 for SNAP protein tags was constructed using a molecular rotor as a viscosity-sensitive fluorescent dye.

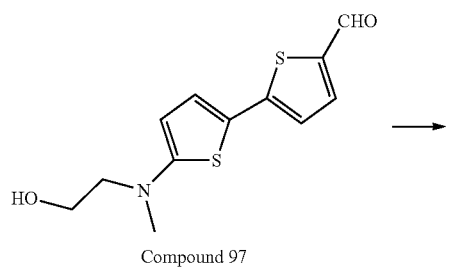

Compound 97

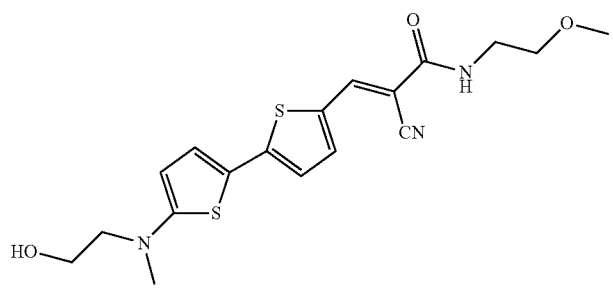

Compound 99

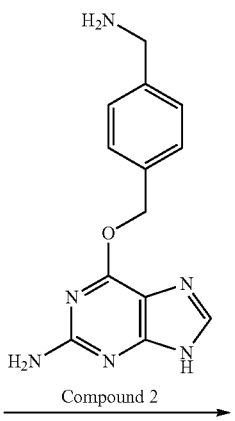

Compound 2

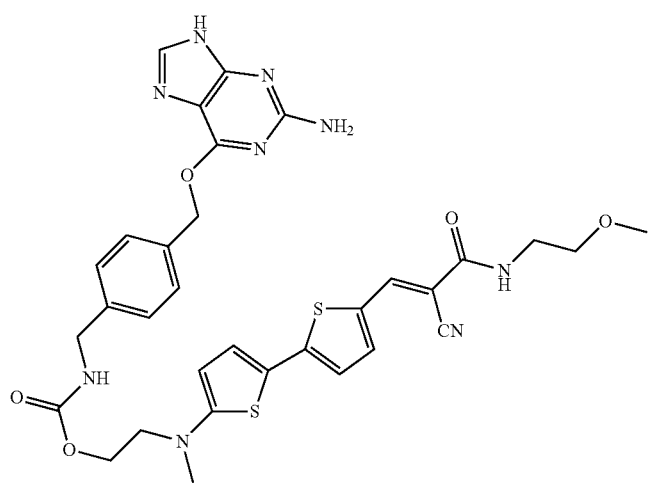

Probe 78

Compound 99

This compound was obtained by following the general procedure for compound 1, and the yield was 96%. $^1$H-NMR (400 MHz, DMSO-d$_6$): δ=12.42 (s, 1H), 10.01 (s, 1H), 8.00 (s, 1H), 7.81 (s, 1H), 7.57 (d, 1H, J=4.00 Hz), 7.40 (m, 4H), 7.13 (d, 1H, J=4.00 Hz), 6.95 (d, 1H, J=4.00 Hz), 6.29 (s, 2H), 5.81 (d, 1H, J=4.00 Hz), 5.46 (s, 2H), 4.40 (d, 2 H, J=4.8 Hz), 3.67 (t, 2H, J=5.60 Hz), 3.48-3.52 (m, 4H), 3.38 (s, 3H), 3.35 (t, 2H, J=5.60 Hz), 3.13 (s, 3H).

Probe 78

This probe was obtained by following the general procedure for probe 1, and the yield was 56%. $^1$H-NMR (400 MHz, DMSO-d$_6$): δ=8.00 (s, 1H), 7.57 (d, 1H, J=4.00 Hz), 7.13 (d, 1H, J=4.00 Hz), 6.95 (d, 1H, J=4.00 Hz), 5.81 (d, 1H, J=4.00 Hz), 3.67 (t, 2H, J=5.60 Hz), 3.48-3.52 (m, 4H), 3.38 (s, 3H), 3.35 (t, 2H, J=5.60 Hz), 3.13 (s, 3H).

Example 79

A fluorescence-activated covalently labeling fluorescent probe 79 for SNAP protein tags was constructed using a molecular rotor as a viscosity-sensitive fluorescent dye.

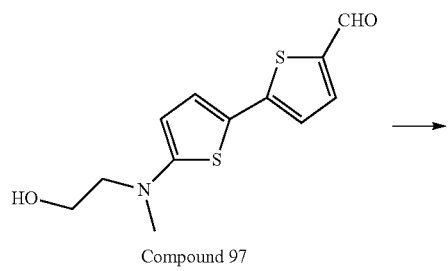

Compound 97

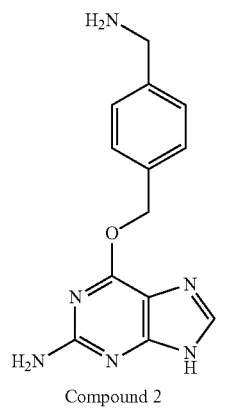

Compound 2

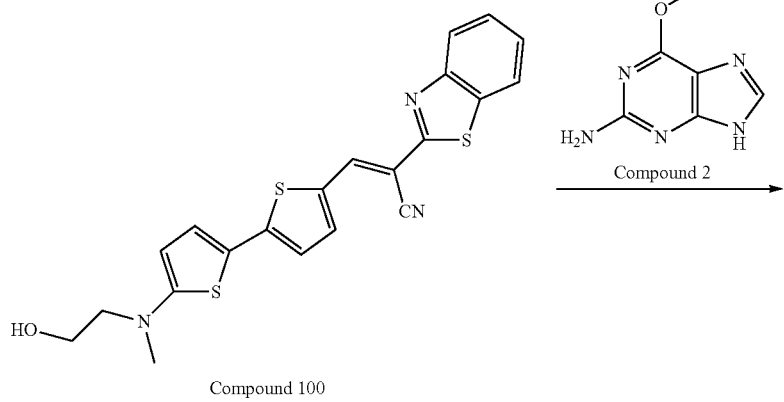

Compound 100

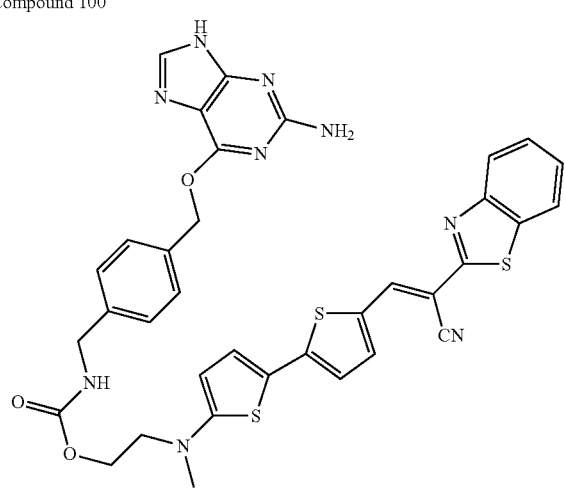

Probe 79

Compound 100

This compound was obtained by following the general procedure for compound 1, and the yield was 97%. ¹H-NMR (400 MHz, DMSO-d$_6$): δ=8.04 (d, 1H, J=8.0 Hz), 7.94 (d, 1H, J=8.0 Hz), 7.89 (s, 1H), 7.57 (d, 1H, J=4.00 Hz), 7.53 (t, 1H, J=8.0 Hz), 7.45 (t, 1H, J=8.0 Hz), 7.13 (d, 1H, J=4.00 Hz), 6.95 (d, 1H, J=4.00 Hz), 5.81 (d, 1H, J=4.00 Hz), 3.67 (t, 2H, J=5.60 Hz), 3.35 (t, 2H, J=5.60 Hz), 3.13 (s, 3H).

Probe 79

This probe was obtained by following the general procedure for probe 1, and the yield was 48%. ¹H-NMR (400 MHz, DMSO-d$_6$): δ=11.82 (s, 1H), 10.21 (s, 1H), 8.04 (d, 1H, J=8.0 Hz), 7.94 (d, 1H, J=8.0 Hz), 7.89 (s, 1H), 7.81 (s, 1H), 7.57 (d, 1H, J=4.00 Hz), 7.53 (t, 1H, J=8.0 Hz), 7.45 (t, 1H, J=8.0 Hz), 7.40 (m, 4H), 7.13 (d, 1H, J=4.00 Hz), 6.95 (d, 1H, J=4.00 Hz), 6.29 (s, 2H), 5.81 (d, 1H, J=4.00 Hz), 5.46 (s, 2H), 4.40 (d, 2H, J=4.8 Hz), 3.67 (t, 2H, J=5.60 Hz), 3.35 (t, 2H, J=5.60 Hz), 3.13 (s, 3H).

Example 80

A fluorescence-activated covalently labeling fluorescent probe 80 for CLIP protein tags was constructed using a molecular rotor as a viscosity-sensitive fluorescent dye.

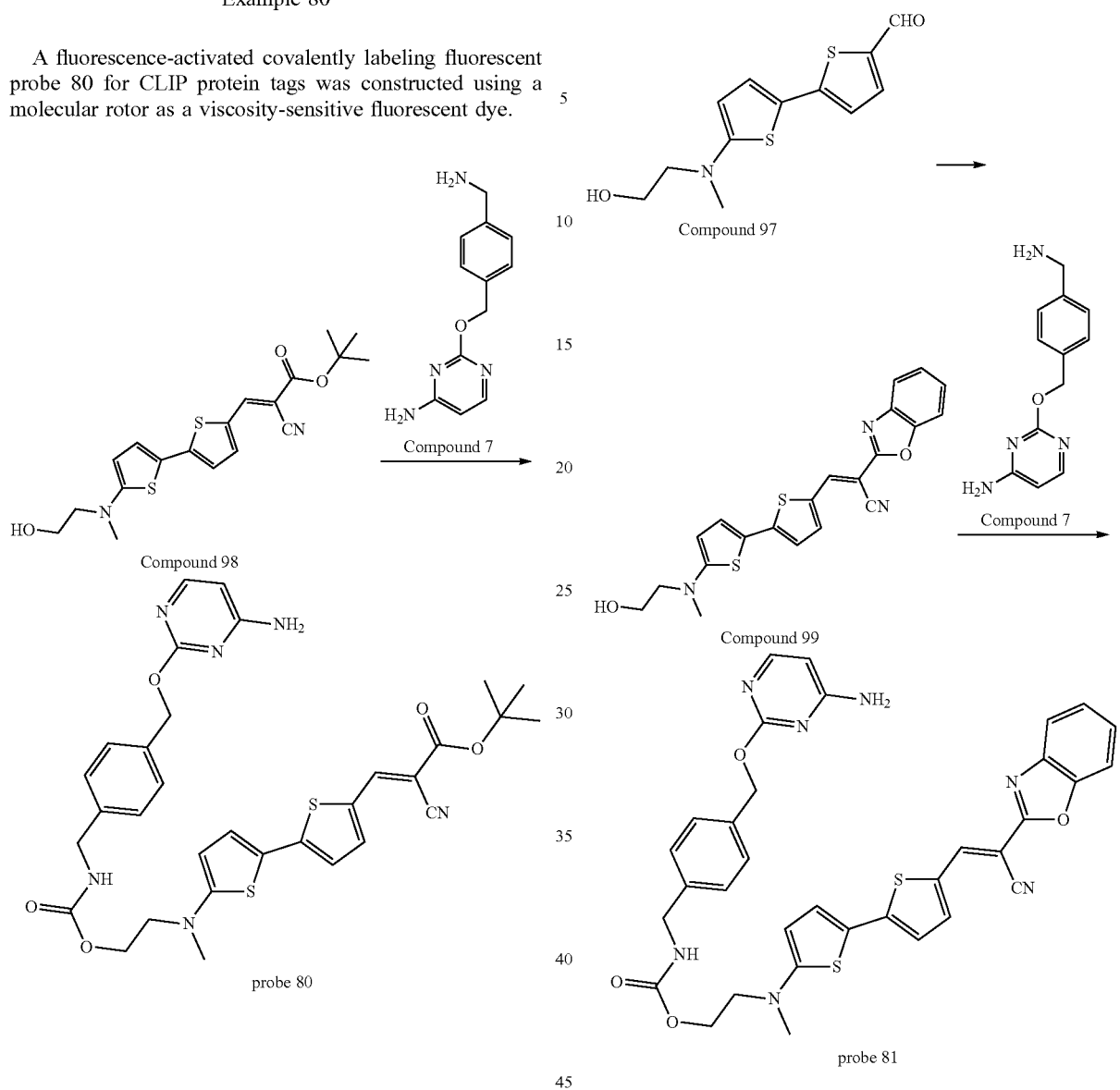

Probe 80

This probe was obtained by following the general procedure for probe 1, and the yield was 56%. $^1$H-NMR (400 MHz, DMSO-d$_6$): δ=8.00 (s, 1H), 7.93 (d, 1H, J=5.6), 7.75 (s, 1H), 7.57 (d, 1H, J=4.00 Hz), 7.33 (d, 2H, J=8.0 Hz), 7.19 (d, 2H, J=8.0 Hz), 7.13 (d, 1H, J=4.00 Hz), 6.95 (d, 1H, J=4.00 Hz), 6.06 (d, 1H, J=5.6 Hz), 5.81 (d, 1H, J=4.00 Hz), 5.27 (s, 2H), 5.16 (s, 2H), 4.45 (d, 2H, J=5.6 Hz), 3.67 (t, 2H, J=5.60 Hz), 3.35 (t, 2H, J=5.60 Hz), 3.13 (s, 3H), 1.50 (s, 9H).

Example 81

A fluorescence-activated covalently labeling fluorescent probe 81 for CLIP protein tags was constructed using a molecular rotor as a viscosity-sensitive fluorescent dye.

Compound 99

This compound was obtained by following the general procedure for compound 1, and the yield was 96%. $^1$H-NMR (400 MHz, DMSO-d$_6$): δ=8.00 (s, 1H), 7.74 (d, 1H, J=4.0 Hz), 7.57 (d, 1H, J=4.00 Hz), 7.51 (d, 1H, J=4.0 Hz), 7.36-7.42 (m, 2H), 7.13 (d, 1H, J=4.00 Hz), 6.95 (d, 1H, J=4.00 Hz), 5.81 (d, 1H, J=4.00 Hz), 3.67 (t, 2H, J=5.60 Hz), 3.35 (t, 2H, J=5.60 Hz), 3.13 (s, 3H).

Probe 81

This probe was obtained by following the general procedure for probe 1, and the yield was 58%. $^1$H-NMR (400 MHz, DMSO-d$_6$): δ=8.00 (s, 1H), 7.93 (d, 1H, J=5.6), 7.79 (s, 1H), 7.74 (d, 1H, J=4.0 Hz), 7.57 (d, 1H, J=4.00 Hz), 7.51 (d, 1H, J=4.0 Hz), 7.36-7.42 (m, 4H), 7.19 (d, 2H, J=8.0 Hz), 7.13 (d, 1H, J=4.00 Hz), 6.95 (d, 1H, J=4.00 Hz), 6.06 (d, 1H, J=5.6 Hz), 5.81 (d, 1H, J=4.00 Hz), 5.27 (s, 2H), 5.16

(s, 2H), 4.45 (d, 2H, J=5.6 Hz), 3.67 (t, 2H, J=5.60 Hz), 3.35 (t, 2H, J=5.60 Hz), 3.13 (s, 3H).

Example 82

A fluorescence-activated covalently labeling fluorescent probe 82 for CLIP protein tags was constructed using a molecular rotor as a viscosity-sensitive fluorescent dye.

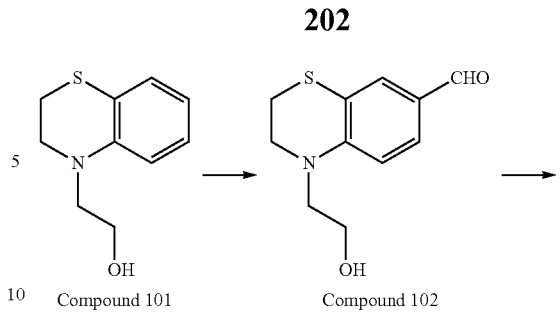

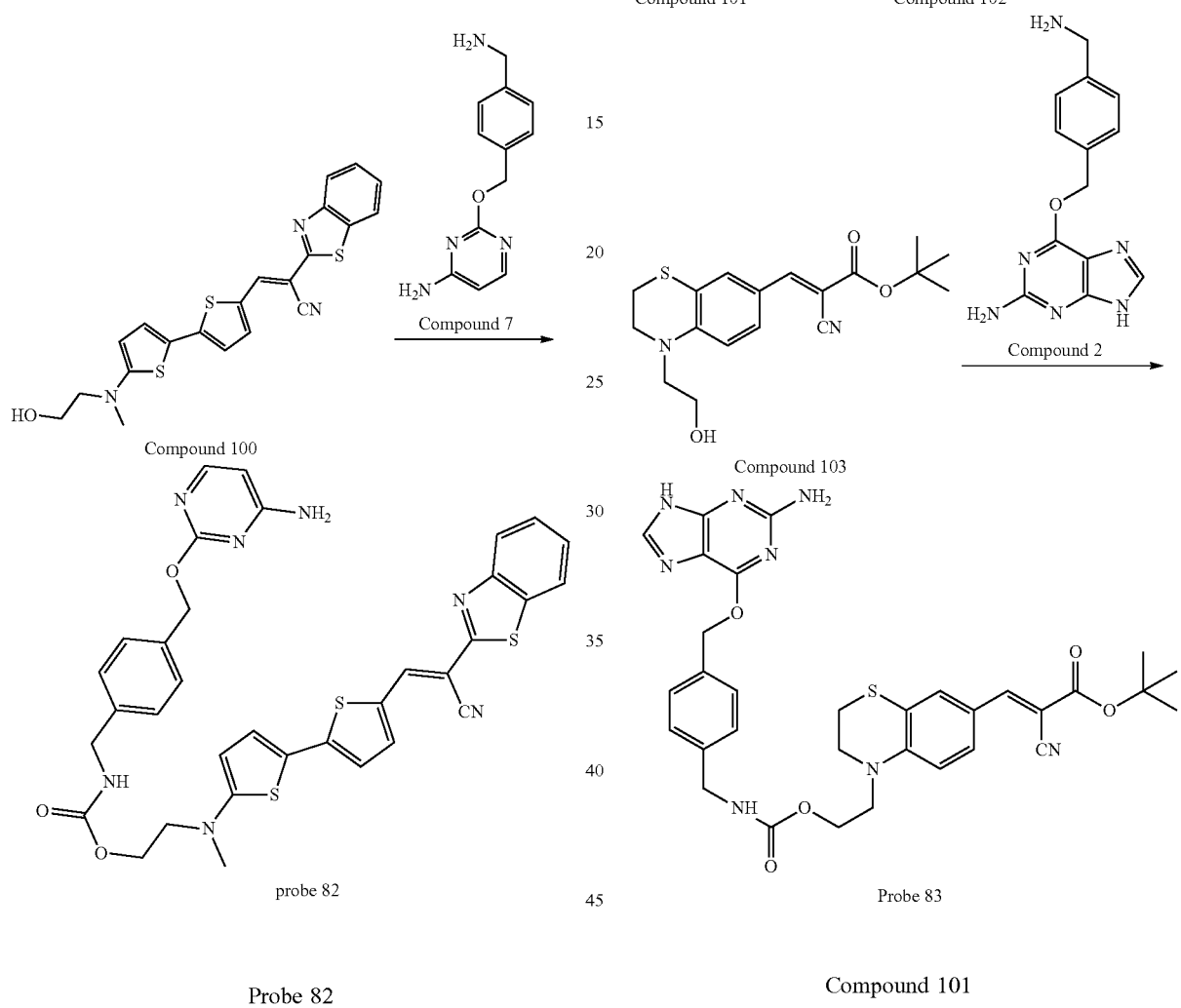

Probe 82

This probe was obtained by following the general procedure for probe 1, and the yield was 57%. $^1$H-NMR (400 MHz, DMSO-d$_6$): δ=8.04 (d, 1H, J=8.0 Hz), 7.94 (d, 2H, J=8.0 Hz), 7.89 (s, 1H), 7.75 (s, 1H), 7.57 (d, 1H, J=4.00 Hz), 7.53 (t, 1H, J=8.0 Hz), 7.45 (t, 1H, J=8.0 Hz), 7.33 (d, 2H, J=8.0 Hz), 7.19 (d, 2H, J=8.0 Hz), 7.13 (d, 1H, J=4.00 Hz), 6.95 (d, 1H, J=4.00 Hz), 6.06 (d, 1H, J=5.6 Hz), 5.81 (d, 1H, J=4.00 Hz), 5.27 (s, 2H), 5.16 (s, 2H), 4.45 (d, 2H, J=5.6 Hz), 3.67 (t, 2H, J=5.60 Hz), 3.35 (t, 2H, J=5.60 Hz), 3.13 (s, 3H).

Example 83

A fluorescence-activated covalently labeling fluorescent probe 83 for SNAP protein tags was constructed using a molecular rotor as a viscosity-sensitive fluorescent dye.

Compound 101

The synthesis was carried out by the method disclosed in the literature (WO2002020499 (A1). Apr. 14, 2002). $^1$H-NMR (400 MHz, DMSO-d$_6$): δ=6.91 (m, 2H), 6.71 (d, 1H, J=8.0 Hz), 6.50 (m, 1H) 4.71 (t, 1H, J=5.6 Hz), 3.62 (m, 2H), 3.56 (m, 2H), 3.35 (m, 2H), 3.00 (m, 2H).

Compound 102

This compound was obtained by following the general procedure for compound 22, and the yield was 57%. $^1$H-NMR (400 MHz, DMSO-d$_6$): δ=9.89 (s, 1H), 7.21 (s, 1H), 6.71 (d, 1H, J=8.0 Hz), 6.50 (m, 1H) 4.71 (t, 1H, J=5.6 Hz), 3.62 (m, 2H), 3.56 (m, 2H), 3.35 (m, 2H), 3.00 (m, 2H).

Compound 103

This compound was obtained by following the general procedure for compound 1, and the yield was 88%. $^1$H-NMR (400 MHz, DMSO-d₆): δ=7.99 (s, 1H), 7.21 (s, 1H), 6.71 (d, 1H, J=8.0 Hz), 6.50 (m, 1H) 4.71 (t, 1H, J=5.6 Hz), 3.62 (m, 2H), 3.56 (m, 2H), 3.35 (m, 2H), 3.00 (m, 2H), 1.49 (s, 9H).

Probe 83

This probe was obtained by following the general procedure for probe 1, and the yield was 68%. ¹H-NMR (400 MHz, DMSO-d₆): δ=11.42 (s, 1H), 10.01 (s, 1H), 7.99 (s, 1H), 7.81 (s, 1H), 7.40 (m, 4H), 7.21 (s, 1H), 6.71 (d, 1H, J=8.0 Hz), 6.50 (m, 1H), 6.29 (s, 2H), 5.46 (s, 2H), 4.40 (d, 2H, J=4.8 Hz), 3.62 (m, 2H), 3.56 (m, 2H), 3.35 (m, 2H), 3.00 (m, 2H), 1.49 (s, 9H).

Example 84

A fluorescence-activated covalently labeling fluorescent probe 84 for CLIP protein tags was constructed using a molecular rotor as a viscosity-sensitive fluorescent dye.

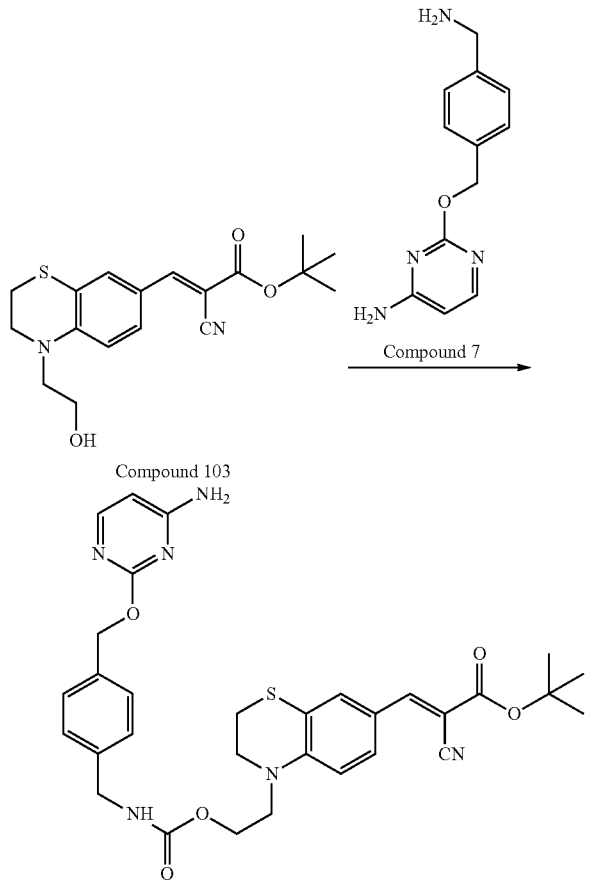

Probe 84

Probe 84

This probe was obtained by following the general procedure for probe 1, and the yield was 48%. ¹H-NMR (400 MHz, DMSO-d₆): δ=7.99 (s, 1H), 7.93 (d, 1H, J=5.6), 7.75 (s, 1H), 7.33 (d, 2H, J=8.0 Hz), 7.21 (s, 1H), 7.19 (d, 2H, J=8.0 Hz), 6.71 (d, 1H, J=8.0 Hz), 6.50 (m, 1H), 6.06 (d, 1H, J=5.6 Hz), 5.27 (s, 2H), 5.16 (s, 2H), 4.45 (d, 2H, J=5.6 Hz), 3.62 (m, 2H), 3.56 (m, 2H), 3.35 (m, 2H), 3.00 (m, 2H), 1.49 (s, 9H).

Example 85

A fluorescence-activated covalently labeling fluorescent probe 85 for SNAP protein tags was constructed using a molecular rotor as a viscosity-sensitive fluorescent dye.

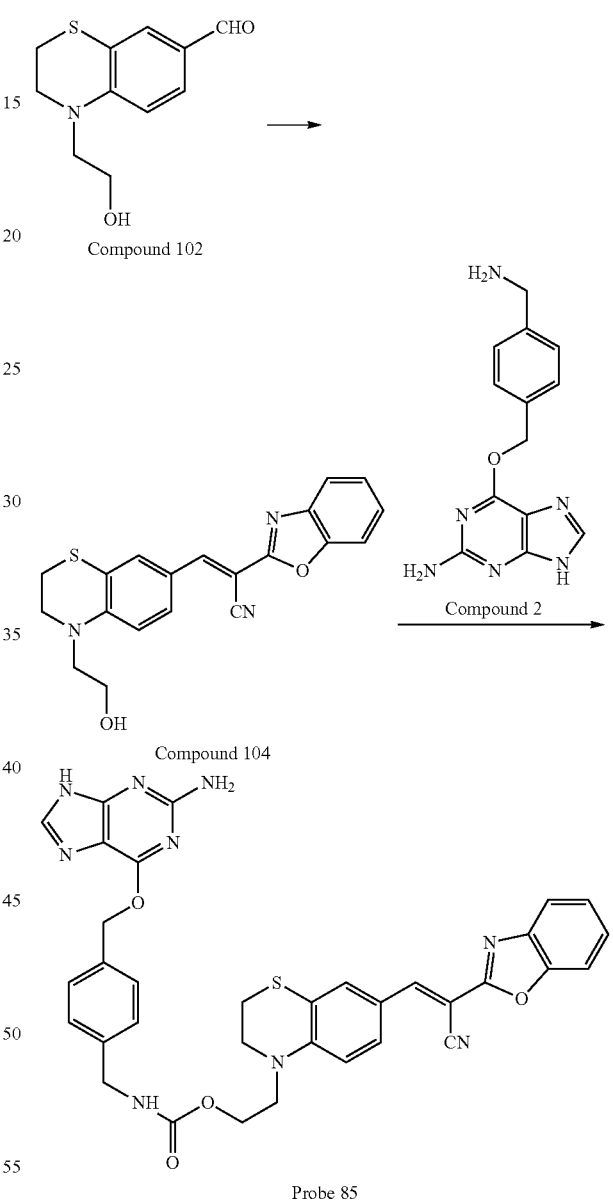

Compound 104

This compound was obtained by following the general procedure for compound 1, and the yield was 88%. ¹H-NMR (400 MHz, DMSO-d₆): δ=7.99 (s, 1H), 7.74 (d, 1H, J=4.0 Hz), 7.55 (d, 1H, J=4.0 Hz), 7.36-7.42 (m, 2H), 7.21 (s, 1H), 6.71 (d, 1H, J=8.0 Hz), 6.50 (m, 1H) 4.71 (t, 1H, J=5.6 Hz), 3.62 (m, 2H), 3.56 (m, 2H), 3.35 (m, 2H), 3.00 (m, 2H).

Probe 85

This probe was obtained by following the general procedure for probe 1, and the yield was 49%. $^1$H-NMR (400 MHz, DMSO-$d_6$): δ=11.82 (s, 1H), 10.51 (s, 1H), 7.99 (s, 1H), 7.81 (s, 1H), 7.74 (d, 1H, J=4.0 Hz), 7.55 (d, 1H, J=4.0 Hz), 7.47 (m, 4H), 7.36-7.42 (m, 2H), 7.21 (s, 1H), 6.71 (d, 1H, J=8.0 Hz), 6.50 (m, 1H), 6.29 (s, 2H), 5.46 (s, 2H), 4.40 (d, 2H, J=4.8 Hz), 3.62 (m, 2H), 3.56 (m, 2H), 3.35 (m, 2H), 3.00 (m, 2H).

Example 86

A fluorescence-activated covalently labeling fluorescent probe 86 for SNAP protein tags was constructed using a molecular rotor as a viscosity-sensitive fluorescent dye.

Probe 86

This probe was obtained by following the general procedure for probe 1, and the yield was 91%. $^1$H-NMR (400 MHz, DMSO-$d_6$): δ=8.04 (d, 1H, J=8.0 Hz), 8.02 (s, 1H), 7.90 (d, 1H, J=8.0 Hz), 7.53 (t, 1H, J=8.0 Hz), 7.45 (t, 1H, J=8.0 Hz), 7.21 (s, 1H), 6.71 (d, 1H, J=8.0 Hz), 6.50 (m, 1H) 4.71 (t, 1H, J=5.6 Hz), 3.62 (m, 2H), 3.56 (m, 2H), 3.35 (m, 2H), 3.00 (m, 2H).

Example 87

A fluorescence-activated covalently labeling fluorescent probe 87 for SNAP protein tags was constructed using a molecular rotor as a viscosity-sensitive fluorescent dye.

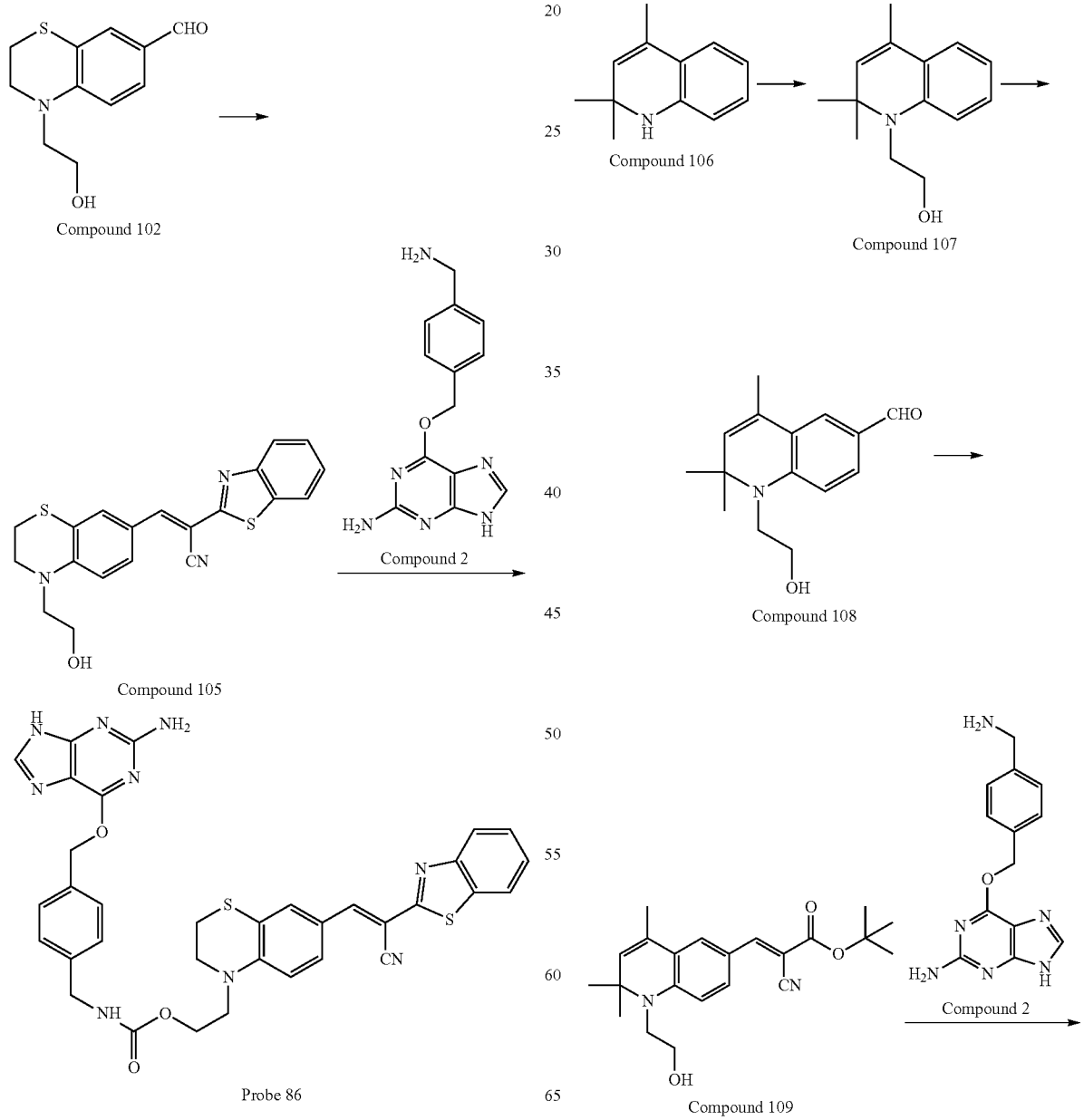

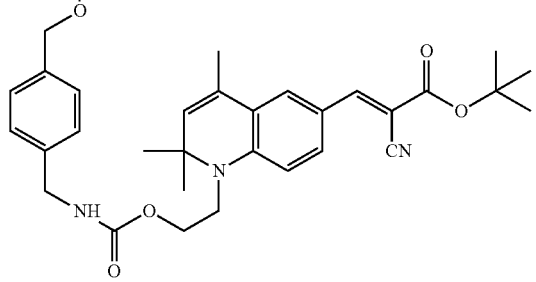

Probe 87

Compound 106

The synthesis was carried out by the method disclosed in Hao Y et al. Tetrahedron 2012. 68.552-558. $^1$H-NMR (400 MHz, CDCl₃): δ=7.06 (d, 1H, J=7.6 Hz), 6.94 (t, 1H, J=7.6H), 6.58 (t, 1H, J=7.2 Hz), 6.4 (d, 1H, 7.8 Hz), 5.19 (s, 1H), 2.35 (s, 3H), 1.36 (s, 6H).

Compound 107

Compound 106 (1.73 g, 10 mmol) was added to a 250 ml round bottom flask, potassium carbonate (2.76 g, 20 mol), bromoethanol (2.48 g, 20 mmol) was added, and 120 ml of acetonitrile was added. The mixture was heated to reflux in an oil bath for 48 h under the protection of Ar. After completion of the reaction, the system was filtered, and the solvent was completely removed by rotary evaporation. The residue was dissolved in 100 ml of dichloromethane, washed three times with 50 ml of water, and the organic phase was dried over anhydrous sodium sulfate. The solvent was removed by rotary evaporation, and the residue was purified by gel silica gel column chromatography to give a brown product 1.76 g, and the yield was 81%. $^1$H-NMR (400 MHz, CDCl₃): δ=7.06 (d, 1H, J=7.6 Hz), 6.94 (t, 1H, J=7.6H), 6.58 (t, 1H, J=7.2 Hz), 6.49 (d, 1H, 7.8 Hz), 3.46 (m, 4H), 2.35 (s, 3H), 1.36 (s, 6H).

Compound 108

This compound was obtained by following the general procedure for compound 22, and the yield was 65%. $^1$H-NMR (400 MHz, CDCl₃): δ=9.89 (s, 1H), 7.36 (d, 1H, J=7.6 Hz), 6.78 (t, 1H, J=7.2 Hz), 6.49 (d, 1H, 7.8 Hz), 3.46 (m, 4H), 2.35 (s, 3H), 1.36 (s, 6H).

Compound 109

This compound was obtained by following the general procedure for compound 1, and the yield was 99%. $^1$H-NMR (400 MHz, CDCl₃): δ=8.03 (s, 1H), 7.36 (d, 1H, J=7.6 Hz), 6.78 (t, 1H, J=7.2 Hz), 6.49 (d, 1H, 7.8 Hz), 3.46 (m, 4H), 2.35 (s, 3H), 1.50 (s, 9H), 1.36 (s, 6H).

Probe 87

This probe was obtained by following the general procedure for probe 1, and the yield was 61%. $^1$H-NMR (400 MHz, CDCl₃): δ=11.82 (s, 1H), 9.73 (s, 1H), 8.03 (s, 1H), 7.81 (s, 1H), 7.40 (m, 4H), 7.36 (d, 1H, J=7.6 Hz), 6.78 (t, 1H, J=7.2 Hz), 6.49 (d, 1H, 7.8 Hz), 6.29 (s, 2H), 5.46 (s, 2H), 4.40 (d, 2H, J=4.8 Hz), 3.46 (m, 4H), 2.35 (s, 3H), 1.50 (s, 9H), 1.36 (s, 6H).

Example 88

A fluorescence-activated covalently labeling fluorescent probe 88 for SNAP protein tags was constructed using a molecular rotor as a viscosity-sensitive fluorescent dye.

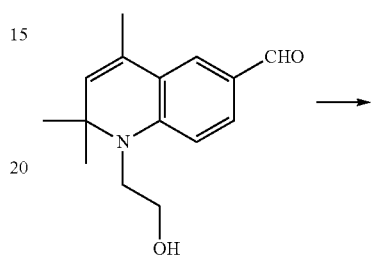

Compound 108

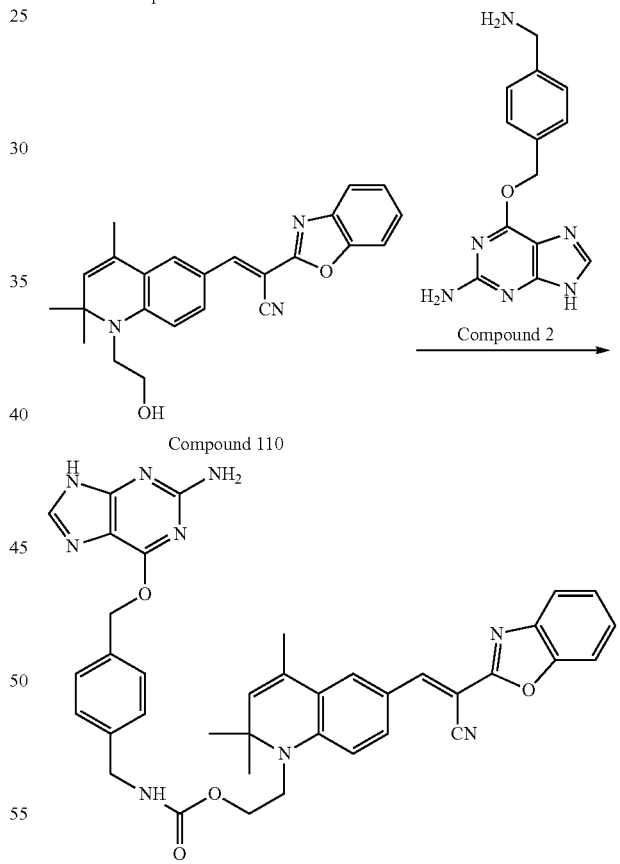

Probe 88

Compound 110

This compound was obtained by following the general procedure for compound 1, and the yield was 96%. $^1$H-NMR (400 MHz, CDCl₃): δ=8.03 (s, 1H), 7.74 (d, 1H, J=4.0 Hz), 7.55 (d, 1H, J=4.0 Hz), 7.36-7.42 (m, 2H), 7.30 (d, 1H, J=7.6

Hz), 6.78 (t, 1H, J=7.2 Hz), 6.49 (d, 1H, 7.8 Hz), 3.46 (m, 4H), 2.35 (s, 3H), 1.36 (s, 6H).

Probe 88

This probe was obtained by following the general procedure for probe 1, and the yield was 56%. $^1$H-NMR (400 MHz, DMSO-$d_6$): δ=11.72 (s, 1H), 9.56 (s, 1H), 8.03 (s, 1H), 7.81 (s, 1H), 7.74 (d, 1H, J=4.0 Hz), 7.55 (d, 1H, J=4.0 Hz), 7.49 (m, 4H), 7.36-7.42 (m, 2H), 7.30 (d, 1H, J=7.6 Hz), 6.78 (t, 1H, J=7.2 Hz), 6.49 (d, 1H, 7.8 Hz), 6.29 (s, 2H), 5.46 (s, 2H), 4.40 (d, 2H, J=4.8 Hz), 3.46 (m, 4H), 2.35 (s, 3H), 1.36 (s, 6H).

Example 89

A fluorescence-activated covalently labeling fluorescent probe 89 for SNAP protein tags was constructed using a molecular rotor as a viscosity-sensitive fluorescent dye.

Compound 111

This compound was obtained by following the general procedure for compound 1, and the yield was 99%. $^1$H-NMR (400 MHz, CDCl$_3$): δ=8.04 (d, 1H, J=8.0 Hz), 7.99 (s, 1H), 7.90 (d, 1H, J=8.0 Hz), 7.53 (t, 1H, J=8.0 Hz), 7.45 (t, 1H, J=8.0 Hz), 7.36 (d, 1H, J=7.6 Hz), 6.78 (t, 1H, J=7.2 Hz), 6.49 (d, 1H, 7.8 Hz), 3.46 (m, 4H), 2.35 (s, 3H), 1.36 (s, 6H).

Probe 89

This probe was obtained by following the general procedure for probe 1, and the yield was 61%. $^1$H-NMR (400 MHz, DMSO-$d_6$): δ=11.76 (s, 1H), 9.86 (s, 1H), 8.04 (d, 1H, J=8.0 Hz), 7.99 (s, 1H), 7.90 (d, 1H, J=8.0 Hz), 7.81 (s, 1H), 7.53 (t, 1H, J=8.0 Hz), 7.40 (m, 4H), 7.45 (t, 1H, J=8.0 Hz), 7.36 (d, 1H, J=7.6 Hz), 6.78 (t, 1H, J=7.2 Hz), 6.49 (d, 1H, 7.8 Hz), 6.29 (s, 2H), 5.46 (s, 2H), 4.40 (d, 2H, J=4.8 Hz), 3.46 (m, 4H), 2.35 (s, 3H), 1.36 (s, 6H).

Example 90

A fluorescence-activated covalently labeling fluorescent probe 90 for CLIP protein tags was constructed using a molecular rotor as a viscosity-sensitive fluorescent dye.

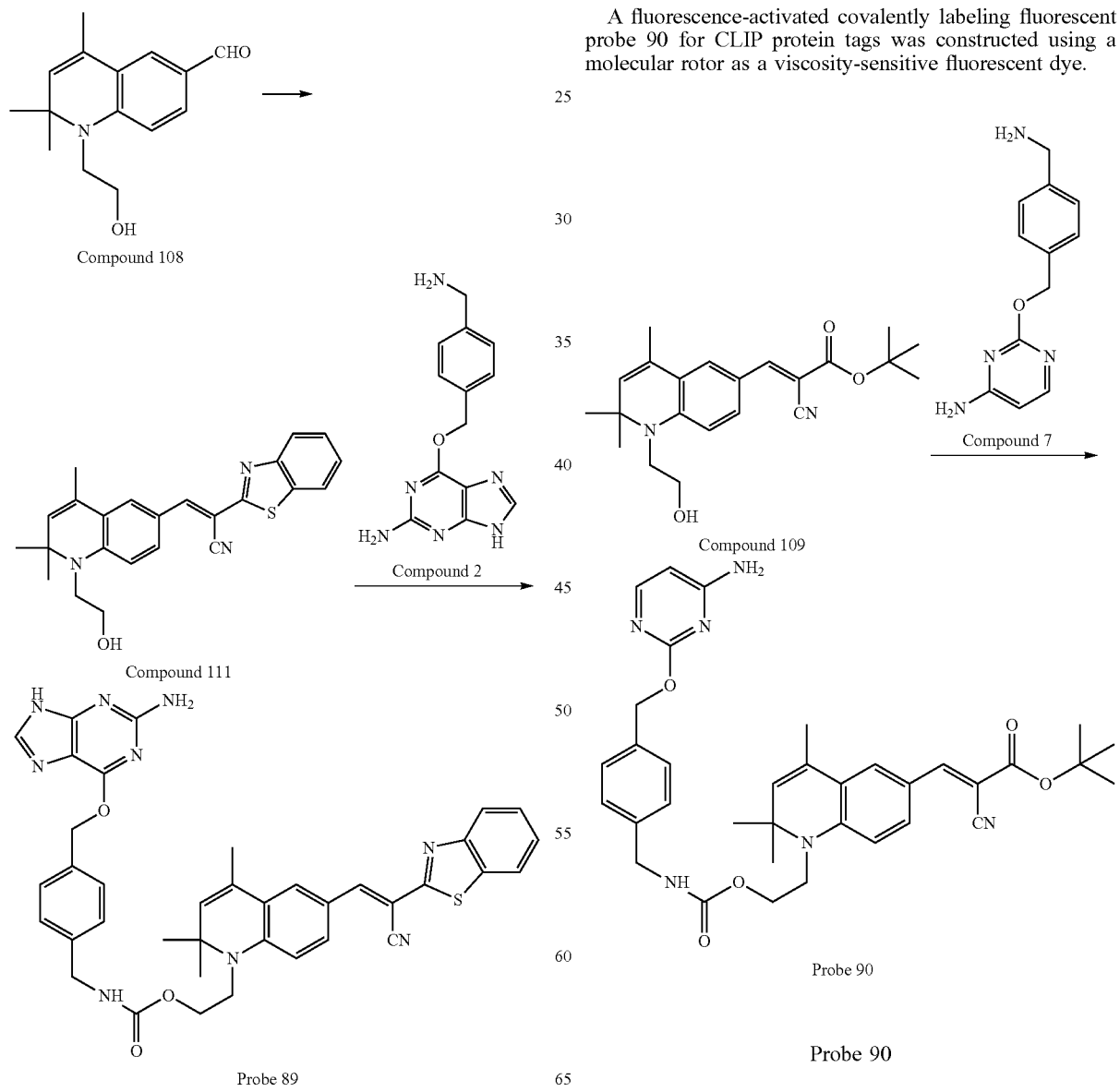

Probe 90

This probe was obtained by following the general procedure for probe 1, and the yield was 52%. $^1$H-NMR (400

MHz, DMSO-d$_6$): δ=8.03 (s, 1H), 7.93 (d, 1H, J=5.6), 7.75 (s, 1H), 7.38 (d, 1H, J=7.6 Hz), 7.31 (d, 2H, J=8.0 Hz), 7.19 (d, 2H, J=8.0 Hz), 6.78 (t, 1H, J=7.2 Hz), 6.49 (d, 1H, 7.8 Hz), 6.06 (d, 1H, J=5.6 Hz), 5.27 (s, 2H), 5.16 (s, 2H), 4.45 (d, 2H, J=5.6 Hz), 3.46 (m, 4H), 2.35 (s, 3H), 1.50 (s, 9H), 1.36 (s, 6H).

Example 91

A fluorescence-activated covalently labeling fluorescent probe 91 for CLIP protein tags was constructed using a molecular rotor as viscosity-sensitive fluorescent dye.

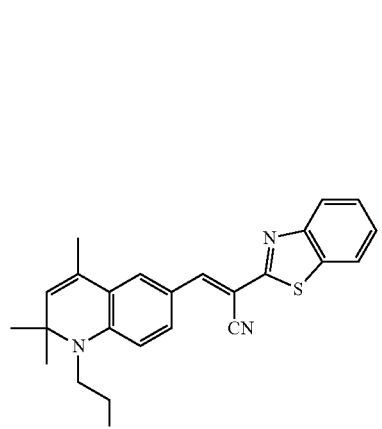

Probe 91

This probe was obtained by following the general procedure for probe 1, and the yield was 59%. $^1$H-NMR (400 MHz, DMSO-d$_6$): δ=8.04 (d, 1H, J=8.0 Hz), 7.99 (s, 1H), 7.93 (d, 1H, J=5.6), 7.90 (d, 1H, J=8.0 Hz), 7.75 (s, 1H), 7.53 (t, 1H, J=8.0 Hz), 7.45 (t, 1H, J=8.0 Hz), 7.36 (d, 1H, J=7.6 Hz), 7.33 (d, 2H, J=8.0 Hz), 7.19 (d, 2H, J=8.0 Hz), 6.78 (t, 1H, J=7.2 Hz), 6.49 (d, 1H, 7.8 Hz), 6.06 (d, 1H, J=5.6 Hz), 5.27 (s, 2H), 5.16 (s, 2H), 4.45 (d, 2H, J=5.6 Hz), 3.46 (m, 4H), 2.35 (s, 3H), 1.36 (s, 6H).

Example 92

A fluorescence-activated covalently labeling fluorescent probe 92 for SNAP protein tags was constructed using a molecular rotor as a viscosity-sensitive fluorescent dye.

Compound 112

Compound 113

Compound 114

Compound 152

Probe 92

Compound 112

The synthesis was carried out by the method disclosed in the literature (Ping Yan. et al. J. Org. Chem. 2008, 73, 6587-6594). $^1$H-NMR (400 MHz, CDCl$_3$): δ=7.18 (s, 1H), 6.96 (d, 2H, J=5.6 Hz), 1.50 (s, 6H).

Compound 113

This compound was obtained by following the general procedure for compound 21, and the yield was 76%. $^1$H-NMR (400 MHz, CDCl$_3$): δ=7.18 (s, 1H), 6.96 (d, 2H, J=5.6 Hz) 3.85 (t, 2H, J=5.6 Hz), 3.60 (t, 2H, J=5.6 Hz), 3.10 (s, 3H), 1.50 (s, 6H).

Compound 114

This compound was obtained by following the general procedure for compound 22, and the yield was 66%. $^1$H-NMR (400 MHz, CDCl$_3$): δ=9.89 (s, 1H), 7.18 (s, 1H), 6.96 (d, 2H, J=5.6 Hz), 3.85 (t, 2H, J=5.6 Hz), 3.60 (t, 2H, J=5.6 Hz), 3.10 (s, 3H), 1.50 (s, 6H).

Compound 115

This compound was obtained by following the general procedure for compound 1, and the yield was 98%. $^1$H-NMR (400 MHz, CDCl$_3$): δ=7.89 (s, 1H), 7.18 (s, 1H), 6.96 (d, 2H, J=5.6 Hz), 3.85 (t, 2H, J=5.6 Hz), 3.60 (t, 2H, J=5.6 Hz), 3.10 (s, 3H), 1.50 (m, 15H).

Probe 92

This probe was obtained by following the general procedure for probe 1, and the yield was 45%. $^1$H-NMR (400 MHz, DMSO-d6): δ=12.42 (s, 1H), 10.01 (s, 1H), 7.89 (s, 1H), 7.18 (s, 1H), 7.81 (s, 1H), 7.4 (m, 4H), 6.96 (d, 2H, J=5.6 Hz), 6.29 (s, 2H), 5.46 (s, 2H), 4.40 (d, 2H, J=4.8 Hz), 3.85 (t, 2H, J=5.6 Hz), 3.60 (t, 2H, J=5.6 Hz), 3.10 (s, 3H), 1.50 (m, 15H).

Example 93

A fluorescence-activated covalently labeling fluorescent probe 93 for SNAP protein tags was constructed using a molecular rotor as a viscosity-sensitive fluorescent dye.

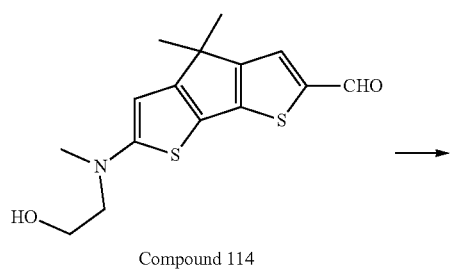

Compound 114

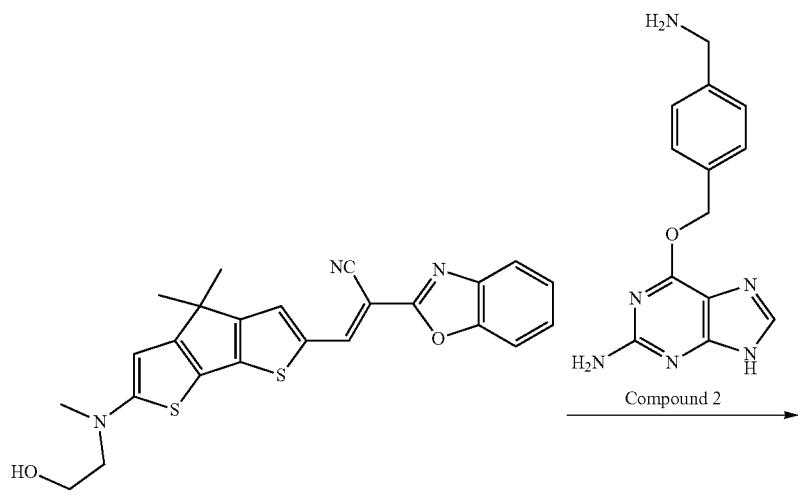

Compound 116

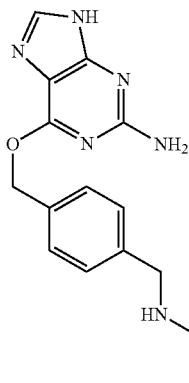

Probe 93

Compound 116

This compound was obtained by following the general procedure for compound 1, and the yield was 98%. $^1$H-NMR (400 MHz, CDCl$_3$): δ=7.89 (s, 1H), 7.74 (d, 1H, J=4.0 Hz), 7.55 (d, 1H, J=4.0 Hz), 7.36-7.42 (m, 2H), 7.18 (s, 1H), 6.96 (d, 2H, J=5.6 Hz), 3.85 (t, 2H, J=5.6 Hz), 4.12 (s, 2H), 3.60 (t, 2H, J=5.6 Hz), 3.10 (s, 3H), 1.50 (s, 6H).

Probe 93

This probe was obtained by following the general procedure for probe 1, and the yield was 45%. $^1$H-NMR (400 MHz, DMSO-d$_6$): δ=12.42 (s, 1H), 10.01 (s, 1H), 7.89 (s, 1H), 7.81 (s, 1H), 7.74 (d, 1H, J=4.0 Hz), 7.55 (d, 1H, J=4.0 Hz), 7.36-7.42 (m, 6H), 7.18 (s, 1H), 6.96 (d, 2H, J=5.6 Hz), 6.29 (s, 2H), 5.46 (s, 2H), 4.40 (d, 2H, J=4.8 Hz), 3.85 (t, 2H, J=5.6 Hz), 4.12 (s, 2H), 3.60 (t, 2H, J=5.6 Hz), 3.10 (s, 3H), 1.50 (s, 6H).

Example 94

A fluorescence-activated covalently labeling fluorescent probe 94 for SNAP protein tags was constructed using a molecular rotor as a viscosity-sensitive fluorescent dye.

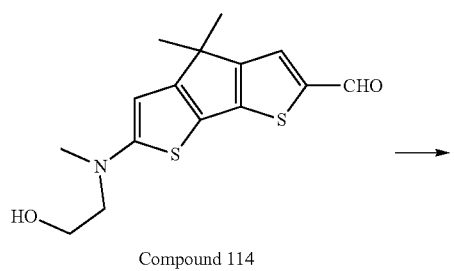

Compound 114

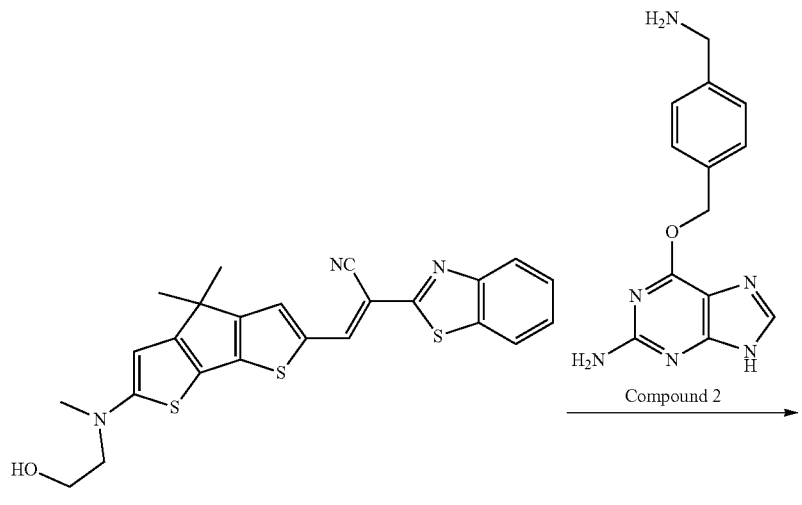

Compound 117

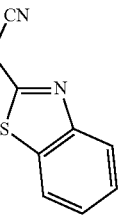
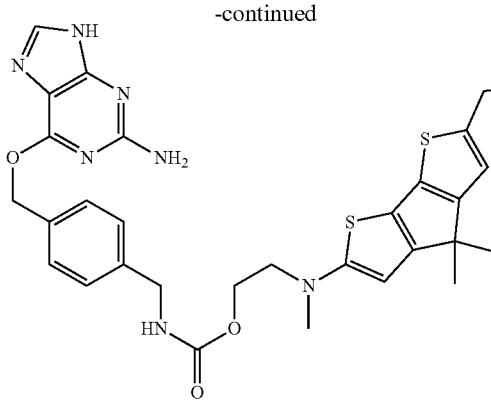

Probe 94

Compound 117

This compound was obtained by following the general procedure for compound 1, and the yield was 98%. $^1$H-NMR (400 MHz, CDCl$_3$): δ=8.04 (d, 1H, J=8.0 Hz), 7.93 (d, 1H, J=8.0 Hz), 7.89 (s, 1H), 7.53 (t, 1H, J=8.0 Hz), 7.45 (t, 1H, J=8.0 Hz), 7.18 (s, 1H), 6.96 (d, 2H, J=5.6 Hz), 4.24 (s, 2H), 3.85 (t, 2H, J=5.6 Hz), 3.60 (t, 2H, J=5.6 Hz), 3.10 (s, 3H), 1.50 (s, 6H).

Probe 94

This probe was obtained by following the general procedure for probe 1, and the yield was 45%. $^1$H-NMR (400 MHz, DMSO-d$_6$): 12.42 (s, 1H), 10.01 (s, 1H), δ=8.04 (d, 1H, J=8.0 Hz), 7.93 (d, 1H, J=8.0 Hz), 7.89 (s, 1H), 7.81 (s, 1H), 7.53 (t, 1H, J=8.0 Hz), 7.45 (t, 1H, J=8.0 Hz), 7.40 (m, 4H), 7.18 (s, 1H), 6.96 (d, 2H, J=5.6 Hz), 6.29 (s, 2H), 5.46 (s, 2H), 4.40 (d, 2H, J=4.8 Hz), 4.24 (s, 2H), 3.85 (t, 2H, J=5.6 Hz), 3.60 (t, 2H, J=5.6 Hz), 3.10 (s, 3H), 1.50 (s, 6H).

Example 95

A fluorescence-activated covalently labeling fluorescent probe 95 for CLIP protein tags was constructed using a molecular rotor as a viscosity-sensitive fluorescent dye.

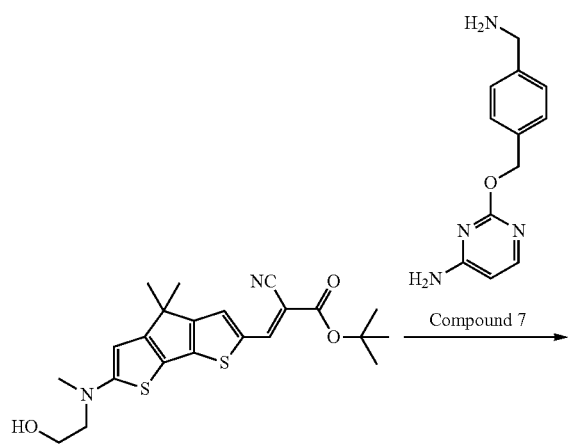

Compound 115

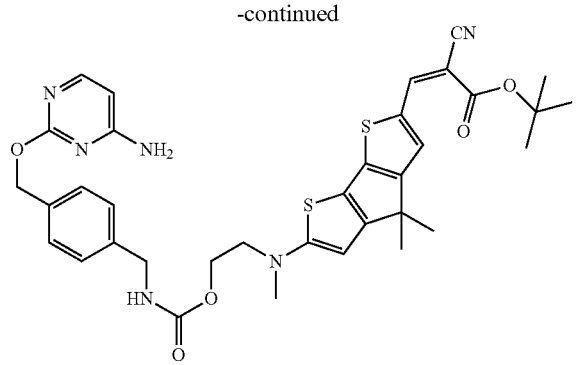

Probe 95

Probe 95

This probe was obtained by following the general procedure for probe 1, and the yield was 58%. $^1$H-NMR (400 MHz, DMSO-d$_6$): δ=7.93 (d, 1H, J=7.2 Hz), 7.89 (s, 1H), 7.75 (s, 1H), 7.33 (d, 2H, J=8.0 Hz), 7.23 (d, 2H, J=8.0 Hz), 7.18 (s, 1H), 6.96 (d, 2H, J=5.6 Hz), 6.06 (d, 1H, J=5.6 Hz), 5.27 (s, 2H), 5.15 (s, 2H), 4.45 (d, 2H, J=5.6 Hz), 3.85 (t, 2H, J=5.6 Hz), 3.60 (t, 2H, J=5.6 Hz), 3.10 (s, 3H), 1.50 (m, 15H).

Example 96

A fluorescence-activated covalently labeling fluorescent probe 96 for CLIP protein tags was constructed using a molecular rotor as a viscosity-sensitive fluorescent dye.

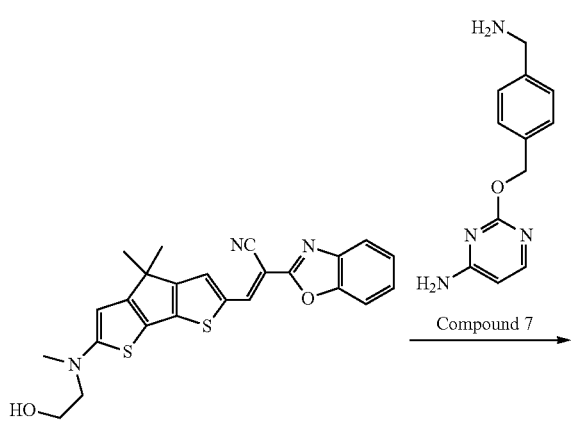

Compound 116

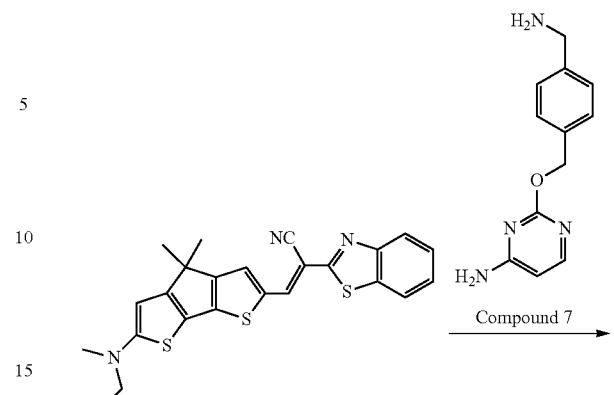

Compound 136

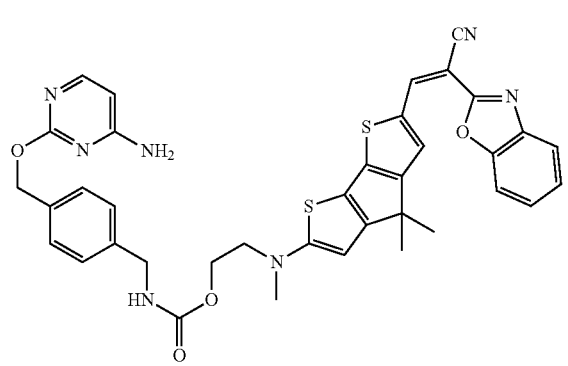

Probe 96

Probe 96

This probe was obtained by following the general procedure for probe 1, and the yield was 55%. $^1$H-NMR (400 MHz, DMSO-d$_6$): δ=7.93 (d, 1H, J=7.2 Hz), 7.89 (s, 1H), 7.79 (s, 1H), 7.74 (d, 1H, J=4.0 Hz), 7.55 (d, 1H, J=4.0 Hz), 7.36-7.42 (m, 2H), 7.31 (d, 2H, J=8.0 Hz), 7.18 (m, 3H), 6.96 (d, 2H, J=5.6 Hz), 6.06 (d, 1H, J=5.6 Hz), 5.27 (s, 2H), 5.15 (s, 2H), 4.45 (d, 2H, J=5.6 Hz), 3.85 (t, 2H, J=5.6 Hz), 4.12 (s, 2H), 3.60 (t, 2H, J=5.6 Hz), 3.10 (s, 3H), 1.50 (s, 6H).

Example 97

A fluorescence-activated covalently labeling fluorescent probe 97 for CLIP protein tags was constructed using a molecular rotor as a viscosity-sensitive fluorescent dye.

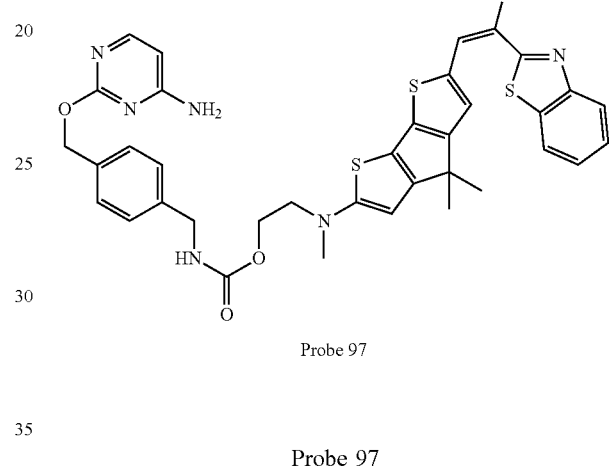

Probe 97

Probe 97

This probe was obtained by following the general procedure for probe 1, and the yield was 98%. $^1$H-NMR (400 MHz, DMSO-d$_6$): δ=8.04 (d, 1H, J=8.0 Hz), 7.93 (m, 2H), 7.89 (s, 1H), 7.75 (s, 1H), 7.53 (t, 1H, J=8.0 Hz), 7.45 (t, 1H, J=8.0 Hz), 7.33 (d, 2H, J=8.0 Hz), 7.23 (d, 2H, J=8.0 Hz), 7.18 (s, 1H), 6.96 (d, 2H, J=5.6 Hz), 6.06 (d, 1H, J=5.6 Hz), 5.27 (s, 2H), 5.15 (s, 2H), 4.45 (d, 2H, J=5.6 Hz), 4.24 (s, 2H), 3.85 (t, 2H, J=5.6 Hz), 3.60 (t, 2H, J=5.6 Hz), 3.10 (s, 3H), 1.50 (s, 6H).

Example 98

A fluorescence-activated covalently labeling fluorescent probe 98 for SNAP protein tags was constructed using a molecular rotor as a viscosity-sensitive fluorescent dye.

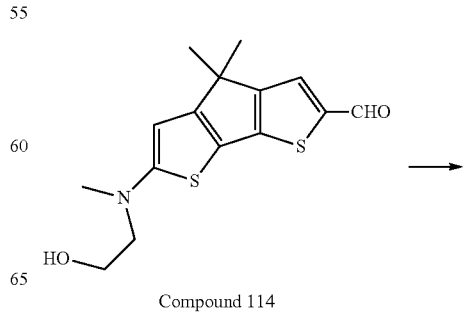

Compound 114

-continued

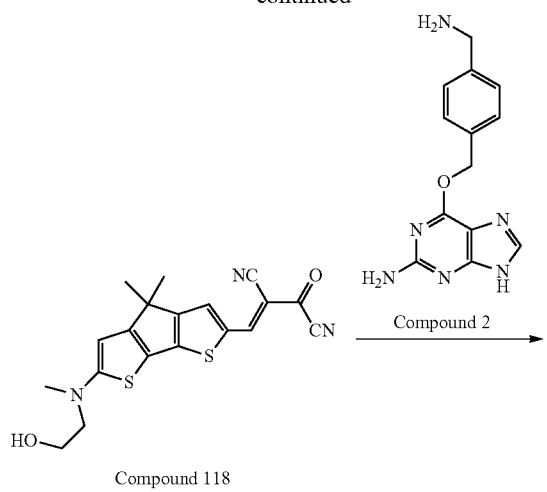

Compound 118

Probe 98

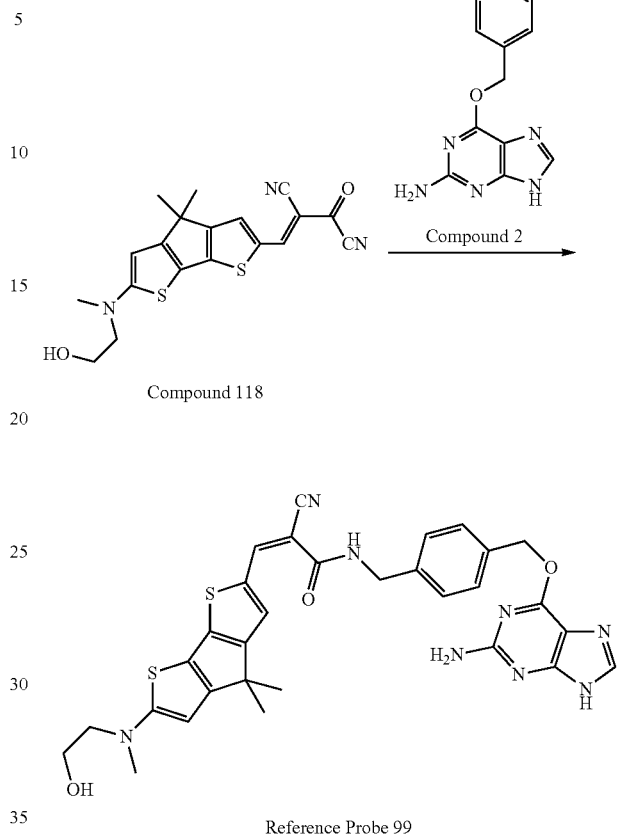

Compound 118

Reference Probe 99

Compound 118

This compound was obtained by following the general procedure for compound 1, and the yield was 98%. $^1$H-NMR (400 MHz, CDCl$_3$): δ=7.89 (s, 1H), 7.18 (s, 1H), 6.96 (d, 2H, J=5.6 Hz), 3.85 (t, 2H, J=5.6 Hz), 3.60 (t, 2H, J=5.6 Hz), 3.10 (s, 3H).

Probe 98

This probe was obtained by following the general procedure for probe 1, and the yield was 33%. $^1$H-NMR (400 MHz, DMSO-d$_6$): δ=12.12 (s, 1H), 10.05 (s, 1H), 7.89 (s, 1H), 7.81 (s, 1H), 7.4 (m, 4H), 7.18 (s, 1H), 6.96 (d, 2H, J=5.6 Hz), 6.29 (s, 2H), 5.46 (s, 2H), 4.40 (d, 2H, J=4.8 Hz), 3.85 (t, 2H, J=5.6 Hz), 3.60 (t, 2H, J=5.6 Hz), 3.10 (s, 3H).

Comparative Example 99

A fluorescence-activated covalently labeling fluorescent reference probe 99 for SNAP protein tags was constructed using a molecular rotor as a viscosity-sensitive fluorescent dye.

Comparative Probe 99

Compound 112 (0.375 g, 1 mmol), Compound 2 (0.297 g, 1.1 mmol) and benzotriazol-1-yl-oxytripyrrolidinylphosphonium hexafluorophosphate (0.625 g, 1.2 mmol) were dissolved in 15 ml of anhydrous dimethylformamide, and 0.2 ml of triethylamine was added, and the mixture was stirred at room temperature for 2 hrs under the protection of Ar. After the completion of the reaction, the solvent was completely removed by rotary evaporation, and the residue was purified by gel silica gel column chromatography to give a yellow solid 0.458, and the yield was 73%. $^1$H-NMR (400 MHz, DMSO-d$_6$): δ=12.12 (s, 1H), 10.05 (s, 1H), 7.89 (s, 1H), 7.81 (s, 1H), 7.4 (m, 4H), 7.18 (s, 1H), 6.96 (d, 2H, J=5.6 Hz), 6.29 (s, 2H), 5.46 (s, 2H), 4.40 (d, 2H, J=4.8 Hz), 3.85 (t, 2H, J=5.6 Hz), 3.60 (t, 2H, J=5.6 Hz), 3.10 (s, 3H).

Comparative Example 100

A fluorescence-activated covalently labeling fluorescent reference probe 100 for SNAP protein tags was constructed using a molecular rotor as a viscosity-sensitive fluorescent dye.

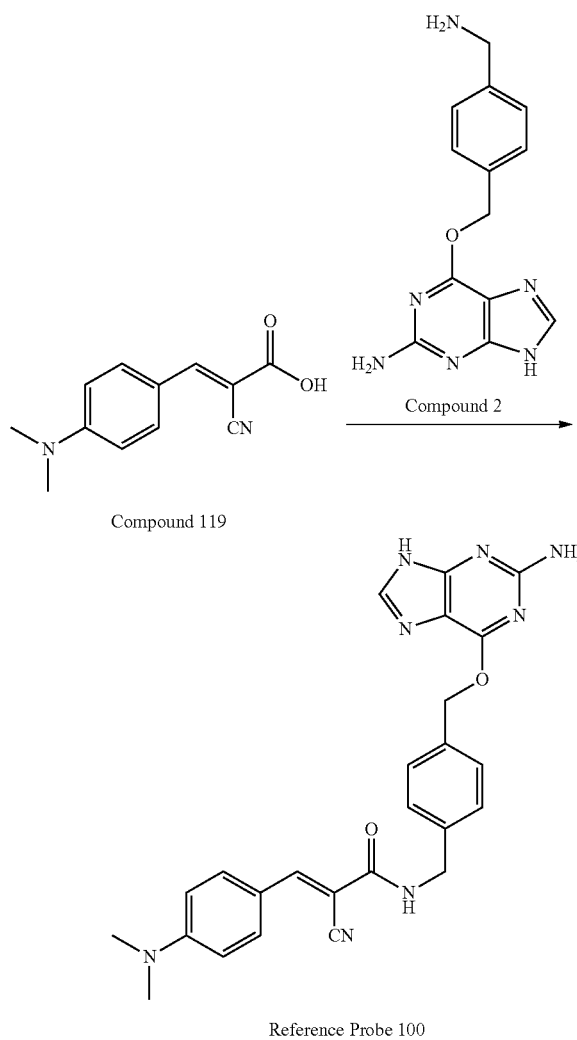

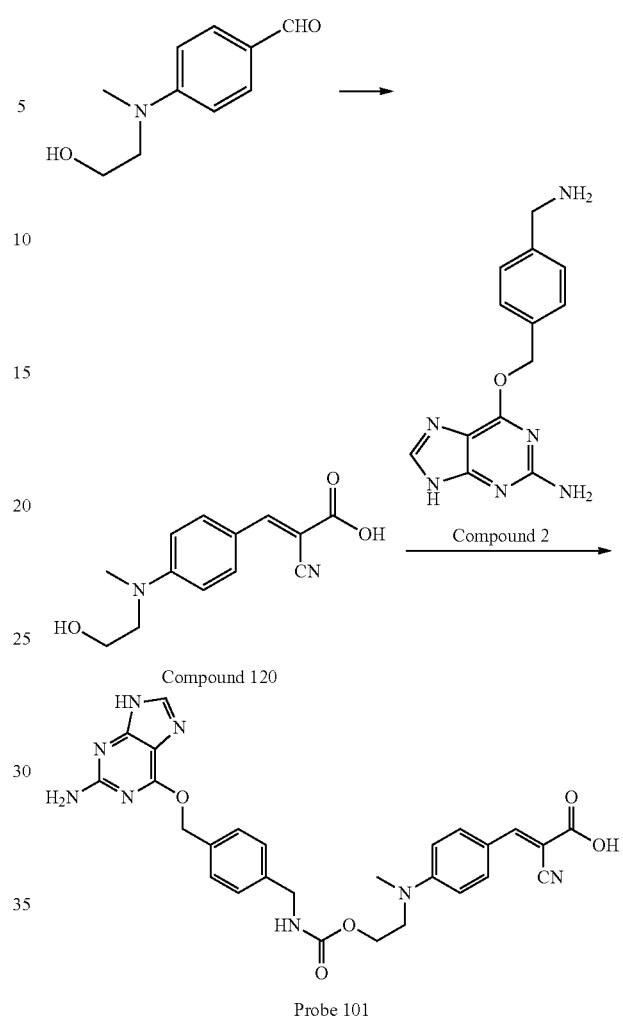

Compound 119

The synthesis was carried out by the method disclosed in (Shirisha Gurrapu et al. ACS Med. Chem. Lett. 2015. 6.558-561). $^1$H-NMR (400 MHz, DMSO-$d_6$): δ=8.11 (s, 1H), 7.97 (d, 2H, J=9.0 Hz), 6.69 (d, 2H, J=9.6 Hz), 3.20 (s, 6H).

Comparative Probe 100

This probe was obtained by following the general procedure for the reference probe 99, and the yield was 81%. $^1$H-NMR (400 MHz, DMSO-$d_6$): δ=11.52 (s, 1H), 10.01 (s, 1H), 8.11 (s, 1H), 7.97 (d, 2H, J=9.0 Hz), 7.81 (s, 1H), 7.40 (m, 4H), 6.69 (d, 2H, J=9.6 Hz), 6.29 (s, 2H), 5.46 (s, 2H), 4.40 (d, 2H, J=4.8 Hz), 3.20 (s, 6H).

Example 101

A fluorescence-activated covalently labeling fluorescent probe 101 for SNAP protein tags was constructed using a molecular rotor as a viscosity-sensitive fluorescent dye.

Compound 120

This compound was obtained by following the general procedure for compound 1, and the yield was 95%. $^1$H-NMR (400 MHz, DMSO-$d_6$): δ=8.07 (s, 1H), 7.93 (d, 2H, J=9.2 Hz), 6.85 (d, 2H, J=9.2 Hz), 3.55-3.59 (m, 4H), 3.08 (s, 3H).

Probe 101

This probe was obtained by following the general procedure for probe 1, and the yield was 35%. $^1$H-NMR (400 MHz, DMSO-$d_6$): δ=12.22 (s, 1H), 10.01 (s, 1H), 8.07 (s, 1H), 7.93 (d, 2H, J=9.2 Hz), 7.81 (s, 1H), 7.4 (m, 4H), 6.85 (d, 2H, J=9.2 Hz), 6.29 (s, 2H), 5.46 (s, 2H), 4.40 (d, 2H, J=4.8 Hz), 3.55-3.59 (m, 4H), 3.08 (s, 3H).

Comparative Example 102

A fluorescence-activated covalently labeling fluorescent reference probe 102 for SNAP protein tags was constructed using a molecular rotor as a viscosity-sensitive fluorescent dye.

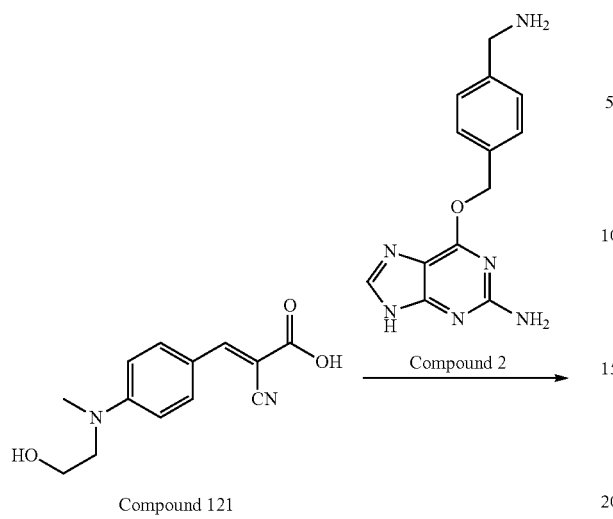

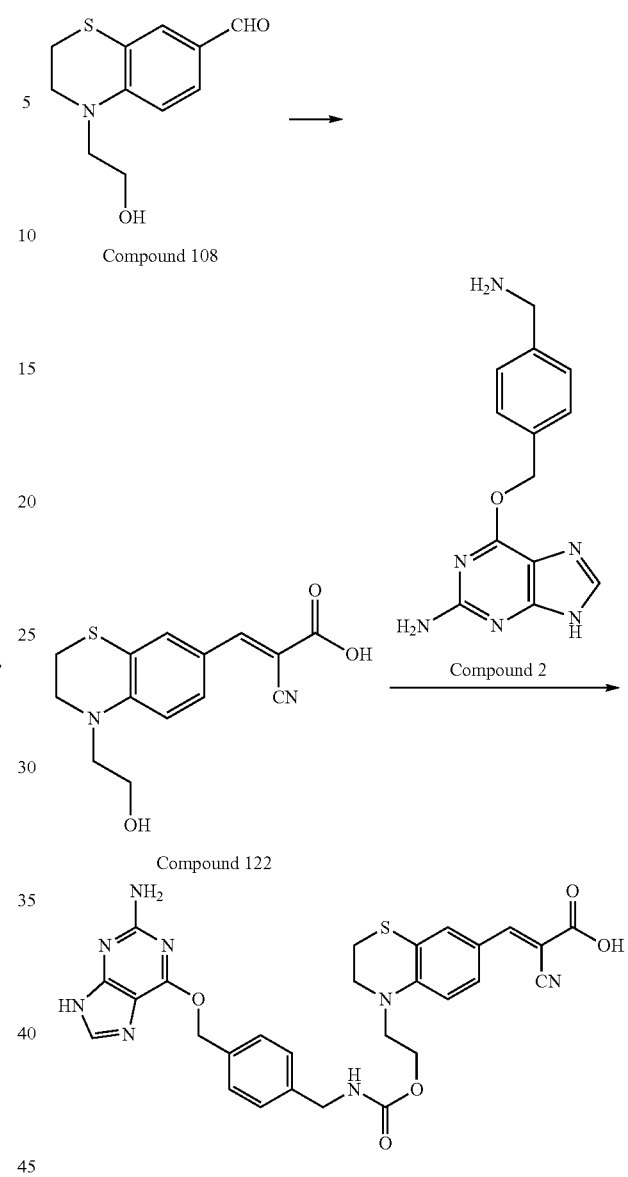

Compound 122

This compound was obtained by following the general procedure for compound 1, and the yield was 89%. $^1$H-NMR (400 MHz, CDCl$_3$): δ=8.09 (s, 1H), 7.36 (d, 1H, J=7.6 Hz), 6.78 (t, 1H, J=7.2 Hz), 6.49 (d, 1H, 7.8 Hz), 3.46 (m, 4H), 2.35 (s, 3H), 1.36 (s, 6H).

Probe 103

This probe was obtained by following the general procedure for probe 1, and the yield was 89%. $^1$H-NMR (400 MHz, CDCl$_3$): δ=11.22 (s, 1H), 9.87 (s, 1H), 8.09 (s, 1H), 7.81 (s, 1H), 7.40 (m, 4H), 7.36 (d, 1H, J=7.6 Hz), 6.78 (t, 1H, J=7.2 Hz), 6.49 (d, 1H, 7.8 Hz), 6.29 (s, 2H), 5.46 (s, 2H), 4.40 (d, 2H, J=4.8 Hz), 3.46 (m, 4H), 2.35 (s, 3H), 1.36 (s, 6H).

Comparative Probe 102

This probe was obtained by following the general procedure for the reference probe 99, and the yield was 65%. $^1$H-NMR (400 MHz, DMSO-d$_6$): δ=12.22 (s, 1H), 10.01 (s, 1H), 8.07 (s, 1H), 7.93 (d, 2H, J=9.2 Hz), 7.81 (s, 1H), 7.4 (m, 4H), 6.85 (d, 2H, J=9.2 Hz), 6.29 (s, 2H), 5.46 (s, 2H), 4.40 (d, 2H, J=4.8 Hz), 3.55-3.59 (m, 4H), 3.08 (s, 3H).

Example 103

A fluorescence-activated covalently labeling fluorescent probe 103 for SNAP protein tags was constructed using a molecular rotor as a viscosity-sensitive fluorescent dye.

Comparative Example 104

A fluorescence-activated covalently labeling fluorescent reference probe 104 for SNAP protein tags was constructed using a molecular rotor as a viscosity-sensitive fluorescent dye.

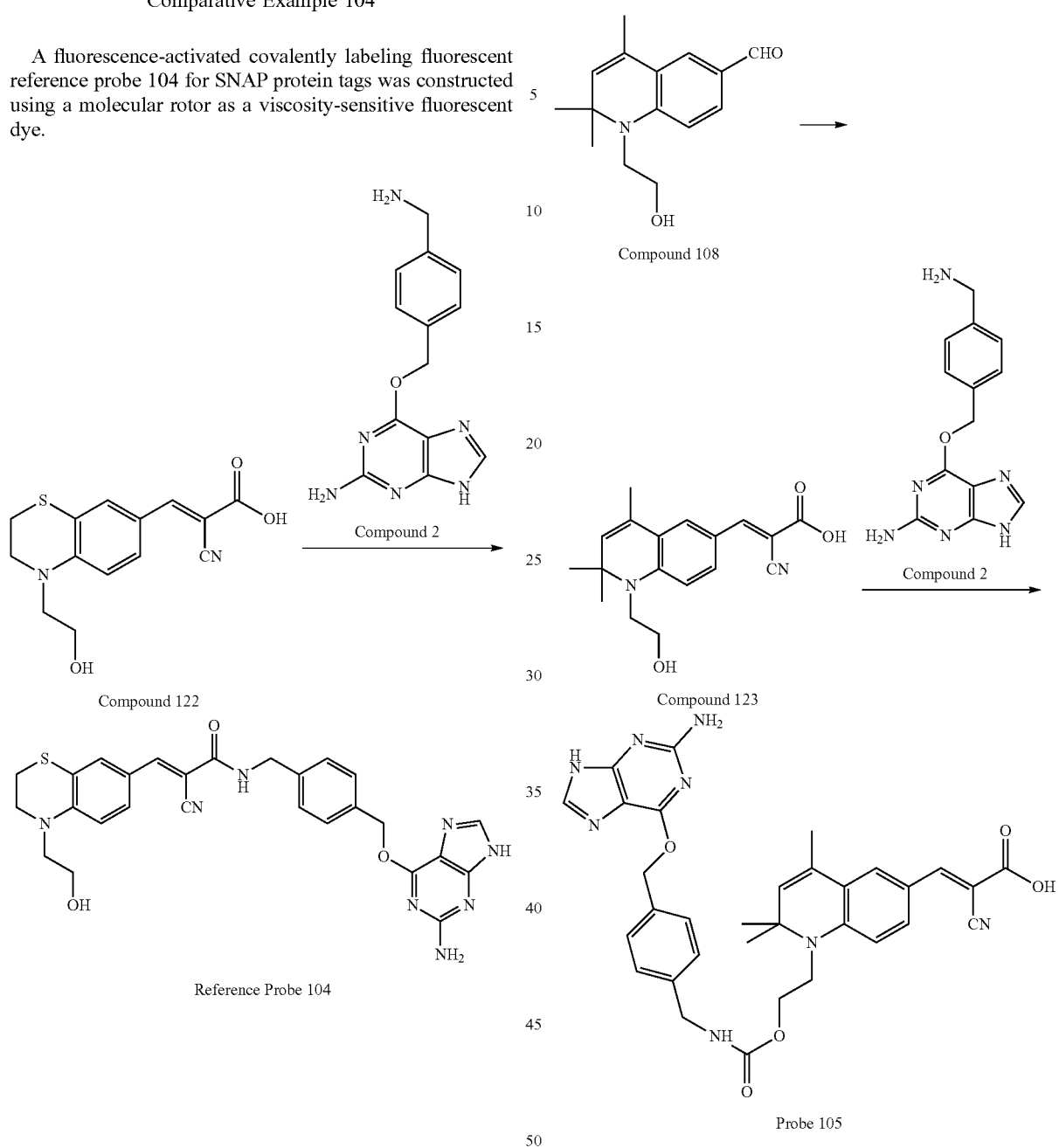

Comparative Probe 104

This probe was obtained by following the general procedure for probe 1, and the yield was 89%. $^1$H-NMR (400 MHz, CDCl$_3$): δ=11.22 (s, 1H), 9.87 (s, 1H), 8.09 (s, 1H), 7.81 (s, 1H), 7.40 (m, 4H), 7.36 (d, 1H, J=7.6 Hz), 6.78 (t, 1H, J=7.2 Hz), 6.49 (d, 1H, 7.8 Hz), 6.29 (s, 2H), 5.46 (s, 2H), 4.40 (d, 2H, J=4.8 Hz), 3.46 (m, 4H), 2.35 (s, 3H), 1.36 (s, 6H).

Example 105

A fluorescence-activated covalently labeling fluorescent probe 105 for SNAP protein tags was constructed using a molecular rotor as a viscosity-sensitive fluorescent dye.

Compound 123

This compound was obtained by following the general procedure for compound 1, and the yield was 99%. $^1$H-NMR (400 MHz, CDCl$_3$): δ=8.03 (s, 1H), 7.36 (d, 1H, J=7.6 Hz), 6.78 (t, 1H, J=7.2 Hz), 6.49 (d, 1H, 7.8 Hz), 3.11 (m, 4H), 2.35 (s, 3H), 1.36 (s, 6H).

Probe 105

This probe was obtained by following the general procedure for probe 99, and the yield was 95%. $^1$H-NMR (400 MHz, DMSO-d$_6$): δ=11.72 (s, 1H), 9.89 (s, 1H), 8.03 (s, 1H), 7.81 (s, 1H), 7.40 (m, 4H), 7.36 (d, 1H, J=7.6 Hz), 6.78

(t, 1H, J=7.2 Hz), 6.49 (d, 1H, 7.8 Hz), 6.29 (s, 2H), 5.46 (s, 2H), 4.40 (d, 2H, J=4.8 Hz), 3.11 (m, 4H), 2.35 (s, 3H), 1.36 (s, 6H).

Comparative Example 106

A fluorescence-activated covalently labeling fluorescent probe 106 for SNAP protein tags was constructed using a molecular rotor as a viscosity-sensitive fluorescent dye.

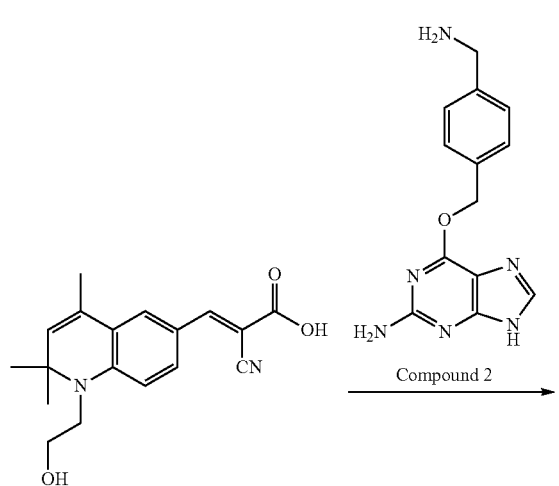

Comparative Probe 106

This probe was obtained by following the general procedure for the reference probe 99, and the yield was 95%. $^1$H-NMR (400 MHz, DMSO-d$_6$): δ=11.72 (s, 1H), 9.89 (s, 1H), 8.03 (s, 1H), 7.81 (s, 1H), 7.40 (m, 4H), 7.36 (d, 1H, J=7.6 Hz), 6.78 (t, 1H, J=7.2 Hz), 6.49 (d, 1H, 7.8 Hz), 6.29 (s, 2H), 5.46 (s, 2H), 4.40 (d, 2H, J=4.8 Hz), 3.11 (m, 4H), 2.35 (s, 3H), 1.36 (s, 6H).

Example 107

A fluorescence-activated covalently labeling fluorescent probe 107 for SNAP protein tags was constructed using a molecular rotor as a viscosity-sensitive fluorescent dye.

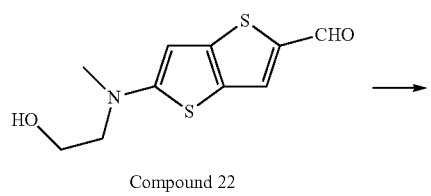

Compound 22

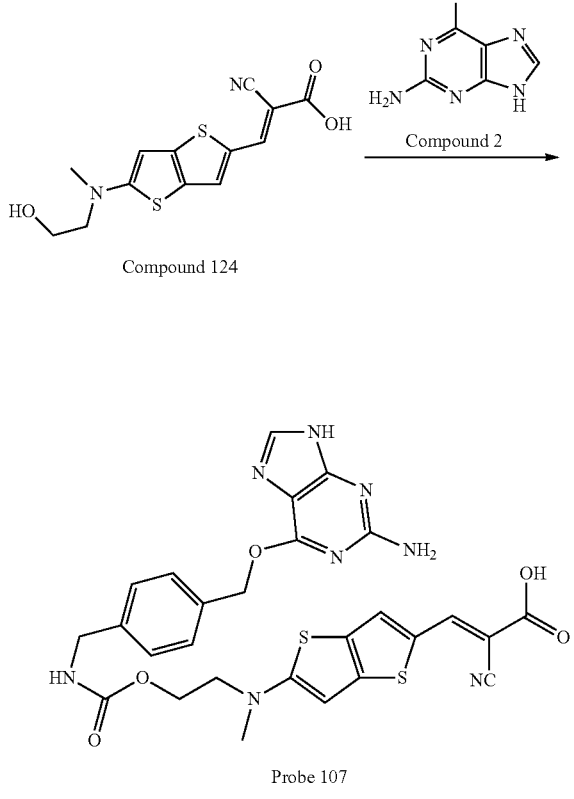

Compound 124

This compound was obtained by following the general procedure for compound 1, and the yield was 96%. $^1$H-NMR (400 MHz, DMSO-d$_6$): δ=8.22 (s, 1H), 8.02 (s, 1H), 6.43 (s, 1H), 3.85 (t, 2H, J=5.6 Hz), 3.60 (t, 2H, J=5.6 Hz), 3.10 (s, 3H).

Probe 107

This probe was obtained by following the general procedure for probe 1, and the yield was 39%. $^1$H-NMR (400 MHz, DMSO-d$_6$): δ=11.72 (s, 1H), 9.79 (s, 1H), 8.22 (s, 1H), 8.02 (s, 1H), 7.81 (s, 1H), 7.40 (m, 4H), 6.43 (s, 1H), 6.29 (s, 2H), 5.46 (s, 2 H), 4.40 (d, 2H, J=4.8 Hz), 3.85 (t, 2H, J=5.6 Hz), 3.60 (t, 2H, J=5.6 Hz), 3.10 (s, 3H).

Comparative Example 108

A fluorescence-activated covalently labeling fluorescent reference probe 6 for SNAP protein tags was constructed using a molecular rotor as a viscosity-sensitive fluorescent dye.

231

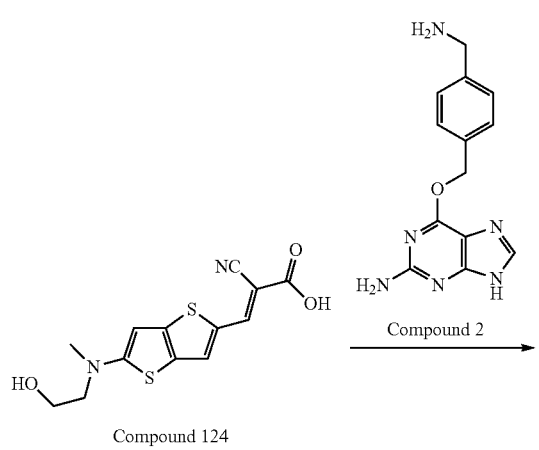

Comparative Probe 108

This probe was obtained by following the general procedure for probe 92, and the yield was 89%. ¹H-NMR (400 MHz, DMSO-d₆): δ=11.72 (s, 1H), 9.79 (s, 1H), 8.22 (s, 1H), 8.02 (s, 1H), 7.81 (s, 1H), 7.40 (m, 4H), 6.43 (s, 1H), 6.29 (s, 2H), 5.46 (s, 2H), 4.40 (d, 2H, J=4.8 Hz), 3.85 (t, 2H, J=5.6 Hz), 3.60 (t, 2H, J=5.6 Hz), 3.10 (s, 3H).

Example 109

A fluorescence-activated covalently labeling fluorescent probe 109 for SNAP protein tags was constructed using a molecular rotor as a viscosity-sensitive fluorescent dye.

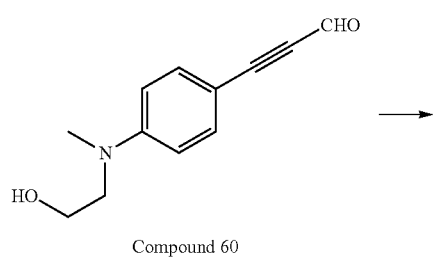

Compound 60

232

-continued

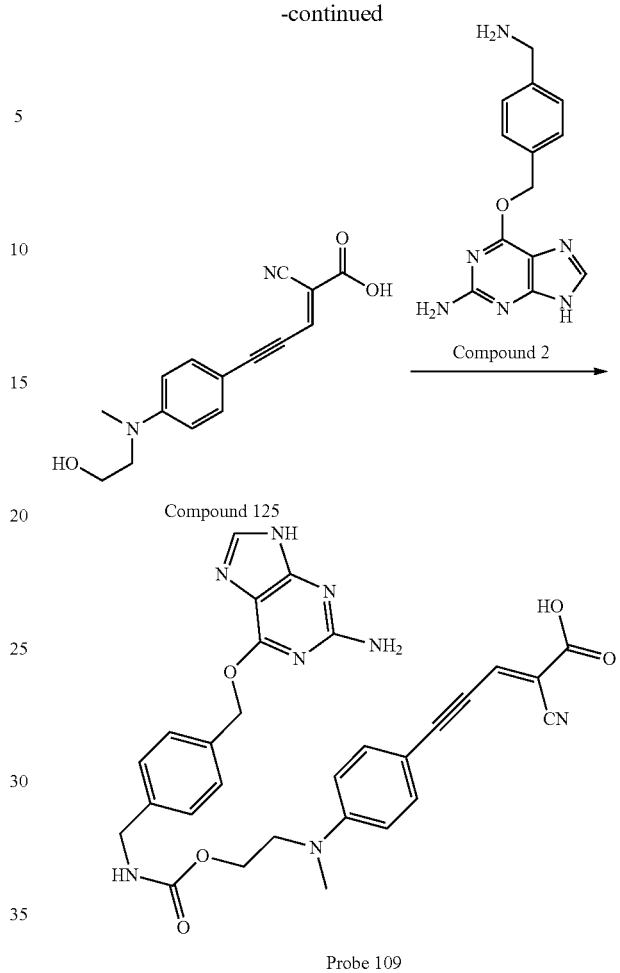

Compound 125

This compound was obtained by following the general procedure for compound 1, and the yield was 89%. ¹H-NMR (400 MHz, CDCl₃): δ=8.00 (s, 1H), 7.49 (d, 2H, J=8.8 Hz), 6.74 (d, 2H, J=8.8 Hz), 3.85 (t, 2H, J=5.6 Hz), 3.60 (t, 2H, J=5.6 Hz), 3.10 (s, 3H).

Probe 109

This probe was obtained by following the general procedure for probe 99, and the yield was 93%. ¹H-NMR (400 MHz, CDCl₃): δ=11.51 (s, 1H), 9.72 (s, 1H), 8.00 (s, 1H), 7.81 (s, 1H), 7.49 (d, 2H, J=8.8 Hz), 7.40 (m, 4H), 6.74 (d, 2H, J=8.8 Hz), 6.29 (s, 2H), 5.46 (s, 2H), 4.40 (d, 2H, J=4.8 Hz), 3.85 (t, 2H, J=5.6 Hz), 3.60 (t, 2H, J=5.6 Hz), 3.10 (s, 3H).

Comparative Example 110

A fluorescence-activated covalently labeling fluorescent reference probe 110 for SNAP protein tags was constructed using a molecular rotor as a viscosity-sensitive fluorescent dye.

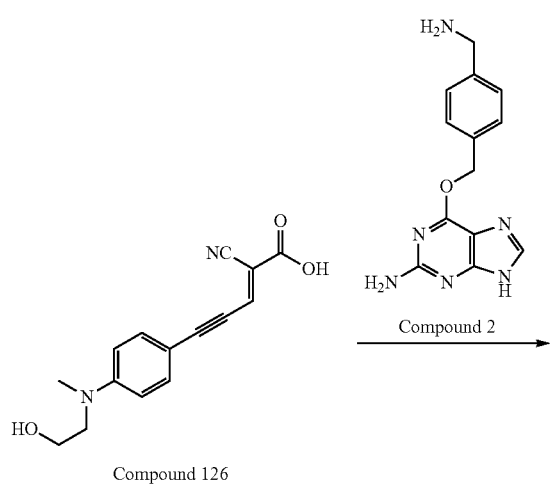

Comparative Probe 110

This probe was obtained by following the general procedure for the reference probe 99, and the yield was 93%. ¹H-NMR (400 MHz, CDCl₃): δ=11.51 (s, 1H), 9.72 (s, 1H), 8.00 (s, 1H), 7.81 (s, 1H), 7.49 (d, 2H, J=8.8 Hz), 7.40 (m, 4H), 6.74 (d, 2H, J=8.8 Hz), 6.29 (s, 2H), 5.46 (s, 2H), 4.40 (d, 2H, J=4.8 Hz), 3.85 (t, 2H, J=5.6 Hz), 3.60 (t, 2H, J=5.6 Hz), 3.10 (s, 3H).

Example 111

A fluorescence-activated covalently labeling fluorescent probe 111 for SNAP protein tags was constructed using a molecular rotor as a viscosity-sensitive fluorescent dye.

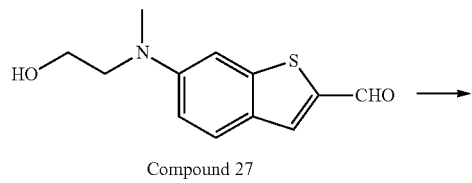

Compound 27

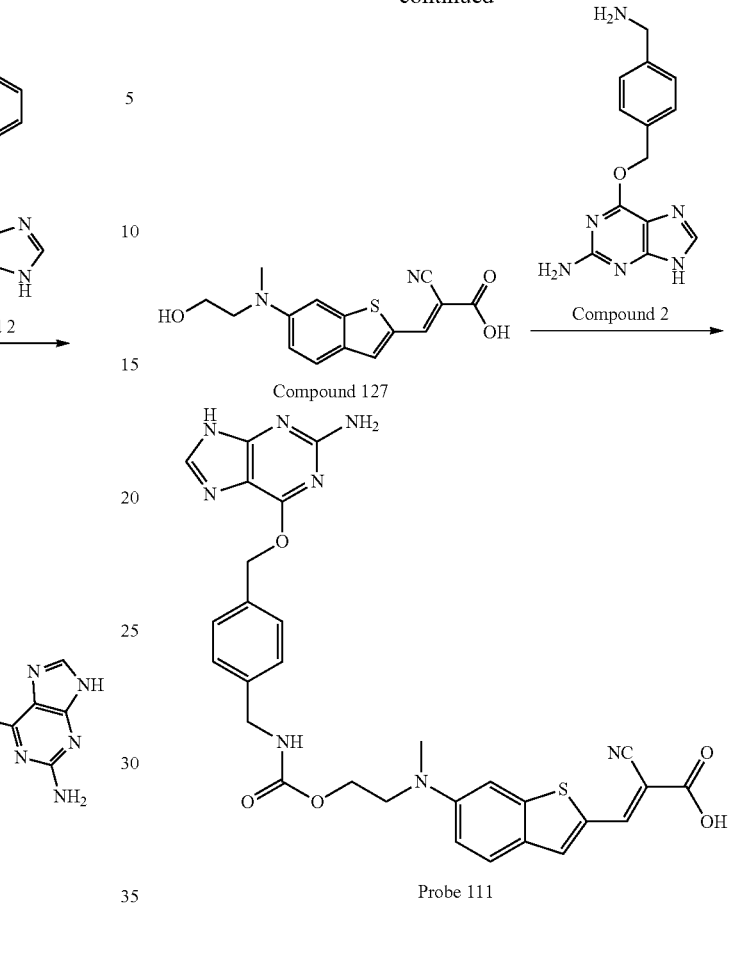

Compound 127

This compound was obtained by following the general procedure for compound 1, and the yield was 98%. ¹H-NMR (400 MHz, CDCl₃): δ=7.95 (s, 1H), 7.81 (s, 1H), 7.68 (d, 1H, J=9.0 Hz), 6.92 (d, 1H, J=2.0), 6.82 (d, 1H, J=9.2 Hz), 3.85 (t, 2H, J=5.6 Hz), 3.60 (t, 2H, J=5.6 Hz), 3.10 (s, 3H)

Probe 111

This probe was obtained by following the general procedure for probe 99, and the yield was 91%. ¹H-NMR (400 MHz, CDCl₃): δ=12.12 (s, 1H), 10.09 (s, 1H), 7.95 (s, 1H), 7.81 (m, 2H), 7.68 (d, 1H, J=9.0 Hz), 7.40 (m, 4H), 6.92 (d, 1H, J=2.0), 6.82 (d, 1H, J=9.2 Hz), 6.29 (s, 2H), 5.46 (s, 2H), 4.40 (d, 2H, J=4.8 Hz), 3.85 (t, 2H, J=5.6 Hz), 3.60 (t, 2H, J=5.6 Hz), 3.10 (s, 3H).

Comparative Example 112

A fluorescence-activated covalently labeling fluorescent reference probe 112 for SNAP protein tags was constructed using a molecular rotor as a viscosity-sensitive fluorescent dye.

235

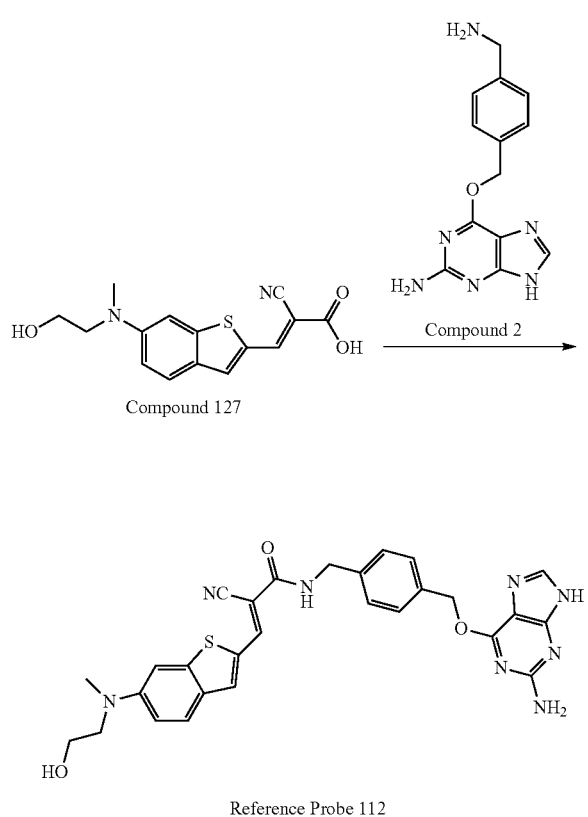 [SMILES: CN(CCO)c1ccc2cc(/C=C(\C#N)C(=O)O)sc2c1 ; NCc1ccc(COc2nc(N)nc3[nH]cnc23)cc1 ; CN(CCO)c1ccc2cc(/C=C(\C#N)C(=O)NCc3ccc(COc4nc(N)nc5[nH]cnc45)cc3)sc2c1]

Compound 127

Reference Probe 112

Comparative Probe 112

This probe was obtained by following the general procedure for the reference probe 99, and the yield was 91%. ¹H-NMR (400 MHz, CDCl₃): δ=12.12 (s, 1H), 10.09 (s, 1H), 7.95 (s, 1H), 7.81 (m, 2H), 7.68 (d, 1H, J=9.0 Hz), 7.40 (m, 4H), 6.92 (d, 1H, J=2.0), 6.82 (d, 1H, J=9.2 Hz), 6.29 (s, 2H), 5.46 (s, 2H), 4.40 (d, 2H, J=4.8 Hz), 3.85 (t, 2H, J=5.6 Hz), 3.60 (t, 2H, J=5.6 Hz), 3.10 (s, 3H).

Comparative Example 113

A fluorescence-activated covalently labeling fluorescent reference probe 113 for SNAP protein tags was constructed using a molecular rotor as a viscosity-sensitive fluorescent dye.

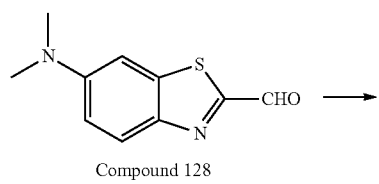

Compound 128

236

-continued

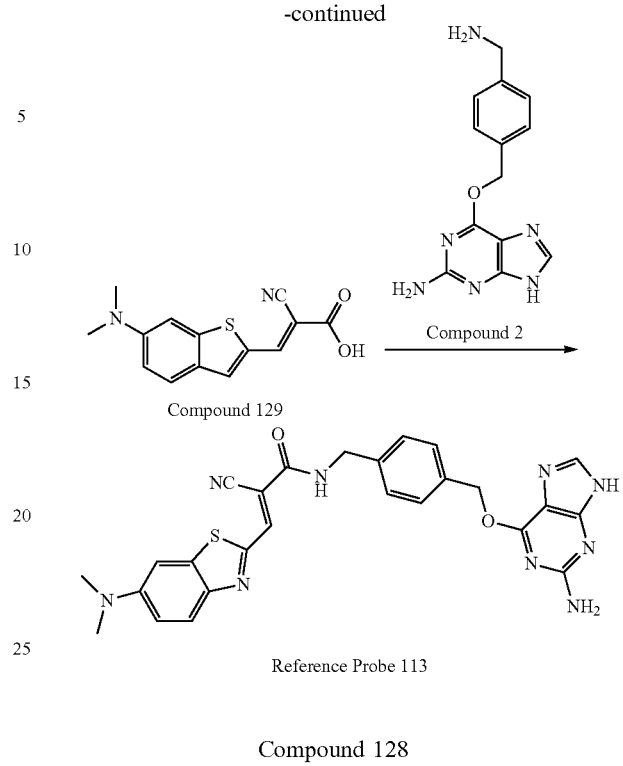

Compound 129

Reference Probe 113

Compound 128

This compound was synthesized according to the method disclosed in the literature (Masahiro Ono et al. Bioorg. Med. Chem. 2009, 17, 7002-7007). ¹H-NMR (400 MHz, CDCl₃): δ=10.06 (s, 1H), 8.03 (d, 1H, J=10.0 Hz), 7.07-7.04 (m, 2H), 3.85 (t, 2H, J=5.6 Hz), 3.60 (t, 2H, J=5.6 Hz), 3.10 (s, 3H).

Compound 129

This compound was obtained by following the general procedure for compound 1, and the yield was 96%. ¹H-NMR (400 MHz, CDCl₃): δ=8.06 (s, 1H), 8.03 (d, 1H, J=10.0 Hz), 7.07-7.04 (m, 2H), 3.85 (t, 2H, J=5.6 Hz), 3.60 (t, 2H, J=5.6 Hz), 3.10 (s, 3H).

Comparative Probe 113

This probe was obtained by following the general procedure for the reference probe 99, and the yield was 89%. ¹H-NMR (400 MHz, DMSO-d₆): δ=11.42 (s, 1H), 9.89 (s, 1H), 8.06 (s, 1H), 8.03 (d, 1H, J=10.0 Hz), 7.81 (s, 1H), 7.40 (m, 4H), 7.07-7.04 (m, 2H), 6.29 (s, 2H), 5.46 (s, 2H), 4.40 (d, 2H, J=4.8 Hz), 3.85 (t, 2H, J=5.6 Hz), 3.60 (t, 2H, J=5.6 Hz), 3.10 (s, 3H).

Example 114

A fluorescence-activated covalently labeling fluorescent probe 114 for SNAP protein tags was constructed using a molecular rotor as a viscosity-sensitive fluorescent dye.

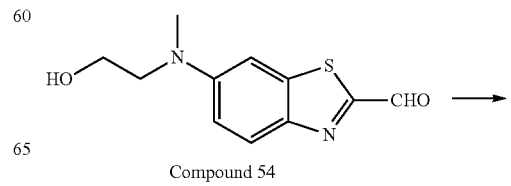

Compound 54

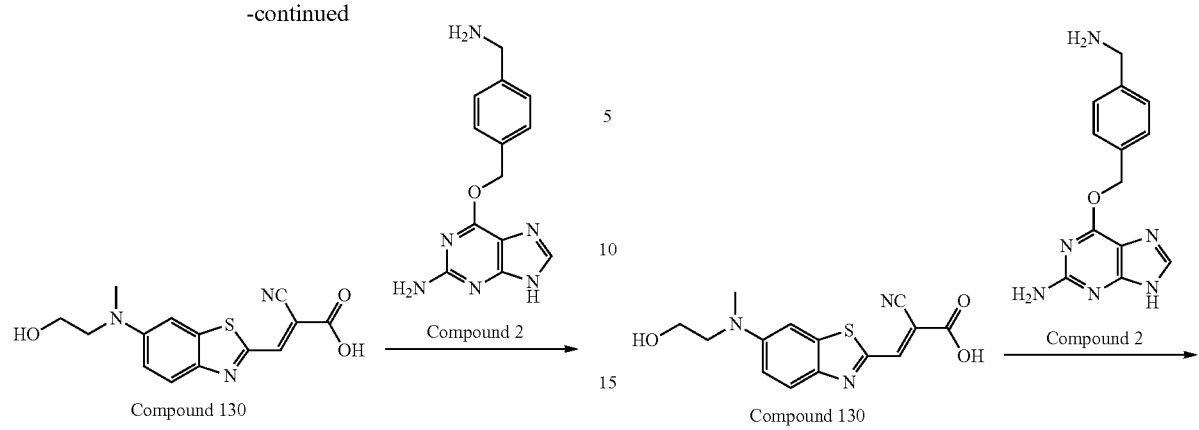

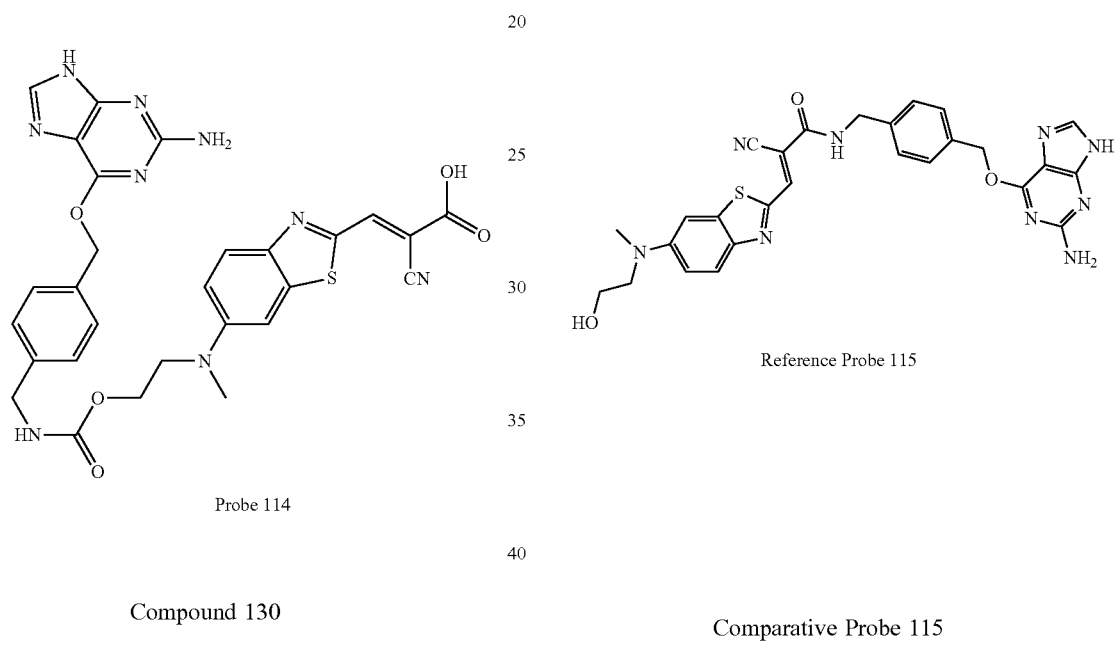

Compound 130

This compound was obtained by following the general procedure for compound 1, and the yield was 96%. ¹H-NMR (400 MHz, CDCl₃): δ=8.06 (s, 1H), 8.03 (d, 1H, J=10.0 Hz), 7.07-7.04 (m, 2H), 3.85 (t, 2H, J=5.6 Hz), 3.60 (t, 2H, J=5.6 Hz), 3.10 (s, 3H).

Probe 114

This probe was obtained by following the general procedure for probe 92, and the yield was 89%. ¹H-NMR (400 MHz, DMSO-d₆): δ=11.42 (s, 1H), 9.89 (s, 1H), 8.06 (s, 1H), 8.03 (d, 1H, J=10.0 Hz), 7.81 (s, 1H), 7.40 (m, 4H), 7.07-7.04 (m, 2H), 6.29 (s, 2H), 5.46 (s, 2H), 4.40 (d, 2H, J=4.8 Hz), 3.85 (t, 2H, J=5.6 Hz), 3.60 (t, 2H, J=5.6 Hz), 3.10 (s, 3H).

Comparative Example 115

A fluorescence-activated covalently labeling fluorescent reference probe 115 for SNAP protein tags was constructed using a molecular rotor as a viscosity-sensitive fluorescent dye.

Comparative Probe 115

This probe was obtained by following the general procedure for probe 99, the yield was 89%. ¹H-NMR (400 MHz, DMSO-d₆): δ=11.42 (s, 1H), 9.89 (s, 1H), 8.06 (s, 1H), 8.03 (d, 1H, J=10.0 Hz), 7.81 (s, 1H), 7.40 (m, 4H), 7.07-7.04 (m, 2H), 6.29 (s, 2H), 5.46 (s, 2H), 4.40 (d, 2H, J=4.8 Hz), 3.85 (t, 2H, J=5.6 Hz), 3.60 (t, 2H, J=5.6 Hz), 3.10 (s, 3H).

Comparative Example 116

A fluorescence-activated covalently labeling fluorescent reference probe 116 for SNAP protein tags was constructed using a molecular rotor as a viscosity-sensitive fluorescent dye.

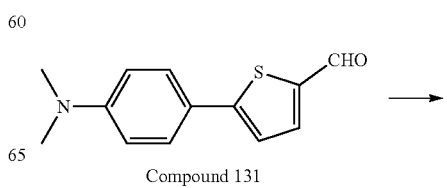

Compound 131

-continued

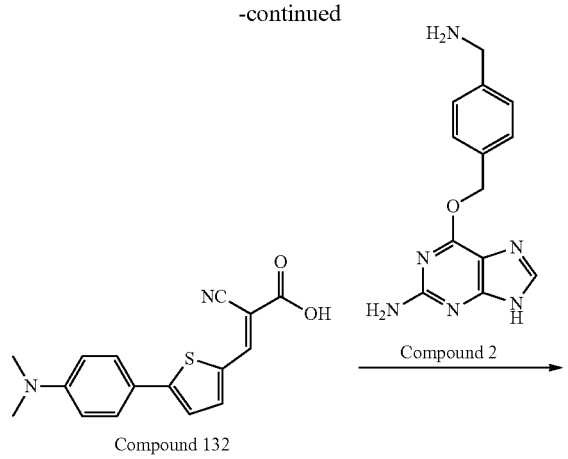

Compound 132

Reference Probe 116

Compound 131

The synthesis was carried out by the method disclosed in the literature (Marian. Z. J. et. al. Tetrahedron., 2008, 64, 10605-10618). $^1$H-NMR (400 MHz, CDCl$_3$): δ=9.98 (s, 1H), 7.68 (d, 1H, J=4.0 Hz), 7.56 (d, 2H, J=9.0 Hz), 7.24 (d, 1H, J=4.0 Hz), 6.72 (d, 2H, J=9.0 Hz), 3.03 (s, 6H).

Compound 132

This compound was obtained by following the general procedure for compound 1, and the yield was 91%. $^1$H-NMR (400 MHz, CDCl$_3$): δ=8.00 (s, 1H), 7.68 (d, 1H, J=4.0 Hz), 7.56 (d, 2H, J=9.0 Hz), 7.24 (d, 1H, J=4.0 Hz), 6.72 (d, 2H, J=9.0 Hz), 3.03 (s, 6H).

Comparative Probe 116

This probe was obtained by following the general procedure for probe 92, and the yield was 97%. $^1$H-NMR (400 MHz, DMSO-d$_6$): δ=11.02 (s, 1H), 9.56 (s, 1H), 8.00 (s, 1H), 7.81 (s, 1H), 7.68 (d, 1H, J=4.0 Hz), 7.56 (d, 2H, J=9.0 Hz), 7.40 (m, 4H), 7.24 (d, 1H, J=4.0 Hz), 6.72 (d, 2H, J=9.0 Hz), 6.29 (s, 2H), 5.46 (s, 2H), 4.40 (d, 2H, J=4.8 Hz), 3.03 (s, 6H).

Example 117

A fluorescence-activated covalently labeling fluorescent probe 117 for SNAP protein tags was constructed using a molecular rotor as a viscosity-sensitive fluorescent dye.

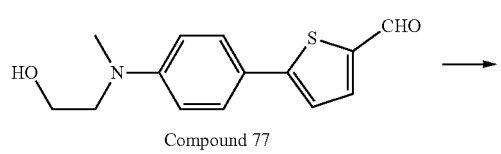

Compound 77

-continued

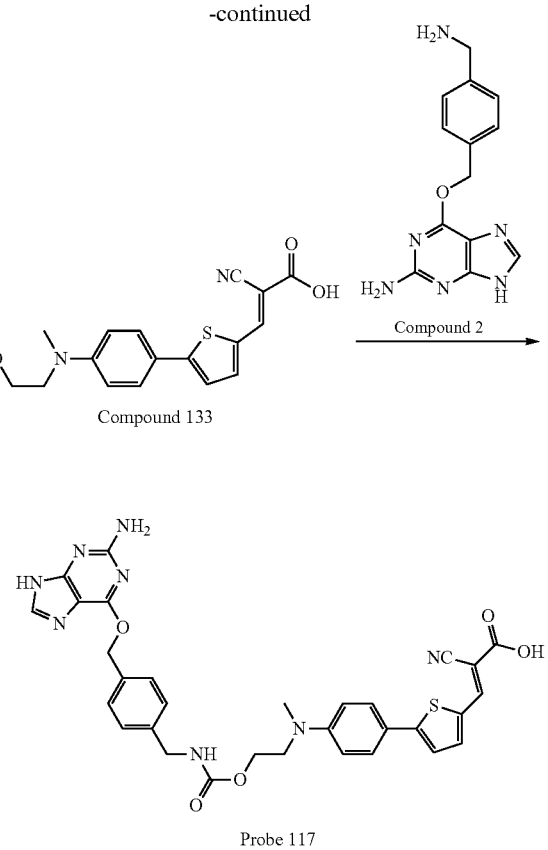

Compound 133

Probe 117

Compound 133

This compound was obtained by following the general procedure for compound 1, and the yield was 91%. $^1$H-NMR (400 MHz, CDCl$_3$): δ=8.00 (s, 1H), 7.68 (d, 1H, J=4.0 Hz), 7.56 (d, 2H, J=9.0 Hz), 7.24 (d, 1H, J=4.0 Hz), 6.72 (d, 2H, J=9.0 Hz), 3.85 (t, 2H, J=5.6 Hz), 3.60 (t, 2H, J=5.6 Hz), 3.10 (s, 3H).

Probe 117

This probe was obtained by following the general procedure for probe 99, and the yield was 97%. $^1$H-NMR (400 MHz, DMSO-d$_6$): δ=11.02 (s, 1H), 9.56 (s, 1H), 8.00 (s, 1H), 7.81 (s, 1H), 7.68 (d, 1H, J=4.0 Hz), 7.56 (d, 2H, J=9.0 Hz), 7.40 (m, 4H), 7.24 (d, 1H, J=4.0 Hz), 6.72 (d, 2H, J=9.0 Hz), 6.29 (s, 2H), 5.46 (s, 2H), 4.40 (d, 2H, J=4.8 Hz), 3.85 (t, 2H, J=5.6 Hz), 3.60 (t, 2H, J=5.6 Hz), 3.10 (s, 3H).

Comparative Example 118

A fluorescence-activated covalently labeling fluorescent reference probe 118 for SNAP protein tags was constructed using a molecular rotor as a viscosity-sensitive fluorescent dye.

241

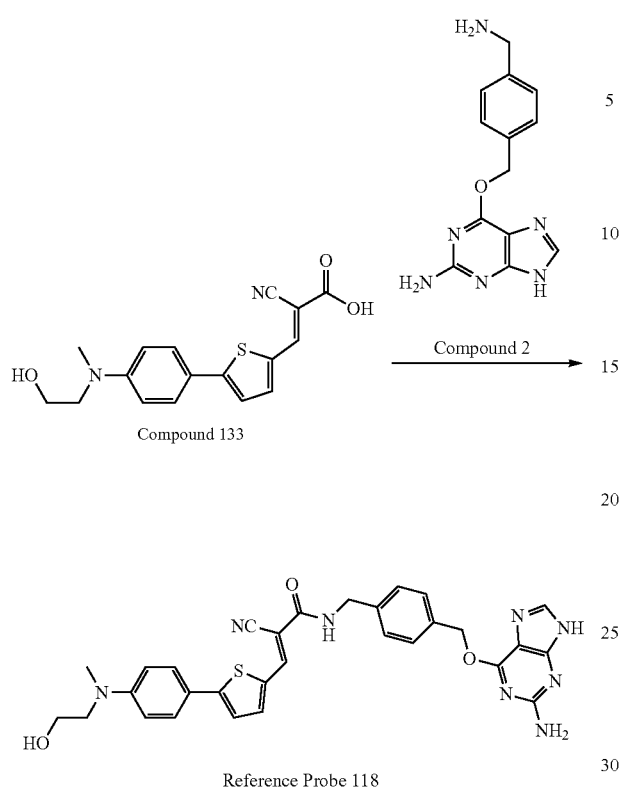

Comparative Probe 118

This probe was obtained by following the general procedure for probe 92, and the yield was 97%. ¹H-NMR (400 MHz, DMSO-d$_6$): δ=11.02 (s, 1H), 9.56 (s, 1H), 8.00 (s, 1H), 7.81 (s, 1H), 7.68 (d, 1H, J=4.0 Hz), 7.56 (d, 2H, J=9.0 Hz), 7.40 (m, 4H), 7.24 (d, 1H, J=4.0 Hz), 6.72 (d, 2H, J=9.0 Hz), 6.29 (s, 2H), 5.46 (s, 2H), 4.40 (d, 2H, J=4.8 Hz), 3.85 (t, 2H, J=5.6 Hz), 3.60 (t, 2H, J=5.6 Hz), 3.10 (s, 3H).

Comparative Example 119

A fluorescence-activated covalently labeling fluorescent reference probe 119 for SNAP protein tags was constructed using a molecular rotor as a viscosity-sensitive fluorescent dye.

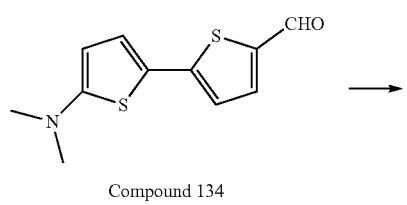

Compound 134

242

-continued

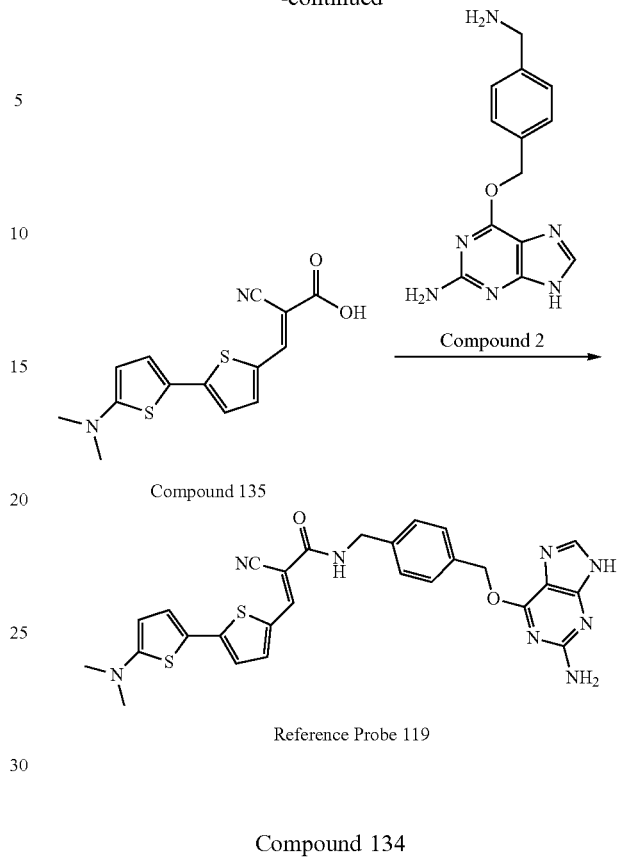

Compound 134

The synthesis was carried out by the method disclosed in the literature (US 20090042227 (A1). 2009 Dec. 12). ¹H-NMR (400 MHz, CDCl$_3$): δ=9.75 (s, 1H), 7.57 (d, 1H, J=4.0 Hz), 7.13 (d, 1H, J=4.0 Hz), 6.95 (d, 1H, J=4.0 Hz), 5.81 (d, 1H, J=4.0 Hz), 3.00 (s, 6H).

Compound 135

This compound was obtained by following the general procedure for compound 1, and the yield was 94%. ¹H-NMR (400 MHz, CDCl$_3$): δ=7.99 (s, 1H), 7.57 (d, 1H, J=4.0 Hz), 7.13 (d, 1H, J=4.0 Hz), 6.95 (d, 1H, J=4.0 Hz), 5.81 (d, 1H, J=4.0 Hz), 3.00 (s, 6H).

Reference Probe 119

This probe was obtained by following the general procedure for the reference probe 99. ¹H-NMR (400 MHz, CDCl$_3$): δ=11.32 (s, 1H), 9.75 (s, 1H), 7.99 (s, 1H), 7.81 (s, 1H), 7.57 (d, 1H, J=4.0 Hz), 7.40 (m, 4H), 7.13 (d, 1H, J=4.0 Hz), 6.95 (d, 1H, J=4.0 Hz), 6.29 (s, 2H), 5.81 (d, 1H, J=4.0 Hz), 5.46 (s, 2H), 4.40 (d, 2H, J=4.8 Hz), 3.00 (s, 6H).

Example 120

A fluorescence-activated covalently labeling fluorescent probe 120 for SNAP protein tags was constructed using a molecular rotor as a viscosity-sensitive fluorescent dye.

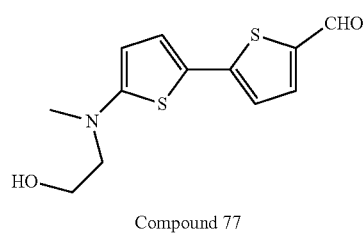

Compound 77

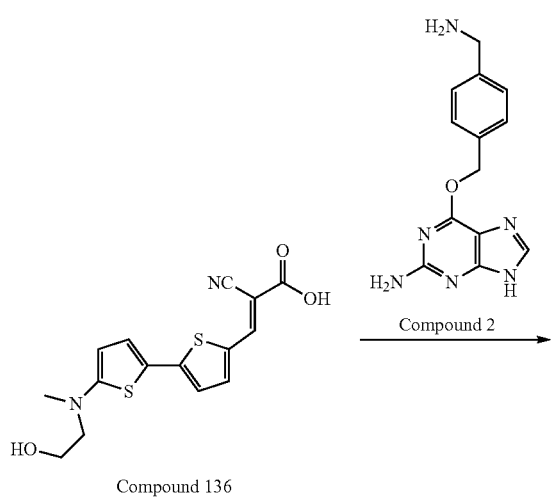

Compound 136

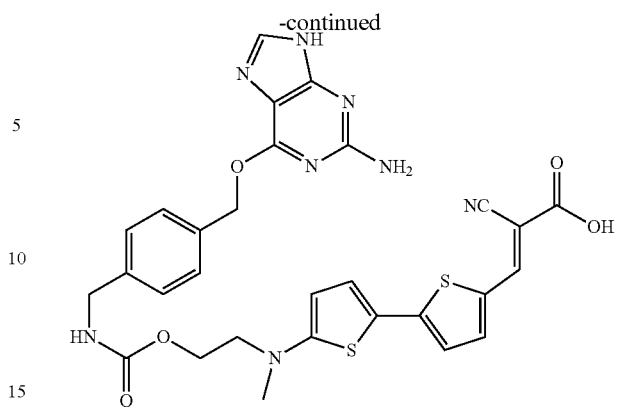

Probe 120

Compound 136

This compound was obtained by following the general procedure for compound 1, and the yield was 94%. $^1$H-NMR (400 MHz, CDCl$_3$): δ=7.99 (s, 1H), 7.57 (d, 1H, J=4.0 Hz), 7.13 (d, 1H, J=4.0 Hz), 6.95 (d, 1H, J=4.0 Hz), 5.81 (d, 1H, J=4.0 Hz), 3.85 (t, 2H, J=5.6 Hz), 3.60 (t, 2H, J=5.6 Hz), 3.10 (s, 3H).

Probe 120

This probe was obtained by following the general procedure for probe 1. $^1$H-NMR (400 MHz, CDCl$_3$): δ=11.32 (s, 1H), 9.75 (s, 1H), 7.99 (s, 1H), 7.81 (s, 1H), 7.57 (d, 1H, J=4.0 Hz), 7.40 (m, 4H), 7.13 (d, 1H, J=4.0 Hz), 6.95 (d, 1H, J=4.0 Hz), 6.29 (s, 2H), 5.81 (d, 1H, J=4.0 Hz), 5.46 (s, 2H), 4.40 (d, 2H, J=4.8 Hz), 3.85 (t, 2H, J=5.6 Hz), 3.60 (t, 2H, J=5.6 Hz), 3.10 (s, 3H).

Comparative Example 121

A fluorescence-activated covalently labeling fluorescent reference probe 121 for SNAP protein tags was constructed using a molecular rotor as a viscosity-sensitive fluorescent dye.

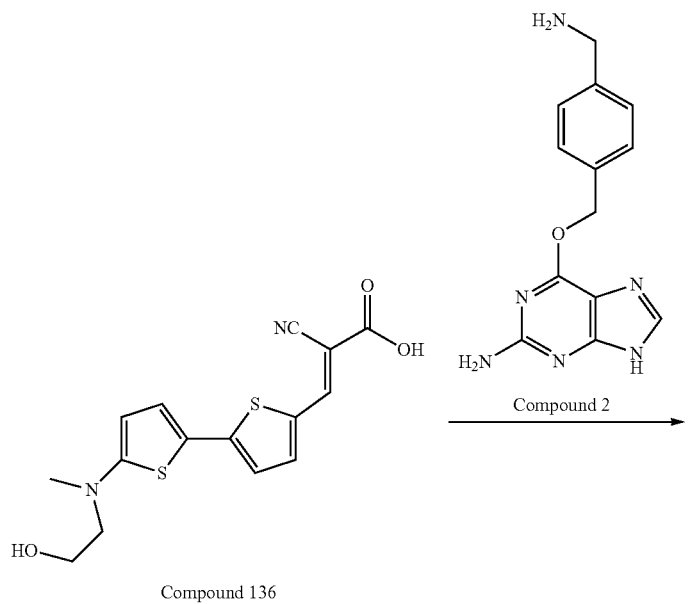

Compound 136

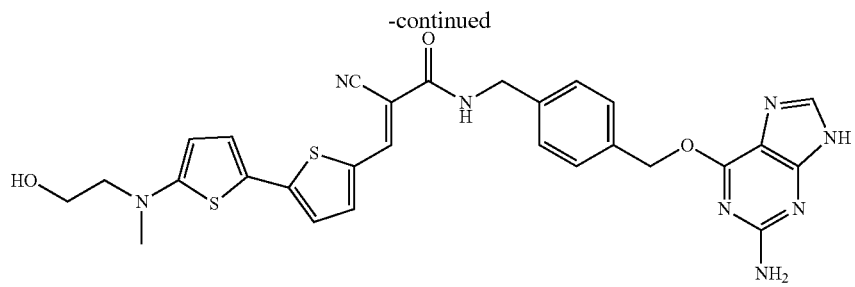

Reference Probe 121

Reference Probe 121

This probe was obtained by following the general procedure for probe 99. $^1$H-NMR (400 MHz, CDCl$_3$): δ=11.32 (s, 1H), 9.75 (s, 1H), 7.99 (s, 1H), 7.81 (s, 1H), 7.57 (d, 1H, J=4.0 Hz), 7.40 (m, 4H), 7.13 (d, 1H, J=4.0 Hz), 6.95 (d, 1H, J=4.0 Hz), 6.29 (s, 2H), 5.81 (d, 1H, J=4.0 Hz), 5.46 (s, 2H), 4.40 (d, 2H, J=4.8 Hz), 3.85 (t, 2H, J=5.6 Hz), 3.60 (t, 2H, J=5.6 Hz), 3.10 (s, 3H).

Example 122

Reference probes BG-CCVJ and BG-gly-CCVJ were prepared by the method reported in literature (T. Y. Wang et al. Chem Sci. 2016, 7, 301-307).

Probes 1 to 98, 101, 103, 105, 107, 109, 111, 114, 117, and 120, and the reference probes 99, 100, 102, 104, 106, 108, 110, 112, 113, 115, 116, 118, 119, 121, BG-CCVJ and BG-Gly-CCVJ were dissolved in dimethyl sulfoxide, respectively, to prepare mother liquors having a concentration of 1×10$^{-2}$ M, to each of which glycerol and methanol were added and uniformly mixed, to prepare solutions finally having a concentration of 1×10$^{-5}$ M. Depending on the probes, fluorescence emission spectra of the probes were detected successively with the maximum excitation wavelength of each probe under the same conditions, and the results were shown in Table 1.

As can be seen from Table 1, the probes of the Examples have fluorescence emission wavelength in a wide range, and have fluorescence intensity in glycerol significantly different from that in methanol. That is, these probes are sensitive to viscosity changes and have viscosity responsiveness.

Example 123

Probes were mixed with corresponding protein tags to obtain mixed samples, in which the final probe concentration was 5 μM, and the final protein tag concentration was 10 μM. The mixed samples were incubated 37° C. for 1 hr, fluorescence spectrophotometer was used to detect the change in fluorescence intensity, and the results are shown in Table 1.

It can be seen from the quantum yield of free probe in Table 1 that the probes of the Examples and the reference probes had extremely low fluorescence prior to binding to a protein tag, close to the background fluorescence level of a PBS buffer, which indicates that prior to binding to the protein tag, the fluorescence of the viscosity-sensitive fluorescent probes has not been activated. From the quantum yield of probe bound to protein tag, after reacting with the protein tags, the probes of the Examples could be detected to have significant signal enhancement in corresponding excitation transmission channels, the fluorescence activation multiple reached several hundreds to a thousand or more, and the brightness was high, which illustrates that after the probes of the Examples are bound to the protein tags, fluorescence of the probes can be activated, and the probes have good fluorescent molecular switching properties. In contrast, though the fluorescence of the reference probes could also be activated, the quantum yield of activated fluorescence was very low, and the brightness was very poor. In particular, in view of comparison results between probe 98 and reference probe 99, probe 101 and reference probe 102, probe 103 and reference probe 104, probe 105 and reference probe 106, probe 107 and reference probe 108, probe 109 and reference probe 110, probe 111 and reference probe 112, probe 114 and reference probe 115, probe 117 and reference probe 118, probe 120 and reference probe 121 in Table 1, for the same fluorescent dye, when the ligand is connected to the electron donor part of the fluorescent dye, the fluorescence activation brightness of the probe is much higher than the reference probe in which ligand is connected to the electron acceptor part of the fluorescent dye.

Accordingly, it can be seen that the fluorescence of the probe binding protein tag of the embodiment can be activated and has good fluorescence molecular switching properties. Compared with the reference probes formed by binding a ligand to an electron acceptor of the fluorescent dyes, the probes formed by binding a ligand to an electron donor of the fluorescent dyes in the Examples have significantly improved fluorescence activation brightness.

TABLE 1

| | fluorescence emission spectra of different probes | | | | |
|---|---|---|---|---|---|
| Name | Quantum yield of free probe | Quantum yield of probe bound to protein tag | Emission wavelength/ nm | Fluorescence activation multiple | Fluorescence ratio in glycerol to methanol |
| probe 1 | <0.001 | 0.35 | 480 | 360 | 560 |
| probe 2 | 0.001 | 0.15 | 510 | 146 | 410 |
| probe 3 | 0.0019 | 0.27 | 532 | 139 | 399 |

TABLE 1-continued fluorescence emission spectra of different probes

| Name | Quantum yield of free probe | Quantum yield of probe bound to protein tag | Emission wavelength/ nm | Fluorescence activation multiple | Fluorescence ratio in glycerol to methanol |
|---|---|---|---|---|---|
| probe 4 | <0.001 | 0.35 | 480 | 490 | 562 |
| probe 5 | <0.001 | 0.15 | 555 | 1174 | 790 |
| probe 6 | <0.001 | 0.37 | 610 | 989 | 1183 |
| probe 7 | <0.001 | 0.23 | 480 | 1502 | 1455 |
| probe 8 | 0.0018 | 0.12 | 510 | 68 | 320 |
| probe 9 | <0.001 | 0.21 | 531 | 745 | 851 |
| probe 10 | <0.001 | 0.39 | 482 | 431 | 655 |
| probe 11 | 0.0013 | 0.36 | 481 | 270 | 422 |
| probe 12 | 0.0012 | 0.41 | 482 | 351 | 405 |
| probe 13 | <0.001 | 0.29 | 483 | 315 | 391 |
| probe 14 | <0.001 | 0.18 | 531 | 771 | 560 |
| probe 15 | <0.001 | 0.21 | 580 | 277 | 320 |
| probe 16 | <0.001 | 0.21 | 580 | 359 | 311 |
| probe 17 | <0.001 | 0.15 | 580 | 498 | 402 |
| probe 18 | 0.0017 | 0.45 | 535 | 265 | 301 |
| probe 19 | 0.0012 | 0.45 | 535 | 361 | 299 |
| probe 20 | <0.001 | 0.32 | 535 | 398 | 341 |
| probe 21 | <0.001 | 0.48 | 555 | 560 | 1481 |
| probe 22 | <0.001 | 0.36 | 590 | 610 | 1821 |
| probe 23 | <0.001 | 0.42 | 610 | 712 | 1235 |
| probe 24 | <0.001 | 0.48 | 555 | 590 | 1681 |
| probe 25 | <0.001 | 0.36 | 590 | 670 | 1621 |
| probe 26 | <0.001 | 0.42 | 610 | 910 | 1123 |
| probe 27 | <0.001 | 0.39 | 555 | 665 | 1134 |
| probe 28 | <0.001 | 0.31 | 590 | 551 | 1132 |
| probe 29 | <0.001 | 0.33 | 610 | 621 | 998 |
| probe 30 | <0.001 | 0.55 | 570 | 535 | 1125 |
| probe 31 | <0.001 | 0.41 | 607 | 421 | 1135 |
| probe 32 | <0.001 | 0.46 | 609 | 638 | 997 |
| probe 33 | <0.001 | 0.55 | 570 | 957 | 1781 |
| probe 34 | <0.001 | 0.48 | 570 | 857 | 1774 |
| probe 35 | 0.0012 | 0.53 | 570 | 433 | 972 |
| probe 36 | 0.001 | 0.50 | 570 | 488 | 1258 |
| probe 37 | 0.0012 | 0.56 | 570 | 469 | 1135 |
| probe 38 | 0.0011 | 0.56 | 570 | 503 | 1011 |
| probe 39 | 0.0016 | 0.55 | 570 | 335 | 892 |
| probe 40 | 0.001 | 0.41 | 570 | 421 | 759 |
| probe 41 | 0.0015 | 0.31 | 575 | 212 | 101 |
| probe 42 | 0.0013 | 0.38 | 600 | 298 | 178 |
| probe 43 | <0.001 | 0.37 | 602 | 982 | 1028 |
| probe 44 | <0.001 | 0.37 | 603 | 1586 | 1459 |
| probe 45 | <0.001 | 0.29 | 603 | 958 | 752 |
| probe 46 | <0.001 | 0.21 | 620 | 563 | 682 |
| probe 47 | <0.001 | 0.26 | 627 | 358 | 235 |
| probe 48 | <0.001 | 0.16 | 625 | 428 | 180 |
| probe 49 | <0.001 | 0.11 | 601 | 541 | 210 |
| probe 50 | <0.001 | 0.29 | 612 | 416 | 358 |
| probe 51 | <0.001 | 0.25 | 625 | 392 | 359 |
| probe 52 | <0.001 | 0.25 | 625 | 435 | 270 |
| probe 53 | <0.001 | 0.18 | 625 | 579 | 401 |
| probe 54 | <0.001 | 0.17 | 650 | 498 | 391 |
| probe 55 | <0.001 | 0.25 | 651 | 382 | 211 |
| probe 56 | <0.001 | 0.39 | 566 | 989 | 436 |
| probe 57 | <0.001 | 0.31 | 566 | 1026 | 762 |
| probe 58 | <0.001 | 0.27 | 590 | 519 | 419 |
| probe 59 | <0.001 | 0.39 | 600 | 498 | 370 |
| probe 60 | 0.0011 | 0.81 | 620 | 751 | 1199 |
| probe 61 | 0.0012 | 0.77 | 620 | 668 | 817 |
| probe 62 | <0.001 | 0.32 | 640 | 592 | 711 |
| probe 63 | 0.0015 | 0.73 | 620 | 486 | 531 |
| probe 64 | <0.001 | 0.48 | 620 | 519 | 632 |
| probe 65 | <0.001 | 0.66 | 650 | 798 | 391 |
| probe 66 | <0.001 | 0.37 | 620 | 512 | 386 |
| probe 67 | <0.001 | 0.36 | 620 | 576 | 276 |
| probe 68 | <0.001 | 0.36 | 620 | 681 | 381 |
| probe 69 | <0.001 | 0.27 | 620 | 491 | 217 |
| probe 70 | 0.0026 | 0.68 | 640 | 258 | 131 |
| probe 71 | 0.0028 | 0.67 | 640 | 239 | 121 |
| probe 72 | 0.001 | 0.47 | 640 | 486 | 268 |
| probe 73 | 0.0031 | 0.76 | 680 | 248 | 325 |
| probe 74 | 0.0025 | 0.78 | 680 | 311 | 297 |
| probe 75 | 0.0021 | 0.44 | 700 | 211 | 105 |
| probe 76 | 0.0011 | 0.37 | 680 | 351 | 186 |

TABLE 1-continued fluorescence emission spectra of different probes

| Name | Quantum yield of free probe | Quantum yield of probe bound to protein tag | Emission wavelength/ nm | Fluorescence activation multiple | Fluorescence ratio in glycerol to methanol |
|---|---|---|---|---|---|
| probe 77 | 0.0014 | 0.38 | 655 | 268 | 279 |
| probe 78 | <0.001 | 0.28 | 672 | 369 | 189 |
| probe 79 | <0.001 | 0.31 | 681 | 419 | 298 |
| probe 80 | 0.0011 | 0.38 | 655 | 349 | 218 |
| probe 81 | <0.001 | 0.29 | 672 | 391 | 235 |
| probe 82 | <0.001 | 0.21 | 681 | 321 | 241 |
| probe 83 | <0.001 | 0.18 | 515 | 209 | 103 |
| probe 84 | <0.001 | 0.16 | 515 | 431 | 121 |
| probe 85 | <0.001 | 0.15 | 535 | 391 | 187 |
| probe 86 | <0.001 | 0.17 | 550 | 413 | 214 |
| probe 87 | <0.001 | 0.45 | 575 | 515 | 209 |
| probe 88 | <0.001 | 0.29 | 595 | 621 | 298 |
| probe 89 | <0.001 | 0.32 | 612 | 421 | 129 |
| probe 90 | <0.001 | 0.28 | 575 | 541 | 109 |
| probe 91 | 0.0013 | 0.24 | 612 | 192 | 163 |
| probe 92 | <0.001 | 0.65 | 645 | 923 | 241 |
| probe 93 | <0.001 | 0.56 | 675 | 753 | 362 |
| probe 94 | <0.001 | 0.47 | 700 | 569 | 158 |
| probe 95 | <0.001 | 0.42 | 645 | 553 | 431 |
| probe 96 | <0.001 | 0.31 | 675 | 435 | 125 |
| probe 97 | <0.001 | 0.23 | 700 | 812 | 261 |
| probe 98 | <0.001 | 0.78 | 650 | 893 | 182 |
| Reference Probe 99 | <0.001 | 0.01 | 649 | 53 | 129 |
| Reference Probe 100 | <0.001 | 0.011 | 480 | 43 | 213 |
| probe 101 | <0.001 | 0.37 | 481 | 463 | 362 |
| Reference Probe 102 | <0.001 | 0.02 | 480 | 31 | 212 |
| probe 103 | <0.001 | 0.27 | 515 | 651 | 321 |
| Reference Probe 104 | <0.001 | 0.02 | 515 | 23 | 351 |
| probe 105 | <0.001 | 0.41 | 510 | 549 | 328 |
| Reference Probe 106 | <0.001 | 0.01 | 555 | 62 | 215 |
| probe 107 | <0.001 | 0.47 | 555 | 564 | 526 |
| Reference Probe 108 | <0.001 | 0.02 | 555 | 30 | 329 |
| probe 109 | <0.001 | 0.33 | 566 | 546 | 341 |
| Reference Probe 110 | <0.001 | 0.01 | 567 | 23 | 218 |
| probe 111 | <0.001 | 0.49 | 570 | 681 | 621 |
| Reference Probe 112 | <0.001 | 0.01 | 570 | 41 | 211 |
| Reference Probe 113 | <0.001 | 0.01 | 625 | 36 | 129 |
| probe 114 | <0.001 | 0.27 | 625 | 328 | 230 |
| Reference Probe 115 | <0.001 | 0.01 | 625 | 38 | 113 |
| Reference Probe 116 | <0.001 | 0.01 | 620 | 29 | 125 |
| probe 117 | <0.001 | 0.39 | 620 | 562 | 321 |
| Reference Probe 118 | <0.001 | 0.02 | 621 | 29 | 158 |
| Reference Probe 119 | <0.001 | 0.01 | 655 | 15 | 362 |
| probe 120 | <0.001 | 0.42 | 656 | 469 | 421 |
| Reference Probe 121 | <0.001 | 0.01 | 655 | 39 | 219 |
| Reference Probe BG-CCVJ | <0.001 | 0.02 | 501 | 170 | 260 |
| Reference Probe BG-Gly-CCVJ | <0.001 | — | — | 60 | 260 |

Example 124

SNAP protein tags were added to 30 µM the solutions of probe 1, probe 14, probe 21, probe 30, probe 48, probe 43, probe 56, respectively, to produce mixed sample solutions in which the final concentration of the SNAP protein tags was 0.1 µM, 0.5 µM, 0.7 µM, 1.2 µM, 4.5 µM, 8.1 µM, 13.1 µM and 14.8 µM. The mixed sample solutions were placed at 37° C. to react for 1 hr. A fluorescence spectrophotometer was used to detect the change in excitation emission spectrum of the sample, and the relationship between SNAP protein tag concentration and fluorescence intensity was drawn according to the emission spectrum intensity, and the results were shown in FIGS. 2 to 11, respectively.

Figure 2:
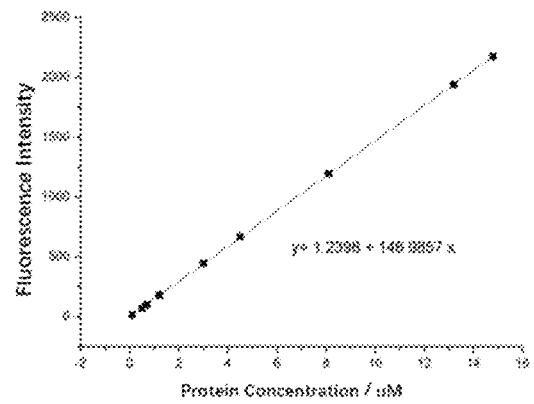
FIG. 2 to FIG. 11 are standard curves of the corresponding fluorescence intensity versus different SNAP protein tag concentrations for probe 1, probe 14, probe 21, probe 30, probe 43, probe 48, probe 56, probe 63, probe 70, and probe 88, respectively.
Figure 3:
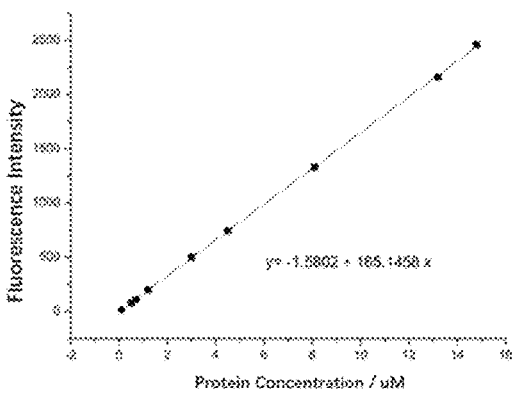
Figure 4:
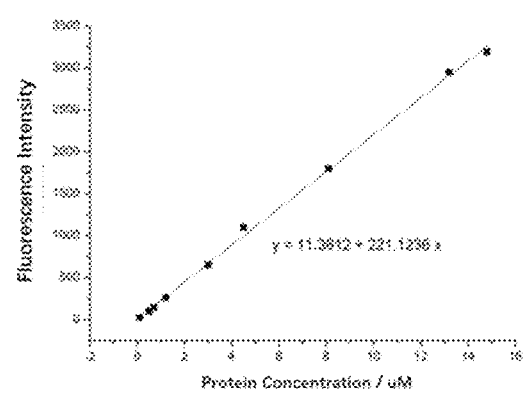
Figure 5:
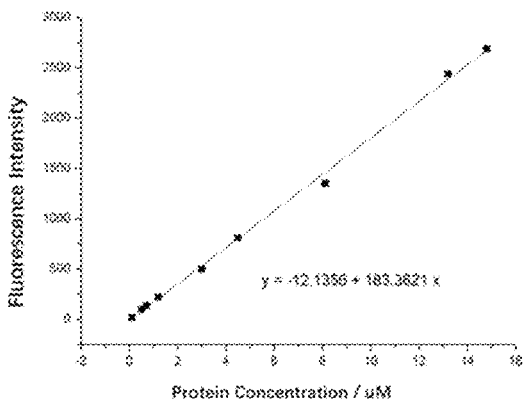
Figure 6:
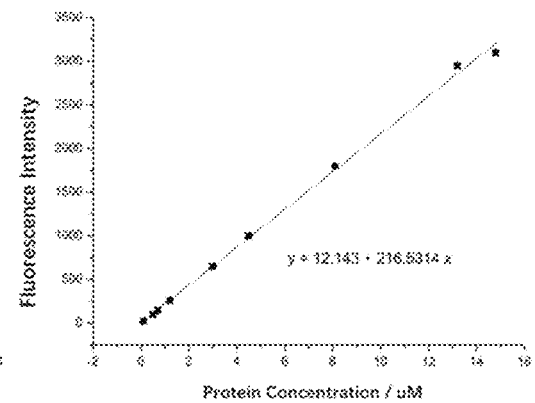
Figure 7:
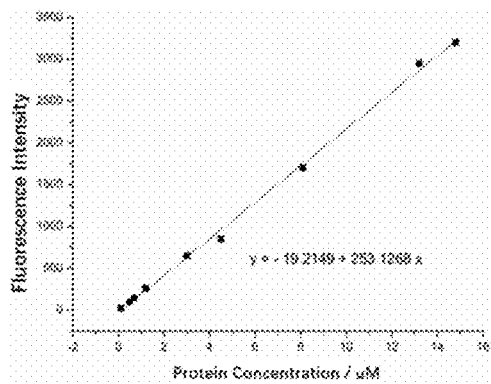
Figure 8:
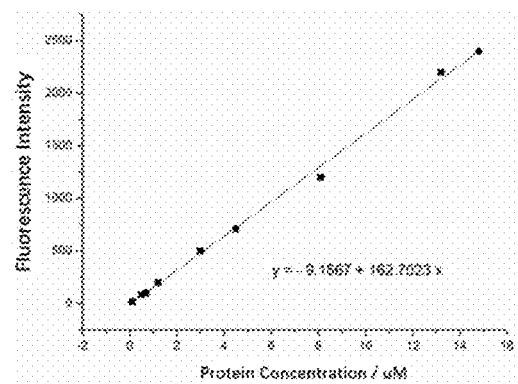
Figure 9:
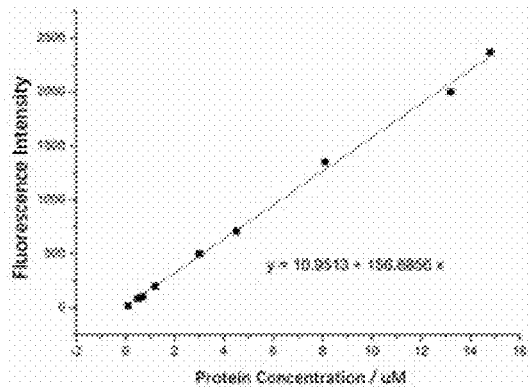
Figure 10:
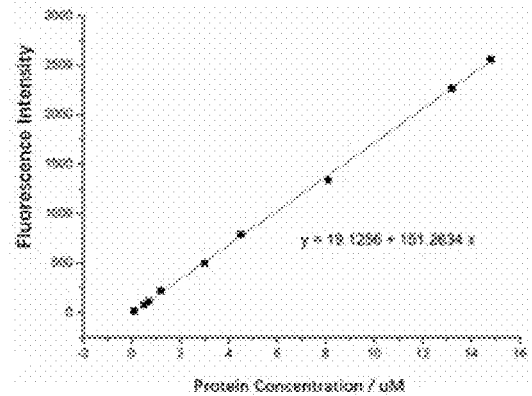
Figure 11:
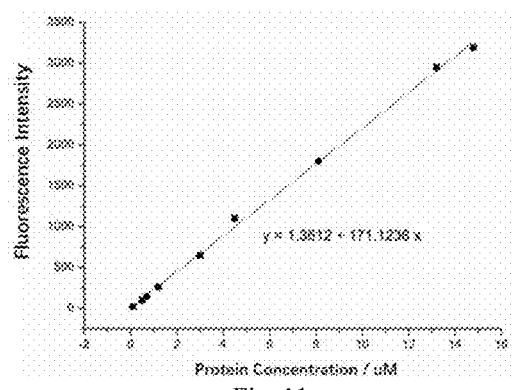

As can be seen from FIG. 2, SNAP protein tag concentration within the range of 0.1 um to 14.8 um has a good linear relationship with the fluorescence intensity of the probe, so protein tags can be quantitatively detected according to the standard curve.

Example 125

Figure 12:
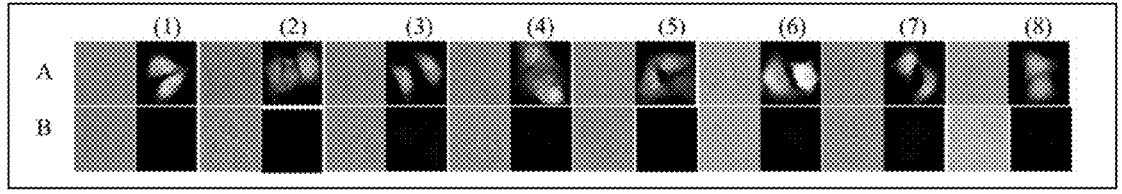
FIG. 12 is a fluorescence spectrum of cell labeled with different probes, wherein (1) to (8) are probe 1, probe 15, probe 21, probe 30, probe 56, probe 60, probe 63, Probe 88, respectively, group A is a HeLa cell with a protein tag expressed, and group B is a HeLa-WT cell (original HeLa cell, without a protein tag expressed)

HeLa cells were taken as an example to exhibit the labeling effect of the compound in mammalian cells. HeLa cells with stable expression of protein tags and HeLa-WT cells (HeLa primitive cells, with no protein tag expressed) were implanted in a 14 mm glass-bottom 96-well cell culture plate and stabilized for 10 hrs. Probes 1, 15, 21, 30, 56, 60, 63, 88 were added to the media, respectively and diluted to 5 μMs. The cells were incubated in a carbon dioxide incubator at 37° C. for 2 hrs, and then a Leica TPS-8 confocal microscopy was used to image the fluorescent changes of the labeled cells. The results of group B in FIG. 12 show that no corresponding fluorescence signal was detected in HeLa-WT cells after the addition of the aforesaid probes, indicating that the fluorescence of the probes was not affected by the intracellular environment. However, for HeLa cells with protein tags expressed shown by group A in FIG. 12, strong fluorescent signals could be detected, which are nearly 300 times stronger.

The above experiments indicate that the probe can specifically label intracellular protein tags and achieve fluorescence specific lighting, and meanwhile, the fluorescence of the probe is not affected by the intracellular environment.

Example 126

Figure 13:
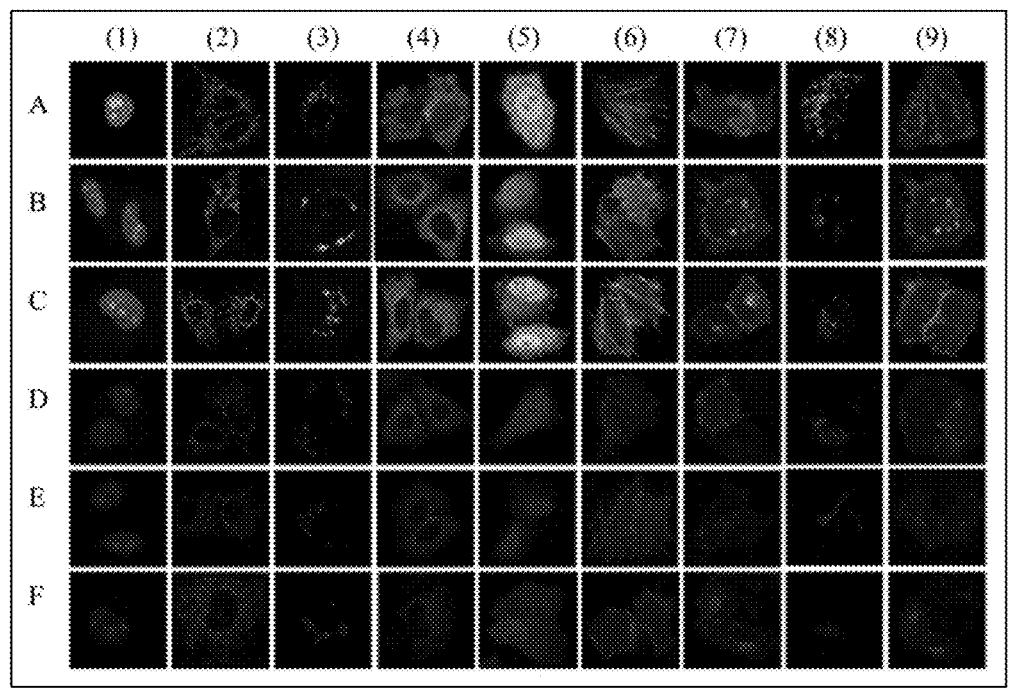
FIG. 13 shows micrographs of different organelles labeled with different probes, wherein group A to group F are probe 1, probe 21, probe 48, probe 60, probe 66, probe 77 respectively, (1) to (9) are the nucleus, mitochondria, Golgi, endoplasmic reticulum, whole cells, cytoskeleton, extracellular membrane, lysosome, and intracellular membrane, respectively.
Figure 14:
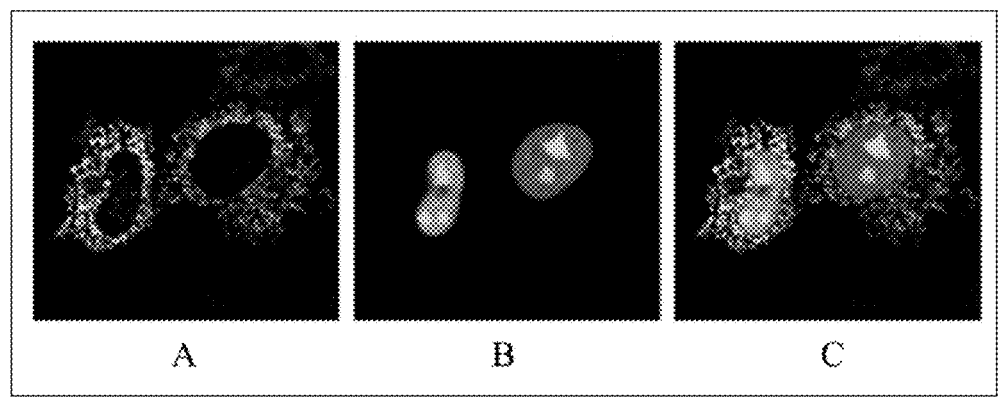
FIG. 14 shows the two-color labeling of the same cell by different probes, wherein A is probe 1 labeled mitochondrion, B is probe 43 labeled nucleus, and C is an orthogonal imaging of A and B.

To verify that probes 1, 21, 48, 60, 66 and 77 can be used to label target proteins located by different organelles, HeLa cells were taken as an example to detect the effect of probes on labeling different subcellular proteins. HeLa cells were implanted 5000 cells per well in a 96-well glass-bottom cell culture plate. 14 hrs later, the cells were transfected with the plasmids encoding different organelle localized protein tags using Lipo2000; the original medium was removed 24 hrs after transfection, washed with a phenol-free red DMEM medium twice, and incubated with a phenol-free red medium containing 0.2 μM probes for 2 hrs, and then the cell labeling effects were detected by imaging with a leica TCS-8 confocal microscopy. Results are shown in FIG. 13. The probes can clearly display a variety of subcellular organelle structures without washing, including but not limited to nucleus, mitochondria, golgi body, endoplasmic reticulum, whole cell, cytoskeleton, extracellular membrane, lysosome, and endometrium.

These results indicate that the probe can be used as a powerful tool for labeling cell subcellular organelles.

Example 127

HeLa cells were implanted 5000 cells per well in a 96-well glass-bottom cell culture plate. 14 hrs later, the cells were transfected with pcdna3.1-clip-nls (The plasmid encoding nucleus localized CLIP tag), pcdna3.1-mito-snap (The plasmid encoding mitochondrial localized SNAP tag) using Lipo2000, 0.1 μM per well. The original medium was removed 24 hrs after transfection, washed twice with a phenol-free red DMEM medium. Then, the cells were incubated respectively with a phenol-free red media containing 0.2 μM probe 1 and probe 43 for two hrs, and then the cell labeling effects were detected by imaging with a leica TCS-8 confocal microscopy. Results are shown in FIG. 13. The probe 1 and problem 43 respectively can clearly display the structures of mitochondrial and nuclear without washing, and the co-localization coefficient of the fluorescence channel of nuclear labeled by probe 43 and the fluorescence channel of mitochondria labeled by probe 1 is less than 0.1, indicating that the two fluorescence channels will not interfere with each other.

The above experiments indicated that the spectra of fluorescence groups of different probes would not interfere with each other, and orthogonal labeling imaging could be performed simultaneously.

Example 128

Figure 15:
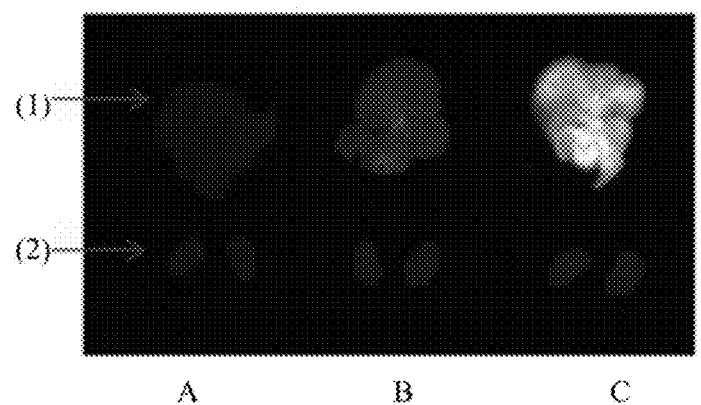
FIG. 15 shows labeling with probe 88 in living mice, wherein group A is a blank group, group B is a control group, group C is a sample group, (1) is a liver, and (2) is a kidney.

First, a SNAP protein tag expressing plasmid, pcdna3.1-SNAP (sample group), and a control plasmid without SNAP protein tag expressing, pcdna3.1-CAT (control group), were introduced into mice. This method dissolves plasmids in a large volume of solution and rapidly injects them into mice through tail vein injection. The mouse liver and kidneys absorb DNA and then express the target protein. 20 hrs after plasmid injection, 0.4 μM probe 88 dissolved in 200 μl PBS was injected into mice through tail vein injection to label the SNAP protein tag. 6 hrs later, the mice were dissected, and the fluorescence differences in the liver parts of different mouse samples were detected by KODAK multi-spectral in vivo imaging system. Results are shown in FIG. 15. The liver fluorescence of the control plasmid pcdna3.1-CAT injected with probe 88 was very low, close to the background fluorescence level of the blank liver without the probe, while the liver of SNAP plasmid pcdna3.1-SNAP injected with probe 88 had strong fluorescence, and the signal intensity was more than 20 times higher than that of the control group.

The above experiments showed that the fluorescence of the probe was not affected by the internal environment of animals, and it could be applied to live animals in vivo, and it could specifically label SNAP protein tags expressed in liver parts and generate strong fluorescence signals.

Example 129

Through the directed evolution displayed by phage, after six rounds of SNAP-tag screening, two SNAP-tag mutants were cloned, which were SNAP F33G and SNAP V164E, respectively. The two SNAP-tag mutants were labeled by probes 1, 21, 40, respectively in accordance with the method described in Example 123. As shown by the results, under the same conditions, the quantum yield after fluorescence activation of the probes was 2.1 to 1.6 times of the original yield, as compared with the sequences disclosed by a literature (Bright Mollwitz et al. Biochem 2012, 51, 986-986).

Attached is the DNA sequences of SNAP F33G and SNAP V164E:

DNA sequence of SNAP F33G (SEQ ID NO: 1):

ATGGACAAAGACTGCGAAATGAAGCGCACCACCCTGGATAGCCCTCTGGG

CAAGCTGGAACTGTCTGGGTGCGAACAGGGCCTGCACCGTATCATCGGCC

-continued

```
TGGGCAAAGGAACATCTGCCGCCGACGCCGTGGAAGTGCCTGCCCCAGCC

GCCGTGCTGGGCGGACCAGAGCCACTGATGCAGGCCACCGCCTGGCTCAA

CGCCTACTTTCACCAGCCTGAGGCCATCGAGGAGTTCCCTGTGCCAGCCC

TGCACCACCCAGTGTTCCAGCAGGAGAGCTTTACCCGCCAGGTGCTGTGG

AAACTGCTGAAAGTGGTGAAGTTCGGAGAGGTCATCAGCTACAGCCACCT

GGCCGCCCTGGCCGGCAATCCCGCCGCCACCGCCGCCGTGAAAACCGCCC

TGAGCGGAAATCCCGTGCCCATTCTGATCCCCTGCCACCGGGTGGTGCAG

GGCGACCTGGACGTGGGGGGCTACGAGGGCGGGCTCGCCGTGAAAGAGTG

GCTGCTGGCCCACGAGGGCCACAGACTGGGCAAGCCTGGGCTGGGTTAA
```

DNA sequence of SNAP V164E (SEQ ID NO: 2):

```
ATGGACAAAGACTGCGAAATGAAGCGCACCACCCTGGATAGCCCTCTGGG

CAAGCTGGAACTGTCTGGGTGCGAACAGGGCCTGCACCGTATCATCTTCC

TGGGCAAAGGAACATCTGCCGCCGACGCCGTGGAAGTGCCTGCCCCAGCC

GCCGTGCTGGGCGGACCAGAGCCACTGATGCAGGCCACCGCCTGGCTCAA

CGCCTACTTTCACCAGCCTGAGGCCATCGAGGAGTTCCCTGTGCCAGCCC

TGCACCACCCAGTGTTCCAGCAGGAGAGCTTTACCCGCCAGGTGCTGTGG

AAACTGCTGAAAGTGGTGAAGTTCGGAGAGGTCATCAGCTACAGCCACCT

GGCCGCCCTGGCCGGCAATCCCGCCGCCACCGCCGCCGTGAAAACCGCCC

TGAGCGGAAATCCCGTGCCCATTCTGATCCCCTGCCACCGGGTGGTGCAG

GGCGACCTGGACGTGGGGGGCTACGAGGGCGGGCTCGCCGAGAAAGAGTG

GCTGCTGGCCCACGAGGGCCACAGACTGGGCAAGCCTGGGCTGGGTTAA
```

Example 130

Figure 16:
FIG. 16 shows the fluorescence changes of probe 21 in mammalian cells with the protein degradation.

To verify the correlation between the fluorescent activation of the probe of the present invention and the existence of proteins, SNAP protein in mammalian cells was taken as an example, and the fluorescence changes of SNAP protein binding probes after protein degradation were detected in HeLa cells by taking AID degradation system as an example. Firstly, HeLa cells were implanted 20,000/cm$^2$ in a 20 mm glass-bottom cell culture dish, and 14 hrs later, plasmids pcdna3.1-TIR1 and pcdna3.1-SNAP-IAA17-H2B were transfected by invitrogen's lipofectmain2000 transfection reagent. 24 hrs after the cell transfection, the original cell culture medium was replaced with a phenol-free red DMEM medium containing 1 µM of probe 21 to label the cells. The cell samples were incubated in a carbon dioxide incubator at 37° C. for 1 hour. After the labeling was completed, the fluorescence signal of labeled cells was detected by imaging with a Leica SP8 laser confocal microscopy, and indoleacetic acid (IAA) was added to induce SNAP-IAA17-H2B protein to degrade, and the cell fluorescence changes were detected during the protein degradation. Results are as shown in FIG. 16, the SNAP-IAA17-H2B protein was located in the nucleus (0 min), and protein degradation was induced by indoleacetic acid. With the increase of time, the fluorescence signal of SNAP-IAA17-H2B protein was gradually decreased. When indoleacetic acid was added for 120 min, the fluorescence signal was basically invisible, and the protein degradation rate was consistent with the results reported in literature. The above experiment indicates that the fluorescent properties of probes in mammalian cells also depend on the presence of proteins. When proteins exist, the fluorescence is activated, and when proteins are degraded, the fluorescence disappears, which can be used to track and monitor the degradation process of target proteins.

Example 131

Figure 17:
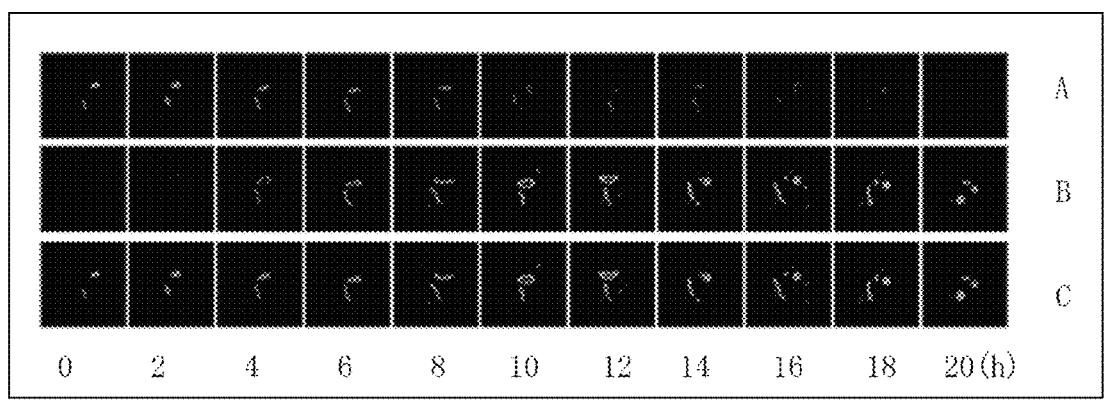
FIG. 17 shows tracing cell gap assembly process with different probes, wherein, A is the fluorescent channel of probe 21, B is the fluorescent channel of probe 1, and C is the superimposed fluorescent channel of probe 21 and probe 1.

To verify that the probe of the present invention can be used to monitor the assembly and degradation process of biological macromolecules in mammalian cells in real time, the process of tracing the assembly of intercellular protein CX43 to form intercellular channels in mammalian cells by the probe was detected by taking HeLa cells as an example. The C-terminal of CX43 gene was fused with SNAP gene, and HeLa cell line with stable expression of fusion protein CX43-SNAP was constructed and obtained by lentivirus infection technology. HeLa-CX43-SNAP cell lines were implanted in a 20 mm glass-bottom cell culture dish 10 hrs before the probe labeling. To conduct labeling, a phenol-free red DMEM medium was first used to dilute the probe 21 to 2 µM to replace the original cell culture medium. Cells were incubated in a carbon dioxide incubator at 37° C. for 1 hour. The cells were then washed twice using a fresh phenol-free red DMEM medium, with unbound probe 21 removed at 2-minute intervals. Then, DMEM phenol-free red culture medium containing 1 µM probe 1 was added to label cells. Leica SP8 confocal microscopy was used to monitor for a long time the fluorescence intensity and position changes of labeled cell samples at the corresponding fluorescence channels of probes 21 and 1, as shown in FIGS. 17A and 17B, respectively. A long-columnar specific fluorescence signal between two cells can be seen in the fluorescence channel of probe 21, as shown in FIG. 17A, consistent with the results reported in the literature (Guido Gaietta et al. Science 2002, 296, 503-507). When probe 1 was just added, the fluorescence signal could not be detected in its corresponding fluorescence channel, as shown in FIG. 17B, indicating that probe 21 labeled all CX43 proteins present in the cell. With the extension of culture time, new CX43-SNAP proteins were synthesized and labeled by probe 1. After labeling for 2 hrs, a fluorescent signal of probe 1 appeared and gradually increased at the edge of intercellular channels labeled by probe 21, while the fluorescent signal of probe 21 originally at the intercellular channels gradually decreased, indicating that the CX43-SNAP protein newly synthesized in intercellular channels replaced the original CX43-SNAP protein gradually from the surrounding to the center. The superimposed channel are as shown in FIG. 17C, consistent with the results reported in literature. The above experimental results demonstrate that SNAP series of compounds can be applied to real-time monitoring of the assembly and degradation of biomacromolecules in cells.

The invention claimed is:

1. A fluorescent probe, which has a structure as shown in formula (I);

wherein,

R is selected from

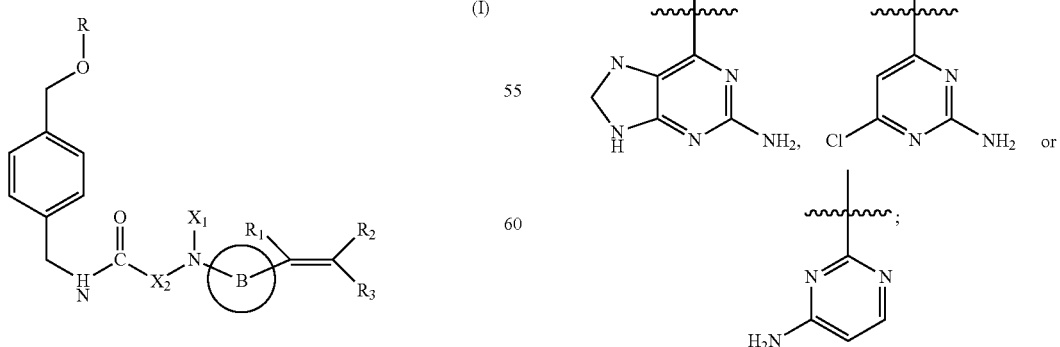

$X_1$ is selected from hydrogen, a saturated aliphatic straight or branched alkyl group of 1 to 10 carbon atoms,

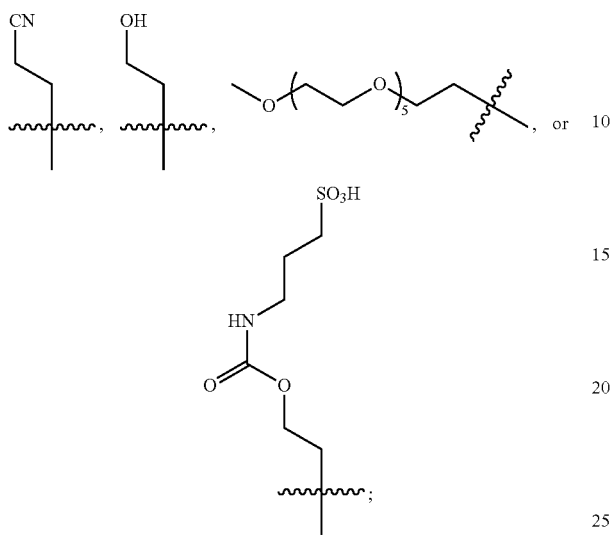

$X_2$ is selected from —$CH_2CH_2CH_2$— or —$CH_2CH_2O$—;

the moiety B is selected from the following Formulas containing the thiophene ring:

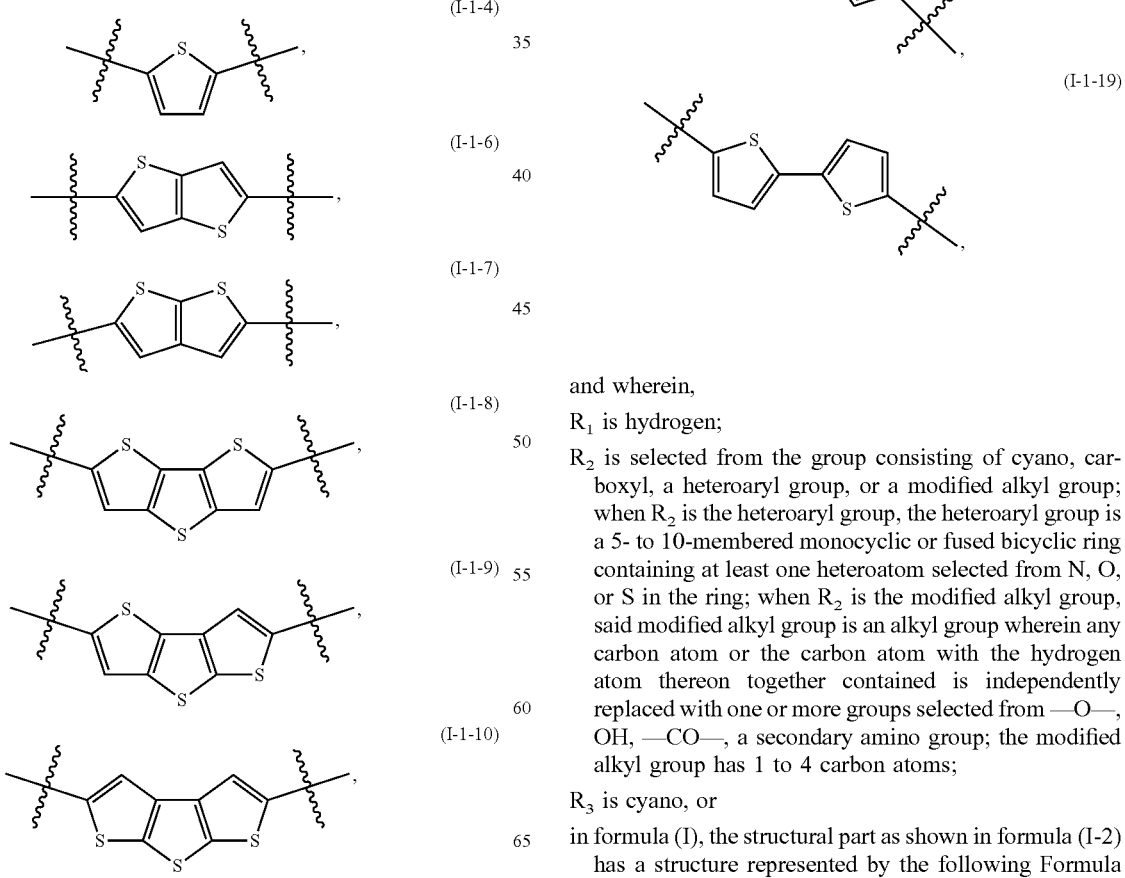

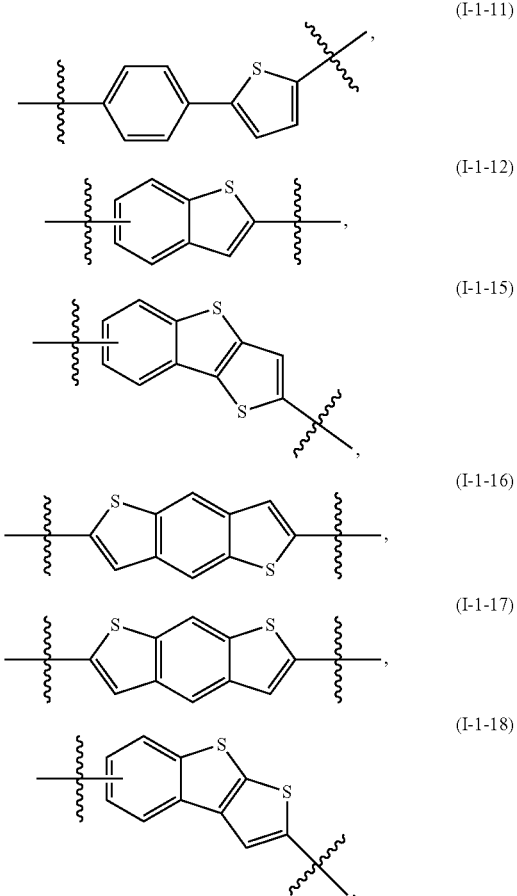

and wherein, $R_1$ is hydrogen;

$R_2$ is selected from the group consisting of cyano, carboxyl, a heteroaryl group, or a modified alkyl group; when $R_2$ is the heteroaryl group, the heteroaryl group is a 5- to 10-membered monocyclic or fused bicyclic ring containing at least one heteroatom selected from N, O, or S in the ring; when $R_2$ is the modified alkyl group, said modified alkyl group is an alkyl group wherein any carbon atom or the carbon atom with the hydrogen atom thereon together contained is independently replaced with one or more groups selected from —O—, OH, —CO—, a secondary amino group; the modified alkyl group has 1 to 4 carbon atoms;

$R_3$ is cyano, or in formula (I), the structural part as shown in formula (I-2) has a structure represented by the following Formula (I-2-b):

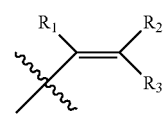
(I-2)

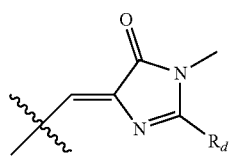
(I-2-b)

wherein, $R_d$ is methyl or phenyl.

2. The fluorescent probe according to claim 1, wherein the $R_2$ is selected from the following structures, or a bicyclic fused aromatic ring or fused aromatic heterocyclic ring formed by the following structures themselves or fused with each other:

3. The fluorescent probe according to claim 1, characterized in that the fluorescent probe is selected from the following structures:

Probe 21

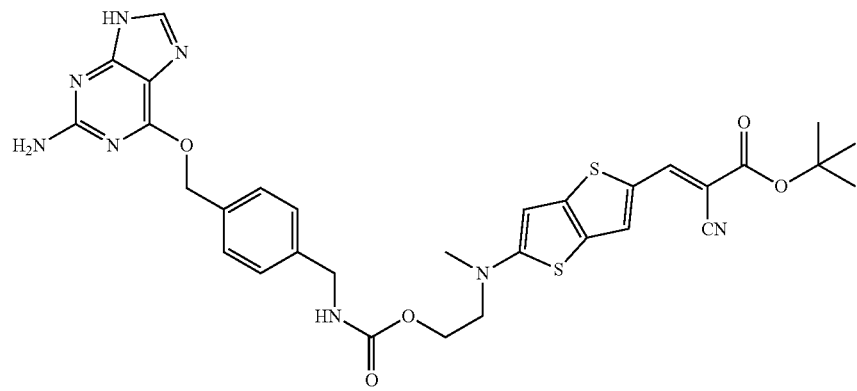

Probe 22

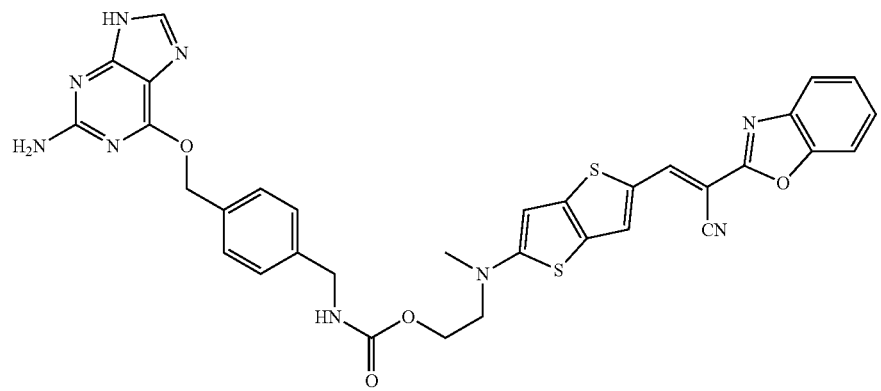

Probe 23

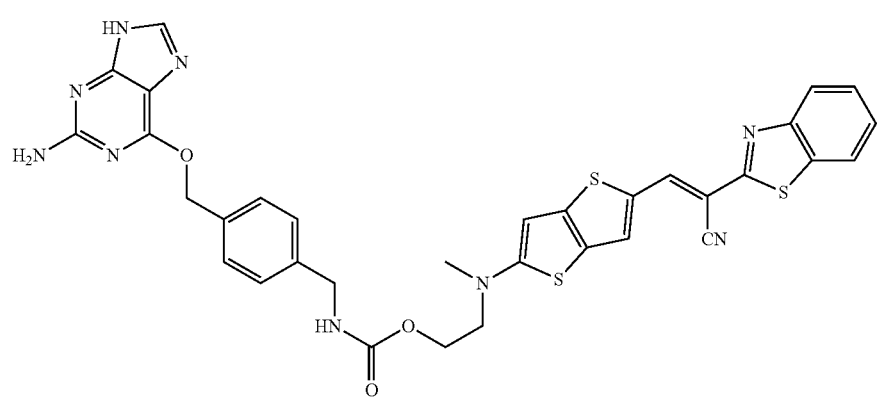

Probe 24
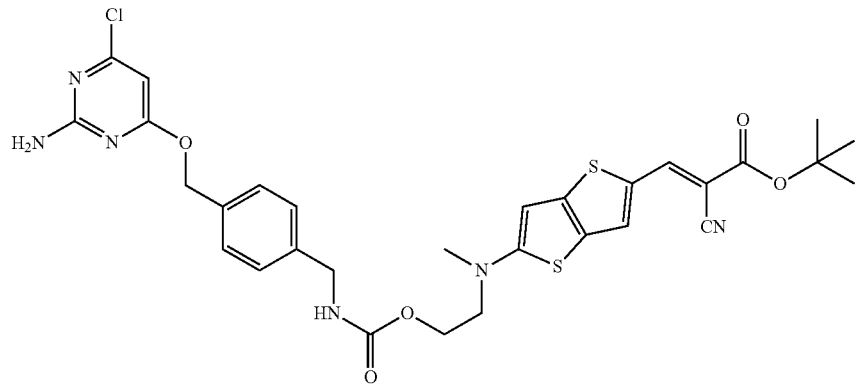
Probe 25
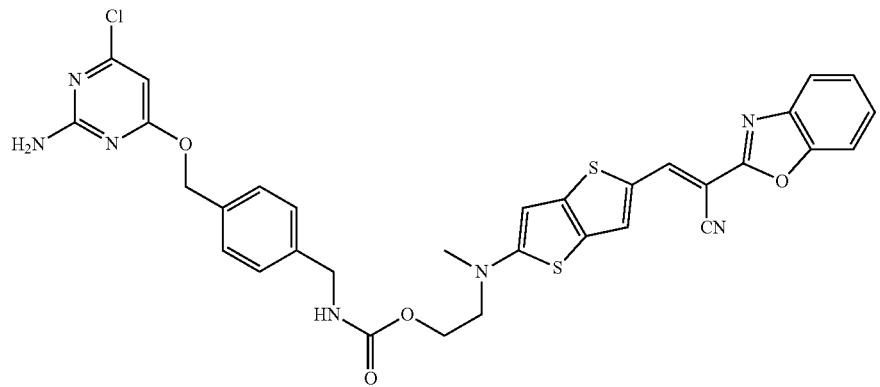
Probe 26
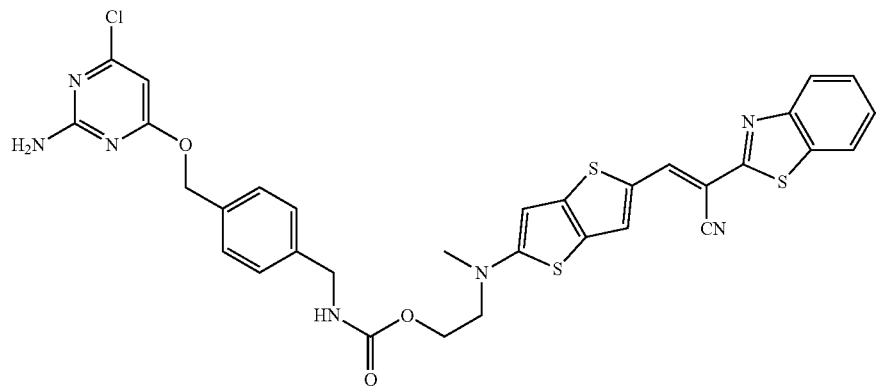
Probe 27
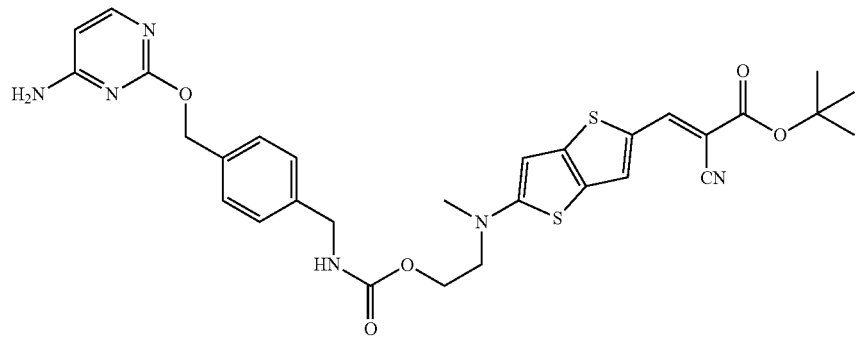

-continued
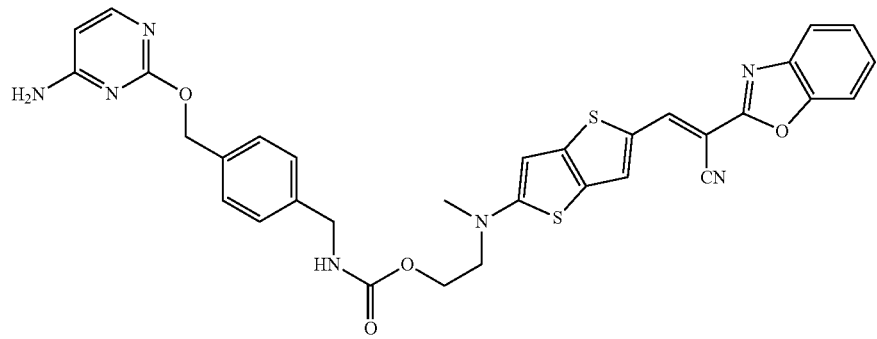
Probe 28
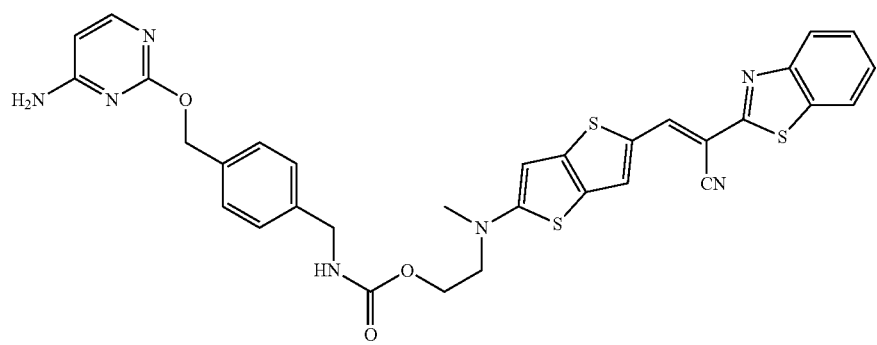
Probe 29
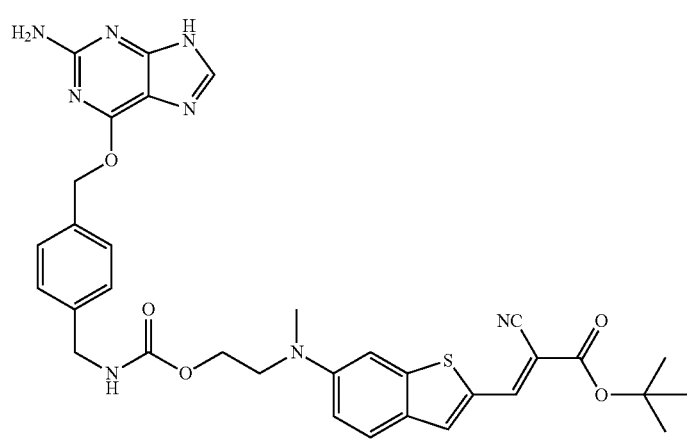
Probe 30
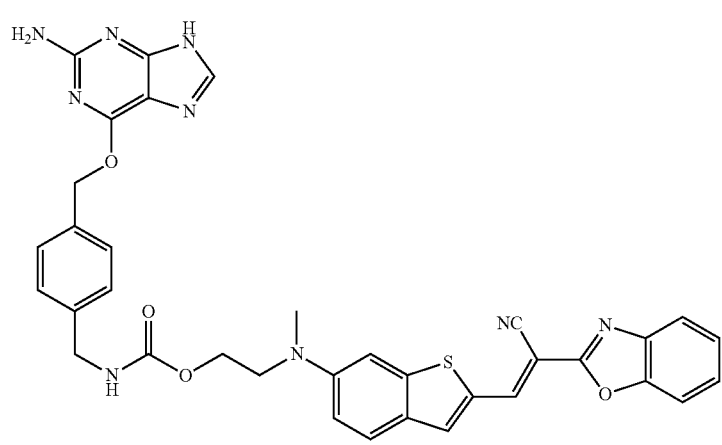
Probe 31

Probe32
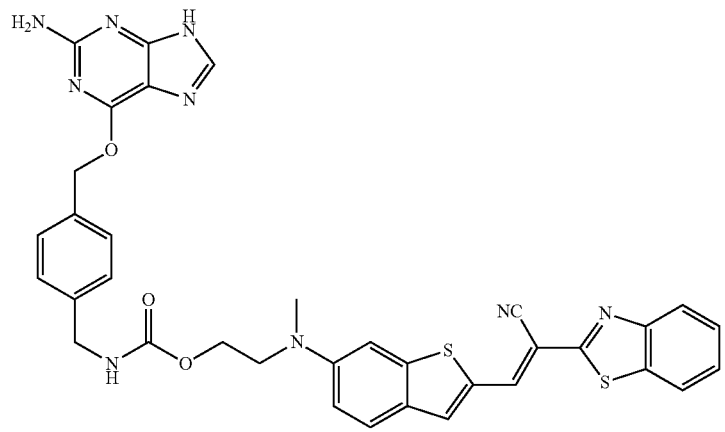
Probe 33
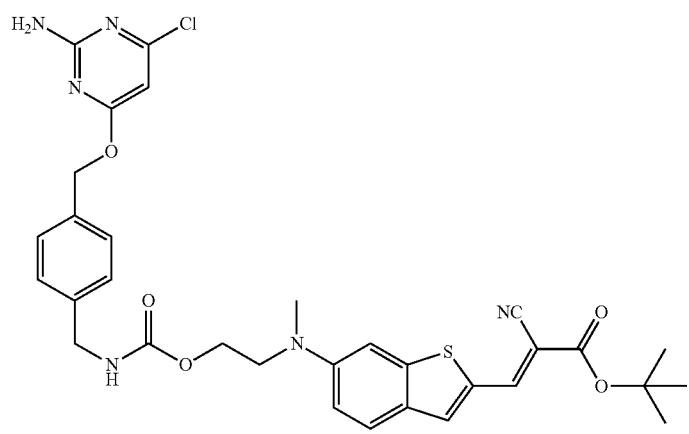
Probe 34
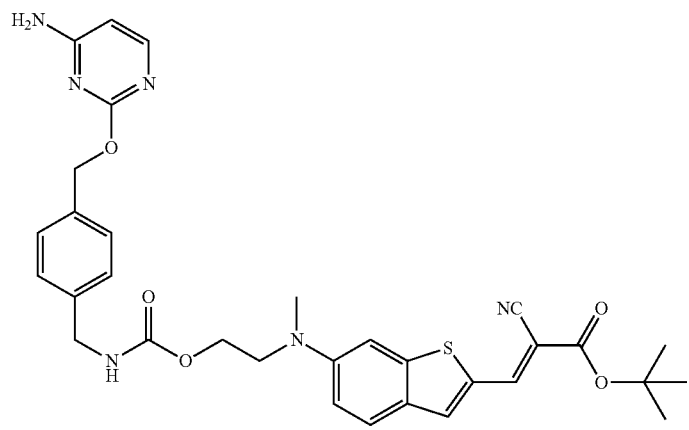

Probe 35
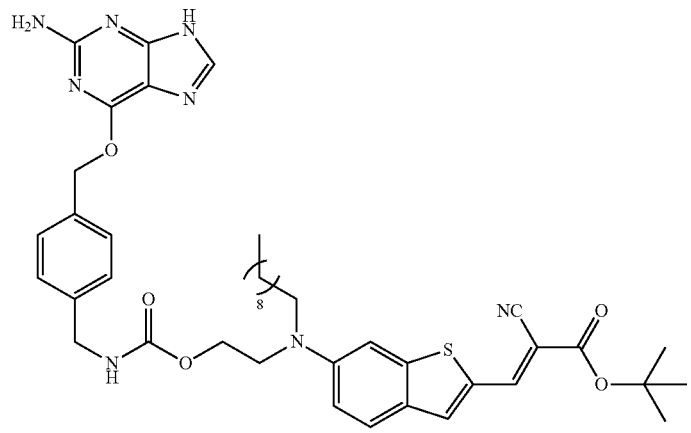
Probe 36
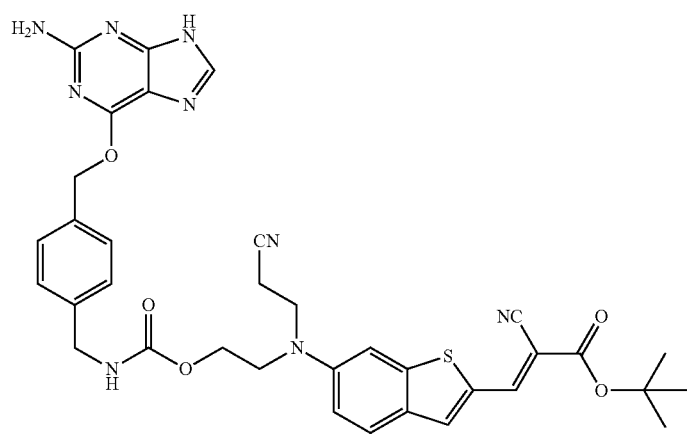
Probe 37
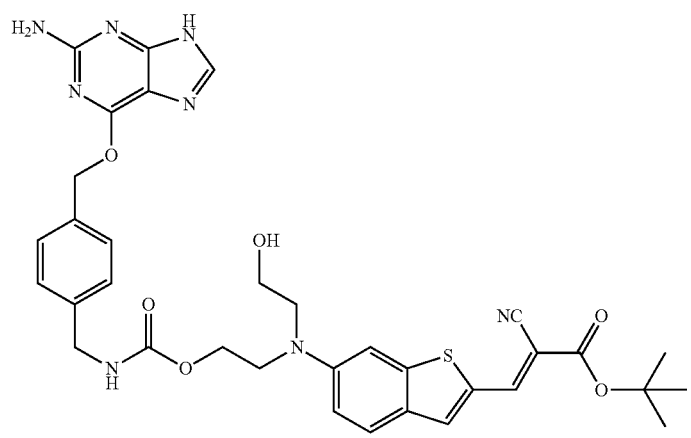

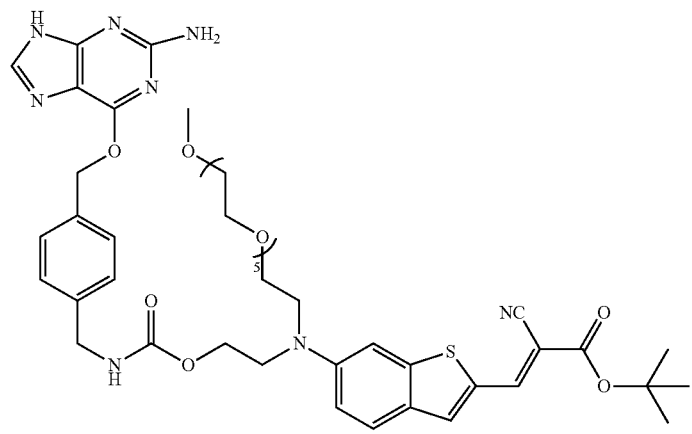
Probe 38
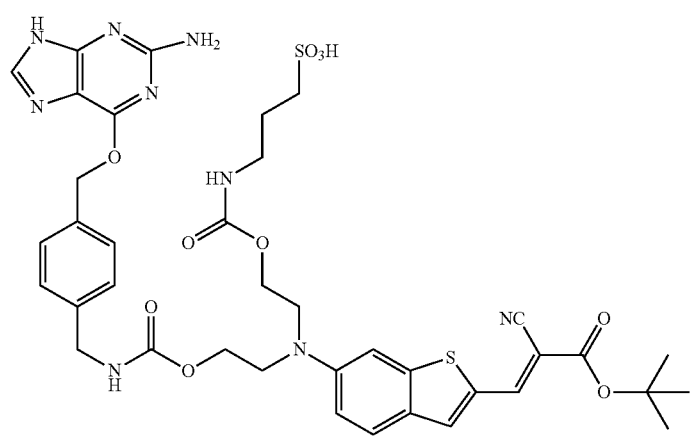
Probe 39
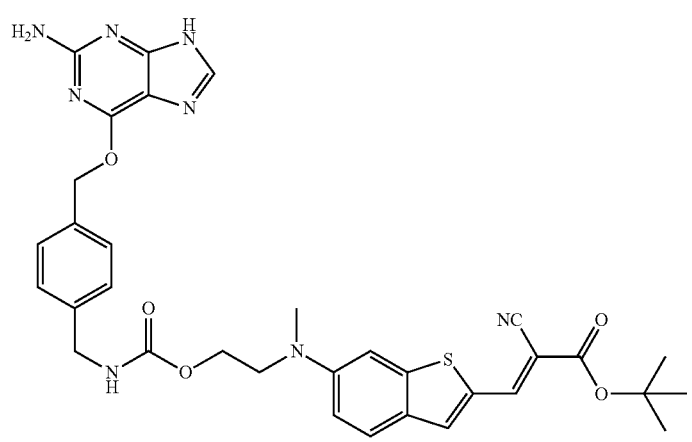
Probe 40

-continued
Probe 41
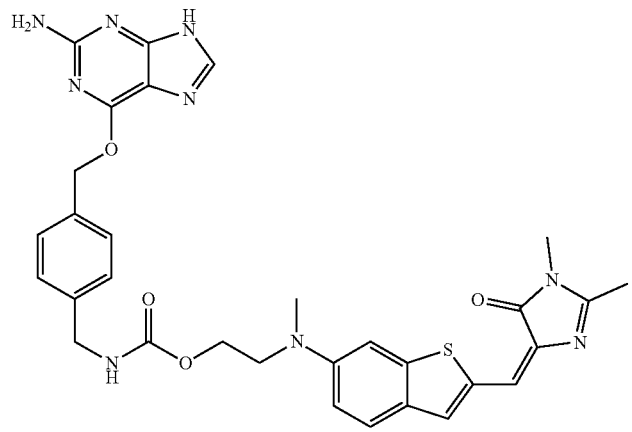
Probe 42
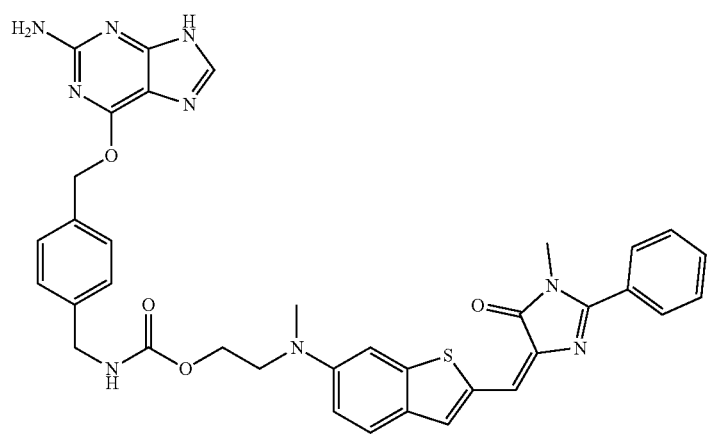
Probe 60
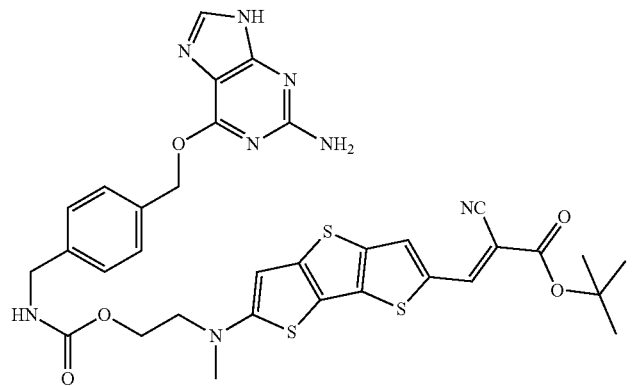
Probe 61
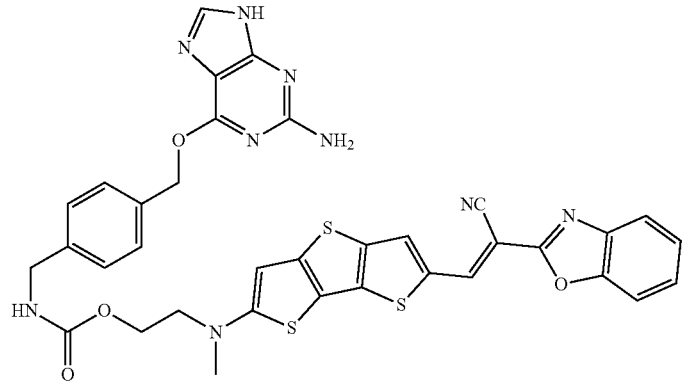

Probe 62
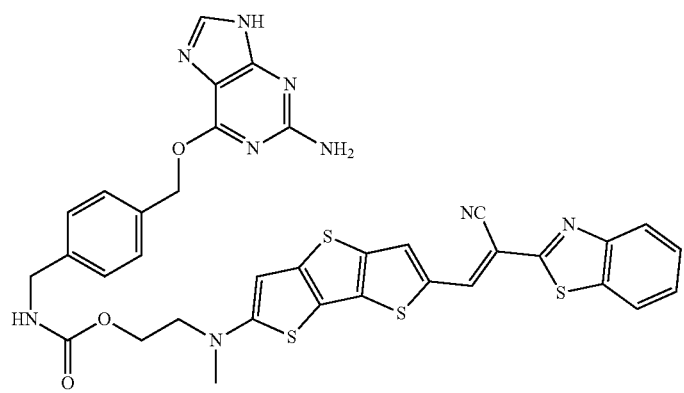
Probe 63
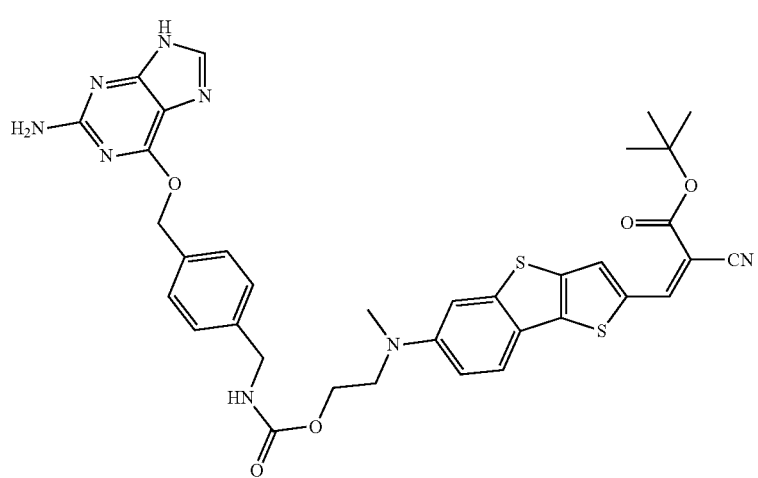
Probe 64
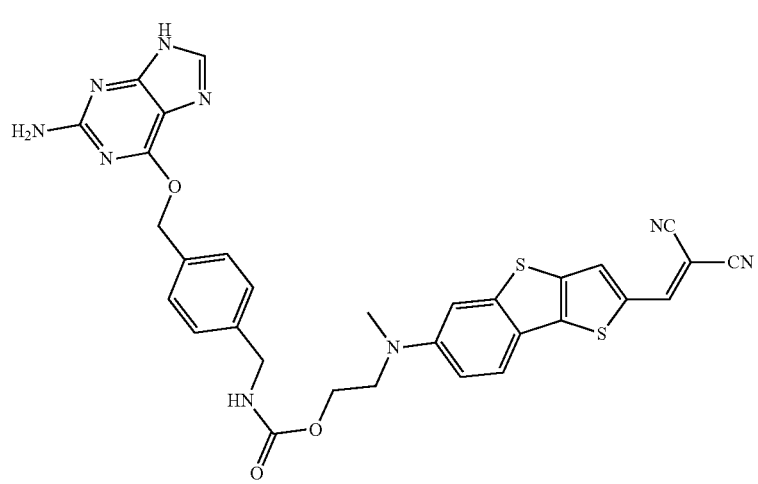

-continued
Probe 65
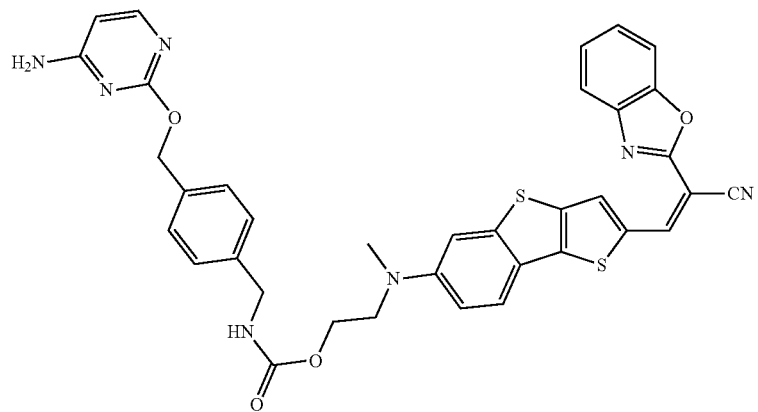
Probe 66
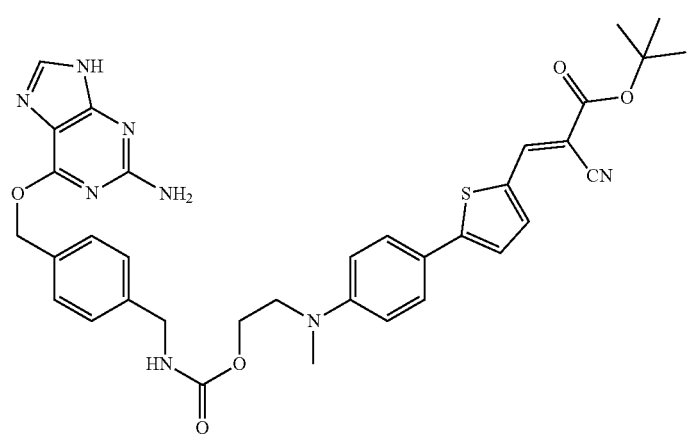
Probe 67
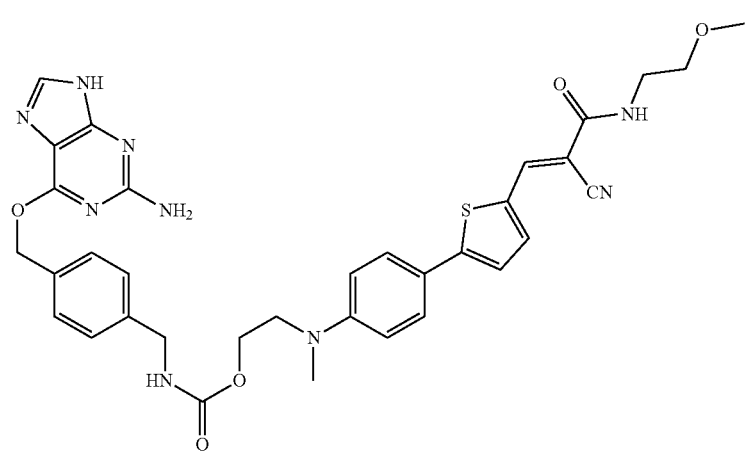

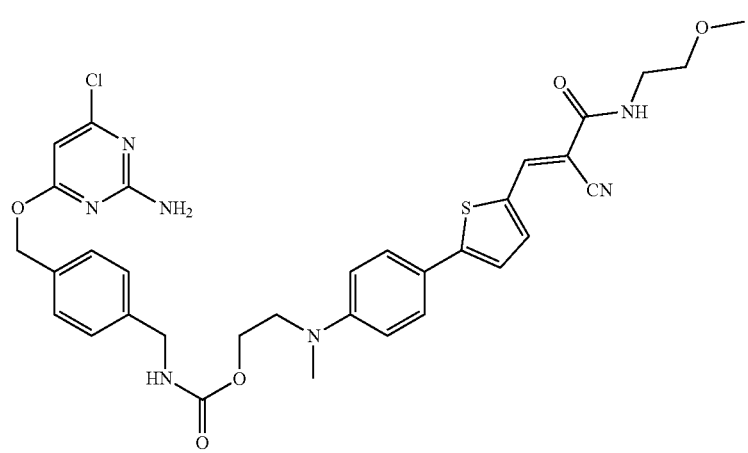
Probe 68
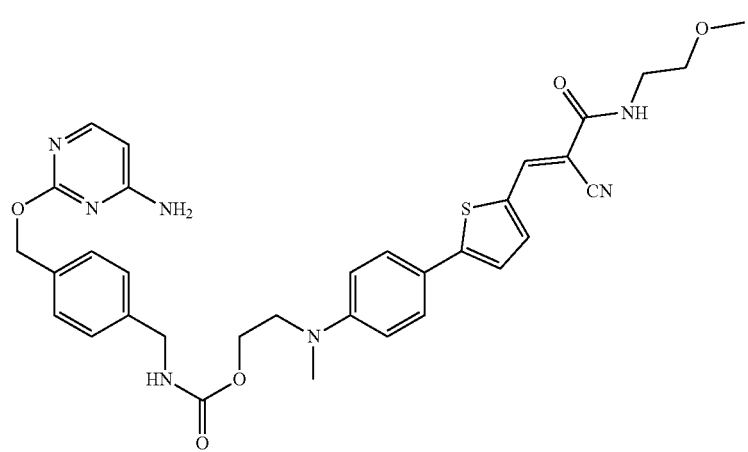
Probe 69
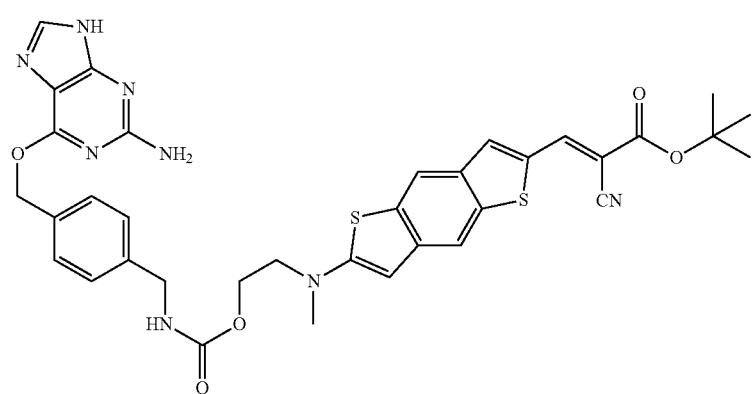
Probe 70
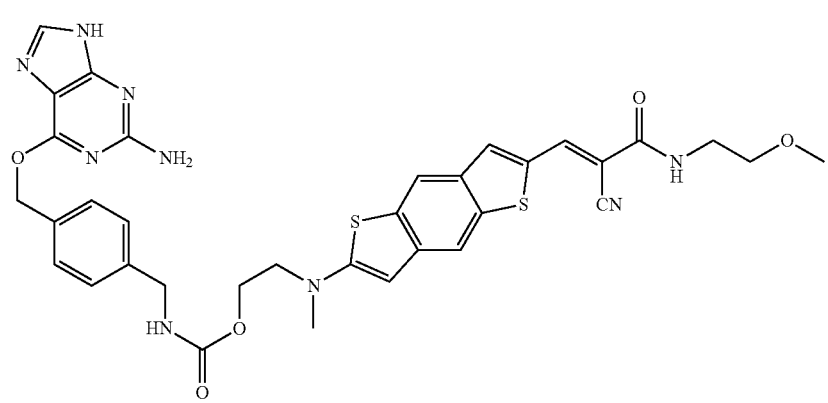
Probe 71

-continued
Probe 72
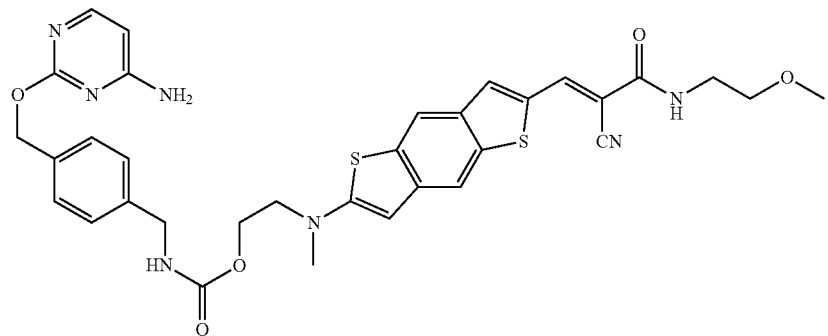
Probe 77
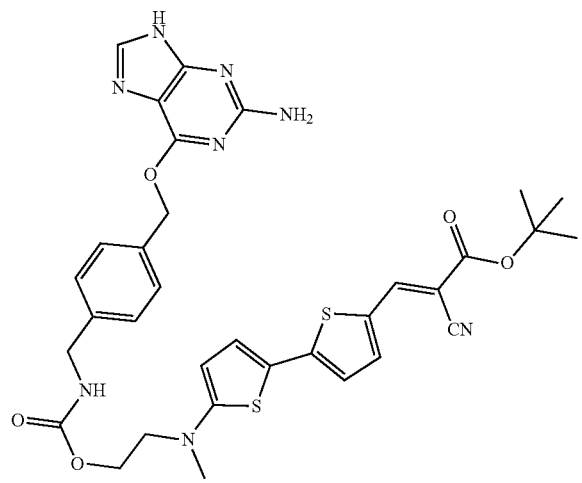
Probe 78
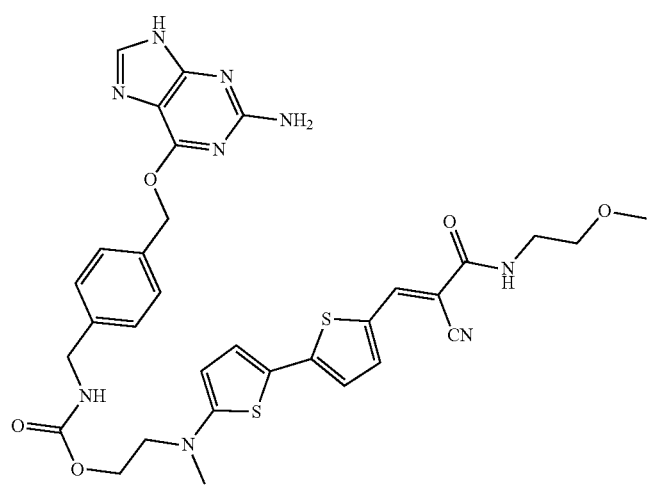

-continued
Probe 79
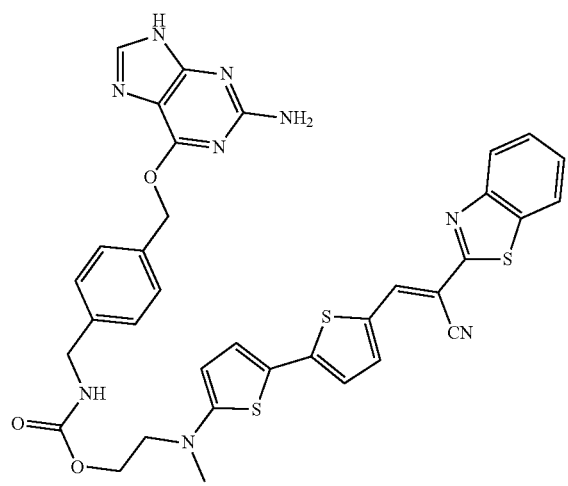
Probe 80
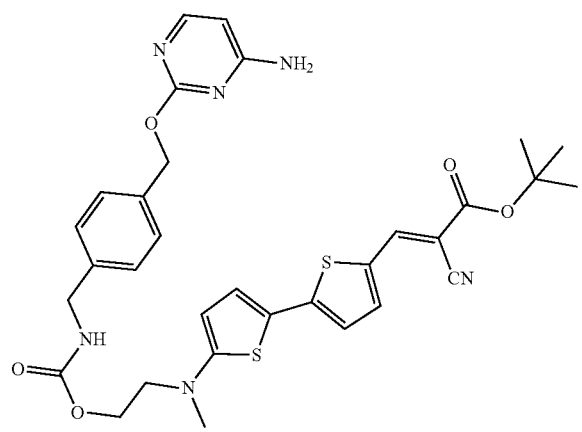
Probe 81
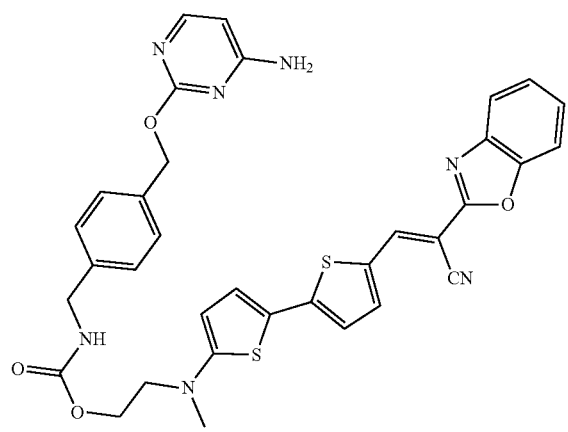
Probe 82
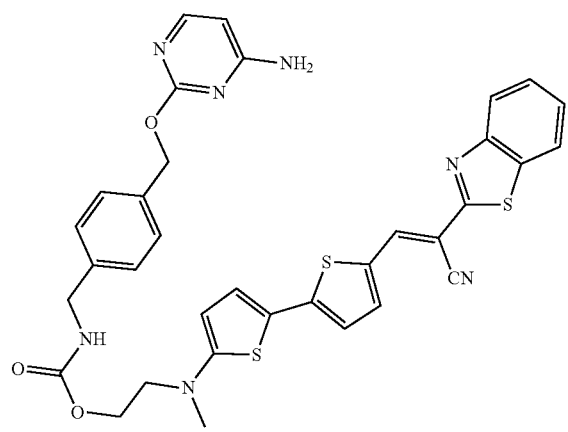
Probe 92
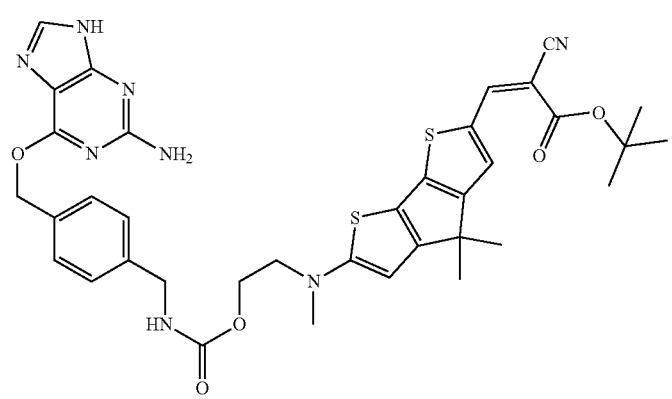

-continued
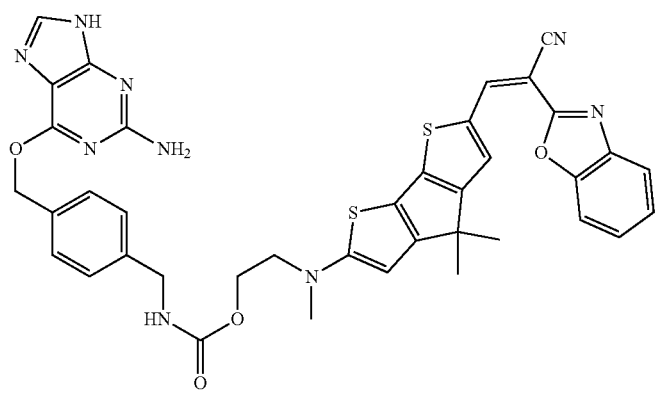
Probe 93
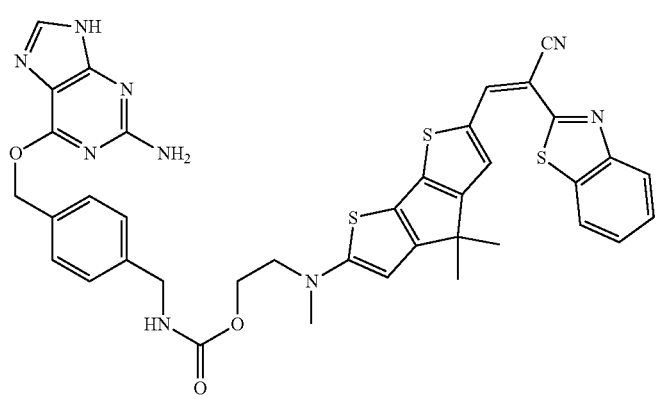
Probe 94
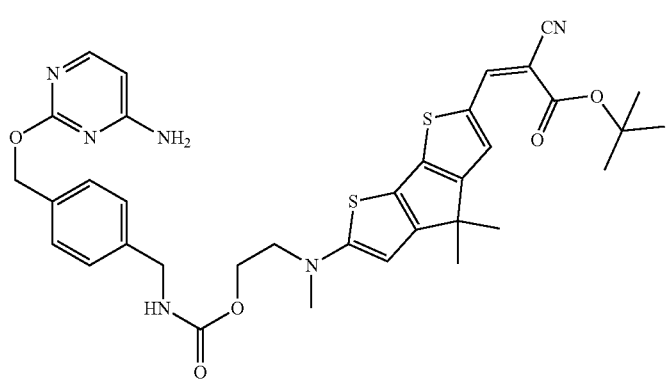
Probe 95
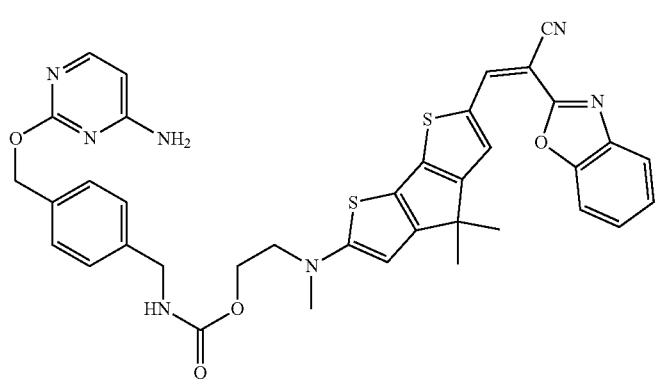
Probe 96

Probe 97
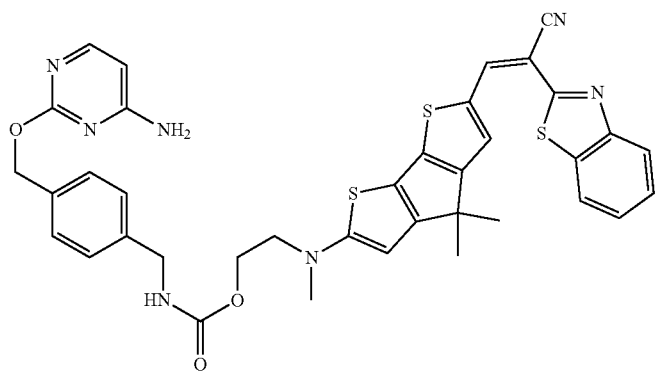
Probe 98
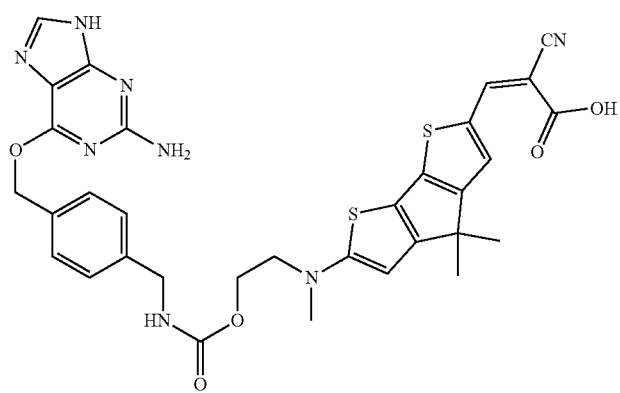
Probe 107
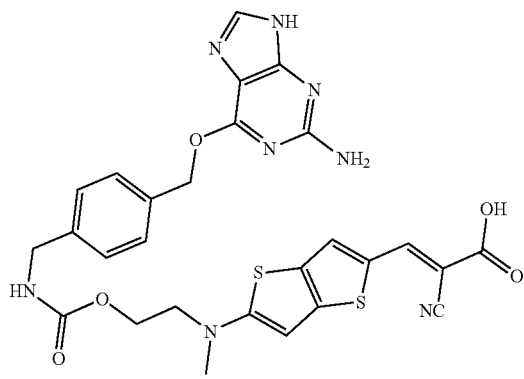
Probe 111
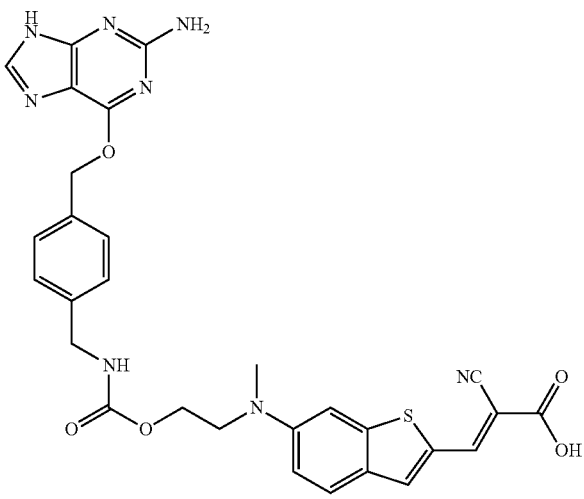

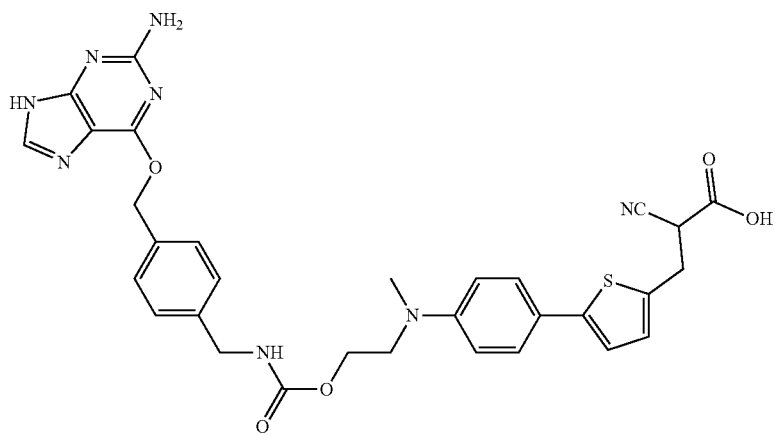

Probe 117

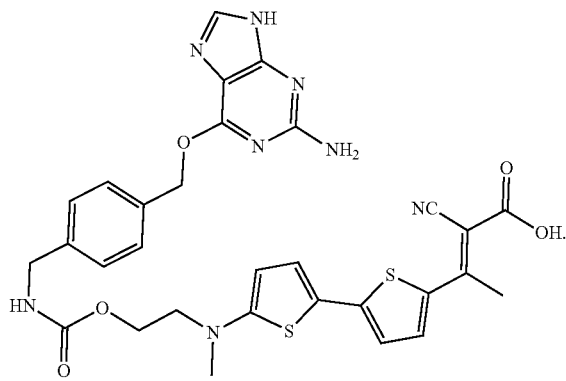

Probe 120

4. A process for preparing the fluorescent probe according to claim 1, comprising a step of reacting a fluorescent dye of formula (II) with a ligand and a linker:

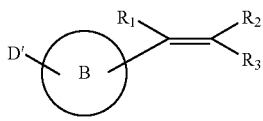
(II)

wherein, after reaction, D' forms —X$_2$—NX$_1$-group that bonds to the formula (II')

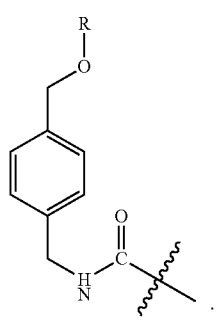
(II')

5. A fluorescent activated protein specific labeling method, comprising the following steps: contacting the fluorescent probe according to claim 1 with a target protein of a protein tag or a fusion protein tag, labeling reaction taking place at the ligand moiety of the fluorescent probe with the protein tag, and the fluorescent probe is labeled onto the protein tag; optionally, the fluorescent probe is covalently labeled on the protein tag;
optionally, a reaction medium of the labeling reaction is selected from a pure protein solution, a cell lysate or an in situ medium in which the target protein of the protein tag or the fused protein tag is located; optionally, the in situ medium is intracellular media, organelle media, living tissue media, Hood or body fluids.

6. A probe kit comprising the fluorescent probe according to claim 1, optionally further comprising a biocompatible medium which is at least one selected from dimethyl sulfoxide, a buffer, and physiological saline; optionally the buffer is phosphate buffer.

7. A fluorescent activated protein specific labeling method, comprising the following steps: contacting the fluorescent probe according to claim 1 with a target protein of a protein tag or a fusion protein tag, labeling reaction taking place at the ligand moiety of the fluorescent probe with the protein tag, and the fluorescent probe is labeled onto the protein tag; optionally, the fluorescent probe is covalently labeled on the protein tag;
optionally, a reaction medium of the labeling reaction is selected from a pure protein solution, a cell lysate or an in situ medium in which the target protein of the protein tag or the fused protein tag is located; optionally, the in situ medium is intracellular media, organelle media, living tissue media, blood or body fluids.

8. A fluorescent activated protein specific labeling method, comprising the following steps: contacting the fluorescent probe according to claim 2 with a target protein of a protein tag or a fusion protein tag, labeling reaction taking place at the ligand moiety of the fluorescent probe with the protein tag, and the fluorescent probe is labeled onto the protein tag; optionally, the fluorescent probe is covalent's/labeled on the protein tag;

optionally, a reaction medium of the labeling reaction is selected from a pure protein solution, a cell lysate or an in situ medium in which the target protein of the protein tag or the fused protein tag is located; optionally, the in situ medium is intracellular media, organelle media, living tissue media, blood or body fluids.

9. A fluorescent activated protein specific labeling method, comprising the following steps: contacting the fluorescent probe according to claim 3 with a target protein of a protein tag or a fusion protein tag, labeling reaction taking place at the ligand moiety of the fluorescent probe with the protein tag, and the fluorescent probe is labeled onto the protein tag; optionally, the fluorescent probe is covalently labeled on the protein tag;

optionally, a reaction medium of the labeling reaction is selected from a pure protein solution, a cell lysate or an in situ medium in which the target protein of the protein tag or the fused protein tag is located; optionally, the in situ medium is intracellular media, organelle media, living tissue media, blood or body fluids.

10. A probe kit, comprising the fluorescent probe according to claim 2, optionally, the probe kit further comprises a biocompatible medium; optionally, the biocompatible medium is at least one selected from dimethyl sulfoxide, a buffer, and physiological saline; optionally, the buffer includes phosphate buffer.

11. A probe kit, comprising the fluorescent probe according to claim 1, optionally, the probe kit further comprises a biocompatible medium; optionally, the biocompatible medium is at least one selected from dimethyl sulfoxide, a buffer, and physiological saline; optionally, the buffer includes phosphate buffer.

12. A probe kit, comprising the fluorescent probe according to claim 3, optionally, the probe kit further comprises a biocompatible medium; optionally, the biocompatible medium is at least one selected from dimethyl sulfoxide, a buffer, and physiological saline; optionally, the buffer includes phosphate buffer.

13. The fluorescent probe according to claim 1, wherein, the structure of the Formula (I-2) is selected from the group consisting of the following Formulas:

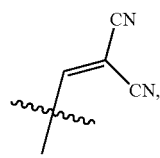

(I-2-1)

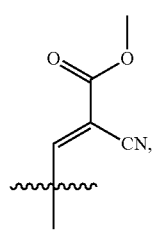

(I-2-2)

-continued

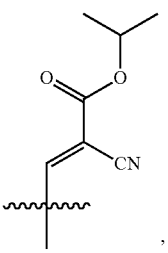

(I-2-3)

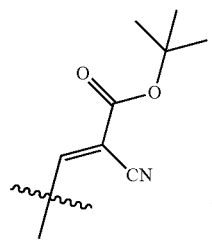

(I-2-4)

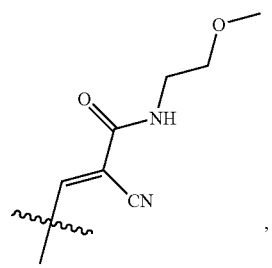

(I-2-6)

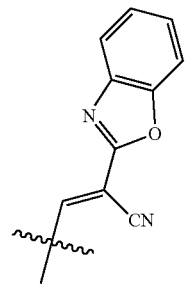

(I-2-7)

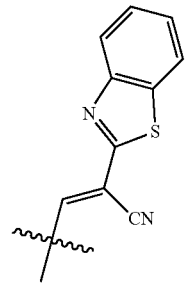

(I-2-9)

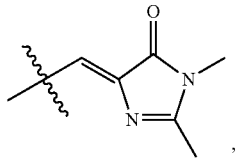

(I-2-11)

(I-2-12)
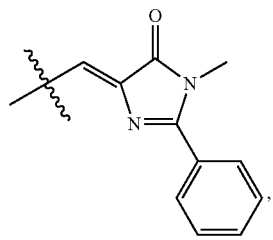
(I-2-17)
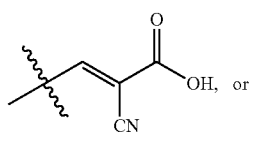
(I-2-18)
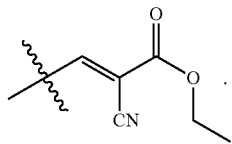
14. The fluorescent probe according to claim 1, wherein said modified alkyl group is a group containing one or more substituents from $C_1$ to $C_4$ alkyl groups, —O—, —O—CO—, or —NH—CO—.
15. The fluorescent probe according to claim 14, wherein the $C_1$ to $C_4$ alkyl groups are methyl, ethyl, propyl, isopropyl, and isobutyl.
* * * * *